US007563948B2

(12) United States Patent
Haertel et al.

(10) Patent No.: US 7,563,948 B2
(45) Date of Patent: Jul. 21, 2009

(54) SUGAR AND LIPID METABOLISM REGULATORS IN PLANTS

(75) Inventors: Heiko A. Haertel, Durham, NC (US); Volker Mittendorf, Hillsborough, NC (US); Ruoying Chen, Apex, NC (US); Karin Shank, Raleigh, NC (US)

(73) Assignee: BASF Plant Science GmbH (DE)

( * ) Notice: Subject to any disclaimer, the term of this patent is extended or adjusted under 35 U.S.C. 154(b) by 262 days.

(21) Appl. No.: 11/277,204

(22) Filed: Mar. 22, 2006

(65) Prior Publication Data

US 2006/0179515 A1    Aug. 10, 2006

Related U.S. Application Data

(62) Division of application No. 10/100,294, filed on Mar. 18, 2002, now Pat. No. 7,105,723.

(60) Provisional application No. 60/276,993, filed on Mar. 16, 2001.

(51) Int. Cl.
*A01H 5/00* (2006.01)
*C12N 15/82* (2006.01)
*C07H 21/04* (2006.01)

(52) U.S. Cl. .................. 800/298; 800/281; 435/410; 536/23.1

(58) Field of Classification Search ............... None
See application file for complete search history.

(56) References Cited

U.S. PATENT DOCUMENTS

| 5,880,334 | A | * | 3/1999 | Suzuki et al. | 800/298 |
|-----------|---|---|--------|---------------|---------|
| 5,955,650 | A | | 9/1999 | Hitz | 800/281 |
| 6,084,164 | A | | 7/2000 | Bidney et al. | 800/322 |
| 6,777,539 | B2 | | 8/2004 | Sprecher et al. | |

FOREIGN PATENT DOCUMENTS

| WO | WO 01/26459 | 4/2001 |
| WO | WO 01/38484 | 5/2001 |
| WO | WO 01/45493 | 6/2001 |
| WO | WO 01/77356 | 10/2001 |
| WO | WO 02/22675 | 3/2002 |

OTHER PUBLICATIONS

Brenner, S.E., TIG, vol. 15, No. 4, (1999), pp. 132-133.
Bork, et al., TIG, vol. 12, No. 10, (1996), pp. 425-427.
Deluca, V., AgBiotech News and Information, vol. 5, No. 6, (1993), pp. 225N-229N.
Mindrinos et al., Database GenEMBL, Accession U12857, (1994).
Broun et al., Science, vol. 282, (1998), ppl. 1315-1317.
Van De Loo et al., PNAS, USA, vol. 92, (1995), pp. 6743-6747.
Doerks et al., TIG, vol. 14, No. 6, (1998), pp. 248-250.
Smith et al., Nature Biotechnology, vol. 15, (1997), pp. 1222-1223.
Buhr et al., 2002, Ribozyme termination of RNA transcripts downregulate seed fatty acid genes in transgenic soybean", The Plant Journal. 30(2):155-163.

EBI Database Accession No. AW098572, "ga02b09.y1 Moss EST library CPU *Ceratodon purpureus* cDNA clone PEP_Source_ID:CPU010518 5' similar to TR:Q9ZUL5 Q9ZUL5 Putative DNA-Binding Protein, mRNA sequence."
EBI Database Accession No. AAC42914, "*Arabidopsis thaliana* DNA fragment Seq ID No.37333," Oct. 17, 2000.
EBI Database Accession No. AAG31130, "Arabidopsis thaliana protein fragment Seq ID No. 37334", Oct. 17, 2000.
Girke et al., 1998, "Identification of a novel Δ6-acyl-group desaturase by targeted gene disruption in *Physcomitrella patens*", The Plant Journal, 15(1):39-48.
Lawton et al., 1989, "Molecular cloning of plant transcripts encoding protein kinase homologs", Proc. Natl. Acad. Sci, USA, 86:3140-3144.
Ohlrogge et al., 2002, "Fatty acid synthesis: from CO2 to functional genomics", Biochem. Society Trans. 28(6):568-573.
Sperling et al., 2000, "A bifunctional $\Delta^6$ -fatty acyl acetylenase/desaturase from the moss *Ceratodon purpureus*", Eur. J. Biochem. 267:3801-3811.
Stein et al., 1993, "A Plant Receptor-Like Gene, the S-Locus Receptor Kinase of *Brassica oleracea* L., Encodes a Functional Serine/Threonine Kinase," Plant Physiol., 101:1103-1106.
Zank et al., 2000. "Cloning and functional expression of the first plant fatty acid elongase specific for $\Delta^6$-polyunsaturated fatty acids", Biochemical Society Trans,28(6):654-658.
Lawton et al., 1989, "Molecular cloning of plant transcripts encoding protein kinase homologs", Proc. Natl. Acad. Sci, USA, 86:3140-3144.
Stein et al., 1993, "A Plant Receptor-Like Gene, the S-Locus Receptor Kinase of *Brassica oleracea* L., Encodes a Functional Serine/Threonine Kinase," Plant Physiol., 101:1103-1106.
Kinney et al., 1994, "Genetic Modification of the Storage Lipids of Plants," Current Opin. in Biotech. 5:144-151.
Hatje et al., "World Importance of Oil Crops and Their Products", Oil Crops of the World-Their Breeding and Utilization, 1989, eds. Röbbelen, Downey, and Ashri, pp. 1-21.
Quatrano et al., gb19e01.y1 Moss EST library, Accession No. AW699058, Apr. 18, 2000, pp. 8-9.
Töpfer et al., "Modification of Plant Lipid Synthesis", 1995, Science, vol. 268, 681-86.
Cahoon et al., "Expression of a coriander desaturase results in petroselinic acid production in transgenic tobacco,", 1992, Proc. Natl. Acad. Sci. USA, vol. 89, 11184-88.
Van de Loo et al., 1993, "Unusual Fatty Acids" in Lipid Metabolism in Plants, ed. Thomas S Moore Jr., CRC Press.

(Continued)

*Primary Examiner*—Elizabeth F McElwain
(74) *Attorney, Agent, or Firm*—Connolly Bove Lodge & Hutz LLP

(57) ABSTRACT

The present invention is directed to novel nucleic acid and amino acid sequences associated with the metabolism of seed storage compounds in plants. More particularly novel lipid metabolism protein (LMP) sequences are provided herein. Preferably, the seed storage compounds are lipids, fatty acids, starches or seed storage proteins.

31 Claims, 25 Drawing Sheets

OTHER PUBLICATIONS

Millar et al., "All fatty acids are not equal: discrimination in plant membrane lipids", 2000, Trends in Plant Science, vol. 5, 95-101.

Browse et al., "Fluxes through the prokaryotic and eukaryotic pathways of lipid synthesis in the '16:3' plant *Arabidopsis thaliana*", 1986, Biochemical Journal, vol. 235, 25-31.

Ohlrogge & Browse, "Lipid Biosynthesis", 1995, Plant Cell, vol. 7, 957-70.

Voelker, 1996, "Plant acyl-ACP thioesterases: chain-length determining enzymes in plant fatty acid biosynthesis" in Genetic Engineering, ed. Jane K. Setlow, vol. 18, 111-33.

Shanklin & Cahoon, "Desaturation and related modifications of fatty acids", 1998, Annu. Rev. Plant Physiol. Plant Mol. Biol., vol. 49, 611-641.

Frentzen, "Acyltransferases from basic science to modified seed oils", 1998, Lipid, vol. 100, 161-66.

Van de Loo et al., "An oleate 12-hydroxylase from *Ricinus communis* L. is a fatty acyl desaturase homolog", 1995, Proc. Natl. Acad. Sci. USA, vol. 92, 6743-47.

Brenner, "Regulatory function of Δ6 desaturase—key enzyme of polyunsaturated fatty acid synthesis" 1977, Adv. Exp. Med. Biol., vol. 83, 85-101.

Plaxton, "The organization and regulation of plant glycolysis", 1996, Annu. Rev. Plant Physiol. Plant Mol. Biol., vol. 47, 185-214.

Kang & Rawsthorne, "Starch and fatty acid synthesis in plastids from developing embryos of oilseed rape (*Brassica napus* L.)", 1994, Plant J., vol. 6, 795-805.

Focks & Benning, "*wrinkled1*: A Novel, Low-Seed-Oil Mutant of Arabidopsis with a Deficiency in the Seed-Specific Regulation of Carbohydrate Metabolism", 1998, Plant Physiol., vol. 118, 91-101.

Cohen, "Signal integration at the level of protein kinases, protein phosphatases and their substrates", 1992, Trends Biochem, Sci., vol. 17, 408-13.

Roberts & Harmon, "Calcium-modulated proteins: targets of intracellular calcium signals in higher plants", 1992, Annu. Rev. Plant Physiol. Plant Mol. Biol., vol. 43, 375-414.

Kuo et al., "Okadaic Acid, a Protein Phosphatase Inhibitor, Blocks Calcium Changes, Gene Expression, and Cell Death Induced by Gibberellin in Wheat Aleurone Cells", 1996, Plant Cell, vol. 8, 259-69.

Ritchie & Gilroy, "Calcium-Dependent Protein Phosphorylation May Mediate the Gibberellic Acid Response in Barley Aleurone", 1998, Plant Physiol., vol. 116, 765-76.

Mitsukawa, et al., "Overexpression on an *Arabidopsis thaliana* high-affinity phosphate transporter gene in tobacco cultured cells enhances cell growth under phosphate-limited conditions", 1997, Proc. Natl. Acad. Sci. USA, vol. 94, No. 13., 7098-7102.

Hurry, et al., "The role of inorganic phosphate in the development of freezing tolerance and the acclimatization of photosynthesis to low temperature is revealed by the *pho* mutants of *Arabidopsis thaliana*", 2000, The Plant Journal, 24(3), 383-396.

Hartel, et al., "DGD1—independent biosynthesis of extraplastidic galactolipids after phosphate deprivation in *Arbidopsis*", 2000, Proc. Natl. Acad. Sci. USA, vol. 97, No. 19, 10649-10654.

Savage & Ohlrogge, "Phosphorylation of pea chloroplast acetyl-CoA carboxylase", 1999, The Plant Journal, 18(5), 521-527.

Mueller, et al., "Lipid Phosphorylation in Chloroplast Envelopes", 2000, The Journal of Biological Chemistry, vol. 275, No. 26, 19475-19481.

Merlot, et al., "The ABI1 and ABI2 protein phosphatases 2C act in a negative feedback regulatory loop of the abscisic acid signaling pathway", 2001, The Plant Journal, 15(3), 295-303.

\* cited by examiner

Figure 1A

SEQ ID NO:1, Nucleotide sequence of s_pp001031077f

CGATGGTGCGTTCGAGATCGTAAGGTTGCCGACGAAGGCGTAACTTGGAAGTCC
TCTGTGTCCCGGCGATGTCCCAATGTTGGCCCGATTTTCTGTTTTAGCGAGCTGT
GGGCTAGTTTGTGGGTATGATCCGGGGAATGAGACGAGATGTCTGTCTGAGTGA
GACCACTCTAGGGGCTGTTGGAGGATGAGGAGGGAAGCGCAGAAGTTGGCCATT
CTTTTCAGTGACTGGACTCTGTGCGAGTGGTCAGCTTTCGGGAGCTGCTGTTGCA
TTGACCGGTGATTCTTTCGAGATCGTAGAGACAGCAGCTGGCAAGGGTTTTGGA
GGCTTTTCAAATGAAGGGCATTCAAGAGCTTTCAGATGATGAAGATTATATTCCG
CCTGTCAATGCATCGCGATATTTCAACAGGGGCAAAGCGCTCTCAAAGACATCAT
CCAATCATGCCAATGGAAATGGAAATCCAAACGGAACGAGTTTTGGAGTTTCAA
CTTCTTCAGCAAGTGACTCTGACAAAGATAAGAAATCCGAAGTTTCAGGTTCTTT
ACTAAGCGATTCTGGCAAGAATCAAAAGTCCGTTACTGAATTGGATTCGTTCGCA
TTTAACCGCAAGTCCAGAATTGCCAAGCGACCTATCGAGCTACTCGAAGACGAG
GAGGACGTGGACGTTGGAGCTGCAAAGGTTGTAGACATTGAGCCGACTAACGGA
AACAAGAGGCGGAGACGGTATCACACCATCGAAGACAGTGACGATGAAGAGTT
GGATGAGAAGAAATCGTTTGGTGATAATCTGACCCCAGGAACGGAAATCGATCA
ATGTGCAGCCGATGAATCCTTAGCAAAAAGGTTGCAGGATTTAGAGCACCGGGC
AGTTCTGGCCGTAATCGCCTGGTTCAAATTTTGTCAGATTCCGATGAAGAAGAA
GAGGAAGAAGTAAATCCCATAACCATCACCCTACAAAGGTGTGACCAGATTGCA
GCATCATTGCGAGAAGAGCTGCAGGCCAGCAGTTCAAGTGATAACTCGGTTAAT
GAAGATCGTTATGCAGAGGTTGATGTAGCAGCAGCAAAAATTGTGAGCCAGGCA
GATGTCTGTGCAGCTTGTGGCATTGCCGAGAATGATACACAACGAATGCTCAAGC
CATATCAGCTTGTAGGCGTCAATTTCATGCTGCTACTTCACCGCAAACATGTTGG
GGGTGCTATACTTGCGGATGAAATGGGCCTAGGAAAGACTGTGCAGGCAGTTGC
GTATCTTGCCCTTCTGAAACATCTTGATGGAGATGCTGGTCCTCATCTTTTAGTTG
CACCTGCTTCTCTTTTAGAAAACTGGCAAAGAGAACTCAAGAAGTGGTGTCCTGC
ATTTAAGGTGGAGCTCTATCATGGCTCAGGAAGGGCAGCTTTAAACAGGAGGCT
TCAGTATGCTGCAAAATCTAAAGGGCCTGCACCCTTTAACGTGATGCTGACGTGC
TACTCCCTTTTTGAGAGGCAGAGTGCTCAGACAAAAGATGACCGCAAATTCCTTA
AGAAATGGAATTGGCGCTGTGTGGTTATGGACGAGGCTCATCTTTTGAAGGACA
GAAGCAGCTTTCGCAGCAAAAAGTTGCGAGATATAGCTCACAAAGCAATTCAAA
GACTGATGCTGACTGGTACTCCACTCCAGAACGATTTGCAGGAGCTATGGTCACT
TCTGGAGTTCATGATGCCTGATGTGTTCAACACAAATGGCGTTGATTTAGATCAA
TATCTGGGAACCAGGAACGATACCTCAGGGATTGTTGTGCAGGATACGAACTTG
ATGACTCGGATCAAAGGAATACTAGGACCTTTTGTATTACGGAGAATGAAAACT
GATGTTATGCGCCAGCTTGTATCAAAGATTCAGGAGGTGGAGTGTGTGGAGATG
CTAGACGAGCAATCAATGGCATATAAAAAGCTGTGAATGAGTATAGAGCCCTT
GCTGAGTCCGCACGTGCCGCTAAAGCTGCAAAGAAATCCTCAGTTAGCGTAGTA
GATGTCCTTCCTCGTCGACAAGTGACCAATATCTTTACTCAATTGAGAAAGCTCG
GTAATCATCCCTTGTTGATACGCCGTTTGTATTCTGACGAGACAGTCAAGAAATT
GGCTAAGAAATTTCATCCATTAGGAGTTTTTGGATATGAATGCGATTTGCAGCGT
GTGGAGGAAGAATTGACTAGTTACAGCGATTTTGACCTCCACAAGTTGTGTATTC
AATATGGAGGCGCTGCGGGAGGGCAAGGAAAGCTTGATGATGATCATGCACTAG
CTTCTGCAAAGTGCCAGGCTTTAGCACGTCTACTTCCCAAGTTACAGCAAGGTGG
CCATCGCACATTGATATTCAGCCAGTGGACAAGCATGCTGGATATTTTAGAATGG

Figure 1A Continued

GCTCTTGACGTCATGGGTTTTTCTTACACTCGCCTAGATGGAAGCACTCAAGTAA
GTGAACGCCAAACCCTAGTGGACGAGTTCAACAATGACCCTAGCATATTTGTGTT
TCTCCTGTCTACTCGAGCTGGAGGTCAAGGTCTAAATTTAACAGGAGCAGACACA
GTCATTTTACATGATTTGGACTTCAATCCCCAAATGGATCGACAGGCTGAGGATC
GCTGTCATCGGATTGGCCAGTCTAAACCTGTTACGATATACCGACTTGTAACAAA
AGATACGGTCGATGAAAGTATATACAAGATAGCCCAACAGAAGCTGGTCCTCGA
TGCGGCAGTTCTTGAAGGAAAAGAGTCATCCTCTGATCTTAATGATGGTGATGCT
CGCACGATGGGTGAAATTCTTTCTGCATTATTGGATGTTCCACCGACATGATCCT
GGAGTCCAGAACACATTTTTAATTTATTTTCATTATCTTTATCTGGCACTGCGAGA
AAGCTCGTTAACGC

Figure 1B

SEQ ID NO:2, Nucleotide sequence of the open reading frame of s_pp001031077f

ATGAAGGGCATTCAAGAGCTTTCAGATGATGAAGATTATATTCCGCCTGTCAATG
CATCGCGATATTTCAACAGGGGCAAAGCGCTCTCAAAGACATCATCCAATCATGC
CAATGGAAATGGAAATCCAAACGGAACGAGTTTTGGAGTTTCAACTTCTTCAGCA
AGTGACTCTGACAAAGATAAGAAATCCGAAGTTTCAGGTTCTTTACTAAGCGATT
CTGGCAAGAATCAAAAGTCCGTTACTGAATTGGATTCGTTCGCATTTAACCGCAA
GTCCAGAATTGCCAAGCGACCTATCGAGCTACTCGAAGACGAGGAGGACGTGGA
CGTTGGAGCTGCAAAGGTTGTAGACATTGAGCCGACTAACGGAAACAAGAGGCG
GAGACGGTATCACACCATCGAAGACAGTGACGATGAAGAGTTGGATGAGAAGA
AATCGTTTGGTGATAATCTGACCCCAGGAACGGAAATCGATCAATGTGCAGCCG
ATGAATCCTTAGCAAAAAGGTTGCAGGATTTAGAGCACCGGGCAGTTCTGGCC
GTAATCGCCTGGTTCAAATTTGTCAGATTCCGATGAAGAAGAAGAGGAAGAAG
TAAATCCCATAACCATCACCCTACAAAGGTGTGACCAGATTGCAGCATCATTGCG
AGAAGAGCTGCAGGCCAGCAGTTCAAGTGATAACTCGGTTAATGAAGATCGTTA
TGCAGAGGTTGATGTAGCAGCAGCAAAAATTGTGAGCCAGGCAGATGTCTGTGC
AGCTTGTGGCATTGCCGAGAATGATACACAACGAATGCTCAAGCCATATCAGCTT
GTAGGCGTCAATTTCATGCTGCTACTTCACCGCAAACATGTTGGGGGTGCTATAC
TTGCGGATGAAATGGGCCTAGGAAAGACTGTGCAGGCAGTTGCGTATCTTGCCCT
TCTGAAACATCTTGATGGAGATGCTGGTCCTCATCTTTTAGTTGCACCTGCTTCTC
TTTTAGAAAACTGGCAAAGAGAACTCAAGAAGTGGTGTCCTGCATTTAAGGTGG
AGCTCTATCATGGCTCAGGAAGGGCAGCTTTAAACAGGAGGCTTCAGTATGCTGC
AAAATCTAAAGGGCCTGCACCCTTTAACGTGATGCTGACGTGCTACTCCCTTTTT
GAGAGGCAGAGTGCTCAGACAAAAGATGACCGCAAATTCCTTAAGAAATGGAAT
TGGCGCTGTGTGGTTATGGACGAGGCTCATCTTTTGAAGGACAGAAGCAGCTTTC
GCAGCAAAAAGTTGCGAGATATAGCTCACAAAGCAATTCAAAGACTGATGCTGA
CTGGTACTCCACTCCAGAACGATTTGCAGGAGCTATGGTCACTTCTGGAGTTCAT
GATGCCTGATGTGTTCAACACAAATGGCGTTGATTTAGATCAATATCTGGGAACC
AGGAACGATACCTCAGGGATTGTTGTGCAGGATACGAACTTGATGACTCGGATC
AAAGGAATACTAGGACCTTTTGTATTACGGAGAATGAAAACTGATGTTATGCGCC
AGCTTGTATCAAAGATTCAGGAGGTGGAGTGTGTGGAGATGCTAGACGAGCAAT
CAATGGCATATAAAAAAGCTGTGAATGAGTATAGAGCCCTTGCTGAGTCCGCAC
GTGCCGCTAAAGCTGCAAAGAAATCCTCAGTTAGCGTAGTAGATGTCCTTCCTCG
TCGACAAGTGACCAATATCTTTACTCAATTGAGAAAGCTCGGTAATCATCCCTTG

Figure 1B Continued

```
TTGATACGCCGTTTGTATTCTGACGAGACAGTCAAGAAATTGGCTAAGAAATTTC
ATCCATTAGGAGTTTTTGGATATGAATGCGATTTGCAGCGTGTGGAGGAAGAATT
GACTAGTTACAGCGATTTTGACCTCCACAAGTTGTGTATTCAATATGGAGGCGCT
GCGGGAGGGCAAGGAAAGCTTGATGATGATCATGCACTAGCTTCTGCAAAGTGC
CAGGCTTTAGCACGTCTACTTCCCAAGTTACAGCAAGGTGGCCATCGCACATTGA
TATTCAGCCAGTGGACAAGCATGCTGGATATTTTAGAATGGGCTCTTGACGTCAT
GGGTTTTTCTTACACTCGCCTAGATGGAAGCACTCAAGTAAGTGAACGCCAAACC
CTAGTGGACGAGTTCAACAATGACCCTAGCATATTTGTGTTTCTCCTGTCTACTCG
AGCTGGAGGTCAAGGTCTAAATTTAACAGGAGCAGACACAGTCATTTTACATGA
TTTGGACTTCAATCCCCAAATGGATCGACAGGCTGAGGATCGCTGTCATCGGATT
GGCCAGTCTAAACCTGTTACGATATACCGACTTGTAACAAAAGATACGGTCGATG
AAAGTATATCAAGATAGCCCAACAGAAGCTGGTCCTCGATGCGGCAGTTCTTG
AAGGAAAAGAGTCATCCTCTGATCTTAATGATGGTGATGCTCGCACGATGGGTG
AAATTCTTTCTGCATTATTGGATGTTCCACCGACA
```

Figure 1C

SEQ ID NO:3, Amino acid sequence of the open reading frame of s_pp001031077f

```
MKGIQELSDDEDYIPPVNASRYFNRGKALSKTSSNHANGNGNPNGTSFGVSTSSASD
SDKDKKSEVSGSLLSDSGKNQKSVTELDSFAFNRKSRIAKRPIELLEDEEDVDVGAAK
VVDIEPTNGNKRRRRYHTIEDSDDEELDEKKSFGDNLTPGTEIDQCAADESLAKRLQ
DLEHRAVSGRNRLVQILSDSDEEEEEEVNPITITLQRCDQIAASLREELQASSSSDNSV
NEDRYAEVDVAAAKIVSQADVCAACGIAENDTQRMLKPYQLVGVNFMLLLHRKHV
GGAILADEMGLGKTVQAVAYLALLKHLDGDAGPHLLVAPASLLENWQRELKKWCP
AFKVELYHGSGRAALNRRLQYAAKSKGPAPFNVMLTCYSLFERQSAQTKDDRKFLK
KWNWRCVVMDEAHLLKDRSSFRSKKLRDIAHKAIQRLMLTGTPLQNDLQELWSLL
EFMMPDVFNTNGVDLDQYLGTRNDTSGIVVQDTNLMTRIKGILGPFVLRRMKTDVM
RQLVSKIQEVECVEMLDEQSMAYKKAVNEYRALAESARAAKAAKKSSVSVVDVLP
RRQVTNIFTQLRKLGNHPLLIRRLYSDETVKKLAKKFHPLGVFGYECDLQRVEEELTS
YSDFDLHKLCIQYGGAAGGQGKLDDDHALASAKCQALARLLPKLQQGGHRTLIFSQ
WTSMLDILEWALDVMGFSYTRLDGSTQVSERQTLVDEFNNDPSIFVFLLSTRAGGQG
LNLTGADTVILHDLDFNPQMDRQAEDRCHRIGQSKPVTIYRLVTKDTVDESIYKIAQ
QKLVLDAAVLEGKESSSDLNDGDARTMGEILSALLDVPPT
```

Figure 2A

SEQ ID NO:4, Nucleotide sequence of s_pp001117032r

```
TGGGTTTGGGTAGTTGCTTGACGCCATAAATTTCTCCCTTGAGTTGCAGTTATTGG
AGGGGGAGCTCAAGTCCAGACGTCCAGACGAGAGCAGTTCGTTTGCATTAATCT
GAAAGCGCAAAGTATCCGAAGATGAACAAGACAGTGTGTCCTGAGTGTCGGAAG
GCGACAGAGGTGGTAGTGGACCATGCCGCGGGGACATGGTGTGTGCAGAATGC
GGATTAGTCTTAGAGCAGCATTCCGTAGATGAAAGCTCGGAATGGCGAACGTTTT
CGGATTCAACTTCCAGCGACCCAGTCCGTGTCGGTGGTCCTTCCAATCCCCTCCTC
ACAGATGGTGGGCTGTCAACCATCATATCCAAGCCCAACGGTGCGCAGGGCGAT
TTCATGTCATCTCTTGGACGTTGGCAGAACAGGGGCTCAAATCCTGATCGGCCTC
TTATCATTGCTTTTCGATCAATTGGAACCATGGCAGACAGGCTCGGACTAGTGTC
```

Figure 2A Continued

```
AACAATCAAGGATCGGGCCAATGAGATATATAAGAAGGTGGAAGACCTGAAATC
TATCCGTGGTCGAAGTCAGGATGCGATACTGGCTGCCTGCTTATACATCGCTTGC
CGACAGGAAGATAAACCTCGAACATTCAAAGAAATATGCTCAGTTGCTAATGGA
GCATCGAAGAAGGACATTGGGAGAGCAACCAAGTTTATTGTGAAGCAATTAGAA
GAGGATATGGGTATTTCTATGGAGATGGGAACAATCCATGCTGGTGACTTCTTGA
GGAGATTCTGCTCGCATCTGAATATGGAAAACAACGAGGTCAGAGCTGCCACAG
AGACGGTAAAGAAGTCAGAGATGCTGGATATCCGAAAAAGTCCAATATCAGTTG
CTGCTGCTGCTATATACATGATCTCACAGCTTAATGAAAAAGATAAGAAAGCCCT
AAAAGACATATCAAGGGTGGCTGGGGTGGCTGAAGTGACTATCCGAAATTCTTA
CAAGGATCTCTATCCCCACGCAGCCAAGCTCATACCCGACTGGTTTCTTAAAGAA
GTTGATTTGAAGAATTTGCCAGCTCCTTAGAGCTTTTCTGTTCTTCGCTAGAGTGG
AAGAGTATAGGCAGGCGGTCCTTGAACC
```

Figure 2B

SEQ ID NO:5, Nucleotide sequence of the open reading frame of s_pp001117032r

```
ATGAACAAGACAGTGTGTCCTGAGTGTCGGAAGGCGACAGAGGTGGTAGTGGAC
CATGCCGCGGGGGACATGGTGTGTGCAGAATGCGGATTAGTCTTAGAGCAGCAT
TCCGTAGATGAAAGCTCGGAATGGCGAACGTTTTCGGATTCAACTTCCAGCGACC
CAGTCCGTGTCGGTGGTCCTTCCAATCCCCTCCTCACAGATGGTGGGCTGTCAAC
CATCATATCCAAGCCCAACGGTGCGCAGGGCGATTTCATGTCATCTCTTGGACGT
TGGCAGAACAGGGGCTCAAATCCTGATCGGCCTCTTATCATTGCTTTTCGATCAA
TTGGAACCATGGCAGACAGGCTCGGACTAGTGTCAACAATCAAGGATCGGGCCA
ATGAGATATATAAGAAGGTGGAAGACCTGAAATCTATCCGTGGTCGAAGTCAGG
ATGCGATACTGGCTGCCTGCTTATACATCGCTTGCCGACAGGAAGATAAACCTCG
AACATTCAAAGAAATATGCTCAGTTGCTAATGGAGCATCGAAGAAGGACATTGG
GAGAGCAACCAAGTTTATTGTGAAGCAATTAGAAGAGGATATGGGTATTTCTAT
GGAGATGGGAACAATCCATGCTGGTGACTTCTTGAGGAGATTCTGCTCGCATCTG
AATATGGAAAACAACGAGGTCAGAGCTGCCACAGAGACGGTAAAGAAGTCAGA
GATGCTGGATATCCGAAAAAGTCCAATATCAGTTGCTGCTGCTGCTATATACATG
ATCTCACAGCTTAATGAAAAAGATAAGAAAGCCCTAAAAGACATATCAAGGGTG
GCTGGGGTGGCTGAAGTGACTATCCGAAATTCTTACAAGGATCTCTATCCCCACG
CAGCCAAGCTCATACCCGACTGGTTTCTTAAAGAAGTTGATTTGAAGAATTTGCC
AGCTCCT
```

Figure 2C

SEQ ID NO:6, Amino acid sequence of the open reading frame of s_pp001117032r

```
MNKTVCPECRKATEVVVDHAAGDMVCAECGLVLEQHSVDESSEWRTFSDSTSSDP
VRVGGPSNPLLTDGGLSTIISKPNGAQGDFMSSLGRWQNRGSNPDRPLIIAFRSIGTM
ADRLGLVSTIKDRANEIYKKVEDLKSIRGRSQDAILAACLYIACRQEDKPRTFKEICSV
ANGASKKDIGRATKFIVKQLEEDMGISMEMGTIHAGDFLRRFCSHLNMENNEVRAA
TETVKKSEMLDIRKSPISVAAAIYMISQLNEKDKKALKDISRVAGVAEVTIRNSYKD
LYPHAAKLIPDWFLKEVDLKNLPAP
```

Figure 3A

SEQ ID NO:7, Nucleotide sequence of c_pp001113065r

GAGCTGCTGTCAGTTCGTCAACGGATTGATGCGGAGTCTTGAATCGGAGTCGAGT
TGGCGGTGACTGAAAAGAATTATCGCTCAAGAAACGATCGACTGTTCGGGTTCG
ACTTGTGATTTGCTTACTGTAGTCGGGTTGACAACGCTTCGACGCGTTCACGTTCT
GTGTGTTATTGATATTCCTGAGACGACTTCTGGATGTGTGTGGGGAGGCTGGAC
TGGTTAGTTCGATTTCGGTGCTCGAGGTTTCATTAATGAAAATTATACCTTAGGA
ATATGAAACAATCGTTATAGGTATCTCTTTTCTTCGACAAGGGATTGATTCATCG
CTTGCAAGCAGCCGCTGGTAACATCACTGCGTCAGTTATCTCTGAAGTTTACATA
GTTTCTTTAGATTTACTAGAGGGTGGAGAATTTTCTAACAGAGATCAAGGGGT
AGAAGACTTATAATATCGAAGGGTTTGCTGCATGAAAGTCTTATTTCACTTGCG
AAGCTTCCGTCCAGCTAGCGTGAGTTTGGATCGTTCGTAATTTTCCTATGTGTTG
CTCAATCGGAAGGGCGCCAGCAAAGTGGAGCGAGCACGGGTTAGGATTAGTATT
CCACTCAGGAAAGTGCAACTCAGGGAAGGGTAGAGAGAAACAGGAACTTGCTTA
TAACGAAAAGTTAGACTTAGAGTTCCTCCACATTTCCCGACAATCTATTTTCTTT
AGAATATGAATCGCATATCTTCCGTTGACGACATCCTGAGCGCATACTGGAACGA
GTCGTCTATGACTTCTCCTGTGAAGGGCAGCATGAACCGCAGTGCTTCTGAGTTC
GCTTTTCAAGAATTTATTAAGGAGAACATGACTGCCACATCTTGCTTCGGAGGCC
GCTCCAAGAGCCGCTTCTATCAATCGCAGGCGGATGAGGGGAAAGCTCTTAACG
ATCAAAGTCGTGACAATCTTATGATCTCGGCAAAATCTGAATCAGAGTTCACTCC
TCCGATGTTCGCAAGCACCGAGGAGCTGCGTGCGATGAATAACGTCGTGGACCC
TGTTGAAGTCGACGATATTGTGGGGATTGAGGGGGCGCTGAACCCCCTCTTCTCC
CGTGTCCAAAATGATGCGGATAAAAAATATTCCAATTTCCCCTCTGCTGCGTTAT
CTGCGGGTGACTGTGGTGGTCAAGACTATGAGGACATCCTTAAGCAGAAGTTGG
AAAGGGCGTGCGCTGCAGCGGCTCTCTCTAGACAGGTGAATGGCGAGGGTGCAA
TAATTGGACAATCGGTTGGAGCTATTTGTCAGAAGAGTTTTGCTATCGAATCATC
TGCCGCTAGTGCTTGTCCAAGTGGAGTTCAATGCGCACCCATGAGCGCTAAGTCT
CCTTCTCCAAAACCTGAAGTGGATGCATCAACCGGGAAGGTCAAACTTACGACC
AGTGGTTCGGAACTTTCTGATGACGACGAACATGATTTGTTAAACCAAAGCCTAC
CAGGCGGTGACCTTAAGCGTGTGAAGAGAATGTTGTCAAACCGTGAATCTGCCC
GACGCTCGCGCAGAAGGAAACAGGCACACTTGAGTGATCTAGAAATGCAGGTTG
CGCAATTGCGAGTTGAAAATACTACGCTTATGCAAAGATTGCAAGAGATTACCC
ACATGCATAAAGATGCATCTGTCGACAACCGAATTCTAAAGGCAGATGTGGAGG
CGTTGCGTGCTAAGGTGAAAATGGCTGAAGACATGGTGGCCCGTCAAGGACAGC
CCATGTCAAATCTCATTCCCGACCCCAGTTTAAGCTTTATGACACCGTTCAATGTG
AATGATATGGAAAGACCATTCTGCAACAGATGAGGCACAGTTCCATGCTACGC
CATGATCAGCAACAGCAGCCTGCTAGTGGCATTAGGGGTAAGATGGGACGTGCA
CCTTCAATGCAACGGGTTGCCAGCCTGGAGCATCTGACGAAGCGTATCCGCAAC
GGGAGTTCCTGCAACGTACCGGCTTGGGGTGGCTGGGACATGGACAGACCTGCC
ATGGTACAGGAACACGGCATCTGATCAATGTTCCGCGCTGACTATGTAGTAGAA
TCGATGTAACTTACATTTACTCCGCTTATTTCAAGCGAGAGCGAGAGTTCAGGGC
AAGTGGAAGATCCGAGATTATTATTTATTTTAGACTTGGGTTGAAGGGGAATAGA
TTTACGCTAAGAAGGGACTTCACCTTAGTTTTCAGAAGTGGCGTAGAATTCTTCT
GATAAGTAGGCATGGAAAGGATCATATTGTTGTTGCTTCAGAGGAAGAGAAGAT
TCATACTTTGGAGGGTGAACATAGAACTTGTTTTTTGGCAGGGTGCAAACGTTGC
TTGTAATCTCCTAGCTGAGATTGATGTTGTTGCTTGTAAATAGCTACTGCTGTCGT
CCTGGTCAAC

Figure 3B

SEQ ID NO:8, Nucleotide sequence of the open reading frame of c_pp001113065r

ATGAATCGCATATCTTCCGTTGACGACATCCTGAGCGCATACTGGAACGAGTCGT
CTATGACTTCTCCTGTGAAGGGCAGCATGAACCGCAGTGCTTCTGAGTTCGCTTT
TCAAGAATTTATTAAGGAGAACATGACTGCCACATCTTGCTTCGGAGGCCGCTCC
AAGAGCCGCTTCTATCAATCGCAGGCGGATGAGGGGAAAGCTCTTAACGATCAA
AGTCGTGACAATCTTATGATCTCGGCAAAATCTGAATCAGAGTTCACTCCTCCGA
TGTTCGCAAGCACCGAGGAGCTGCGTGCGATGAATAACGTCGTGGACCCTGTTG
AAGTCGACGATATTGTGGGGATTGAGGGGGCGCTGAACCCCCTCTTCTCCCGTGT
CCAAAATGATGCGGATAAAAAATATTCCAATTTCCCCTCTGCTGCGTTATCTGCG
GGTGACTGTGGTGGTCAAGACTATGAGGACATCCTTAAGCAGAAGTTGGAAAGG
GCGTGCGCTGCAGCGGCTCTCTAGACAGGTGAATGGCGAGGGTGCAATAATT
GGACAATCGGTTGGAGCTATTTGTCAGAAGAGTTTTGCTATCGAATCATCTGCCG
CTAGTGCTTGTCCAAGTGGAGTTCAATGCGCACCCATGAGCGCTAAGTCTCCTTC
TCCAAAACCTGAAGTGGATGCATCAACCGGGAAGGTCAAACTTACGACCAGTGG
TTCGGAACTTTCTGATGACGACGAACATGATTTGTTAAACCAAAGCCTACCAGGC
GGTGACCTTAAGCGTGTGAAGAGAATGTTGTCAAACCGTGAATCTGCCCGACGCT
CGCGCAGAAGGAAACAGGCACACTTGAGTGATCTAGAAATGCAGGTTGCGCAAT
TGCGAGTTGAAAATACTACGCTTATGCAAAGATTGCAAGAGATTACCCACATGC
ATAAAGATGCATCTGTCGACAACCGAATTCTAAAGGCAGATGTGGAGGCGTTGC
GTGCTAAGGTGAAAATGGCTGAAGACATGGTGGCCCGTCAAGGACAGCCCATGT
CAAATCTCATTCCCGACCCCAGTTTAAGCTTTATGACACCGTTCAATGTGAATGA
TATGGAAAGACCATTTCTGCAACAGATGAGGCACAGTTCCATGCTACGCCATGAT
CAGCAACAGCAGCCTGCTAGTGGCATTAGGGGTAAGATGGGACGTGCACCTTCA
ATGCAACGGGTTGCCAGCCTGGAGCATCTGACGAAGCGTATCCGCAACGGGAGT
TCCTGCAACGTACCGGCTTGGGGTGGCTGGGACATGGACAGACCTGCCATGGTA
CAGGAACACGGCATC

Figure 3C

SEQ ID NO:9, Amino acid sequence of the open reading frame of c_pp001113065r

MNRISSVDDILSAYWNESSMTSPVKGSMNRSASEFAFQEFIKENMTATSCFGGRSKSR
FYQSQADEGKALNDQSRDNLMISAKSESEFTPPMFASTEELRAMNNVVDPVEVDDIV
GIEGALNPLFSRVQNDADKKYSNFPSAALSAGDCGGQDYEDILKQKLERACAAAAL
SRQVNGEGAIIGQSVGAICQKSFAIESSAASACPSGVQCAPMSAKSPSPKPEVDASTG
KVKLTTSGSELSDDDEHDLLNQSLPGGDLKRVKRMLSNRESARRSRRKQAHLSDL
EMQVAQLRVENTTLMQRLQEITHMHKDASVDNRILKADVEALRAKVKMAEDMVA
RQGQPMSNLIPDPSLSFMTPFNVNDMERPFLQQMRHSSMLRHDQQQPASGIRGKM
GRAPSMQRVASLEHLTKRIRNGSSCNVPAWGGWDMDRPAMVQEHGI

Figure 4A

SEQ ID NO:10, Nucleotide sequence of c_pp004047195r

GGCGTCGTCTTCGATGGAACCCCGCGTCGGCAACAAGTATCGCCTTGGCCGGAA
AATTGGGAGTGGTTCCTTTGGTGAGATCTACCTGGGGACCAATCTCGTGACTCAT

Figure 4A Continued

GAGGAGGTCGGCATCAAGCTGGAGAGCATCAAGGCCAAGCATCCACAATTGCTT
TATGAGTCCAAGTTGTACCGTATTCTTCAAGGAGGAACTGGGATTCCCAACATCA
GATGGTACGGAATTGAAGGAGACTATAATGTGATGGTTCTTGATCTTCTGGGACC
CAGTCTTGAAGATCTTTTCAATTTCTGCAGCCGGAAATTCTCTTTGAAGACAGTTC
TCATGCTTGCCGACCAGCTGATCAATCGAGTGGAGTATGTGCATGCCAAGAGTTT
CCTCCACAGGGACATAAAGCCTGACAATTTCTTGATGGGGCTAGGCAGGCGAGC
AAATCAGGTCTATATGATTGACTTTGGTCTTGCAAAGAAGTATCGCGATCCCACT
ACTCATCAGCACATTCCTTATAGAGAGAACAAAAATCTTACTGGAACCGCTCGAT
ATGCAAGTATCAACACTCATCTTGGTATTGAACAAAGCAGGAGAGATGATCTGG
AGTCTCTTGGATATGTTCTCATGTATTTCTTGAGAGGCAGCCTGCCTTGGCAAGG
AATGAAAGCAGGAACCAAGAAGCAGAAGTATGAAAAAATCAGTGAGAAAAGA
TGTCCACCCCTATAGAGTTCCTTTGTAAAGCTTACCCGTCTGAGTTTGCTTCATAC
TTCCACTACTGTCGGTCTCTTCGGTTCGATGACAAACCGGACTATGCTTACCTGA
AGAGAATTTTCCGAGATCTCTTCATTCGTGAGGGTTTTCAGTTTGATTATGTTTC
GACTGGACGATTTTGAAGTATCAGCAAACACATTTTTCTGGTGGTCCTCTCCGTC
CAGCGGCTGCGGCGGGAGGTTCAAGTGGAGCAGCAGCAGCAGCGGCAGCAGGA
ATTGGTACAGTCCCAAGAGACGCCCAGCGAGCAATTGAGCCTACTGATGTTGCC
GCTCGAACTCGAATGGTTGGTGCGACTCGCTCTAGTGGATTAAATCCACTGGACG
CGTCAAAGCATAAGAGTACTAGCCCAGATGAAGCCGCTTCTAAGGACATAGCCC
TTAGCGGTCTTGCAGAACCAGAGCGCACGCATGCTTCTTCGTTTGTGCGGGGGAG
CTCATCATCAAGGAGAGCTGTTGTTGGATGTGCTAGGCCAGCAGGGTCAACAGA
GGCGGGAGATGGAACGCGGGTGTTGGCTGGCAAAATGGGCCCCACTAGCCTGCG
CACATCAGCAGGAATGCAGAGGAGCTCTCCGGTGGCATCTACGGATCCCAAGCG
GACGGGACGAGATTCTTATGCTGGAAACTCCGGAAGAAATCCTAGTTCCTCTCGA
AATTCGAAAGAGTGAGCACATTGGTTGAACTGGGTCCTGCATCTTGTTCGAAGAG
CATTACAACTGTATCTGGCCTTGGTATCTGCTGTGGTTTAGGAATTTGGCCTTGTA
CTTGATTTGAAGAACAGGTTCGTAAGAAATTGATCAAATTTCAATGTCGTGGGCG
TCCAGTTCAGGATATGGTTGGTGGCTTGTGATGGATATATTATCTGTTTCTATCTT
TGAAGGTGTTGCCCCAGCCGTATAGTTTTCATCTTTCATAGCTTGTAGTTGGCAA
AGCCCATTGCCATCTGTCAATATTCAGAGTGTGGTTGAGGGAGCTGTTTAGCCTT
CTAGATAAGAGATCTGGATTGCGTTCTGGATTGCTGCACAGACCTTGAAGATTTG
TGGCTGTTCG

Figure 4B

SEQ ID NO:11, Nucleotide sequence of the open reading frame of c_pp004047195r

ATGGAACCCCGCGTCGGCAACAAGTATCGCCTTGGCCGGAAAATTGGGAGTGGT
TCCTTTGGTGAGATCTACCTGGGGACCAATCTCGTGACTCATGAGGAGGTCGGCA
TCAAGCTGGAGAGCATCAAGGCCAAGCATCCACAATTGCTTTATGAGTCCAAGTT
GTACCGTATTCTTCAAGGAGGAACTGGGATTCCCAACATCAGATGGTACGGAATT
GAAGGAGACTATAATGTGATGGTTCTTGATCTTCTGGGACCCAGTCTTGAAGATC
TTTTCAATTTCTGCAGCCGGAAATTCTCTTTGAAGACAGTTCTCATGCTTGCCGAC
CAGCTGATCAATCGAGTGGAGTATGTGCATGCCAAGAGTTTCCTCCACAGGGAC
ATAAAGCCTGACAATTTCTTGATGGGGCTAGGCAGGCGAGCAAATCAGGTCTAT
ATGATTGACTTTGGTCTTGCAAAGAAGTATCGCGATCCCACTACTCATCAGCACA
TTCCTTATAGAGAGAACAAAAATCTTACTGGAACCGCTCGATATGCAAGTATCAA
CACTCATCTTGGTATTGAACAAAGCAGGAGAGATGATCTGGAGTCTCTTGGATAT

Figure 4B Continued

```
GTTCTCATGTATTTCTTGAGAGGCAGCCTGCCTTGGCAAGGAATGAAAGCAGGAA
CCAAGAAGCAGAAGTATGAAAAAATCAGTGAGAAAAAGATGTCCACCCCTATAG
AGTTCCTTTGTAAAGCTTACCCGTCTGAGTTTGCTTCATACTTCCACTACTGTCGG
TCTCTTCGGTTCGATGACAAACCGGACTATGCTTACCTGAAGAGAATTTTCCGAG
ATCTCTTCATTCGTGAGGGTTTTCAGTTTGATTATGTTTTCGACTGGACGATTTTG
AAGTATCAGCAAACACATTTTTCTGGTGGTCCTCTCCGTCCAGCGGCTGCGGCGG
GAGGTTCAAGTGGAGCAGCAGCAGCAGCGGCAGCAGGAATTGGTACAGTCCCAA
GAGACGCCCAGCGAGCAATTGAGCCTACTGATGTTGCCGCTCGAACTCGAATGG
TTGGTGCGACTCGCTCTAGTGGATTAAATCCACTGGACGCGTCAAAGCATAAGAG
TACTAGCCCAGATGAAGCCGCTTCTAAGGACATAGCCCTTAGCGGTCTTGCAGAA
CCAGAGCGCACGCATGCTTCTTCGTTTGTGCGGGGAGCTCATCATCAAGGAGAG
CTGTTGTTGGATGTGCTAGGCCAGCAGGGTCAACAGAGGCGGGAGATGGAACGC
GGGTGTTGGCTGGCAAAATGGGCCCCACTAGCCTGCGCACATCAGCAGGAATGC
AGAGGAGCTCTCCGGTGGCATCTACGGATCCCAAGCGGACGGGACGAGATTCTT
ATGCTGGAAACTCCGGAAGAAATCCTAGTTCCTCTCGAAATTCGAAAGAG
```

Figure 4C

SEQ ID NO:12, Amino acid sequence of the open reading frame of c_pp004047195r

MEPRVGNKYRLGRKIGSGSFGEIYLGTNLVTHEEVGIKLESIKAKHPQLLYESKLYRI
LQGGTGIPNIRWYGIEGDYNVMVLDLLGPSLEDLFNFCSRKFSLKTVLMLADQLINR
VEYVHAKSFLHRDIKPDNFLMGLGRRANQVYMIDFGLAKKYRDPTTHQHIPYRENK
NLTGTARYASINTHLGIEQSRRDDLESLGYVLMYFLRGSLPWQGMKAGTKKQKYEK
ISEKKMSTPIEFLCKAYPSEFASYFHYCRSLRFDDKPDYAYLKRIFRDLFIREGFQFDY
VFDWTILKYQQTHFSGGPLRPAAAAGGSSGAAAAAAGIGTVPRDAQRAIEPTDVA
ARTRMVGATRSSGLNPLDASKHKSTSPDEAASKDIALSGLAEPERTHASSFVRGSSSS
RRAVVGCARPAGSTEAGDGTRVLAGKMGPTSLRTSAGMQRSSPVASTDPKRTGRDS
YAGNSGRNPSSSRNSKE

Figure 5A

SEQ ID NO:13, Nucleotide sequence of c_pp001058012r

```
AGCACGAGGGCAAGAGGGGATAGAGACTTGAAAGGAAAGGGGAGGGAAGGGTG
TAAGGAGGCCCACGGGCAGGGTCAAGGTGTCCAATGCACCTGCAAGATCAGGAA
GCTTGAAGTAGATCAGGGAAAAAACGATGGTAGTCCCTAGTTTACCCGCCTTCGG
AGGACAGAACGCCATGCTCAGACGCAACATTGACAACAACACCGACACTCTGAT
TTCTCTGCTTCAAGGGTCCTGCTCCCTCGCGTGAGCATGCAACAAGTGCCGCGT
TCATCGGAGAGTCTCGAAAACATGATGGGGCTTGTGGGCAAAAACTGCCTTAC
TTTTCGTCATTTGATGGGCCGAGTGTAGAAGAGCAAGAGGATGTCGACGAAGGT
ATCGACGAATTCGCACACCACGTGGAGAAAAGAGGAGATTGTCATTAGAACAA
GTGCGATCATTAGAACGGAATTTTGAAGTGGAAAACAAGCTTGAGCCCGAGAGG
AAAATGCAACTAGCTAAGGAGCTTGGACTGCGACCTCGTCAAGTGGCGGTGTGG
TTCCAGAATAGACGGGCAAGGTGGAAAACCAAACAGCTCGAGCACGACTACGAG
ACCCTGAAGAAAGCCTACGACAGGCTTAAAGCAGACTTCGAAGCCGTTACTCTA
GACACAAATGCTCTTAAAGCTGAGGTGAGTCGCCTCAAGGGAATCTCTAATGAC
GACGTCAAGCCCGCCGAATTCGTTCAGGGCAAGTGTGACACAACGAGTCACCCT
```

Figure 5A Continued

GCCTCCCCTGCGCAATCGGAGAGGTCCGACATTGTGTCATCGAGGAATCGCACA
ACTCCTACCATACATGTGGATCCCGTGGCACCCGAGGAAGCCGGCGCTCACTTAA
CCATGAGCTCGGATAGCAATTCCAGCGAGGTCATGGACGCTGATAGCCCTCGCA
CGAGCCACACCAGCGCTAGTAGGAGCACTTTGTCCACAAGTGTGGTGCAGCCTG
ACGAGGGCCTGGGAGTGGCCCAGTACCCCACTTTTCTCCCGAAAACTTCGTGGG
TCCCAATATGCCAGAGATTTGCGCTGATCAGTCACTTGCATCTCAAGTGAAGCTG
GAAGAGATCCACAGCTTCAATCCCGACCAAACCTTCCTGCTCTTGCCCAACTGGT
GGGATTGGGCTTGATTCGTTTCTTCATCTGTACCCATACACTTTTCCTTGAATCC
AAGTTGAATTCACTTTAGGCAGTGTTTTTTCACGATGTACCACTTGTTATTCTTCC
ACCATGTGCAATCCAACGTCAAC

Figure 5B

SEQ ID NO:14, Nucleotide sequence of the open reading frame of c_pp001058012r

ATGGTAGTCCCTAGTTTACCCGCCTTCGGAGGACAGAACGCCATGCTCAGACGCA
ACATTGACAACAACACCGACACTCTGATTTCTCTGCTTCAAGGGTCCTGCTCCCC
TCGCGTGAGCATGCAACAAGTGCCGCGTTCATCGGAGAGTCTCGAAAACATGAT
GGGGGCTTGTGGGCAAAAACTGCCTTACTTTTCGTCATTTGATGGGCCGAGTGTA
GAAGAGCAAGAGGATGTCGACGAAGGTATCGACGAATTCGCACCACGTGGAG
AAAAAGAGGAGATTGTCATTAGAACAAGTGCGATCATTAGAACGGAATTTTGAA
GTGGAAAACAAGCTTGAGCCCGAGAGGAAAATGCAACTAGCTAAGGAGCTTGGA
CTGCGACCTCGTCAAGTGGCGGTGTGGTTCCAGAATAGACGGGCAAGGTGGAAA
ACCAAACAGCTCGAGCACGACTACGAGACCCTGAAGAAAGCCTACGACAGGCTT
AAAGCAGACTTCGAAGCCGTTACTCTAGACACAAATGCTCTTAAAGCTGAGGTG
AGTCGCCTCAAGGGAATCTCTAATGACGACGTCAAGCCCGCCGAATTCGTTCAGG
GCAAGTGTGACACAACGAGTCACCCTGCCTCCCCTGCGCAATCGGAGAGGTCCG
ACATTGTGTCATCGAGGAATCGCACAACTCCTACCATACATGTGGATCCCGTGGC
ACCCGAGGAAGCCGGCGCTCACTTAACCATGAGCTCGGATAGCAATTCCAGCGA
GGTCATGGACGCTGATAGCCCTCGCACGAGCCACACCAGCGCTAGTAGGAGCAC
TTTGTCCACAAGTGTGGTGCAGCCTGACGAGGGCCTGGGAGTGGCCCAGTACCCC
CACTTTTCTCCCGAAAACTTCGTGGGTCCCAATATGCCAGAGATTTGCGCTGATC
AGTCACTTGCATCTCAAGTGAAGCTGGAAGAGATCCACAGCTTCAATCCCGACCA
AACCTTCCTGCTCTTGCCCAACTGGTGGGATTGGGCT

Figure 5C

SEQ ID NO:15, Amino acid sequence of the open reading frame of c_pp001058012r

MVVPSLPAFGGQNAMLRRNIDNNTDTLISLLQGSCSPRVSMQQVPRSSESLENMMG
ACGQKLPYFSSFDGPSVEEQEDVDEGIDEFAHHVEKKRRLSLEQVRSLERNFEVENK
LEPERKMQLAKELGLRPRQVAVWFQNRRARWKTKQLEHDYETLKKAYDRLKADFE
AVTLDTNALKAEVSRLKGISNDDVKPAEFVQGKCDTTSHPASPAQSERSDIVSSRNRT
TPTIHVDPVAPEEAGAHLTMSSDSNSSEVMDADSPRTSHTSASRSTLSTSVVQPDEGL
GVAQYPHFSPENFVGPNMPEICADQSLASQVKLEEIHSFNPDQTFLLLPNWWDWA

Figure 6A

SEQ ID NO:16, Nucleotide sequence of s_pp001009079f

GGCCTTCAAGCACTCTCTGCATGTGTGCCCGTATTGCCTTGAGTCACCCTCGGCG
CTCTTTTGAGGCTACACAACTGGAAGGCAATAATTCGCAGCGCAGGCAACGCCA
TCTATGGCGCCCGCGGAACAACTCAAGACCAGAAGTGAATCTGGTAGTAGTGGG
GTAAGGAGTACAACCCCTACAGTTATCGTCATCGGCGCTGGTTTTGGAGGCCTCG
CTGCCGCCCGATTTCTCTACAACTCGAACGTGAAGGTTGTGGTGTTGGAGTCTCG
TGAACGGATTGGGGGTCGTGTTTACACTGACTATTCTTTTGGATTCCCCGTCGATA
TGGGGGCTTCATGGTTACATGGAGTATGCAAGGACAACCCTCTCGCACCTGTTAT
CGGCAAGCTACGATTGCCTTTGTATCGAACATGTGGCGATAATTCAGTTTTGTAT
GACCATGACTTAGAGAGCTATGCGCTATTTGACATGGATGGTCACCAAGTTCCAC
AATCTCTGGTCACGGAGGTCGGGGAGGTGTTCGAGAGTTTATTGGAAGAGACAA
AGAAACTCAGGGATGAGCACTCGGATGACATGTCAGTAATGAAGGCGTTTACAC
TAGTCTTGGAGAAACGGCCAGATCTGAGGCAAGAGGGGATGGCATTCAAAGTTC
TGCAGTGGTATTTGTGTCGCATGGAAGGATGGTTTGCAGCCGACGCAGACAACAT
CTCCGTTCAAAGTTGGGACGAGGAGGAGTTGCTTCAAGGTGGGCACGGTTTGAT
GGTGAAGGGTTATGAGCCCGTTATCAGCTCCCTTGCTGAAGGTCTTGATATCAGA
TTCAATCATAGGGTTACGAAGATCAGTCGGCGCCTGCATGGAGTGCGAGTGGGC
ACCGAAGATGGGAAGGTATTCGAAGCTGATGCTTGTGTTGTAGCATTACCTCTGG
GAGTGTTGAAAGCAAATGTGGTGCGGTTTGAGCCGAGATTGCCGGAGTGGAAGG
AGGCAGCAATTGCTGATTTAGGGGTGGGCAACGAGAATAAGATCGCCCTGTTCTT
TGAGGAAGTGTGCTGGCCGAACGTAGAGTTCCTTGGAGTTGTTGCCCCGACTTCG
TACGGTTGCAGCTACTTTTTGAACCTTCACAAGGCAACAGGGCACCCTGTGTTGG
TATACATGCCTGCAGGACGTCTTGCCAATGATATTGAGCAGCTGTCAAATGAGGC
TGCTGCCAACTTCGCTATCAGGCAGTTGAAAAGAATATTGCCGAATGCTGCAGAG
CCGATCAAATATCTGGTGTCGAGGTGGGGGACGGACCCAAACTCGAGGGGGTGC
TACAGCTATGACGCAGTGGGCAAGCCCCACGATCTGTACGAACGGCTACGCACA
CCAGTTGACAATTTGTTCTGGGCTGGGGAAGCCACCAGCGAGAGGTTCCCTGGA
ACTGTGCATGGTGCGTTTCATACAGGTGTGATGGCAGGAAGTGAGTGTCTGAAA
AGATTTGCTGAAAGGTGCCGGGATCTGGAGATGTTTCAGCCCGTGATGGCGAAA
GAAGACGAACTGATCACGCCATTGTTGATTTCTCGGATGTGAAGAACGCACAAG
CTACCTACTTCGTTGTGGGCCGTGCGGGTGGGTCGTCCATGAGA

Figure 6B

SEQ ID NO:17, Nucleotide sequence of the open reading frame of s_pp001009079f

ATGGCGCCCGCGGAACAACTCAAGACCAGAAGTGAATCTGGTAGTAGTGGGGTA
AGGAGTACAACCCCTACAGTTATCGTCATCGGCGCTGGTTTTGGAGGCCTCGCTG
CCGCCCGATTTCTCTACAACTCGAACGTGAAGGTTGTGGTGTTGGAGTCTCGTGA
ACGGATTGGGGGTCGTGTTTACACTGACTATTCTTTTGGATTCCCCGTCGATATGG
GGCTTCATGGTTACATGGAGTATGCAAGGACAACCCTCTCGCACCTGTTATCGG
CAAGCTACGATTGCCTTTGTATCGAACATGTGGCGATAATTCAGTTTTGTATGAC
CATGACTTAGAGAGCTATGCGCTATTTGACATGGATGGTCACCAAGTTCCACAAT
CTCTGGTCACGGAGGTCGGGGAGGTGTTCGAGAGTTTATTGGAAGAGACAAAGA
AACTCAGGGATGAGCACTCGGATGACATGTCAGTAATGAAGGCGTTTACACTAG
TCTTGGAGAAACGGCCAGATCTGAGGCAAGAGGGGATGGCATTCAAAGTTCTGC
AGTGGTATTTGTGTCGCATGGAAGGATGGTTTGCAGCCGACGCAGACAACATCTC

Figure 6B Continued

CGTTCAAAGTTGGGACGAGGAGGAGTTGCTTCAAGGTGGGCACGGTTTGATGGT
GAAGGGTTATGAGCCCGTTATCAGCTCCCTTGCTGAAGGTCTTGATATCAGATTC
AATCATAGGGTTACGAAGATCAGTCGGCGCCTGCATGGAGTGCGAGTGGGCACC
GAAGATGGGAAGGTATTCGAAGCTGATGCTTGTGTTGTAGCATTACCTCTGGGAG
TGTTGAAAGCAAATGTGGTGCGGTTTGAGCCGAGATTGCCGGAGTGGAAGGAGG
CAGCAATTGCTGATTTAGGGGTGGGCAACGAGAATAAGATCGCCCTGTTCTTTGA
GGAAGTGTGCTGGCCGAACGTAGAGTTCCTTGGAGTTGTTGCCCCGACTTCGTAC
GGTTGCAGCTACTTTTTGAACCTTCACAAGGCAACAGGGCACCCTGTGTTGGTAT
ACATGCCTGCAGGACGTCTTGCCAATGATATTGAGCAGCTGTCAAATGAGGCTGC
TGCCAACTTCGCTATCAGGCAGTTGAAAAGAATATTGCCGAATGCTGCAGAGCC
GATCAAATATCTGGTGTCGAGGTGGGGGACGGACCCAAACTCGAGGGGGTGCTA
CAGCTATGACGCAGTGGGCAAGCCCCACGATCTGTACGAACGGCTACGCACACC
AGTTGACAATTTGTTCTGGGCTGGGGAAGCCACCAGCGAGAGGTTCCCTGGAACT
GTGCATGGTGCGTTTCATACAGGTGTGATGGCAGGAAGTGAGTGTCTGAAAAGA
TTTGCTGAAGGTGCCGGGATCTGGAGATGTTTCAGCCCGTGATGGCGAAAGAA
GACGAACTGATCACGCCATTGTTGATTTCTCGGATG

Figure 6C

SEQ ID NO:18, Amino acid sequence of the open reading frame of s_pp001009079f

MAPAEQLKTRSESGSSGVRSTTPTVIVIGAGFGGLAAARFLYNSNVKVVVLESRERIG
GRVYTDYSFGFPVDMGASWLHGVCKDNPLAPVIGKLRLPLYRTCGDNSVLYDHDLE
SYALFDMDGHQVPQSLVTEVGEVFESLLEETKKLRDEHSDDMSVMKAFTLVLEKRP
DLRQEGMAFKVLQWYLCRMEGWFAADADNISVQSWDEEELLQGGHGLMVKGYEP
VISSLAEGLDIRFNHRVTKISRRLHGVRVGTEDGKVFEADACVVALPLGVLKANVVR
FEPRLPEWKEAAIADLGVGNENKIALFFEEVCWPNVEFLGVVAPTSYGCSYFLNLHK
ATGHPVLVYMPAGRLANDIEQLSNEAAANFAIRQLKRILPNAAEPIKYLVSRWGTDP
NSRGCYSYDAVGKPHDLYERLRTPVDNLFWAGEATSERFPGTVHGAFHTGVMAGS
ECLKRFAERCRDLEMFQPVMAKEDELITPLLISRM

Figure 7A

SEQ ID NO:19, Nucleotide sequence of c_pp004076330r

GTTGCGTTCTCTGCTTCCTTCGAAGGCCTTCGCCTCGGCGATCCCTCTCCCCGATT
CCGTTTGCCCCCGAGTGCAATTGCGGATTCGGATCCCATGCTCCCCTCTTGTTGAG
CCTTCGGTGGAACTTTGCGGTGTGTGATTTGGTGCTCCGTGACTCTGGCCGAACG
TGTCCACTTATTTTCAATCAAAATGGCCTCCAACGGAAACGGAAACGCGTCACAT
GATTTCGAATTTGCGAGCTCTCACGTCCCCAACGGTCTTTCTAAAATCAACACTA
AACCTGGAGAGCCAGACATGTGCAAAGATGACACTTCGTCGACGGTAAAGGTGT
CAAACCTTGAACAGCTGCACGCATTGCAGAAGAAGAAAGCGTCTGCTCCGACTA
CGCCACGCAACGCTACAAACCCATCTACACCCAAGAACTTGACTCCTCGTGCCTA
CTTATCAGAGGAAGAACGTCAGAAGCAGCAGATGCAGTCTGTTAGTGCATCCTT
GGCTTCTCTGACTCGTCAAAGCGGTCCTCAAGTTATCAAGGGCGAACCAGGCAG
AAAGAAATCTCCTCCCAAGACTGTGACTGCTCCCAGGCTGGACATTAGTGACAGC
GCTCTGAAGTTCACACACGTCCTCTACAACCTGTCTCCTTCTGAGTTGTACGAGC
AAGCTATTAAGTTCGAGAAGGGCTCATTCATTACCTCGAGTGGAGCTCTTGCTAC

Figure 7A Continued

```
ACTTTCTGGAGCTAAGACTGGGCGATCTCCCAAGGACAAACGTGTGGTGAAAGA
AGAGACATCCAAGGATGACTTGTGGTGGGGAAGGGGTTCTCCAAATATCGAAAT
GGACGAGGAGACATTCTTGGTCAATCGTGAGAGGGCAGTTGACTACCTGAACTC
ATTGGAGAAGGTTTTTGTAAATGACCAGTTCCTGAACTGGGACCCTCAGAACCGA
ATTAAAGTCCGGATCATATCAGCCCGTGCTTATCATTCGCTTTTTATGCACAATAT
GTGCATTCGCCCTACACCTGAGGAGCTCGAAGACTTTGGAACTCCTGATTTTACA
ATTTACAATGCCGGACAATTTCCTTGCAACCGTTACACCCACTACATGTCGTCGT
CAACTAGCATAGATCTGAACCTGAAACGCAAAGAGATGGTGATTTTGGGGACAC
AATATGCCGGAGAGATGAAGAAGGGACTTTTCAGTCTTATGCACTACTTGATGCC
CAAAAGAGGCATTTTGTCGTTGCATTCTGGTTGCAACATGGGAAAGGAAGGGGA
TGTGACATTATTTTTGGATTATCAGGTACTGGGAAGACGACTCTGTCAACTGAT
CCTAACCGGCAGCTTATTGGTGATGATGAGCATTGCTGGAGTGACAACGGAGTTT
CAAATATTGAGGGAGGATGCTATGCAAAATGCATCGATCTTTCTAAAGAAAAGG
AGCCGGAAATCTGGAATGCAATCAAGTTTGGAACCGTGCTAGAAAATGTGGTCT
TTGAGGAGCACTACAGGGAGGTTGATTACACCGATAAATCTGTGACCGAGAACA
CAAGGGCCGCATACCCTATTGAGTACATTCCCAACGTCAGGTTACCATGCGTTGG
ACCTCATCCAAAGAACATCATCTTGCTTTCGTGTGATGCTTTTGGTGTCTTACCAC
CTGTGAGCAAATTGACACATGCTCAAACCATGTATCACTTCATCAGTGGCTACAC
TGCCTTGGTTGCAGGAACTGTGGAGGGCGTGAAAGAGCCTACGGCCACATTCTC
AGCATGCTTTGGAGCTGCTTTCATTATGCTGCACCCCACTAAGTATGCCACCATG
TTAGCGGAGAAGATGCAGCGACATGGAGCTACTGCATGGTTGGTCAACACCGGC
TGGTCCGGCGGCAGCTATGGTGTCGGATCAAGAATGAAACTCGCATATACGAGG
AAGATCATTAATGCTATTCATGACGGGTCATTGTTGGGCGCTAATTATGCGCAAA
CTCCAATTTTCAACCTGGCTGTGCCAACTGCGGTCAACGGGGTTCCAAGTGAAAT
CTTGCAGCCACAGAATGCGTGGTCAGACAAGACGCAATACGATGCTACTCTGAA
AAAGCTCGCAGGTCTTTTTCAGAAGAATTTTGAGATTTATGCTGATTACCAAGTT
GGTGGAAACAGCCAGCTTACGCAGCAGATTCTTGCAGCTGGGCCTGTTTTACAGT
AGAGACGAGACCGCTGTATGTGTGGAATGATTTGGAGATCAGACGGAAGTCTGT
GAATCCTCATGTAGGGGATTTTTCTCCACCGGCAGAGGTTTGGATACAG
```

Figure 7B

SEQ ID NO:20, Nucleotide sequence of the open reading frame of c_pp004076330r

```
GTGATTTGGTGCTCCGTGACTCTGGCCGAACGTGTCCACTTATTTTCAATCAAAAT
GGCCTCCAACGGAAACGGAAACGCGTCACATGATTTCGAATTTGCGAGCTCTCAC
GTCCCCAACGGTCTTTCTAAAATCAACACTAAACCTGGAGAGCCAGACATGTGCA
AAGATGACACTTCGTCGACGGTAAAGGTGTCAAACCTTGAACAGCTGCACGCAT
TGCAGAAGAAGAAAGCGTCTGCTCCGACTACGCCACGCAACGCTACAAACCCAT
CTACACCCAAGAACTTGACTCCTCGTGCCTACTTATCAGAGGAAGAACGTCAGAA
GCAGCAGATGCAGTCTGTTAGTGCATCCTTGGCTTCTCTGACTCGTCAAAGCGGT
CCTCAAGTTATCAAGGGCGAACCAGGCAGAAAGAAATCTCCTCCCAAGACTGTG
ACTGCTCCCAGGCTGGACATTAGTGACAGCGCTCTGAAGTTCACACACGTCCTCT
ACAACCTGTCTCCTTCTGAGTTGTACGAGCAAGCTATTAAGTTCGAGAAGGGCTC
ATTCATTACCTCGAGTGGAGCTCTTGCTACACTTTCTGGAGCTAAGACTGGGCGA
TCTCCCAAGGACAAACGTGTGGTGAAAGAAGAGACATCCAAGGATGACTTGTGG
TGGGGAAGGGGTTCTCCAAATATCGAAATGGACGAGGAGACATTCTTGGTCAAT
CGTGAGAGGGCAGTTGACTACCTGAACTCATTGGAGAAGGTTTTTGTAAATGACC
```

Figure 7B Continued

```
AGTTCCTGAACTGGGACCCTCAGAACCGAATTAAAGTCCGGATCATATCAGCCCG
TGCTTATCATTCGCTTTTTATGCACAATATGTGCATTCGCCCTACACCTGAGGAGC
TCGAAGACTTTGGAACTCCTGATTTTACAATTTACAATGCCGGACAATTTCCTTGC
AACCGTTACACCCACTACATGTCGTCGTCAACTAGCATAGATCTGAACCTGAAAC
GCAAAGAGATGGTGATTTTGGGGACACAATATGCCGGAGAGATGAAGAAGGGA
CTTTTCAGTCTTATGCACTACTTGATGCCCAAAAGAGGCATTTTGTCGTTGCATTC
TGGTTGCAACATGGGAAGGAAGGGGATGTGACATTATTTTTGGATTATCAGGT
ACTGGGAAGACGACTCTGTCAACTGATCCTAACCGGCAGCTTATTGGTGATGATG
AGCATTGCTGGAGTGACAACGGAGTTTCAAATATTGAGGGAGGATGCTATGCAA
AATGCATCGATCTTTCTAAAGAAAAGGAGCCGGAAATCTGGAATGCAATCAAGT
TTGGAACCGTGCTAGAAAATGTGGTCTTTGAGGAGCACTACAGGGAGGTTGATT
ACACCGATAAATCTGTGACCGAGAACACAAGGGCCGCATACCCTATTGAGTACA
TTCCCAACGTCAGGTTACCATGCGTTGGACCTCATCCAAAGAACATCATCTTGCT
TTCGTGTGATGCTTTTGGTGTCTTACCACCTGTGAGCAAATTGACACATGCTCAA
ACCATGTATCACTTCATCAGTGGCTACACTGCCTTGGTTGCAGGAACTGTGGAGG
GCGTGAAAGAGCCTACGGCCACATTCTCAGCATGCTTTGGAGCTGCTTTCATTAT
GCTGCACCCCACTAAGTATGCCACCATGTTAGCGGAGAAGATGCAGCGACATGG
AGCTACTGCATGGTTGGTCAACACCGGCTGGTCCGGCGGCAGCTATGGTGTCGGA
TCAAGAATGAAACTCGCATATACGAGGAAGATCATTAATGCTATTCATGACGGG
TCATTGTTGGGCGCTAATTATGCGCAAACTCCAATTTTCAACCTGGCTGTGCCAA
CTGCGGTCAACGGGGTTCCAAGTGAAATCTTGCAGCCACAGAATGCGTGGTCAG
ACAAGACGCAATACGATGCTACTCTGAAAAAGCTCGCAGGTCTTTTTCAGAAGA
ATTTTGAGATTTATGCTGATTACCAAGTTGGTGGAAACAGCCAGCTTACGCAGCA
GATTCTTGCAGCTGGGCCTGTTTTACAG
```

Figure 7C

SEQ ID NO:21, Amino acid sequence of the open reading frame of c_pp004076330r

```
VIWCSVTLAERVHLFSIKMASNGNGNASHDFEFASSHVPNGLSKINTKPGEPDMCKD
DTSSTVKVSNLEQLHALQKKKASAPTTPRNATNPSTPKNLTPRAYLSEEERQKQQMQ
SVSASLASLTRQSGPQVIKGEPGRKKSPPKTVTAPRLDISDSALKFTHVLYNLSPSELY
EQAIKFEKGSFITSSGALATLSGAKTGRSPKDKRVVKEETSKDDLWWGRGSPNIEMD
EETFLVNRERAVDYLNSLEKVFVNDQFLNWDPQNRIKVRIISARAYHSLFMHNMCIR
PTPEELEDFGTPDFTIYNAGQFPCNRYTHYMSSSTSIDLNLKRKEMVILGTQYAGEMK
KGLFSLMHYLMPKRGILSLHSGCNMGKEGDVTLFFGLSGTGKTTLSTDPNRQLIGDD
EHCWSDNGVSNIEGGCYAKCIDLSKEKEPEIWNAIKFGTVLENVVFEEHYREVDYTD
KSVTENTRAAYPIEYIPNVRLPCVGPHPKNIILLSCDAFGVLPPVSKLTHAQTMYHFIS
GYTALVAGTVEGVKEPTATFSACFGAAFIMLHPTKYATMLAEKMQRHGATAWLVN
TGWSGGSYGVGSRMKLAYTRKIINAIHDGSLLGANYAQTPIFNLAVPTAVNGVPSEIL
QPQNAWSDKTQYDATLKKLAGLFQKNFEIYADYQVGGNSQLTQQILAAGPVLQ
```

Figure 8A

SEQ ID NO:22, Nucleotide sequence of c_pp004040301r

GGCGAAGGGGAGGTGTCGGAGGGGATTTATTGTGCCGTAGCTGGGTTTGCAAAA
ATGTGTTCTATTCCGTTCGGTCGGAAGAAGTCCAAGAAGGGGGATTTGGCGCAG
GATCTGTTGGGGGATGTGTTCTCGACTTACAGCGAGAATGGGAAGCTGGACGCC
GAGGGGTTGCTGAAGTTCTTGCAGACAGAGCAAGGGGATAGCAAGTCCTCTCTA
GATGACGCCAAGCATTTAGTGGAGTTGATTCGGAATGAGAGACATAAGTCGAAA
TTCCCTGGGTTCATCGTCAGCTCGGACCTGTCAAGGGTGATTTTAAAAACTATG
TACTGAGCCCGGATTTGAATGGGGTTCTTGAAAGCACTGTGCATCAAGACATGAC
GCAGCCGTTATCGCACTACTTCATATTCACTGGTCACAACTCGTACTTGACGGGT
AACCAGCTTAGCAGCGACAGTAGCGACGTTCCCATTGCTGCTGCACTGCAACGTG
GCGTGCGGGTGGTGGAACTGGATTTGTGGCCTGACGATAAAGGCGGCATCAAGG
TCACTCACGGGAACACACTCACCAGTCCAGTTGCTTTCGAGAAGTGCATAAAAGC
CATCAAGGCCAACGCGTTCGTCTCCTCGAAATATCCTGTAGTTATCACTCTTGAG
GATCATCTTTCAAGTCCTTTACAGGCCCTTGCTGCAGAGACTTTGACGAACATTTT
GGGAGAGGACTTGTACTATCCACCCTCATCCGATGGGTTTAAAGAACTGCCTTCT
CCGGAATCATTGAAAGGGAAAATTCTAATATCTACCAAACCGCCGAAAGAATAC
CTTGAAGCCGCTGTCGCACAGAAGTCGGCGTTGAAAGATGAAAGATTTTGAAT
GAGTTCAAGAAGGCAGATAAGTTGCAGGAGCAGTCAACTGCTCCTGTTAAAAGC
CCCGTTGAGAAAAAGATTGCAGTTCCACCATCAGAGAAGACAAAATCCATTTCC
GAAGAGAAGGACTTGAGTGAAAAAGTTGGAAATTTACGTGTTGATTCAGAGGGT
GAATCAGCTGATCCTGCCCCTGCAAGTTCCCCGACGGTAAGAAAGCAACATTG
ACAGCGGATAGTGAAAGTGACGATGACGACAATAAGAAGAATCCTGAGTATGCT
CGGCTTATCACTATCCACCAATCGAAGCCTTCGAAAGGAACTACCGTGGAAGAC
AGACTGAAAGTTGAAGGGACAGTGGTACGGATTAGTCTTTCAGAGACTAAGCTG
GAGAAGGTCACTGAAGAGTTTCCTGAACTTGTGGTCAAGTTCACGCAGAGGAAC
ATTCTACGTGTGTATCCTGCTGGTAACCGAGTAAACTCGTCCAACTATGATCCTA
CTGCGGCTTGGATTCACGGAGCTCAAATGGTGGCTCAAAATATGCAAGGTTATGG
CAAAGAGCTCTGGCAAGCCCACGGCAAGTTCAGGGGAAATGGTGGCTGTGGATA
CATCCTTAAGCCAAAGTATCTATTGGAAGATTTGCCCAATGGTAAACCTTTTAAC
CCTTCAGCTCCTGGAGATACGAAGATGATCTTGAAGGTAAAGGTAATGACAACC
ATGGGATGGGACAAAGCGTTCCCCAAATACCATTTCGACCTTTTCTCGCCTCCAG
ATTTCTTCACTAGGCTGCTTGTGACTGGAGTGCCTGCCGATGTGGCAAAGTGGAA
AACTTCCGTTATAGATGACGTTTGGGAACCCCACTGGAACGAGGATCACGAGTTT
TACCTTAAATGCCCTGAACTTGCACTGCTCCGAATTGAAGTTAGAGATCACGACG
AGGAAAGTCAAGATGAGTTCGAAGGGCAGGCGTGCCTTCCAATGCATGAAATTA
AAGACGGCTATCGATGCGTGCAGATGTATGACAAAAAGGGCAGTGTGTTGAAGG
GCGTGAAAATGTTGTTCCATTTTCAAAAACGTTCGTTTTCTCCGGTCCAGTAATTC

Figure 8B

SEQ ID NO:23, Nucleotide sequence of the open reading frame of c_pp004040301r

GTGTCGGAGGGGATTTATTGTGCCGTAGCTGGGTTTGCAAAAATGTGTTCTATTC
CGTTCGGTCGGAAGAAGTCCAAGAAGGGGGATTTGGCGCAGGATCTGTTGGGGG
ATGTGTTCTCGACTTACAGCGAGAATGGGAAGCTGGACGCCGAGGGGTTGCTGA
AGTTCTTGCAGACAGAGCAAGGGGATAGCAAGTCCTCTCTAGATGACGCCAAGC
ATTTAGTGGAGTTGATTCGGAATGAGAGACATAAGTCGAAATTCCCTGGGTTCAT

Figure 8B Continued

CGTCAGCTCGGACCTGTCGAAGGGTGATTTTAAAAACTATGTACTGAGCCCGGAT
TTGAATGGGGTTCTTGAAAGCACTGTGCATCAAGACATGACGCAGCCGTTATCGC
ACTACTTCATATTCACTGGTCACAACTCGTACTTGACGGGTAACCAGCTTAGCAG
CGACAGTAGCGACGTTCCCATTGCTGCTGCACTGCAACGTGGCGTGCGGGTGGTG
GAACTGGATTTGTGGCCTGACGATAAAGGCGGCATCAAGGTCACTCACGGGAAC
ACACTCACCAGTCCAGTTGCTTTCGAGAAGTGCATAAAAGCCATCAAGGCCAAC
GCGTTCGTCTCCTCGAAATATCCTGTAGTTATCACTCTTGAGGATCATCTTTCAAG
TCCTTTACAGGCCCTTGCTGCAGAGACTTTGACGAACATTTTGGGAGAGGACTTG
TACTATCCACCCTCATCCGATGGGTTTAAAGAACTGCCTTCTCCGGAATCATTGA
AAGGGAAAATTCTAATATCTACCAAACCGCCGAAAGAATACCTTGAAGCCGCTG
TCGCACAGAAGTCGGCGTTGAAAGATGAAAGATTTTGAATGAGTTCAAGAAGG
CAGATAAGTTGCAGGAGCAGTCAACTGCTCCTGTTAAAAGCCCCGTTGAGAAAA
AGATTGCAGTTCCACCATCAGAGAAGACAAAATCCATTTCCGAAGAGAAGGACT
TGAGTGAAAAGTTGGAAATTTACGTGTTGATTCAGAGGGTGAATCAGCTGATCC
TGCCCCTGCAAGTTCCCCCGACGGTAAGAAAGCAACATTGACAGCGGATAGTGA
AAGTGACGATGACGACAATAAGAAGAATCCTGAGTATGCTCGGCTTATCACTAT
CCACCAATCGAAGCCTTCGAAAGGAACTACCGTGGAAGACAGACTGAAAGTTGA
AGGGACAGTGGTACGGATTAGTCTTTCAGAGACTAAGCTGGAGAAGGTCACTGA
AGAGTTTCCTGAACTTGTGGTCAAGTTCACGCAGAGGAACATTCTACGTGTGTAT
CCTGCTGGTAACCGAGTAAACTCGTCCAACTATGATCCTACTGCGGCTTGGATTC
ACGGAGCTCAAATGGTGGCTCAAAATATGCAAGGTTATGGCAAAGAGCTCTGGC
AAGCCCACGGCAAGTTCAGGGGAAATGGTGGCTGTGGATACATCCTTAAGCCAA
AGTATCTATTGGAAGATTTGCCCAATGGTAAACCTTTTAACCCTTCAGCTCCTGG
AGATACGAAGATGATCTTGAAGGTAAAGGTAATGACAACCATGGGATGGGACAA
AGCGTTCCCCAAATACCATTTCGACCTTTTCTCGCCTCCAGATTTCTTCACTAGGC
TGCTTGTGACTGGAGTGCCTGCCGATGTGGCAAAGTGGAAAACTTCCGTTATAGA
TGACGTTTGGGAACCCCACTGGAACGAGGATCACGAGTTTTACCTTAAATGCCCT
GAACTTGCACTGCTCCGAATTGAAGTTAGAGATCACGACGAGGAAAGTCAAGAT
GAGTTCGAAGGGCAGGCGTGCCTTCCAATGCATGAAATTAAAGACGGCTATCGA
TGCGTGCAGATGTATGACAAAAAGGGCAGTGTGTTGAAGGGCGTGAAAATGTTG
TTCCATTTTCAAAAACGTTCGTTTCTCCGGTCCAG

Figure 8C

SEQ ID NO:24, Amino acid sequence of the open reading frame of c_pp004040301r

VSEGIYCAVAGFAKMCSIPFGRKKSKKGDLAQDLLGDVFSTYSENGKLDAEGLLKFL
QTEQGDSKSSLDDAKHLVELIRNERHKSKFPGFIVSSDLSKGDFKNYVLSPDLNGVLE
STVHQDMTQPLSHYFIFTGHNSYLTGNQLSSDSSDVPIAAALQRGVRVVELDLWPDD
KGGIKVTHGNTLTSPVAFEKCIKAIKANAFVSSKYPVVITLEDHLSSPLQALAAETLT
NILGEDLYYPPSSDGFKELPSPESLKGKILISTKPPKEYLEAAVAQKSALKDEKILNEF
KKADKLQEQSTAPVKSPVEKKIAVPPSEKTKSISEEKDLSEKVGNLRVDSEGESADPA
PASSPDGKKATLTADSESDDDDNKKNPEYARLITIHQSKPSKGTTVEDRLKVEGTVV
RISLSETKLEKVTEEFPELVVKFTQRNILRVYPAGNRVNSSNYDPTAAWIHGAQMVA
QNMQGYGKELWQAHGKFRGNGGCGYILKPKYLLEDLPNGKPFNPSAPGDTKMILK
VKVMTTMGWDKAFPKYHFDLFSPPDFFTRLLVTGVPADVAKWKTSVIDDVWEPHW
NEDHEFYLKCPELALLRIEVRDHDEESQDEFEGQACLPMHEIKDGYRCVQMYDKKG
SVLKGVKMLFHFQKRSFSPVQ

Figure 9A

SEQ ID NO:25, Nucleotide sequence of s_pp002024092r

CTGAGTGAGGAACTGGGAGCGATGGAAGCGTGCAATTGCGTAGAGCCGCAATGG
CCTCCAGACGATCTTCTCATGCGGTACCAGTACATATCGAATTTTTTCATCGCGTT
GGCATATTTCTCTATTCCGCTGGAGCTTATTTACTTTGTGAAGAAGTCGTCTATTT
TCCCATATCGATGGGTTCTTGTTCAGTTTGGAGCCTTCATTGTGCTGTGCGGAGCA
ACGCATCTAATATCCTTGTGGACGTTCAGTAGCCGTTCTCGAACAGTGGCCGTCG
TTCTTACAATAGCGAAGGTTCTTACTGCTGTTGTGTCGTGTGCCACAGCACTCATG
CTTGTGCACATTATTCCAGACCTCCTTAGTGTAAAGACCCGAGAATTGTTCTTGA
AGAAGAAGGCTGCAGAACTTGATCGTGAAATGGGATTGATACGTACACAGGAGG
AAACAGGTCGTCACGTTAGGATGCTCACTCATGAAATACGAAGTACCCTAGATC
GACATACAATTTTGAATACCACCCTCATAGAACTCGGAAAAACGCTTTCGCTTGA
GGAGTGTACTTTATGGATGCCAAGCCCAGATGGTCAAGAGCTACAACTCAAAAA
TGCTCTTCGAGCTGAATCTCTTCATGTTACAGTCCCCATACATCACCCAACTATCA
AGCAAGTGTTTAGTACTCCCCGGGCAGTGGTGATATCTCCTAACAGCCCAGTTTG
TGTTACTCGAATTCGTGGAGCGAAGTACATGACTGGGGAGGTCGTGGCAATTCG
AGTCCCACTTCTGCATCTCACAAACTTCCACTTCAGTGATTGGCCTGATGCCGGA
ACACGTCCTTTTGCATTGATGGTGCTGATGTTGCCTTTAAACAGTGCACGAAGGT
GGCACGTTCATGAATTGGAGCTAGTGGAAGTTGTGGCTGATCAGGTGGCTGTGGC
TCTATCACACGCAACAATTCTGGAGGAATCAATGCCTGCTCGAGATCTTTGATG
GAACAAAACGTAGCATTGGAACATGCTAGACAGGAGGCAGAGACAGCTATTCGA
GCCCGCAACGACTTTCTGGCTGTGATGAATCATGAGATGCGCACGCCCATGCATG
CTATCATTGCTCTTTCTTCTTTATTACAAGAAACGGAGTTAACCCCTGAGCAGCG
GTCTATGGTGGAAACTGTTTTGAAAAGCAGTAACCTTTTGGCCACATTGATAAAT
GACGTGCTTGATCTCTCGGCTCGAGGATGGAAGTCTGGAGCTCGATATTCAGA
CATTCAACCTTCCTAATGTCTTCAAAGAGGTTTTGAACCTTGTGAAGCCAATAGC
GTCCGTGAAAAGGTTACAAGTGAACTTGACTATGGGGCCCGACATCCCTGAAATT
GCAGTTGGGGATGATAAGCGGCTTTTACAAACTGCTCTCAATGTTGTTGGAAATG
CGGTGAAGTTTACTAAGGAGGGCCACGTGAACGTAATTGTAGGTCTAGAAAGAC
CTGAATATCCGCGAGACCCTCGTCAGCCAGATTTTCGGCCTTTATCAGGAGACAA
TCATTTTTACCTCAGAGTCCAGGTGCGGGACACAGGTTTAGGTCTCAATCCACAA
GACATCCCTATGCTATTTAACAAGTTTGTACAAGCTGACTCTACCACAACTAGAA
ATTACGGAGGGACAGGACTTGGGTTAGCTATTTGTAAAAGATTTGTTAATCTCAT
GGATGGGCATATATGGATTGAAAGCGAGGGGGTTGGAAGGGGCCGATTGTGAC
CTTCATTGTGAAGTTAAATCTTCCCGAGACTTCAAGTCATCTCTCTATTCATATTG
CGCCTACCTCGCAACCAAGTGGTAGTCAGTCTCGGACAGACTTTTCTGGTGTCAG
AATCTTGGTCACCGATGACAATGGTGTGAACAGGATGGTAACGCGAGGCTTGCT
AATGAGACTAGGGCGTGAAGTGACTTGGCGGCATCTGGACGGGAATGTCTGCA
ATTAATCCAACAGCGAAACCAGGCATTTAACGTGCTTCTACTTGATGTGTGCATG
CCGGAGATGGATGGATATGAAGTTGCTACTCAAATTCAAAAAGATTAACACGT
CGCGATCGGCCGCTTCTTGTTGCCCTTACGGCCAACACTGATCGTATCACCCATG
AGAAATGTCTTCGTCTGGGCATGGACGGAGTGGTCACAAAGCCTATTTCGTTAGA
AAAGATGCGATTGGTGCTCACAGAGCTTTTGGAACGAGGCTCCATTTCTGAACTT
ACTCAAAGATTATGATATTAGTTGTTGAATTCATATCCCCTAATTTGAAAGGCAA
ACGAGTACTGCAAGGG

Figure 9B

SEQ ID NO:26, Nucleotide sequence of the open reading frame of s_pp002024092r

ATGGAAGCGTGCAATTGCGTAGAGCCGCAATGGCCTCCAGACGATCTTCTCATGC
GGTACCAGTACATATCGAATTTTTTCATCGCGTTGGCATATTTCTCTATTCCGCTG
GAGCTTATTTACTTTGTGAAGAAGTCGTCTATTTTCCCATATCGATGGGTTCTTGT
TCAGTTTGGAGCCTTCATTGTGCTGTGCGGAGCAACGCATCTAATATCCTTGTGG
ACGTTCAGTAGCCGTTCTCGAACAGTGGCCGTCGTTCTTACAATAGCGAAGGTTC
TTACTGCTGTTGTGTCGTGTGCCACAGCACTCATGCTTGTGCACATTATTCCAGAC
CTCCTTAGTGTAAAGACCCGAGAATTGTTCTTGAAGAAGAAGGCTGCAGAACTTG
ATCGTGAAATGGGATTGATACGTACACAGGAGGAAACAGGTCGTCACGTTAGGA
TGCTCACTCATGAAATACGAAGTACCCTAGATCGACATACAATTTTGAATACCAC
CCTCATAGAACTCGGAAAAACGCTTTCGCTTGAGGAGTGTACTTTATGGATGCCA
AGCCCAGATGGTCAAGAGCTACAACTCAAAAATGCTCTTCGAGCTGAATCTCTTC
ATGTTACAGTCCCCATACATCACCCAACTATCAAGCAAGTGTTTAGTACTCCCCG
GGCAGTGGTGATATCTCCTAACAGCCCAGTTTGTGTTACTCGAATTCGTGGAGCG
AAGTACATGACTGGGGAGGTCGTGGCAATTCGAGTCCCACTTCTGCATCTCACAA
ACTTCCACTTCAGTGATTGGCCTGATGCCGGAACACGTCCTTTTGCATTGATGGT
GCTGATGTTGCCTTTAAACAGTGCACGAAGGTGGCACGTTCATGAATTGGAGCTA
GTGGAAGTTGTGGCTGATCAGGTGGCTGTGGCTCTATCACACGCAACAATTCTGG
AGGAATCAATGCCTGCTCGAGATCTTTTGATGGAACAAAACGTAGCATTGGAAC
ATGCTAGACAGGAGGCAGAGACAGCTATTCGAGCCCGCAACGACTTTCTGGCTG
TGATGAATCATGAGATGCGCACGCCCATGCATGCTATCATTGCTCTTTCTTCTTTA
TTACAAGAAACGGAGTTAACCCCTGAGCAGCGGTCTATGGTGGAAACTGTTTTGA
AAAGCAGTAACCTTTTGGCCACATTGATAAATGACGTGCTTGATCTCTCGGCT
CGAGGATGGAAGTCTGGAGCTCGATATTCAGACATTCAACCTTCCTAATGTCTTC
AAAGAGGTTTTGAACCTTGTGAAGCCAATAGCGTCCGTGAAAAGGTTACAAGTG
AACTTGACTATGGGGCCCGACATCCCTGAAATTGCAGTTGGGGATGATAAGCGG
CTTTTACAAACTGCTCTCAATGTTGTTGGAAATGCGGTGAAGTTTACTAAGGAGG
GCCACGTGAACGTAATTGTAGGTCTAGAAAGACCTGAATATCCGCGAGACCCTC
GTCAGCCAGATTTTCGGCCTTTATCAGGAGACAATCATTTTTACCTCAGAGTCCA
GGTGCGGGACACAGGTTTAGGTCTCAATCCACAAGACATCCCTATGCTATTTAAC
AAGTTTGTACAAGCTGACTCTACCACAACTAGAAATTACGGAGGGACAGGACTT
GGGTTAGCTATTTGTAAAAGATTTGTTAATCTCATGGATGGGCATATATGGATTG
AAAGCGAGGGGGTTGGAAGGGGGCCGATTGTGACCTTCATTGTGAAGTTAAATC
TTCCCGAGACTTCAAGTCATCTCTCTATTCATATTGCGCCTACCTCGCAACCAAGT
GGTAGTCAGTCTCGGACAGACTTTTCTGGTGTCAGAATCTTGGTCACCGATGACA
ATGGTGTGAACAGGATGGTAACGCGAGGCTTGCTAATGAGACTAGGGCGTGAAG
TGACTTTGGCGGCATCTGGACGGGAATGTCTGCAATTAATCCAACAGCGAAACC
AGGCATTTAACGTGCTTCTACTTGATGTGTGCATGCCGGAGATGGATGGATATGA
AGTTGCTACTCAAATTCAAAAAGATTAACACGTCGCGATCGGCCGCTTCTTGTT
GCCCTTACGGCCAACACTGATCGTATCACCCATGAGAAATGTCTTCGTCTGGGCA
TGGACGGAGTGGTCACAAAGCCTATTTCGTTAGAAAGATGCGATTGGTGCTCAC
AGAGCTTTTGGAACGAGGCTCCATTTCTGAACTTACTCAAAGATTA

Figure 9C

SEQ ID NO:27, Amino acid sequence of the open reading frame of s_pp002024092r

MEACNCVEPQWPPDDLLMRYQYISNFFIALAYFSIPLELIYFVKKSSIFPYRWVLVQF
GAFIVLCGATHLISLWTFSSRSRTVAVVLTIAKVLTAVVSCATALMLVHIIPDLLSVKT
RELFLKKKAAELDREMGLIRTQEETGRHVRMLTHEIRSTLDRHTILNTTLIELGKTLSL
EECTLWMPSPDGQELQLKNALRAESLHVTVPIHHPTIKQVFSTPRAVVISPNSPVCVT
RIRGAKYMTGEVVAIRVPLLHLTNFHFSDWPDAGTRPFALMVLMLPLNSARRWHVH
ELELVEVVADQVAVALSHATILEESMPARDLLMEQNVALEHARQEAETAIRARNDF
LAVMNHEMRTPMHAIIALSSLLQETELTPEQRSMVETVLKSSNLLATLINDVLDLSRL
EDGSLELDIQTFNLPNVFKEVLNLVKPIASVKRLQVNLTMGPDIPEIAVGDDKRLLQT
ALNVVGNAVKFTKEGHVNVIVGLERPEYPRDPRQPDFRPLSGDNHFYLRVQVRDTG
LGLNPQDIPMLFNKFVQADSTTTRNYGGTGLGLAICKRFVNLMDGHIWIESEGVGRG
PIVTFIVKLNLPETSSHLSIHIAPTSQPSGSQSRTDFSGVRILVTDDNGVNRMVTRGLL
MRLGREVTLAASGRECLQLIQQRNQAFNVLLLDVCMPEMDGYEVATQIQKRLTRRD
RPLLVALTANTDRITHEKCLRLGMDGVVTKPISLEKMRLVLTELLERGSISELTQRL

Figure 10A

SEQ ID NO:28, Nucleotide sequence of s_pp001031042f

AGTGGGTGGTTGGACTGTAAGGAGCTAGCGTTTTAGAGCTACAGTGCGGTTTGCT
GTGTGAGTGAGTGAGTGAGTGCGTGAGTGAGGATGTCTGTTTCTGGTATGG
ACAACTATGAGAAGCTGGAGAAGGTAGGAGAGGGGACTTACGGAAAGGTGTAT
AAGGCCCGTGATAAACGCTCCGGGCAGCTGGTGGCGCTCAAGAAGACTAGGTTG
GAGATGGAGGAAGAAGGCGTCCCTTCCACCGCTTTGCGCGAAGTTTCGTTGCTAC
AAATGCTCTCCCACAGCATGTATATCGTCAGGCTACTTTGCGTGGAGCACGTCGA
GAAAGGCAGCAAGCCCATGCTCTACTTGGTCTTTGAATATATGGACACTGATCTT
AAGAAGTATATTGACTTGCACGGTCGTGGTCCGAGCGGGAAGCCTCTGCCTCCCA
AAGTGGTCCAGAGTTTCATGTATCAATTGTGCACAGGGCTTGCCCACTGTCATGG
CCACGGAGTAATGCACAGGGATCTGAAACCCCAGAATTTGCTCGTCGACAAGCA
AACCCGTCGTCTTAAGATTGCCGACCTTGGTCTCGGTCGGGCATTCACAGTGCCA
ATGAAGAGTTACACACGAGATTGTTACTCTATGGTACCGAGCTCCTGAAGTTC
TTCTTGGAGCGACCCACTACTCTCTACCTGTGGATATCTGGTCTGTTGGGTGCATC
TTCGCTGAACTCGTCCGGAAAATGCCGCTCTTCACTGGAGACTCCGAACTTCAGC
AGCTTCTTCACATCTTCAGGTTGCTTGGCACCCCGAATGAGACAATCTGGCCTGG
TGTTAGCCAGCACCGTGATTGGCACGAGTTCCTCAATGGAGACCACAAGATCTG
TCCCTTGCTGTTCCCGGACTCAGCGCGGTTGGCTTAGACCTTCTCGCCAAAATGTT
GGTATTCGAGCCCTCAAAGAGAATCTCTGCCAAAGCCGCCTTGAGCCATACTTAT
TTCGCTGATGTTGATAAGMCAGCAACCTAAACACAACAGAACAATTCAAGAGAA
CCAGGTAACCTCTACCTGTCCAAGACGAAG

Figure 10B

SEQ ID NO:29, Nucleotide sequence of the open reading frame of s_pp001031042f

GTGAGGATGTCTGTTTCTGGTATGGACAACTATGAAGAAGCTGGAGAAGGTAGGA
GAGGGGACTTACGGAAAGGTGTATAAGGCCCGTGATAAACGCTCCGGGCAGCTG
GTGGCGCTCAAGAAGACTAGGTTGGAGATGGAGGAAGAAGGCGTCCCTTCCACC
GCTTTGCGCGAAGTTTCGTTGCTACAAATGCTCTCCACAGCATGTATATCGTCA
GGCTACTTTGCGTGGAGCACGTCGAGAAAGGCAGCAAGCCCATGCTCTACTTGGT
CTTTGAATATATGGACACTGATCTTAAGAAGTATATTGACTTGCACGGTCGTGGT
CCGAGCGGGAAGCCTCTGCCTCCCAAAGTGGTCCAGAGTTTCATGTATCAATTGT
GCACAGGGCTTGCCCACTGTCATGGCCACGGAGTAATGCACAGGGATCTGAAAC
CCCAGAATTTGCTCGTCGACAAGCAAACCCGTCGTCTTAAGATTGCCGACCTTGG
TCTCGGTCGGGCATTCACAGTGCCAATGAAGAGTTACACACGAGATTGTTACT
CTATGGTACCGAGCTCCTGAAGTTCTTCTTGGAGCGACCCACTACTCTCTACCTGT
GGATATCTGGTCTGTTGGGTGCATCTTCGCTGAACTCGTCCGGAAAATGCCGCTC
TTCACTGGAGACTCCGAACTTCAGCAGCTTCTTCACATCTTCAGGTTGCTTGGCAC
CCCGAATGAGACAATCTGGCCTGGTGTTAGCCAGCACCGTGATTGGCACGAGTTT
CCTCAATGGAGACCACAAGATCTGTCCCTTGCTGTTCCCGGACTCAGCGCGGTTG
GCTTAGACCTTCTCGCCAAAATGTTGGTATTCGAGCCCTCAAAGAGAATCTCTGC
CAAAGCCGCCTTGAGCCATACTTATTTCGCTGATGTTGATAAGMCAGCAACC

Figure 10C

SEQ ID NO:30, Amino acid sequence of the open reading frame of s_pp001031042f

VRMSVSGMDNYEKLEKVGEGTYGKVYKARDKRSGQLVALKKTRLEMEEEGVPSTA
LREVSLLQMLSHSMYIVRLLCVEHVEKGSKPMLYLVFEYMDTDLKKYIDLHGRGPS
GKPLPPKVVQSFMYQLCTGLAHCHGHGVMHRDLKPQNLLVDKQTRRLKIADLGLG
RAFTVPMKSYTHEIVTLWYRAPEVLLGATHYSLPVDIWSVGCIFAELVRKMPLFTGD
SELQQLLHIFRLLGTPNETIWPGVSQHRDWHEFPQWRPQDLSLAVPGLSAVGLDLLA
KMLVFEPSKRISAKAALSHTYFADVDKXAT

Figure 11A

SEQ ID NO:31, Nucleotide sequence of c_pp032010072r

GCTCTCCTGTGGCCTCAAGCTCTGGCATCGCCCAGAGGAAGCCCGCATCCGCTAA
CTTGGCAGGTTTGCCCGGCACCGCATTCAAGGGCTCCGTCGCTGGTTTGCGATGG
GACAGCAATGGATCCGTTCAAGTCTCCAAGTCTTCACTGGACGTCGGCGTCTTCA
AGGAAGGACGCACCTCTTCGCGCCGGGCTGTCGTGCGCGCCTCAGCAGACTCAG
GCTCTGAGTCCAAGAACATTCTGATGATGGGCGGCACTCGATTCATCGGACTCTT
CCTTGCCCGCGAGCTTGTGAAGGCAGGCCACCAGGTTACATTGTTCACAAGAGG
AAAAGCTCCCATCACCCAGCAACTGCCAGGAGAATCTGATGAGGAGTACGCCGA
GTACTCGTCCAAGGTGAAGCACCTTCAAGGCGATCGTCAAGATTTTGACGGCCTG
AAGGAGAAGCTTAAAGGCACCAACTTCAACATTGTCTACGACATCAACGGTAGG
GAGGGTAAGGAAGTGGAGCCCATCTTGGAGGCTCTACCAGGACTGGAGCAGTAC
ATTTTCTGCTCATCGGCCGGTGTTTACCTGAAATCCGACCAACTTCCTCACTTCGA
GGTTGACGCAGTCGACCCCAAGAGCCGACACAAAGGGAAGTTGGACACGGAAA

Figure 11A Continued

CGCTGCTGCAGAGCAAGGGAGTTGCGTGGACTTCCATCAGACCTGTGTACATTTA
CGGGCCTCTCAACTACAACCCTGTGGAGGAGTGGTTCTTTCAGCGCCTCAAGGAG
GGACGCCCCATTCCGGTCCCCAACTCCGGAATGCAGATCACGCAGCTCGGCCAC
GTCAAGGACCTGGCCAGAGCGTTCGTGTTAGTGCTGGCGAATGAGAAGGCTTAC
GGCCAGATTTACAACATCAGCGGTGCCAAGTATGTGACCTTCGATGGTATCGCCA
AGGCATGTGCTCTTGCTGGTGGGTTCCCCGAGCCTCAAATCGTACACTACAACCC
CAAGGACTTCGACTTCGGCAAGAAGAAGGCTTTCCCACTTCGTGACCAGCATTTC
TTTACCTCCGTCGAGAAGGCCGAGAAGGAGCTAGGCTTCACACCCGAATTCGGA
TTGGTCGAGGGACTTAAGGATTCCTACAGCCTGGACTTTGGGCGTGGAACATTCC
GCAAAGCCGCCGACTTCTCTACTGATGATATGATCCTGGAGAAACTTGGCATCAA
GACCACCGTAGCTGCCTAGATTTCTCGTTTCCAGTGATCAAAGTTGTAGGGAGGG
AATTGTGCAGCAGACGCCG

Figure 11B

SEQ ID NO:32, Nucleotide sequence of the open reading frame of c_pp032010072r

GTGGCCTCAAGCTCTGGCATCGCCCAGAGGAAGCCCGCATCCGCTAACTTGGCA
GGTTTGCCCGGCACCGCATTCAAGGGCTCCGTCGCTGGTTTGCGATGGGACAGCA
ATGGATCCGTTCAAGTCTCCAAGTCTTCACTGGACGTCGGCGTCTTCAAGGAAGG
ACGCACCTCTTCGCGCCGGGCTGTCGTGCGCGCCTCAGCAGACTCAGGCTCTGAG
TCCAAGAACATTCTGATGATGGGCGGCACTCGATTCATCGGACTCTTCCTTGCCC
GCGAGCTTGTGAAGGCAGGCCACCAGGTTACATTGTTCACAAGAGGAAAAGCTC
CCATCACCCAGCAACTGCCAGGAGAATCTGATGAGGAGTACGCCGAGTACTCGT
CCAAGGTGAAGCACCTTCAAGGCGATCGTCAAGATTTTGACGGCCTGAAGGAGA
AGCTTAAAGGCACCAACTTCAACATTGTCTACGACATCAACGGTAGGGAGGGTA
AGGAAGTGGAGCCCATCTTGGAGGCTCTACCAGGACTGGAGCAGTACATTTTCTG
CTCATCGGCCGGTGTTTACCTGAAATCCGACCAACTTCCTCACTTCGAGGTTGAC
GCAGTCGACCCCAAGAGCCGACACAAAGGGAAGTTGGACACGGAAACGCTGCTG
CAGAGCAAGGGAGTTGCGTGGACTTCCATCAGACCTGTGTACATTTACGGGCCTC
TCAACTACAACCCTGTGGAGGAGTGGTTCTTTCAGCGCCTCAAGGAGGGACGCCC
CATTCCGGTCCCCAACTCCGGAATGCAGATCACGCAGCTCGGCCACGTCAAGGA
CCTGGCCAGAGCGTTCGTGTTAGTGCTGGCGAATGAGAAGGCTTACGGCCAGATT
TACAACATCAGCGGTGCCAAGTATGTGACCTTCGATGGTATCGCCAAGGCATGTG
CTCTTGCTGGTGGGTTCCCCGAGCCTCAAATCGTACACTACAACCCCAAGGACTT
CGACTTCGGCAAGAAGAAGGCTTTCCCACTTCGTGACCAGCATTTCTTTACCTCC
GTCGAGAAGGCCGAGAAGGAGCTAGGCTTCACACCCGAATTCGGATTGGTCGAG
GGACTTAAGGATTCCTACAGCCTGGACTTTGGGCGTGGAACATTCCGCAAAGCCG
CCGACTTCTCTACTGATGATATGATCCTGGAGAAACTTGGCATCAAGACCACCGT
AGCTGCC

Figure 11C

SEQ ID NO:33, Amino acid sequence of the open reading frame of c_pp032010072r

VASSSGIAQRKPASANLAGLPGTAFKGSVAGLRWDSNGSVQVSKSSLDVGVFKEGR
TSSRRAVVRASADSGSESKNILMMGGTRFIGLFLARELVKAGHQVTLFTRGKAPITQ
QLPGESDEEYAEYSSKVKHLQGDRQDFDGLKEKLKGTNFNIVYDINGREGKEVEPIL
EALPGLEQYIFCSSAGVYLKSDQLPHFEVDAVDPKSRHKGKLDTETLLQSKGVAWTS
IRPVYTYGPLNYNPVEEWFFQRLKEGRPIPVPNSGMQITQLGHVKDLARAFVLVLANE
KAYGQIYNISGAKYVTFDGIAKACALAGGFPEPQIVHYNPKDFDFGKKKAFPLRDQH
FFTSVEKAEKELGFTPEFGLVEGLKDSYSLDFGRGTFRKAADFSTDDMILEKLGIKTT
VAA

Figure 12A

SEQ ID NO:34, Nucleotide sequence of s_pp001068093r

GCCCTTATCCCGGGCTAGTCGCATTCACAGAGCAGCTGATTTAGAGTCTCCACCG
AATTCCACCATGTTGGCGCTCTTCGAGACGCCCGCGGGGTTCGCCCTGTTCAAGG
TTTTGAATGAGGGTAAACTCGATGCCTCCGAGGAATTGTACAAGGAGTTTGAGAC
TGCGGACCTCGCCCGTAAGATGGTGAAGTTGAAAGCCTTTGAAAAATTCGAGAA
TACCACAGATGCCCTGAATGCTGCGTCACACCTTGTGGAAAGCAAGTTGCCAAA
GGGTCTGCGCAAGTTCCTTAAGAAAGAATGCCAAGGGGAGACTCTAGCTATAGC
TGACTCGAAGCTTGGAAAAGCTATTAGTGACAAGCTGGAAATCAACTGTGTTAA
CAATGCGGCAGTGGCAGAGCTGATGAGGGGTCTAAGATCACAATTGTCGGAACT
AATTTCTGGTCTTGCTGGTCATGATATGGCTCCCATGAGTCTGGGACTGTCTCACA
GTTTATCGCGATACAAACTTAAATTCAGCCCTGACAAGGTGGACACCATGATCGT
GCAAGCCATTGGACTCTTGGACGATTTGGACAAGGAGCTAAATACTTATGCTATG
AGAGTGCGTGAATGGTATGGTTGGCATTTTCCAGAGCTTGCTAAGATCGTTCAAG
ATAATGTTCAATACGCTAAGTCAGTGAAGCTGATGGGCAGTCGCACTAACGCCG
CAGACCTGGATTTCTCTGGGATATTGCAAGAGGAAGTAGAGTCTGAAATGAAAG
AAGCTGCAGTCATTTCCATGGGTACGGAAGTTAGTGACCACGATATGTTGAACAT
CAAGTCCTTGTGCGACCAAGTCATTGCTCTCTCAGAGTACCGAGGCCAACTTTTT
GACTACTTGAGGAGTCGTATGAATGCTATTGCGCCTAATCTTACTGTCATGGTTG
GGGAGTTAGTAGGTGCTAGGTTAATTGCCCATGCTGGAAGTCTCATTAACTTGGC
AAAACACCCGGCAAGCACTGTTCAAATTTTGGGTGCTGAAAAGGCACTTTTTAGG
GCATTGAAGACCAAACATGAACCTCCGAAATATGGGCTTATTTATCACGCCTCTT
TGATAGGACAAGCGGCACCTAAATTCAAGGGTAAAATTTCTCGAGTCCTTGCTGC
AAAGTCGGCGCTGTCGATCCGTATGGATGCTCTGGGAGAGGGCTCGGAAGCTAG
CATTGGTATTGAAAGCCGCGCTAAGGCTGAAGCAAGGTTAAGGCAACTTGAAGG
TAGAGCTCTTGGAAAAACTCCTGTCTCTGCATCCAAGGGCAAGCCCAATATTCAG
GCTTATGAAAAGATAGGAAATCTGGAACTCCTGGATTGCTTTCTGCCGCCAAGG
TTTACAATCCCTCCGCTGATGTTACTATGGATGAACCTACTGATGCCACCCCCGCT
AAGAAGAAAAAGATCAAGGAGGCTGCAGAGGAGCCAGCTGCTGAACCAGCAGC
CGAAGACACTTTACCGAAGAAGAAAAAGAAATCTAAGGAAGCTGCAGCAGAGG
CAGAACCTGAACCAACTACGGATGCCACTTCACCCAAGAAGAAGAAGAAGAAAT
CCAAGCAAGCCGCAGAAGAGGCAGCTGCTGAACCTACCACAGAGGCCACTCCTC
CACCAAAGAAGAAGAAATCAAAGGATGCTGTCACACCTACCGTTGCGGTTGCCG
TGGCTGTCACACCAGAGCTCACCAAGTCTGGGAAGAAGAGGAAAGCTGAGACTG
AAGCTGCCGCCGGGGCTGCAGTAGAGGCCGCAGTGGAGGCAGTCACTGGAGTAG
AGAAGAAGAAGAAAAAGAAAAAGAGCAAGGAAGAATCTGCCTAAGCAAGAGGC
GCCCAAGGATAGTAGTTAGGTTACTTGTAGTGTATACATGGAGCGAAATATGTCA
TTGAAGGGTCAAACGCTGGATATCGCAAGGGC

Figure 12B

SEQ ID NO:35, Nucleotide sequence of the open reading frame of s_pp001068093r

ATGTTGGCGCTCTTCGAGACGCCCGCGGGGTTCGCCCTGTTCAAGGTTTTGAATG
AGGGTAAACTCGATGCCTCCGAGGAATTGTACAAGGAGTTTGAGACTGCGGACC
TCGCCCGTAAGATGGTGAAGTTGAAAGCCTTTGAAAAATTCGAGAATACCACAG
ATGCCCTGAATGCTGCGTCACACCTTGTGGAAAGCAAGTTGCCAAAGGGTCTGCG
CAAGTTCCTTAAGAAAGAATGCCAAGGGGAGACTCTAGCTATAGCTGACTCGAA
GCTTGGAAAAGCTATTAGTGACAAGCTGGAAATCAACTGTGTTAACAATGCGGC
AGTGGCAGAGCTGATGAGGGGTCTAAGATCACAATTGTCGGAACTAATTTCTGGT
CTTGCTGGTCATGATATGGCTCCCATGAGTCTGGGACTGTCTCACAGTTTATCGC
GATACAAACTTAAATTCAGCCCTGACAAGGTGGACACCATGATCGTGCAAGCCA
TTGGACTCTTGGACGATTTGGACAAGGAGCTAAATACTTATGCTATGAGAGTGCG
TGAATGGTATGGTTGGCATTTTCCAGAGCTTGCTAAGATCGTTCAAGATAATGTT
CAATACGCTAAGTCAGTGAAGCTGATGGGCAGTCGCACTAACGCCGCAGACCTG
GATTTCTCTGGGATATTGCAAGAGGAAGTAGAGTCTGAAATGAAAGAAGCTGCA
GTCATTTCCATGGGTACGGAAGTTAGTGACCACGATATGTTGAACATCAAGTCCT
TGTGCGACCAAGTCATTGCTCTCTCAGAGTACCGAGGCCAACTTTTTGACTACTT
GAGGAGTCGTATGAATGCTATTGCGCCTAATCTTACTGTCATGGTTGGGGAGTTA
GTAGGTGCTAGGTTAATTGCCCATGCTGGAAGTCTCATTAACTTGGCAAAACACC
CGGCAAGCACTGTTCAAATTTTGGGTGCTGAAAAGGCACTTTTTAGGGCATTGAA
GACCAAACATGAACCTCCGAAATATGGGCTTATTTATCACGCCTCTTTGATAGGA
CAAGCGGCACCTAAATTCAAGGGTAAAATTTCTCGAGTCCTTGCTGCAAAGTCGG
CGCTGTCGATCCGTATGGATGCTCTGGGAGAGGGCTCGGAAGCTAGCATTGGTAT
TGAAAGCCGCGCTAAGGCTGAAGCAAGGTTAAGGCAACTTGAAGGTAGAGCTCT
TGGAAAAACTCCTGTCTCTGCATCCAAGGGCAAGCCCAATATTCAGGCTTATGAA
AAAGATAGGAAATCTGGAACTCCTGGATTGCTTTCTGCCGCCAAGGTTTACAATC
CCTCCGCTGATGTTACTATGGATGAACCTACTGATGCCACCCCCGCTAAGAAGAA
AAAGATCAAGGAGGCTGCAGAGGAGCCAGCTGCTGAACCAGCAGCCGAAGACA
CTTTACCGAAGAAGAAAAAGAAATCTAAGGAAGCTGCAGCAGAGGCAGAACCT
GAACCAACTACGGATGCCACTTCACCCAAGAAGAAGAAGAAGAAATCCAAGCA
AGCCGCAGAAGAGGCAGCTGCTGAACCTACCACAGAGGCCACTCCTCCACCAAA
GAAGAAGAAATCAAAGGATGCTGTCACACCTACCGTTGCGGTTGCCGTGGCTGT
CACACCAGAGCTCACCAAGTCTGGGAAGAAGAGGAAAGCTGAGACTGAAGCTGC
CGCCGGGGCTGCAGTAGAGGCCGCAGTGGAGGCAGTCACTGGAGTAGAGAAGA
AGAAGAAAAGAAAAAGAGCAAGGAAGAATCTGCC

Figure 12C

SEQ ID NO:36, Amino acid sequence of the open reading frame of s_pp001068093r

MLALFETPAGFALFKVLNEGKLDASEELYKEFETADLARKMVKLKAFEKFENTTDA
LNAASHLVESKLPKGLRKFLKKECQGETLAIADSKLGKAISDKLEINCVNNAAVAEL
MRGLRSQLSELISGLAGHDMAPMSLGLSHSLSRYKLKFSPDKVDTMIVQAIGLLDDL
DKELNTYAMRVREWYGWHFPELAKIVQDNVQYAKSVKLMGSRTNAADLDFSGILQ
EEVESEMKEAAVISMGTEVSDHDMLNIKSLCDQVIALSEYRGQLFDYLRSRMNAIAP
NLTVMVGELVGARLIAHAGSLINLAKHPASTVQILGAEKALFRALKTKHEPPKYGLI
YHASLIGQAAPKFKGKISRVLAAKSALSIRMDALGEGSEASIGIESRAKAEARLRQLE
GRALGKTPVSASKGKPNIQAYEKDRKSGTPGLLSAAKVYNPSADVTMDEPTDATPA
KKKKIKEAAEEPAAEPAAEDTLPKKKKKSKEAAAEAEPEPTTDATSPKKKKKKSKQ
AAEEAAAEPTTEATPPPKKKKSKDAVTPTVAVAVAVTPELTKSGKKRKAETEAAAG
AAVEAAVEAVTGVEKKKKKKSKEESA

Figure 13A

SEQ ID NO:37, Nucleotide sequence of s_pp013010011r

AATTCCCAGATTCCCTCACACACCCACTATGCAATCCCGCATTCTCATTGCGTGCC
CACCTCTCGAACGCCCAGGTCTGGGTTTGAAATCCTGGTAATTGGACGATTTGGA
GGTAAAAGGAGGTGCGCAATTTGGCAGATAGTTTGGAGGTTTGGATAATCGTTG
CGTAGAGGTGGCCATGGCGGGTGTGGCGCTGGGACTCGTGGGACCCGGTTTGGA
ATTGGTGGCCAGCAAGAGGGCACTGTGCCCTGGAGCTTCTTTCTCTTCTCCGTTTT
GCCTCAGTTGCTCTGCGTCTGTGTCATCCAACAGCAGTACTCGTGCCAGGTCTCC
CAAGGCCCTTGTCCTCAGGAGCTCCTTTGTCTCGCGGACCACCCATTCCAGCTTCT
GGGATGGTGGAGTGGGAGCCTGTGTGCTCGCGCTTGCGGTGGAGGACTCAATTA
AGCAAAGGAAACGCGGTGGTGCCCTTTGTGCTCAAGCGAATATTTTTGAGCGTGT
GGTCAGAATTGTGAGGTCCTACGCAAATGCTATAGTGAGCTCAGCTGAAGACCCT
GAAAAGTTACTGGATCAGACTGTGTTGGAAATGAATGAAGACCTGATAAAAATG
CGTCAGGCATCGGCACAGGTGCTAGCTTCCCAAAAGCAGTTGGAGAATAAGTAT
AAAGCAGCTCAAACAGCTGCAGATGATTGGTATAGGAGAGCGAAATTAGCACTT
GAAAAAGGTGATGAGGACTTAGCTAGGGAGGCTCTTAAACGCCGTAAGGATTAT
GAGGAAAGTGCCAAGGCATTGAAAAGTCAGCTGGATCAGCAGAAGGGTGTCGTG
GATAAGCTGATATCGAACACTCGGCTGCTAGAAAGCAAGATCTCAGAGGCTAAG
TCGAAGAAGGACACTTTGAAAGCACGAGCACAATCTGCCAAGACTTCCCAGAAG
GTTAATGAGATGTTGGGAAATATCAATACTAGCGGTGCTCTTGCGGCATTTGAGA
AGATGGAAGAAAAAGTTACTGCATTAGAGGCAGAATCGGAGGCGCTCAATCAAC
TCAGTACTGATGATTTGGCTGCCAAGTTCGCTCTTTTAGAAAGTGATTCTGTAGAT
GACGACTTGGCATCCTTAAAGCAAGACGTGCTGGGTTCATCGAAGAGAAAAGGA
GAGCTGCCGGAAGGCCGGTCCCAAGCAGTTTCAAGTAGCAGCAAAACTCCCTAT
CCTTTCAAGGACTCGGAGATTGAAAGGGAATTGAATGAGCTACGAAAGAGGGCC
AACGATTTTTAAGTCTTCATTTTGATTTTCTCTGCTGTTTAGCAGCAAATCGGAAT
TCTTATGATTGTGTATTTTAGAGTGAAGGGTGGTTGCTGGTCACTGCTGTATCTTA
AATCATTGACGATTTGAAGGTCGGGAACGTGAGTCTTTAGCAATTGGTCATGCAA
GCTACGGCTATACAATTTAATTTGTGCAAATACCTCAATATCTGCTGAAACAGAT
TTTGTGGTGATCATTAAAAATCTTGATTCGACTCGTGCCGAATTC

Figure 13B

SEQ ID NO:38, Nucleotide sequence of the open reading frame of s_pp013010011r

GTGGCCATGGCGGGTGTGGCGCTGGGACTCGTGGGACCCGGTTTGGAATTGGTG
GCCAGCAAGAGGGCACTGTGCCCTGGAGCTTCTTTCTCTTCTCCGTTTTGCCTCAG
TTGCTCTGCGTCTGTGTCATCCAACAGCAGTACTCGTGCCAGGTCTCCCAAGGCC
CTTGTCCTCAGGAGCTCCTTTGTCTCGCGGACCACCCATTCCAGCTTCTGGGATGG
TGGAGTGGGAGCCTGTGTGCTCGCGCTTGCGGTGGAGGACTCAATTAAGCAAAG
GAAACGCGGTGGTGCCCTTTGTGCTCAAGCGAATATTTTTGAGCGTGTGGTCAGA
ATTGTGAGGTCCTACGCAAATGCTATAGTGAGCTCAGCTGAAGACCCTGAAAAG
TTACTGGATCAGACTGTGTTGGAAATGAATGAAGACCTGATAAAAATGCGTCAG
GCATCGGCACAGGTGCTAGCTTCCCAAAAGCAGTTGGAGAATAAGTATAAAGCA
GCTCAAACAGCTGCAGATGATTGGTATAGGAGAGCGAAATTAGCACTTGAAAAA
GGTGATGAGGACTTAGCTAGGGAGGCTCTTAAACGCCGTAAGGATTATGAGGAA
AGTGCCAAGGCATTGAAAAGTCAGCTGGATCAGCAGAAGGGTGTCGTGGATAAG
CTGATATCGAACACTCGGCTGCTAGAAAGCAAGATCTCAGAGGCTAAGTCGAAG

Figure 13B Continued

AAGGACACTTTGAAAGCACGAGCACAATCTGCCAAGACTTCCCAGAAGGTTAAT
GAGATGTTGGGAAATATCAATACTAGCGGTGCTCTTGCGGCATTTGAGAAGATG
GAAGAAAAAGTTACTGCATTAGAGGCAGAATCGGAGGCGCTCAATCAACTCAGT
ACTGATGATTTGGCTGCCAAGTTCGCTCTTTTAGAAAGTGATTCTGTAGATGACG
ACTTGGCATCCTTAAAGCAAGACGTGCTGGGTTCATCGAAGAGAAAGGAGAGC
TGCCGGAAGGCCGGTCCCAAGCAGTTTCAAGTAGCAGCAAAACTCCCTATCCTTT
CAAGGACTCGGAGATTGAAAGGGAATTGAATGAGCTACGAAAGAGGGCCAACG
ATTTT

Figure 13C

SEQ ID NO:39, Amino acid sequence of the open reading frame of s_pp013010011r

VAMAGVALGLVGPGLELVASKRALCPGASFSSPFCLSCSASVSSNSSTRARSPKALVL
RSSFVSRTTHSSFWDGGVGACVLALAVEDSIKQRKRGGALCAQANIFERVVRIVRSY
ANAIVSSAEDPEKLLDQTVLEMNEDLIKMRQASAQVLASQKQLENKYKAAQTAAD
DWYRRAKLALEKGDEDLAREALKRRKDYEESAKALKSQLDQQKGVVDKLISNTRL
LESKISEAKSKKDTLKARAQSAKTSQKVNEMLGNINTSGALAAFEKMEEKVTALEAE
SEALNQLSTDDLAAKFALLESDSVDDDLASLKQDVLGSSKRKGELPEGRSQAVSSSS
KTPYPFKDSEIERELNELRKRANDF

Figure 14A

SEQ ID NO:40, Nucleotide sequence of c_pp004096088r

GCTCTCCTGTGGCCTCAAGCTCTGGCATCGCCCAGAGGAAGCCCGCATCCGCTAA
CTTGGCAGGTTTGCCCGGCACCGCATTCAAGGGCTCCGTCGCTGGTTTGCGATGG
GACAGCAATGGATCCGTTCAAGTCTCCAAGTCTTCACTGGACGTCGGCGTCTTCA
AGGAAGGACGCACCTCTTCGCGCCGGGCTGTCGTGCGCGCCTCAGCAGACTCAG
GCTCTGAGTCCAAGAACATTCTGATGATGGGCGGCACTCGATTCATCGGACTCTT
CCTTGCCCGCGAGCTTGTGAAGGCAGGCCACCAGGTTACATTGTTCACAAGAGG
AAAAGCTCCCATCACCCAGCAACTGCCAGGAGAATCTGATGAGGAGTACGCCGA
GTACTCGTCCAAGGTGAAGCACCTTCAAGGCGATCGTCAAGATTTTGACGGCCTG
AAGGAGAAGCTTAAAGGCACCAACTTCAACATTGTCTACGACATCAACGGTAGG
GAGGGTAAGGAAGTGGAGCCCATCTTGGAGGCTCTACCAGGACTGGAGCAGTAC
ATTTTCTGCTCATCGGCCGGTGTTTACCTGAAATCCGACCAACTTCCTCACTTCGA
GGTTGACGCAGTCGACCCCAAGAGCCGACACAAAGGGAAGTTGGACACGGAAA
CGCTGCTGCAGAGCAAGGGAGTTGCGTGGACTTCCATCAGACCTGTGTACATTTA
CGGGCCTCTCAACTACAACCCTGTGGAGGAGTGGTTCTTTCAGCGCCTCAAGGAG
GGACGCCCCATTCCGGTCCCCAACTCCGGAATGCAGATCACGCAGCTCGGCCAC
GTCAAGGACCTGGCCAGAGCGTTCGTGTTAGTGCTGGCGAATGAGAAGGCTTAC
GGCCAGATTTACAACATCAGCGGTGCCAAGTATGTGACCTTCGATGGTATCGCCA
AGGCATGTGCTCTTGCTGGTGGGTTCCCCGAGCCTCAAATCGTACACTACAACCC
CAAGGACTTCGACTTCGGCAAGAAGAAGGCTTTCCCACTTCGTGACCAGCATTTC
TTTACCTCCGTCGAGAAGGCCGAGAAGGAGCTAGGCTTCACACCCGAATTCGGA
TTGGTCGAGGGACTTAAGGATTCCTACAGCCTGGACTTTGGGCGTGGAACATTCC
GCAAAGCCGCCGACTTCTCTACTGATGATATGATCCTGGAGAAACTTGGCATCAA
GACCACCGTAGCTGCCTAGATTTCTCGTTTCCAGTGATCAAAGTTGTAGGGAGGG
AATTGTGCAGCAGACGCCG

Figure 14B

SEQ ID NO:41, Nucleotide sequence of the open reading frame of c_pp004096088r

GTGGCCTCAAGCTCTGGCATCGCCCAGAGGAAGCCCGCATCCGCTAACTTGGCA
GGTTTGCCCGGCACCGCATTCAAGGGCTCCGTCGCTGGTTTGCGATGGGACAGCA
ATGGATCCGTTCAAGTCTCCAAGTCTTCACTGGACGTCGGCGTCTTCAAGGAAGG
ACGCACCTCTTCGCGCCGGGCTGTCGTGCGCGCCTCAGCAGACTCAGGCTCTGAG
TCCAAGAACATTCTGATGATGGGCGGCACTCGATTCATCGGACTCTTCCTTGCCC
GCGAGCTTGTGAAGGCAGGCCACCAGGTTACATTGTTCACAAGAGGAAAAGCTC
CCATCACCCAGCAACTGCCAGGAGAATCTGATGAGGAGTACGCCGAGTACTCGT
CCAAGGTGAAGCACCTTCAAGGCGATCGTCAAGATTTTGACGGCCTGAAGGAGA
AGCTTAAAGGCACCAACTTCAACATTGTCTACGACATCAACGGTAGGGAGGGTA
AGGAAGTGGAGCCCATCTTGGAGGCTCTACCAGGACTGGAGCAGTACATTTTCTG
CTCATCGGCCGGTGTTTACCTGAAATCCGACCAACTTCCTCACTTCGAGGTTGAC
GCAGTCGACCCCAAGAGCCGACACAAAGGGAAGTTGGACACGGAAACGCTGCTG
CAGAGCAAGGGAGTTGCGTGGACTTCCATCAGACCTGTGTACATTTACGGCCTC
TCAACTACAACCCTGTGGAGGAGTGGTTCTTTCAGCGCCTCAAGGAGGGACGCCC
CATTCCGGTCCCCAACTCCGGAATGCAGATCACGCAGCTCGGCCACGTCAAGGA
CCTGGCCAGAGCGTTCGTGTTAGTGCTGGCGAATGAGAAGGCTTACGGCCAGATT
TACAACATCAGCGGTGCCAAGTATGTGACCTTCGATGGTATCGCCAAGGCATGTG
CTCTTGCTGGTGGGTTCCCCGAGCCTCAAATCGTACACTACAACCCCAAGGACTT
CGACTTCGGCAAGAAGAAGGCTTTCCCACTTCGTGACCAGCATTTCTTTACCTCC
GTCGAGAAGGCCGAGAAGGAGCTAGGCTTCACACCCGAATTCGGATTGGTCGAG
GGACTTAAGGATTCCTACAGCCTGGACTTTGGGCGTGGAACATTCCGCAAAGCCG
CCGACTTCTCTACTGATGATATGATCCTGGAGAAACTTGGCATCAAGACCACCGT
AGCTGCC

Figure 14C

SEQ ID NO:42, Amino acid sequence of the open reading frame of c_pp004096088r

VASSSGIAQRKPASANLAGLPGTAFKGSVAGLRWDSNGSVQVSKSSLDVGVFKEGR
TSSRRAVVRASADSGSESKNILMMGGTRFIGLFLARELVKAGHQVTLFTRGKAPITQ
QLPGESDEEYAEYSSKVKHLQGDRQDFDGLKEKLKGTNFNIVYDINGREGKEVEPIL
EALPGLEQYIFCSSAGVYLKSDQLPHFEVDAVDPKSRHKGKLDTETLLQSKGVAWTS
IRPVYIYGPLNYNPVEEWFFQRLKEGRPIPVPNSGMQITQLGHVKDLARAFVLVLANE
KAYGQIYNISGAKYVTFDGIAKACALAGGFPEPQIVHYNPKDFDFGKKKAFPLRDQH
FFTSVEKAEKELGFTPEFGLVEGLKDSYSLDFGRGTFRKAADFSTDDMILEKLGIKTT
VAA

SEQUENCE LISTING

<160> NUMBER OF SEQ ID NOS: 73

<210> SEQ ID NO 1
<211> LENGTH: 2908
<212> TYPE: DNA
<213> ORGANISM: Physcomitrella patens

<400> SEQUENCE: 1

```
cgatggtgcg ttcgagatcg taaggttgcc gacgaaggcg taacttggaa gtcctctgtg      60
tcccggcgat gtcccaatgt tggcccgatt ttctgttttt agcgagctgt gggctagttt     120
gtgggtatga tccggggaat gagacgagat gtctgtctga gtgagaccac tctaggggct     180
gttggaggat gaggagggaa gcgcagaagt tggccattct tttcagtgac tggactctgt     240
gcgagtggtc agctttcggg agctgctgtt gcattgaccg tgattctttt cgagatcgta     300
gagacagcag ctggcaaggg ttttggggag cttttcaaat gaagggcatt caagagcttt     360
cagatgatga agattatatt ccgcctgtca atgcatcgcg atatttcaac aggggcaaag     420
cgctctcaaa gacatcatcc aatcatgcca atggaaatgg aaatccaaac ggaacgagtt     480
ttggagtttc aacttcttca gcaagtgact ctgacaaaga taagaaatcc gaagtttcag     540
gttcttact aagcgattct ggcaagaatc aaaagtccgt tactgaattg gattcgttcg      600
catttaaccg caagtccaga attgccaagc gacctatcga gctactcgaa gacgaggagg     660
acgtggacgt tggagctgca aaggttgtag acattgagcc gactaacgga aacaagaggc     720
ggagacggta tcacaccatc gaagacagtg acgatgaaga gttggatgag aagaaatcgt     780
ttggtgataa tctgacccca ggaacggaaa tcgatcaatg tgcagccgat gaatccttag     840
caaaaaggtt gcaggattta gagcaccggg cagtttctgg ccgtaatcgc ctggttcaaa     900
ttttgtcaga ttccgatgaa gaagaagagg aagaagtaaa tcccataacc atcaccctac     960
aaaggtgtga ccagattgca gcatcattgc gagaagagct gcaggccagc agttcaagtg    1020
ataactcggt taatgaagat cgttatgcag aggttgatgt agcagcagca aaaattgtga    1080
gccaggcaga tgtctgtgca gcttgtggca ttgccgagaa tgatacacaa cgaatgctca    1140
agccatatca gcttgtaggc gtcaatttca tgctgctact tcaccgcaaa catgttgggg    1200
gtgctatact tgcggatgaa atgggcctag gaaagactgt gcaggcagtt gcgtatcttg    1260
cccttctgaa acatcttgat ggagatgctg gtcctcatct tttagttgca cctgcttctc    1320
ttttagaaaa ctggcaaaga gaactcaaga agtggtgtcc tgcatttaag gtggagctct    1380
atcatggctc aggaagggca gctttaaaca ggaggcttca gtatgctgca aaatctaaag    1440
ggcctgcacc ctttaacgtg atgctgacgt gctactccct ttttgagagg cagagtgctc    1500
agacaaaaga tgaccgcaaa ttccttaaga aatggaattg gcgctgtgtg gttatggacg    1560
aggctcatct ttttgaaggac agaagcagct ttcgcagcaa aaagttgcga gatatagctc    1620
acaaagcaat tcaaagactg atgctgactg gtactccact ccagaacgat ttgcaggagc    1680
tatggtcact tctggagttc atgatgcctg atgtgttcaa cacaaatggc gttgatttag    1740
atcaatatct gggaaccagg aacgatacct cagggattgt tgtgcaggat acgaacttga    1800
tgactcggat caaaggaata ctaggaccctt ttgtattacg gagaatgaaa actgatgtta    1860
tgcgccagct tgtatcaaag attcaggagg tggagtgtgt ggagatgcta gacgagcaat    1920
caatggcata taaaaaagct gtgaatgagt atagagcct tgctgagtcc gcacgtgccg    1980
ctaaagctgc aaagaaatcc tcagttagcg tagtagatgt ccttcctcgt cgacaagtga    2040
```

-continued

```
ccaatatctt tactcaattg agaaagctcg gtaatcatcc cttgttgata cgccgtttgt   2100
attctgacga gacagtcaag aaattggcta agaaatttca tccattagga gttttggat    2160 atgaatgcga tttgcagcgt gtggaggaag aattgactag ttacagcgat tttgacctcc   2220
acaagttgtg tattcaatat ggaggcgctg cgggagggca aggaaagctt gatgatgatc   2280
atgcactagc ttctgcaaag tgccaggctt tagcacgtct acttcccaag ttacagcaag   2340
gtggccatcg cacattgata ttcagccagt ggacaagcat gctggatatt ttagaatggg   2400
ctcttgacgt catgggtttt tcttacactc gcctagatgg aagcactcaa gtaagtgaac   2460
gccaaaccct agtggacgag ttcaacaatg accctagcat atttgtgttt ctcctgtcta   2520
ctcgagctgg aggtcaaggt ctaaatttaa caggagcaga cacagtcatt ttacatgatt   2580
tggacttcaa tccccaaatg gatcgacagg ctgaggatcg ctgtcatcgg attggccagt   2640
ctaaacctgt tacgatatac cgacttgtaa caaaagatac ggtcgatgaa agtatataca   2700
agatagccca acagaagctg gtcctcgatg cggcagttct tgaaggaaaa gagtcatcct   2760
ctgatcttaa tgatggtgat gctcgcacga tgggtgaaat tctttctgca ttattggatg   2820
ttccaccgac atgatcctgg agtccagaac acatttttaa tttattttca ttatctttat   2880
ctggcactgc gagaaagctc gttaacgc                                     2908
```

<210> SEQ ID NO 2
<211> LENGTH: 2493
<212> TYPE: DNA
<213> ORGANISM: Physcomitrella patens

<400> SEQUENCE: 2

```
atgaagggca ttcaagagct ttcagatgat gaagattata ttccgcctgt caatgcatcg     60
cgatatttca cagggggcaa agcgctctca aagacatcat ccaatcatgc caatggaaat    120
ggaaatccaa acggaacgag ttttggagtt tcaacttctt cagcaagtga ctctgacaaa    180
gataagaaat ccgaagtttc aggttcttta ctaagcgatt ctggcaagaa tcaaaagtcc    240
gttactgaat tggattcgtt cgcatttaac cgcaagtcca gaattgccaa gcgacctatc    300
gagctactcg aagacgagga ggacgtggac gttggagctg caaaggttgt agacattgag    360
ccgactaacg gaaacaagag gcggagacgg tatcacacca tcgaagacag tgacgatgaa    420
gagttggatg agaagaaatc gtttggtgat aatctgaccc aggaacgga atcgatcaa     480 tgtgcagccg atgaatcctt agcaaaaagg ttgcaggatt tagagcaccg ggcagtttct    540
ggccgtaatc gcctggttca aattttgtca gattccgatg aagaagaaga ggaagaagta    600
aatcccataa ccatcaccct acaaaggtgt gaccagattg cagcatcatt gcagaagag    660 ctgcaggcca gcagttcaag tgataactcg gttaatgaag atcgttatgc agaggttgat    720
gtagcagcag caaaaattgt gagccaggca gatgtctgtg cagcttgtgg cattgccgag    780
aatgatacac aacgaatgct caagccatat cagcttgtag gcgtcaattt catgctgcta    840
cttcaccgca acatgttggg ggtgctata cttgcggatg aaatgggcct aggaaagact    900
gtgcaggcag ttgcgtatct tgcccttctg aaacatcttg atggagatgc tggtcctcat    960
cttttagttg cacctgcttc tcttttagaa aactggcaaa gagaactcaa gaagtggtgt   1020
cctgcattta aggtggagct ctatcatggc tcaggaaggg cagctttaaa caggaggctt   1080
cagtatgctg caaaatctaa agggcctgca ccctttaacg tgatgctgac gtgctactcc   1140 cttttgaga ggcagagtgc tcagacaaaa gatgaccgca aattccttaa gaaatggaat   1200
```

```
tggcgctgtg tggttatgga cgaggctcat cttttgaagg acagaagcag ctttcgcagc   1260
aaaaagttgc gagatatagc tcacaaagca attcaaagac tgatgctgac tggtactcca   1320
ctccagaacg atttgcagga gctatggtca cttctggagt tcatgatgcc tgatgtgttc   1380
aacacaaatg gcgttgattt agatcaatat ctgggaacca ggaacgatac ctcagggatt   1440
gttgtgcagg atacgaactt gatgactcgg atcaaaggaa tactaggacc ttttgtatta   1500
cggagaatga aaactgatgt tatgcgccag cttgtatcaa agattcagga ggtggagtgt   1560
gtggagatgc tagacgagca atcaatggca tataaaaaag ctgtgaatga gtatagagcc   1620
cttgctgagt ccgcacgtgc cgctaaagct gcaaagaaat cctcagttag cgtagtagat   1680
gtccttcctc gtcgacaagt gaccaatatc tttactcaat tgagaaagct cggtaatcat   1740
cccttgttga tacgccgttt gtattctgac gagacagtca agaaattggc taagaaattt   1800
catccattag gagttttttgg atatgaatgc gatttgcagc gtgtggagga agaattgact   1860
agttacagcg attttgacct ccacaagttg tgtattcaat atggaggcgc tgcgggaggg   1920
caaggaaagc ttgatgatga tcatgcacta gcttctgcaa agtgccaggc tttagcacgt   1980
ctacttccca agttacagca aggtggccat cgcacattga tattcagcca gtggacaagc   2040
atgctggata ttttagaatg ggctcttgac gtcatgggtt tttcttacac tcgcctagat   2100
ggaagcactc aagtaagtga acgccaaacc ctagtggacg agttcaacaa tgaccctagc   2160
atatttgtgt ttctcctgtc tactcgagct ggaggtcaag gtctaaattt aacaggagca   2220
gacacagtca ttttacatga tttggacttc aatccccaaa tggatcgaca ggctgaggat   2280
cgctgtcatc ggattggcca gtctaaacct gttacgatat accgacttgt aacaaaagat   2340
acggtcgatg aaagtatata caagatagcc aacagaagc tggtcctcga tgcggcagtt   2400
cttgaaggaa aagagtcatc ctctgatctt aatgatggtg atgctcgcac gatgggtgaa   2460
attctttctg cattattgga tgttccaccg aca                               2493
```

<210> SEQ ID NO 3
<211> LENGTH: 831
<212> TYPE: PRT
<213> ORGANISM: Physcomitrella patens

<400> SEQUENCE: 3

```
Met Lys Gly Ile Gln Glu Leu Ser Asp Asp Glu Asp Tyr Ile Pro Pro
  1               5                  10                  15

Val Asn Ala Ser Arg Tyr Phe Asn Arg Gly Lys Ala Leu Ser Lys Thr
             20                  25                  30

Ser Ser Asn His Ala Asn Gly Asn Gly Asn Pro Asn Gly Thr Ser Phe
         35                  40                  45

Gly Val Ser Thr Ser Ser Ala Ser Asp Ser Asp Lys Asp Lys Lys Ser
     50                  55                  60

Glu Val Ser Gly Ser Leu Leu Ser Asp Ser Gly Lys Asn Gln Lys Ser
 65                  70                  75                  80

Val Thr Glu Leu Asp Ser Phe Ala Phe Asn Arg Lys Ser Arg Ile Ala
                 85                  90                  95

Lys Arg Pro Ile Glu Leu Leu Glu Asp Glu Glu Asp Val Asp Val Gly
            100                 105                 110

Ala Ala Lys Val Val Asp Ile Glu Pro Thr Asn Gly Asn Lys Arg Arg
        115                 120                 125

Arg Arg Tyr His Thr Ile Glu Asp Ser Asp Asp Glu Glu Leu Asp Glu
    130                 135                 140
```

```
Lys Lys Ser Phe Gly Asp Asn Leu Thr Pro Gly Thr Glu Ile Asp Gln
145                 150                 155                 160

Cys Ala Ala Asp Glu Ser Leu Ala Lys Arg Leu Gln Asp Leu Glu His
            165                 170                 175

Arg Ala Val Ser Gly Arg Asn Arg Leu Val Gln Ile Leu Ser Asp Ser
        180                 185                 190

Asp Glu Glu Glu Glu Glu Val Asn Pro Ile Thr Ile Thr Leu Gln
    195                 200                 205

Arg Cys Asp Gln Ile Ala Ala Ser Leu Arg Glu Glu Leu Gln Ala Ser
    210                 215                 220

Ser Ser Ser Asp Asn Ser Val Asn Glu Asp Arg Tyr Ala Glu Val Asp
225                 230                 235                 240

Val Ala Ala Ala Lys Ile Val Ser Gln Ala Asp Val Cys Ala Ala Cys
            245                 250                 255

Gly Ile Ala Glu Asn Asp Thr Gln Arg Met Leu Lys Pro Tyr Gln Leu
        260                 265                 270

Val Gly Val Asn Phe Met Leu Leu His Arg Lys His Val Gly Gly
    275                 280                 285

Ala Ile Leu Ala Asp Glu Met Gly Leu Gly Lys Thr Val Gln Ala Val
290                 295                 300

Ala Tyr Leu Ala Leu Leu Lys His Leu Asp Gly Asp Ala Gly Pro His
305                 310                 315                 320

Leu Leu Val Ala Pro Ala Ser Leu Leu Glu Asn Trp Gln Arg Glu Leu
            325                 330                 335

Lys Lys Trp Cys Pro Ala Phe Lys Val Glu Leu Tyr His Gly Ser Gly
        340                 345                 350

Arg Ala Ala Leu Asn Arg Arg Leu Gln Tyr Ala Ala Lys Ser Lys Gly
    355                 360                 365

Pro Ala Pro Phe Asn Val Met Leu Thr Cys Tyr Ser Leu Phe Glu Arg
370                 375                 380

Gln Ser Ala Gln Thr Lys Asp Asp Arg Lys Phe Leu Lys Lys Trp Asn
385                 390                 395                 400

Trp Arg Cys Val Val Met Asp Glu Ala His Leu Leu Lys Asp Arg Ser
            405                 410                 415

Ser Phe Arg Ser Lys Lys Leu Arg Asp Ile Ala His Lys Ala Ile Gln
        420                 425                 430

Arg Leu Met Leu Thr Gly Thr Pro Leu Gln Asn Asp Leu Gln Glu Leu
    435                 440                 445

Trp Ser Leu Leu Glu Phe Met Met Pro Asp Val Phe Asn Thr Asn Gly
450                 455                 460

Val Asp Leu Asp Gln Tyr Leu Gly Thr Arg Asn Asp Thr Ser Gly Ile
465                 470                 475                 480

Val Val Gln Asp Thr Asn Leu Met Thr Arg Ile Lys Gly Ile Leu Gly
            485                 490                 495

Pro Phe Val Leu Arg Arg Met Lys Thr Asp Val Met Arg Gln Leu Val
        500                 505                 510

Ser Lys Ile Gln Glu Val Glu Cys Val Glu Met Leu Asp Glu Gln Ser
    515                 520                 525

Met Ala Tyr Lys Lys Ala Val Asn Glu Tyr Arg Ala Leu Ala Glu Ser
530                 535                 540

Ala Arg Ala Ala Lys Ala Lys Lys Ser Ser Val Ser Val Asp
545                 550                 555                 560

Val Leu Pro Arg Arg Gln Val Thr Asn Ile Phe Thr Gln Leu Arg Lys
```

```
                565                 570                 575
Leu Gly Asn His Pro Leu Leu Ile Arg Arg Leu Tyr Ser Asp Glu Thr
                580                 585                 590
Val Lys Lys Leu Ala Lys Lys Phe His Pro Leu Gly Val Phe Gly Tyr
            595                 600                 605
Glu Cys Asp Leu Gln Arg Val Glu Glu Glu Leu Thr Ser Tyr Ser Asp
        610                 615                 620
Phe Asp Leu His Lys Leu Cys Ile Gln Tyr Gly Ala Ala Gly Gly
625                 630                 635                 640
Gln Gly Lys Leu Asp Asp His Ala Leu Ala Ser Ala Lys Cys Gln
                645                 650                 655
Ala Leu Ala Arg Leu Leu Pro Lys Leu Gln Gln Gly Gly His Arg Thr
            660                 665                 670
Leu Ile Phe Ser Gln Trp Thr Ser Met Leu Asp Ile Leu Glu Trp Ala
        675                 680                 685
Leu Asp Val Met Gly Phe Ser Tyr Thr Arg Leu Asp Gly Ser Thr Gln
    690                 695                 700
Val Ser Glu Arg Gln Thr Leu Val Asp Glu Phe Asn Asn Asp Pro Ser
705                 710                 715                 720
Ile Phe Val Phe Leu Leu Ser Thr Arg Ala Gly Gly Gln Gly Leu Asn
                725                 730                 735
Leu Thr Gly Ala Asp Thr Val Ile Leu His Asp Leu Asp Phe Asn Pro
            740                 745                 750
Gln Met Asp Arg Gln Ala Glu Asp Arg Cys His Arg Ile Gly Gln Ser
        755                 760                 765
Lys Pro Val Thr Ile Tyr Arg Leu Val Thr Lys Asp Thr Val Asp Glu
    770                 775                 780
Ser Ile Tyr Lys Ile Ala Gln Gln Lys Leu Val Leu Asp Ala Ala Val
785                 790                 795                 800
Leu Glu Gly Lys Glu Ser Ser Asp Leu Asn Asp Gly Asp Ala Arg
                805                 810                 815
Thr Met Gly Glu Ile Leu Ser Ala Leu Leu Asp Val Pro Pro Thr
            820                 825                 830

<210> SEQ ID NO 4
<211> LENGTH: 1122
<212> TYPE: DNA
<213> ORGANISM: Physcomitrella patens

<400> SEQUENCE: 4
tgggtttggg tagttgcttg acgccataaa tttctccctt gagttgcagt tattggaggg      60
ggagctcaag tccagacgtc cagacgagag cagttcgttg tgcattaatc tgaaagcgca    120
aagtatccga agatgaacaa gacagtgtgt cctgagtgtc ggaaggcgac agaggtggta    180
gtggaccatg ccgcggggga catggtgtgt gcagaatgcg gattagtctt agagcagcat    240
tccgtagatg aaagctcgga atggcgaacg ttttcggatt caacttccag cgacccagtc    300
cgtgtcggtg gtccttccaa tcccctcctc acagatggtg gctgtcaac catcatatcc    360
aagcccaacg gtgcgcaggg cgatttcatg tcatctcttg gacgttggca gaacaggggc    420
tcaaatcctg atcggcctct tatcattgct tttcgatcaa ttggaaccat ggcagacagg    480
ctcggactag tgtcaacaat caaggatcgg ccaatgaga tatataagaa ggtggaagac    540
ctgaaatcta tccgtggtcg aagtcaggat gcgatactgg ctgcctgctt atacatcgct    600
tgccgacagg aagataaacc tcgaacattc aaagaaatat gctcagttgc taatggagca    660
```

```
tcgaagaagg acattgggag agcaaccaag tttattgtga agcaattaga agaggatatg      720
ggtatttcta tggagatggg aacaatccat gctggtgact tcttgaggag attctgctcg      780
catctgaata tggaaaacaa cgaggtcaga gctgccacag agacggtaaa gaagtcagag      840
atgctggata tccgaaaaag tccaatatca gttgctgctg ctgctatata catgatctca      900
cagcttaatg aaaaagataa gaaagcccta aagacatat caagggtggc tggggtggct       960
gaagtgacta tccgaaattc ttacaaggat ctctatcccc acgcagccaa gctcataccc     1020
gactggtttc ttaaagaagt tgatttgaag aatttgccag ctccttagag cttttctgtt     1080
cttcgctaga gtggaagagt ataggcaggc ggtccttgaa cc                        1122
```

<210> SEQ ID NO 5
<211> LENGTH: 933
<212> TYPE: DNA
<213> ORGANISM: Physcomitrella patens

<400> SEQUENCE: 5

```
atgaacaaga cagtgtgtcc tgagtgtcgg aaggcgacag aggtggtagt ggaccatgcc       60
gcgggggaca tggtgtgtgc agaatgcgga ttagtcttag agcagcattc cgtagatgaa      120
agctcggaat ggcgaacgtt ttcggattca acttccagcg acccagtccg tgtcggtggt      180
ccttccaatc ccctcctcac agatggtggg ctgtcaacca tcatatccaa gcccaacggt      240
gcgcagggcg atttcatgtc atctcttgga cgttggcaga caggggctc aaatcctgat       300 cggcctctta tcattgcttt tcgatcaatt ggaaccatgg cagacaggct cggactagtg      360
tcaacaatca aggatcgggc caatgagata tataagaagg tggaagacct gaaatctatc      420
cgtggtcgaa gtcaggatgc gatactggct gcctgcttat acatcgcttg ccgacaggaa      480
gataaacctc gaacattcaa agaaatatgc tcagttgcta atggagcatc gaagaaggac      540
attgggagag caaccaagtt tattgtgaag caattagaag aggatatggg tatttctatg      600
gagatgggaa caatccatgc tggtgacttc ttgaggagat ctgctcgca tctgaatatg       660 gaaaacaacg aggtcagagc tgccacagag acggtaaaga agtcagagat gctggatatc      720
cgaaaaagtc aatatcagt tgctgctgct gctatataca tgatctcaca gcttaatgaa       780
aaagataaga agccctaaa agacatatca agggtggctg gggtggctga agtgactatc       840
cgaaattctt acaaggatct ctatcccac gcagccaagc tcatacccga ctggtttctt       900
aaagaagttg atttgaagaa tttgccagct cct                                   933
```

<210> SEQ ID NO 6
<211> LENGTH: 311
<212> TYPE: PRT
<213> ORGANISM: Physcomitrella patens

<400> SEQUENCE: 6

```
Met Asn Lys Thr Val Cys Pro Glu Cys Arg Lys Ala Thr Glu Val Val
 1               5                  10                  15

Val Asp His Ala Ala Gly Asp Met Val Cys Ala Glu Cys Gly Leu Val
             20                  25                  30

Leu Glu Gln His Ser Val Asp Glu Ser Ser Glu Trp Arg Thr Phe Ser
         35                  40                  45

Asp Ser Thr Ser Ser Asp Pro Val Arg Val Gly Gly Pro Ser Asn Pro
     50                  55                  60

Leu Leu Thr Asp Gly Gly Leu Ser Thr Ile Ile Ser Lys Pro Asn Gly
```

```
                65                  70                  75                  80
Ala Gln Gly Asp Phe Met Ser Ser Leu Gly Arg Trp Gln Asn Arg Gly
                        85                  90                  95

Ser Asn Pro Asp Arg Pro Leu Ile Ile Ala Phe Arg Ser Ile Gly Thr
                100                 105                 110

Met Ala Asp Arg Leu Gly Leu Val Ser Thr Ile Lys Asp Arg Ala Asn
            115                 120                 125

Glu Ile Tyr Lys Lys Val Glu Asp Leu Lys Ser Ile Arg Gly Arg Ser
        130                 135                 140

Gln Asp Ala Ile Leu Ala Ala Cys Leu Tyr Ile Ala Cys Arg Gln Glu
145                 150                 155                 160

Asp Lys Pro Arg Thr Phe Lys Glu Ile Cys Ser Val Ala Asn Gly Ala
                165                 170                 175

Ser Lys Lys Asp Ile Gly Arg Ala Thr Lys Phe Ile Val Lys Gln Leu
            180                 185                 190

Glu Glu Asp Met Gly Ile Ser Met Glu Met Gly Thr Ile His Ala Gly
        195                 200                 205

Asp Phe Leu Arg Arg Phe Cys Ser His Leu Asn Met Glu Asn Asn Glu
    210                 215                 220

Val Arg Ala Ala Thr Glu Thr Val Lys Lys Ser Glu Met Leu Asp Ile
225                 230                 235                 240

Arg Lys Ser Pro Ile Ser Val Ala Ala Ala Ile Tyr Met Ile Ser
                245                 250                 255

Gln Leu Asn Glu Lys Asp Lys Lys Ala Leu Lys Asp Ile Ser Arg Val
            260                 265                 270

Ala Gly Val Ala Glu Val Thr Ile Arg Asn Ser Tyr Lys Asp Leu Tyr
        275                 280                 285

Pro His Ala Ala Lys Leu Ile Pro Asp Trp Phe Leu Lys Glu Val Asp
    290                 295                 300

Leu Lys Asn Leu Pro Ala Pro
305                 310

<210> SEQ ID NO 7
<211> LENGTH: 2417
<212> TYPE: DNA
<213> ORGANISM: Physcomitrella patens

<400> SEQUENCE: 7
gagctgctgt cagttcgtca acggattgat gcggagtctt gaatcggagt cgagttggcg    60
gtgactgaaa agaattatcg ctcaagaaac gatcgactgt tcgggttcga cttgtgattt   120
gcttactgta gtcgggttga caacgcttcg acgcgttcac gttctgtgtg ttattgatat   180
tcctgagacg actttctgga tgtgtgtggg gaggctggac tggttagttc gatttcggtg   240
ctcgaggttt cattaatgaa aattataccct taggaatatg aaacaatcgt tataggtatc   300
tcttttcttc gacaagggat tgattcatcg cttgcaagca gccgctggta acatcactgc   360
gtcagttatc tctgaagttt acatagtttc tttagatttt actagagggt ggagaatttt   420
ctcaacagag atcaaggggt agaagactta taatatcgaa gggtttgctg catgaaaagt   480
cttatttcac ttgcgaagct tccgtccagc tagcgtgagt ttggatcgtt cgtaattttt   540
cctatgtgtt gctcaatcgg aagggcgcca gcaaagtgga gcgagcacgg gttaggatta   600
gtattccact caggaaagtg caactcaggg aagggtagag agaaacagga acttgcttat   660
aacgaaaagt tagacttaga gttcctccac atttcccgac aatctatttt tctttagaat   720
```

```
atgaatcgca tatcttccgt tgacgacatc ctgagcgcat actggaacga gtcgtctatg      780
acttctcctg tgaagggcag catgaaccgc agtgcttctg agttcgcttt tcaagaattt      840
attaaggaga acatgactgc cacatcttgc ttcggaggcc gctccaagag ccgcttctat      900
caatcgcagg cggatgaggg gaaagctctt aacgatcaaa gtcgtgacaa tcttatgatc      960
tcggcaaaat ctgaatcaga gttcactcct ccgatgttcg caagcaccga ggagctgcgt     1020
gcgatgaata acgtcgtgga ccctgttgaa gtcgacgata ttgtggggat tgaggggggcg     1080
ctgaacccccc tcttctcccg tgtccaaaat gatgcggata aaaatattc caatttcccc     1140
tctgctgcgt tatctgcggg tgactgtggt ggtcaagact atgaggacat ccttaagcag     1200
aagttggaaa gggcgtgcgc tgcagcggct ctctctagac aggtgaatgg cgagggtgca     1260
ataattggac aatcggttgg agctatttgt cagaagagtt ttgctatcga atcatctgcc     1320
gctagtgctt gtccaagtgg agttcaatgc gcacccatga gcgctaagtc tccttctcca     1380
aaacctgaag tggatgcatc aaccgggaag gtcaaactta cgaccagtgg ttcggaactt     1440
tctgatgacg acgaacatga tttgttaaac caaagcctac caggcggtga ccttaagcgt     1500
gtgaagagaa tgttgtcaaa ccgtgaatct gcccgacgct cgcgcagaag gaaacaggca     1560
cacttgagtg atctagaaat gcaggttgcg caattgcgag ttgaaaatac tacgcttatg     1620
caaagattgc aagagattac ccacatgcat aaagatgcat ctgtcgacaa ccgaattcta     1680
aaggcagatg tggaggcgtt gcgtgctaag gtgaaaatgg ctgaagacat ggtggcccgt     1740
caaggacagc ccatgtcaaa tctcattccc gacccccagtt taagctttat gacaccgttc     1800
aatgtgaatg atatggaaag accatttctg caacagatga ggcacagttc catgctacgc     1860
catgatcagc aacagcagcc tgctagtggc attaggggta agatgggacg tgcaccttca     1920
atgcaacggg ttgccagcct ggagcatctg acgaagcgta tccgcaacgg gagttcctgc     1980
aacgtaccgg cttggggtgg ctgggacatg gacagacctg ccatggtaca ggaacacggc     2040
atctgatcaa tgtttccgcg ctgactatgt agtagaatcg atgtaactta catttactcc     2100
gcttatttca agcgagagcg agagttcagg gcaagtggaa gatccgagat tattatttat     2160
tttagacttg ggttgaaggg gaatagattt acgctaagaa gggacttcac cttagttttc     2220
agaagtggcg tagaattctt ctgataagta ggcatgaaaa ggatcatatt gttgttgctt     2280
cagaggaaga gaagattcat actttggagg gtgaacatag aacttgtttt ttggcagggt     2340
gcaaacgttg cttgtaatct cctagctgag attgatgttg ttgcttgtaa atagctactg     2400
ctgtcgtcct ggtcaac                                                   2417

<210> SEQ ID NO 8
<211> LENGTH: 1323
<212> TYPE: DNA
<213> ORGANISM: Physcomitrella patens

<400> SEQUENCE: 8
atgaatcgca tatcttccgt tgacgacatc ctgagcgcat actggaacga gtcgtctatg       60
acttctcctg tgaagggcag catgaaccgc agtgcttctg agttcgcttt tcaagaattt      120
attaaggaga acatgactgc cacatcttgc ttcggaggcc gctccaagag ccgcttctat      180
caatcgcagg cggatgaggg gaaagctctt aacgatcaaa gtcgtgacaa tcttatgatc      240
tcggcaaaat ctgaatcaga gttcactcct ccgatgttcg caagcaccga ggagctgcgt      300
gcgatgaata acgtcgtgga ccctgttgaa gtcgacgata ttgtggggat tgaggggggcg      360
ctgaacccccc tcttctcccg tgtccaaaat gatgcggata aaaatattc caatttcccc      420
```

```
tctgctgcgt tatctgcggg tgactgtggt ggtcaagact atgaggacat ccttaagcag    480
aagttggaaa gggcgtgcgc tgcagcggct ctctctagac aggtgaatgg cgagggtgca    540
ataattggac aatcggttgg agctatttgt cagaagagtt ttgctatcga atcatctgcc    600
gctagtgctt gtccaagtgg agttcaatgc cacccatga gcgctaagtc tccttctcca     660
aaacctgaag tggatgcatc aaccgggaag gtcaaactta cgaccagtgg ttcggaactt    720
tctgatgacg acgaacatga tttgttaaac caaagcctac caggcggtga ccttaagcgt    780
gtgaagagaa tgttgtcaaa ccgtgaatct gcccgacgct cgcgcagaag gaaacaggca    840
cacttgagtg atctagaaat gcaggttgcg caattgcgag ttgaaaatac tacgcttatg    900
caaagattgc aagagattac ccacatgcat aaagatgcat ctgtcgacaa ccgaattcta    960
aaggcagatg tggaggcgtt gcgtgctaag gtgaaaatgg ctgaagacat ggtggcccgt   1020
caaggacagc ccatgtcaaa tctcattccc gacccagtt taagctttat gacaccgttc    1080
aatgtgaatg atatggaaag accatttctg caacagatga ggcacagttc catgctacgc   1140
catgatcagc aacagcagcc tgctagtggc attaggggta agatgggacg tgcaccttca   1200
atgcaacggg ttgccagcct ggagcatctg acgaagcgta tccgcaacgg gagttcctgc   1260
aacgtaccgg cttggggtgg ctgggacatg acagacctgc catggtaca ggaacacggc    1320 atc                                                                 1323
```

<210> SEQ ID NO 9
<211> LENGTH: 441
<212> TYPE: PRT
<213> ORGANISM: Physcomitrella patens

<400> SEQUENCE: 9

```
Met Asn Arg Ile Ser Ser Val Asp Asp Ile Leu Ser Ala Tyr Trp Asn
 1               5                  10                  15

Glu Ser Ser Met Thr Ser Pro Val Lys Gly Ser Met Asn Arg Ser Ala
            20                  25                  30

Ser Glu Phe Ala Phe Gln Glu Phe Ile Lys Glu Asn Met Thr Ala Thr
        35                  40                  45

Ser Cys Phe Gly Gly Arg Ser Lys Ser Arg Phe Tyr Gln Ser Gln Ala
    50                  55                  60

Asp Glu Gly Lys Ala Leu Asn Asp Gln Ser Arg Asp Asn Leu Met Ile
65                  70                  75                  80

Ser Ala Lys Ser Glu Ser Glu Phe Thr Pro Pro Met Phe Ala Ser Thr
                85                  90                  95

Glu Glu Leu Arg Ala Met Asn Asn Val Val Asp Pro Val Glu Val Asp
            100                 105                 110

Asp Ile Val Gly Ile Glu Gly Ala Leu Asn Pro Leu Phe Ser Arg Val
        115                 120                 125

Gln Asn Asp Ala Asp Lys Lys Tyr Ser Asn Phe Pro Ser Ala Ala Leu
    130                 135                 140

Ser Ala Gly Asp Cys Gly Gly Gln Asp Tyr Glu Asp Ile Leu Lys Gln
145                 150                 155                 160

Lys Leu Glu Arg Ala Cys Ala Ala Ala Leu Ser Arg Gln Val Asn
                165                 170                 175

Gly Glu Gly Ala Ile Ile Gly Gln Ser Val Gly Ala Ile Cys Gln Lys
            180                 185                 190

Ser Phe Ala Ile Glu Ser Ser Ala Ala Ser Ala Cys Pro Ser Gly Val
        195                 200                 205
```

```
Gln Cys Ala Pro Met Ser Ala Lys Ser Pro Pro Lys Pro Glu Val
    210                 215                 220

Asp Ala Ser Thr Gly Lys Val Lys Leu Thr Thr Ser Gly Ser Glu Leu
225                 230                 235                 240

Ser Asp Asp Asp Glu His Asp Leu Leu Asn Gln Ser Leu Pro Gly Gly
                245                 250                 255

Asp Leu Lys Arg Val Lys Arg Met Leu Ser Asn Arg Glu Ser Ala Arg
            260                 265                 270

Arg Ser Arg Arg Arg Lys Gln Ala His Leu Ser Asp Leu Glu Met Gln
        275                 280                 285

Val Ala Gln Leu Arg Val Glu Asn Thr Thr Leu Met Gln Arg Leu Gln
    290                 295                 300

Glu Ile Thr His Met His Lys Asp Ala Ser Val Asp Asn Arg Ile Leu
305                 310                 315                 320

Lys Ala Asp Val Glu Ala Leu Arg Ala Lys Val Lys Met Ala Glu Asp
                325                 330                 335

Met Val Ala Arg Gln Gly Gln Pro Met Ser Asn Leu Ile Pro Asp Pro
            340                 345                 350

Ser Leu Ser Phe Met Thr Pro Phe Asn Val Asn Asp Met Glu Arg Pro
        355                 360                 365

Phe Leu Gln Gln Met Arg His Ser Ser Met Leu Arg His Asp Gln Gln
    370                 375                 380

Gln Gln Pro Ala Ser Gly Ile Arg Gly Lys Met Gly Arg Ala Pro Ser
385                 390                 395                 400

Met Gln Arg Val Ala Ser Leu Glu His Leu Thr Lys Arg Ile Arg Asn
                405                 410                 415

Gly Ser Ser Cys Asn Val Pro Ala Trp Gly Gly Trp Asp Met Asp Arg
            420                 425                 430

Pro Ala Met Val Gln Glu His Gly Ile
        435                 440

<210> SEQ ID NO 10
<211> LENGTH: 1818
<212> TYPE: DNA
<213> ORGANISM: Physcomitrella patens

<400> SEQUENCE: 10
ggcgtcgtct tcgatggaac cccgcgtcgg caacaagtat cgccttggcc ggaaaattgg      60
gagtggttcc tttggtgaga tctacctggg gaccaatctc gtgactcatg aggaggtcgg     120
catcaagctg gagagcatca aggccaagca tccacaattg ctttatgagt ccaagttgta     180
ccgtattctt caaggaggaa ctgggattcc caacatcaga tggtacggaa ttgaaggaga     240
ctataatgtg atggttcttg atcttctggg acccagtctt gaagatcttt caatttctg      300 cagccggaaa ttctctttga agacagttct catgcttgcc gaccagctga tcaatcgagt     360
ggagtatgtg catgccaaga gtttcctcca cagggacata aagcctgaca atttcttgat     420
ggggctaggc aggcgagcaa atcaggtcta tatgattgac tttggtcttg caaagaagta     480
tcgcgatccc actactcatc agcacattcc ttatagagag aacaaaaatc ttactggaac     540
cgctcgatat gcaagtatca acactcatct tggtattgaa caaagcagga gagatgatct     600
ggagtctctt ggatatgttc tcatgtattt cttgagaggc agcctgcctt ggcaaggaat     660
gaaagcagga accaagaagc agaagtatga aaaaatcagt gagaaaaaga tgtccacccc     720
tatagagttc ctttgtaaag cttacccgtc tgagtttgct tcatacttcc actactgtcg     780
```

```
gtctcttcgg ttcgatgaca aaccggacta tgcttacctg aagagaattt tccgagatct    840
cttcattcgt gagggttttc agtttgatta tgttttcgac tggacgattt tgaagtatca    900
gcaaacacat ttttctggtg gtcctctccg tccagcggct gcggcgggag gttcaagtgg    960
agcagcagca gcagcggcag caggaattgg tacagtccca agagacgccc agcgagcaat   1020
tgagcctact gatgttgccg ctcgaactcg aatggttggt gcgactcgct ctagtggatt   1080
aaatccactg gacgcgtcaa agcataagag tactagccca gatgaagccg cttctaagga   1140
catagccctt agcggtcttg cagaaccaga gcgcacgcat gcttcttcgt ttgtgcgggg   1200
gagctcatca tcaaggagag ctgttgttgg atgtgctagg ccagcagggt caacagaggc   1260
gggagatgga acgcgggtgt tggctggcaa aatgggcccc actagcctgc gcacatcagc   1320
aggaatgcag aggagctctc cggtggcatc tacggatccc aagcggacgg gacgagattc   1380
ttatgctgga aactccggaa gaaatcctag ttcctctcga aattcgaaag agtgagcaca   1440
ttggttgaac tgggtcctgc atcttgttcg aagagcatta caactgtatc tggccttggt   1500
atctgctgtg gtttaggaat ttggcccttgt acttgatttg aagaacaggt tcgtaagaaa   1560
ttgatcaaat ttcaatgtcg tgggcgtcca gttcaggata tggttggtgg cttgtgatgg   1620
atatattatc tgtttctatc tttgaaggtg ttgcccccag ccgtatagtt ttcatctttc   1680
atagcttgta gttggcaaag cccattgcca tctgtcaata ttcagagtgt ggttgaggga   1740
gctgtttagc cttctagata agagatctgg attgcgttct ggattgctgc acagaccttg   1800
aagatttgtg gctgttcg                                                  1818

<210> SEQ ID NO 11
<211> LENGTH: 1419
<212> TYPE: DNA
<213> ORGANISM: Physcomitrella patens

<400> SEQUENCE: 11
atggaacccc gcgtcggcaa caagtatcgc cttggccgga aaattgggag tggttccttt     60
ggtgagatct acctggggac caatctcgtg actcatgagg aggtcggcat caagctggag    120
agcatcaagg ccaagcatcc acaattgctt tatgagtcca agttgtaccg tattcttcaa    180
ggaggaactg ggattcccaa catcagatgg tacggaattg aaggagacta taatgtgatg    240
gttcttgatc ttctgggacc cagtcttgaa gatcttttca atttctgcag ccggaaattc    300
tctttgaaga cagttctcat gcttgccgac cagctgatca atcgagtgga gtatgtgcat    360
gccaagagtt tcctccacag ggacataaag cctgacaatt tcttgatggg gctaggcagg    420
cgagcaaatc aggtctatat gattgacttt ggtcttgcaa agaagtatcg cgatcccact    480
actcatcagc acattcctta tagagagaac aaaaatctta ctggaaccgc tcgatatgca    540
agtatcaaca ctcatcttgg tattgaacaa agcaggagag atgatctgga gtctcttgga    600
tatgttctca tgtatttctt gagaggcagc ctgccttggc aaggaatgaa agcaggaacc    660
aagaagcaga agtatgaaaa atcagtgagg aaaaagatgt ccaccccctat agagttcctt    720 tgtaaagctt acccgtctga gtttgcttca tacttccact actgtcggtc tcttcggttc    780
gatgacaaac cggactatgc ttacctgaag agaattttcc gagatctctt cattcgtgag    840
ggttttcagt ttgattatgt tttcgactgg acgattttga agtatcagca aacacatttt    900
tctggtggtc ctctccgtcc agcggctgcg gcggaggtt caagtggagc agcagcagca    960
gcggcagcag gaattggtac agtcccaaga gacgcccagc gagcaattga gcctactgat   1020
```

```
gttgccgctc gaactcgaat ggttggtgcg actcgctcta gtggattaaa tccactggac   1080
gcgtcaaagc ataagagtac tagcccagat gaagccgctt ctaaggacat agcccttagc   1140
ggtcttgcag aaccagagcg cacgcatgct tcttcgtttg tgcgggggag ctcatcatca   1200
aggagagctg ttgttggatg tgctaggcca gcagggtcaa cagaggcggg agatggaacg   1260
cgggtgttgg ctggcaaaat gggcccact  agcctgcgca catcagcagg aatgcagagg   1320
agctctccgg tggcatctac ggatcccaag cggacgggac gagattctta tgctggaaac   1380
tccggaagaa atcctagttc ctctcgaaat tcgaaagag                          1419
```

```
<210> SEQ ID NO 12
<211> LENGTH: 473
<212> TYPE: PRT
<213> ORGANISM: Physcomitrella patens

<400> SEQUENCE: 12

Met Glu Pro Arg Val Gly Asn Lys Tyr Arg Leu Gly Arg Lys Ile Gly
  1               5                  10                  15

Ser Gly Ser Phe Gly Glu Ile Tyr Leu Gly Thr Asn Leu Val Thr His
             20                  25                  30

Glu Glu Val Gly Ile Lys Leu Glu Ser Ile Lys Ala Lys His Pro Gln
         35                  40                  45

Leu Leu Tyr Glu Ser Lys Leu Tyr Arg Ile Leu Gln Gly Gly Thr Gly
     50                  55                  60

Ile Pro Asn Ile Arg Trp Tyr Gly Ile Glu Gly Asp Tyr Asn Val Met
 65                  70                  75                  80

Val Leu Asp Leu Leu Gly Pro Ser Leu Glu Asp Leu Phe Asn Phe Cys
                 85                  90                  95

Ser Arg Lys Phe Ser Leu Lys Thr Val Leu Met Leu Ala Asp Gln Leu
            100                 105                 110

Ile Asn Arg Val Glu Tyr Val His Ala Lys Ser Phe Leu His Arg Asp
        115                 120                 125

Ile Lys Pro Asp Asn Phe Leu Met Gly Leu Gly Arg Arg Ala Asn Gln
    130                 135                 140

Val Tyr Met Ile Asp Phe Gly Leu Ala Lys Lys Tyr Arg Asp Pro Thr
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Leu Arg
        195                 200                 205

Gly Ser Leu Pro Trp Gln Gly Met Lys Ala Gly Thr Lys Lys Gln Lys
    210                 215                 220

Tyr Glu Lys Ile Ser Glu Lys Lys Met Ser Thr Pro Ile Glu Phe Leu
225                 230                 235                 240

Cys Lys Ala Tyr Pro Ser Glu Phe Ala Ser Tyr Phe His Tyr Cys Arg
                245                 250                 255

Ser Leu Arg Phe Asp Asp Lys Pro Asp Tyr Ala Tyr Leu Lys Arg Ile
            260                 265                 270

Phe Arg Asp Leu Phe Ile Arg Glu Gly Phe Gln Phe Asp Tyr Val Phe
        275                 280                 285

Asp Trp Thr Ile Leu Lys Tyr Gln Gln Thr His Phe Ser Gly Gly Pro
    290                 295                 300
```

```
Leu Arg Pro Ala Ala Ala Gly Gly Ser Ser Gly Ala Ala Ala
305                 310                 315                 320

Ala Ala Ala Gly Ile Gly Thr Val Pro Arg Asp Ala Gln Arg Ala Ile
                325                 330                 335

Glu Pro Thr Asp Val Ala Ala Arg Thr Arg Met Val Gly Ala Thr Arg
            340                 345                 350

Ser Ser Gly Leu Asn Pro Leu Asp Ala Ser Lys His Lys Ser Thr Ser
        355                 360                 365

Pro Asp Glu Ala Ala Ser Lys Asp Ile Ala Leu Ser Gly Leu Ala Glu
    370                 375                 380

Pro Glu Arg Thr His Ala Ser Ser Phe Val Arg Gly Ser Ser Ser Ser
385                 390                 395                 400

Arg Arg Ala Val Val Gly Cys Ala Arg Pro Ala Gly Ser Thr Glu Ala
                405                 410                 415

Gly Asp Gly Thr Arg Val Leu Ala Gly Lys Met Gly Pro Thr Ser Leu
            420                 425                 430

Arg Thr Ser Ala Gly Met Gln Arg Ser Ser Pro Val Ala Ser Thr Asp
        435                 440                 445

Pro Lys Arg Thr Gly Arg Asp Ser Tyr Ala Gly Asn Ser Gly Arg Asn
    450                 455                 460

Pro Ser Ser Ser Arg Asn Ser Lys Glu
465                 470
```

<210> SEQ ID NO 13
<211> LENGTH: 1274
<212> TYPE: DNA
<213> ORGANISM: Physcomitrella patens

<400> SEQUENCE: 13

```
agcacgaggg caagagggga tagagacttg aaaggaaagg ggagggaagg gtgtaaggag     60
gcccacgggc agggtcaagg tgtccaatgc acctgcaaga tcaggaagct tgaagtagat    120
cagggaaaaa acgatggtag tccctagttt acccgccttc ggaggacaga acgccatgct    180
cagacgcaac attgacaaca acaccgacac tctgatttct ctgcttcaag ggtcctgctc    240
ccctcgcgtg agcatgcaac aagtgccgcg ttcatcggag agtctcgaaa acatgatggg    300
ggcttgtggg caaaaactgc cttactttt c gtcatttgat gggccgagtg tagaagagca    360
agaggatgtc gacgaaggta tcgacgaatt cgcacaccac gtggagaaaa agaggagatt    420
gtcattagaa caagtgcgat cattagaacg gaattttgaa gtggaaaaca gcttgagcc     480
cgagaggaaa atgcaactag ctaaggagct tggactgcga cctcgtcaag tggcggtgtg    540
gttccagaat agacgggcaa ggtggaaaac caaacagctc gagcacgact acgagaccct    600
gaagaaagcc tacgacaggc ttaaagcaga cttcgaagcc gttactctag acacaaatgc    660
tcttaaagct gaggtgagtc gcctcaaggg aatctctaat gacgacgtca agcccgccga    720
attcgttcag ggcaagtgtg acacaacgag tcaccctgcc tcccctgcgc aatcggagag    780
gtccgacatt gtgtcatcga ggaatcgcac aactcctacc atacatgtgg atcccgtggc    840
acccgaggaa gccggcgctc acttaaccat gagctcggat agcaattcca gcgaggtcat    900
ggacgctgat agccctcgca cgagccacac cagcgctagt aggagcactt tgtccacaag    960
tgtggtgcag cctgacgagg gcctgggagt ggcccagtac ccccactttt ctcccgaaaa   1020
cttcgtgggt cccaatatgc cagagatttg cgctgatcag tcacttgcat ctcaagtgaa   1080
gctggaagag atccacagct tcaatcccga ccaaaccttc ctgctcttgc ccaactggtg   1140
```

```
ggattgggct tgattcgttt cttcatctgt acccatacac ttttccttg aatccaagtt   1200 gaattcactt taggcagtgt ttttcacga tgtaccactt gttattcttc caccatgtgc   1260
aatccaacgt caac                                                    1274
```

<210> SEQ ID NO 14
<211> LENGTH: 1017
<212> TYPE: DNA
<213> ORGANISM: Physcomitrella patens

<400> SEQUENCE: 14

```
atggtagtcc ctagtttacc cgccttcgga ggacagaacg ccatgctcag acgcaacatt    60
gacaacaaca ccgacactct gatttctctg cttcaagggt cctgctcccc tcgcgtgagc   120
atgcaacaag tgccgcgttc atcggagagt ctcgaaaaca tgatggggc ttgtgggcaa    180 aaactgcctt acttttcgtc atttgatggg ccgagtgtag aagagcaaga ggatgtcgac   240
gaaggtatcg acgaattcgc acaccacgtg agaaaaaga ggagattgtc attagaacaa    300
gtgcgatcat tagaacggaa ttttgaagtg aaaacaagc ttgagcccga ggaaaatg     360 caactagcta aggagcttgg actgcgacct cgtcaagtgg cggtgtggtt ccagaataga   420
cgggcaaggt ggaaaaccaa acagctcgag cacgactacg agaccctgaa gaaagcctac   480
gacaggctta agcagacttc gaagccgtt actctagaca caaatgctct taaagctgag   540
gtgagtcgcc tcaagggaat tctaatgac gacgtcaagc ccgccgaatt cgttcagggc    600
aagtgtgaca acgagtca ccctgcctcc cctgcgcaat cggagaggtc cgacattgtg    660
tcatcgagga atcgcacaac tcctaccata catgtggatc ccgtggcacc cgaggaagcc   720
ggcgctcact taaccatgag ctcggatagc aattccagcg aggtcatgga cgctgatagc   780
cctcgcacga gccacaccag cgctagtagg agcactttgt ccacaagtgt ggtgcagcct   840
gacgagggcc tggagtggcc ccagtacccc cactttctc ccgaaaactt cgtgggtccc    900
aatatgccag agatttgcgc tgatcagtca cttgcatctc aagtgaagct ggaagagatc   960
cacagcttca atcccgacca aaccttcctg ctcttgccca actggtggga ttgggct    1017
```

<210> SEQ ID NO 15
<211> LENGTH: 339
<212> TYPE: PRT
<213> ORGANISM: Physcomitrella patens

<400> SEQUENCE: 15

```
Met Val Val Pro Ser Leu Pro Ala Phe Gly Gly Gln Asn Ala Met Leu
  1               5                  10                  15

Arg Arg Asn Ile Asp Asn Asn Thr Asp Thr Leu Ile Ser Leu Leu Gln
             20                  25                  30

Gly Ser Cys Ser Pro Arg Val Ser Met Gln Gln Val Pro Arg Ser Ser
         35                  40                  45

Glu Ser Leu Glu Asn Met Met Gly Ala Cys Gly Gln Lys Leu Pro Tyr
     50                  55                  60

Phe Ser Ser Phe Asp Gly Pro Ser Val Glu Glu Gln Glu Asp Val Asp
 65                  70                  75                  80

Glu Gly Ile Asp Glu Phe Ala His His Val Glu Lys Lys Arg Arg Leu
                 85                  90                  95

Ser Leu Glu Gln Val Arg Ser Leu Glu Arg Asn Phe Glu Val Glu Asn
            100                 105                 110

Lys Leu Glu Pro Glu Arg Lys Met Gln Leu Ala Lys Glu Leu Gly Leu
```

```
                115                 120                 125
Arg Pro Arg Gln Val Ala Val Trp Phe Gln Asn Arg Ala Arg Trp
    130                 135                 140

Lys Thr Lys Gln Leu Glu His Asp Tyr Glu Thr Leu Lys Lys Ala Tyr
145                 150                 155                 160

Asp Arg Leu Lys Ala Asp Phe Glu Ala Val Thr Leu Asp Thr Asn Ala
                165                 170                 175

Leu Lys Ala Glu Val Ser Arg Leu Lys Gly Ile Ser Asn Asp Val
            180                 185                 190

Lys Pro Ala Glu Phe Val Gln Gly Lys Cys Asp Thr Thr Ser His Pro
        195                 200                 205

Ala Ser Pro Ala Gln Ser Glu Arg Ser Asp Ile Val Ser Ser Arg Asn
    210                 215                 220

Arg Thr Thr Pro Thr Ile His Val Asp Pro Val Ala Pro Glu Glu Ala
225                 230                 235                 240

Gly Ala His Leu Thr Met Ser Ser Asp Ser Asn Ser Ser Glu Val Met
                245                 250                 255

Asp Ala Asp Ser Pro Arg Thr Ser His Thr Ser Ala Ser Arg Ser Thr
            260                 265                 270

Leu Ser Thr Ser Val Val Gln Pro Asp Glu Gly Leu Gly Val Ala Gln
        275                 280                 285

Tyr Pro His Phe Ser Pro Glu Asn Phe Val Gly Pro Asn Met Pro Glu
    290                 295                 300

Ile Cys Ala Asp Gln Ser Leu Ala Ser Gln Val Lys Leu Glu Glu Ile
305                 310                 315                 320

His Ser Phe Asn Pro Asp Gln Thr Phe Leu Leu Leu Pro Asn Trp Trp
                325                 330                 335

Asp Trp Ala

<210> SEQ ID NO 16
<211> LENGTH: 1626
<212> TYPE: DNA
<213> ORGANISM: Physcomitrella patens

<400> SEQUENCE: 16
ggccttcaag cactctctgc atgtgtgccc gtattgcctt gagtcaccct cggcgctctt    60
ttgaggctac acaactggaa ggcaataatt cgcagcgcag gcaacgccat ctatggcgcc   120
cgcggaacaa ctcaagacca gaagtgaatc tggtagtagt ggggtaagga gtacaacccc   180
tacagttatc gtcatcggcg ctggttttgg aggcctcgct gccgcccgat tctctacaa    240
ctcgaacgtg aaggttgtgg tgttggagtc tcgtgaacgg attgggggtc gtgtttacac   300
tgactattct tttggattcc ccgtcgatat gggggcttca tggttacatg gagtatgcaa   360
ggacaaccct ctcgcacctg ttatcggcaa gctacgattg cctttgtatc gaacatgtgg   420
cgataattca gttttgtatg accatgactt agagagctat gcgctatttg acatggatgg   480
tcaccaagtt ccacaatctc tggtcacgga ggtcggggag gtgttcgaga gtttattgga   540
agagacaaag aaactcaggg atgagcactc ggatgacatg tcagtaatga aggcgtttac   600
actagtcttg gagaaacggc cagatctgag gcaagagggg atggcattca agttctgca    660
gtggtatttg tgtcgcatgg aaggatggtt tgcagccgac gcagacaaca tctccgttca   720
aagttgggac gaggaggagt tgcttcaagg tgggcacggt tgatggtga  agggttatga    780
gcccgttatc agctcccttg ctgaaggtct tgatatcaga ttcaatcata gggttacgaa   840
```

-continued

```
gatcagtcgg cgcctgcatg gagtgcgagt gggcaccgaa gatgggaagg tattcgaagc      900
tgatgcttgt gttgtagcat tacctctggg agtgttgaaa gcaaatgtgg tgcggtttga      960
gccgagattg ccggagtgga aggaggcagc aattgctgat ttaggggtgg caacgagaa      1020
taagatcgcc ctgttctttg aggaagtgtg ctggccgaac gtagagttcc ttggagttgt     1080
tgccccgact tcgtacggtt gcagctactt tttgaacctt cacaaggcaa cagggcaccc     1140
tgtgttggta tacatgcctg caggacgtct tgccaatgat attgagcagc tgtcaaatga     1200
ggctgctgcc aacttcgcta tcaggcagtt gaaaagaata ttgccgaatg ctgcagagcc     1260
gatcaaatat ctggtgtcga ggtggggggac ggacccaaac tcgagggggt gctacagcta    1320
tgacgcagtg ggcaagcccc acgatctgta cgaacggcta cgcacaccag ttgacaattt     1380
gttctgggct ggggaagcca ccagcgagag gttccctgga actgtgcatg gtgcgtttca     1440
tacaggtgtg atggcaggaa gtgagtgtct gaaaagattt gctgaaaggt gccgggatct     1500
ggagatgttt cagcccgtga tggcgaaaga agacgaactg atcacgccat tgttgatttc     1560
tcggatgtga agaacgcaca agctacctac ttcgttgtgg gccgtgcggg tgggtcgtcc     1620
atgaga                                                                1626

<210> SEQ ID NO 17
<211> LENGTH: 1455
<212> TYPE: DNA
<213> ORGANISM: Physcomitrella patens

<400> SEQUENCE: 17
atggcgcccg cggaacaact caagaccaga agtgaatctg gtagtagtgg ggtaaggagt       60
acaacccta cagttatcgt catcggcgct ggtttttggag gcctcgctgc cgcccgattt      120
ctctacaact cgaacgtgaa ggttgtggtg ttggagtctc gtgaacggat tgggggtcgt      180
gtttacactg actattcttt tggattcccc gtcgatatgg gggcttcatg gttacatgga      240
gtatgcaagg acaaccctct cgcacctgtt atcggcaagc tacgattgcc tttgtatcga      300
acatgtggcg ataattcagt tttgtatgac catgacttag agagctatgc gctatttgac      360
atggatggtc accaagttcc acaatctctg gtcacggagg tcggggaggt gttcgagagt      420
ttattggaag agacaaagaa actcagggat gagcactcgg atgacatgtc agtaatgaag      480
gcgtttacac tagtcttgga gaacggcca gatctgaggc aagaggggat ggcattcaaa      540
gttctgcagt ggtatttgtg tcgcatggaa ggatggtttg cagccgacgc agacaacatc      600
tccgttcaaa gttgggacga ggaggagttg cttcaaggtg gcacggtttt gatggtgaag      660
ggttatgagc ccgttatcag ctcccttgct gaaggtcttg atatcagatt caatcatagg      720
gttacgaaga tcagtcggcg cctgcatgga gtgcgagtgg caccgaaga tgggaaggta      780
ttcgaagctg atgcttgtgt tgtagcatta cctctgggag tgttgaaagc aaatgtggtg      840
cggtttgagc cgagattgcc ggagtggaag gaggcagcaa ttgctgattt aggggtgggc      900
aacgagaata gatcgccct gttctttgag gaagtgtgct ggccgaacgt agagttcctt      960
ggagttgttg ccccgacttc gtacggttgc agctactttt tgaaccttca caaggcaaca     1020
gggcaccctg tgttggtata catgcctgca ggacgtcttg ccaatgatat tgagcagctg     1080
tcaaatgagg ctgctgccaa cttcgctatc aggcagttga aaagaatatt gccgaatgct     1140
gcagagccga tcaaatatct ggtgtcgagg tgggggacgg acccaaactc gaggggggtgc    1200
tacagctatg acgcagtggg caagccccac gatctgtacg aacggctacg cacaccagtt     1260
gacaatttgt tctgggctgg ggaagccacc agcgagaggt tccctggaac tgtgcatggt     1320
```

```
gcgtttcata caggtgtgat ggcaggaagt gagtgtctga aaagatttgc tgaaaggtgc   1380
cgggatctgg agatgtttca gcccgtgatg gcgaaagaag acgaactgat cacgccattg   1440
ttgatttctc ggatg                                                    1455
```

<210> SEQ ID NO 18
<211> LENGTH: 485
<212> TYPE: PRT
<213> ORGANISM: Physcomitrella patens

<400> SEQUENCE: 18

```
Met Ala Pro Ala Glu Gln Leu Lys Thr Arg Ser Glu Ser Gly Ser Ser
 1               5                  10                  15

Gly Val Arg Ser Thr Thr Pro Thr Val Ile Val Ile Gly Ala Gly Phe
            20                  25                  30

Gly Gly Leu Ala Ala Ala Arg Phe Leu Tyr Asn Ser Asn Val Lys Val
        35                  40                  45

Val Val Leu Glu Ser Arg Glu Arg Ile Gly Gly Arg Val Tyr Thr Asp
    50                  55                  60

Tyr Ser Phe Gly Phe Pro Val Asp Met Gly Ala Ser Trp Leu His Gly
65                  70                  75                  80

Val Cys Lys Asp Asn Pro Leu Ala Pro Val Ile Gly Lys Leu Arg Leu
                85                  90                  95

Pro Leu Tyr Arg Thr Cys Gly Asp Asn Ser Val Leu Tyr Asp His Asp
            100                 105                 110

Leu Glu Ser Tyr Ala Leu Phe Asp Met Asp Gly His Gln Val Pro Gln
        115                 120                 125

Ser Leu Val Thr Glu Val Gly Glu Val Phe Glu Ser Leu Leu Glu Glu
    130                 135                 140

Thr Lys Lys Leu Arg Asp Glu His Ser Asp Asp Met Ser Val Met Lys
145                 150                 155                 160

Ala Phe Thr Leu Val Leu Glu Lys Arg Pro Asp Leu Arg Gln Glu Gly
                165                 170                 175

Met Ala Phe Lys Val Leu Gln Trp Tyr Leu Cys Arg Met Glu Gly Trp
            180                 185                 190

Phe Ala Ala Asp Ala Asp Asn Ile Ser Val Gln Ser Trp Asp Glu Glu
        195                 200                 205

Glu Leu Leu Gln Gly Gly His Gly Leu Met Val Lys Gly Tyr Glu Pro
    210                 215                 220

Val Ile Ser Ser Leu Ala Glu Gly Leu Asp Ile Arg Phe Asn His Arg
225                 230                 235                 240

Val Thr Lys Ile Ser Arg Arg Leu His Gly Val Arg Val Gly Thr Glu
                245                 250                 255

Asp Gly Lys Val Phe Glu Ala Asp Ala Cys Val Val Ala Leu Pro Leu
            260                 265                 270

Gly Val Leu Lys Ala Asn Val Val Arg Phe Glu Pro Arg Leu Pro Glu
        275                 280                 285

Trp Lys Glu Ala Ala Ile Ala Asp Leu Gly Val Gly Asn Glu Asn Lys
    290                 295                 300

Ile Ala Leu Phe Phe Glu Glu Val Cys Trp Pro Asn Val Glu Phe Leu
305                 310                 315                 320

Gly Val Val Ala Pro Thr Ser Tyr Gly Cys Ser Tyr Phe Leu Asn Leu
                325                 330                 335

His Lys Ala Thr Gly His Pro Val Leu Val Tyr Met Pro Ala Gly Arg
```

-continued

```
                340                 345                 350
Leu Ala Asn Asp Ile Glu Gln Leu Ser Asn Glu Ala Ala Ala Asn Phe
            355                 360                 365
Ala Ile Arg Gln Leu Lys Arg Ile Leu Pro Asn Ala Ala Glu Pro Ile
        370                 375                 380
Lys Tyr Leu Val Ser Arg Trp Gly Thr Asp Pro Asn Ser Arg Gly Cys
385                 390                 395                 400
Tyr Ser Tyr Asp Ala Val Gly Lys Pro His Asp Leu Tyr Glu Arg Leu
                405                 410                 415
Arg Thr Pro Val Asp Asn Leu Phe Trp Ala Gly Glu Ala Thr Ser Glu
            420                 425                 430
Arg Phe Pro Gly Thr Val His Gly Ala Phe His Thr Gly Val Met Ala
        435                 440                 445
Gly Ser Glu Cys Leu Lys Arg Phe Ala Glu Arg Cys Arg Asp Leu Glu
    450                 455                 460
Met Phe Gln Pro Val Met Ala Lys Glu Asp Glu Leu Ile Thr Pro Leu
465                 470                 475                 480
Leu Ile Ser Arg Met
            485

<210> SEQ ID NO 19
<211> LENGTH: 2291
<212> TYPE: DNA
<213> ORGANISM: Physcomitrella patens

<400> SEQUENCE: 19
gttgcgttct ctgcttcctt cgaaggcctt cgcctcggcg atccctctcc ccgattccgt      60
ttgcccccga gtgcaattgc ggattcggat cccatgctcc cctcttgttg agccttcggt     120
ggaactttgc ggtgtgtgat ttggtgctcc gtgactctgg ccgaacgtgt ccacttattt     180
tcaatcaaaa tggcctccaa cggaaacgga aacgcgtcac atgatttcga atttgcgagc     240
tctcacgtcc ccaacggtct ttctaaaatc aacactaaac ctggagagcc agacatgtgc     300
aaagatgaca cttcgtcgac ggtaaaggtg tcaaaccttg aacagctgca cgcattgcag     360
aagaagaaag cgtctgctcc gactacgcca cgcaacgcta caaacccatc tacacccaag     420
aacttgactc ctcgtgccta cttatcagag gaagaacgtc agaagcagca gatgcagtct     480
gttagtgcat ccttggcttc tctgactcgt caaagcggtc ctcaagttat caagggcgaa     540
ccaggcagaa agaaatctcc tcccaagact gtgactgctc ccaggctgga cattagtgac     600
agcgctctga gttcacaca cgtcctctac aacctgtctc cttctgagtt gtacgagcaa     660
gctattaagt tcgagaaggg ctcattcatt acctcgagtg gagctcttgc tacactttct     720
ggagctaaga ctgggcgatc tcccaaggac aaacgtgtgg tgaaagaaga gacatccaag     780
gatgacttgt ggtggggaag gggttctcca aatatcgaaa tggacgagga gacattcttg     840
gtcaatcgtg agagggcagt tgactacctg aactcattgg agaaggtttt tgtaaatgac     900
cagttcctga actgggaccc tcagaaccga attaaagtcc ggatcatatc agcccgtgct     960
tatcattcgc tttttatgca caatatgtgc attcgcccta cacctgagga gctcgaagac    1020
tttggaactc ctgatttttac aatttacaat gccggacaat ttccttgcaa ccgttacacc    1080
cactacatgt cgtcgtcaac tagcatagat ctgaacctga acgcaaagag gatggtgatt    1140
ttggggacac aatatgccgg agagatgaag aagggacttt tcagtcttat gcactacttg    1200
atgcccaaaa gaggcatttt gtcgttgcat tctggttgca acatgggaaa ggaagggggat    1260
```

```
gtgacattat tttttggatt atcaggtact gggaagacga ctctgtcaac tgatcctaac    1320
cggcagctta ttggtgatga tgagcattgc tggagtgaca acggagtttc aaatattgag    1380
ggaggatgct atgcaaaatg catcgatctt tctaaagaaa aggagccgga atctggaat     1440 gcaatcaagt ttggaaccgt gctagaaaat gtggtctttg aggagcacta cagggaggtt    1500
gattacaccg ataaatctgt gaccgagaac acaagggccg catacccct tgagtacatt     1560 cccaacgtca ggttaccatg cgttggacct catccaaaga acatcatctt gctttcgtgt    1620
gatgcttttg gtgtcttacc acctgtgagc aaattgacac atgctcaaac catgtatcac    1680
ttcatcagtg gctacactgc cttggttgca ggaactgtgg agggcgtgaa agagcctacg    1740
gccacattct cagcatgctt tggagctgct ttcattatgc tgcaccccac taagtatgcc    1800
accatgttag cggagaagat gcagcgacat ggagctactg catggttggt caacaccggc    1860
tggtccggcg gcagctatgg tgtcggatca agaatgaaac tcgcatatac gaggaagatc    1920
attaatgcta ttcatgacgg gtcattgttg ggcgctaatt atgcgcaaac tccaattttc    1980
aacctggctg tgccaactgc ggtcaacggg gttccaagtg aaatcttgca gccacagaat    2040
gcgtggtcag acaagacgca atacgatgct actctgaaaa agctcgcagg tcttttttcag   2100 aagaattttg agatttatgc tgattaccaa gttggtggaa acagccagct acgcagcag    2160 attcttgcag ctgggcctgt tttacagtag agacgagacc gctgtatgtg tggaatgatt    2220
tggagatcag acggaagtct gtgaatcctc atgtagggga ttttctcca ccggcagagg    2280 tttggataca g                                                         2291

<210> SEQ ID NO 20
<211> LENGTH: 2052
<212> TYPE: DNA
<213> ORGANISM: Physcomitrella patens

<400> SEQUENCE: 20
gtgatttggt gctccgtgac tctggccgaa cgtgtccact tatttcaat caaaatggcc      60 tccaacggaa acggaaacgc gtcacatgat ttcgaatttg cgagctctca cgtccccaac    120
ggtctttcta aaatcaacac taaacctgga gagccagaca tgtgcaaaga tgacacttcg    180
tcgacggtaa aggtgtcaaa ccttgaacag ctgcacgcat tgcagaagaa gaaagcgtct    240
gctccgacta cgccacgcaa cgctacaaac ccatctacac ccaagaactt gactcctcgt    300
gcctacttat cagaggaaga acgtcagaag cagcagatgc agtctgttag tgcatccttg    360
gcttctctga ctcgtcaaag cggtcctcaa gttatcaagg gcgaaccagg cagaaagaaa    420
tctcctccca agactgtgac tgctcccagg ctggacatta gtgacagcgc tctgaagttc    480
acacacgtcc tctacaacct gtctccttct gagttgtacg agcaagctat taagttcgag    540
aagggctcat tcattacctc gagtggagct cttgctacac tttctggagc taagactggg    600
cgatctccca aggacaaacg tgtggtgaaa gaagagacat ccaaggatga cttgtggtgg    660
ggaaggggtt ctccaaatat cgaaatggac gaggagacat cttggtcaa tcgtgagagg    720 gcagttgact acctgaactc attggagaag gttttgtaa tgaccagtt cctgaactgg    780 gaccctcaga accgaattaa agtccggatc atatcagccc gtgcttatca ttcgcttttt    840
atgcacaata tgtgcattcg ccctacacct gaggagctcg aagactttgg aactcctgat    900
tttacaattt acaatgccgg acaatttcct tgcaaccgtt acacccacta catgtcgtcg    960
tcaactagca tagatctgaa cctgaaacgc aaagagatgg tgattttggg gacacaatat   1020
gccggagaga tgaagaaggg acttttcagt cttatgcact acttgatgcc caaaagaggc   1080
```

```
attttgtcgt tgcattctgg ttgcaacatg ggaaaggaag gggatgtgac attattttt    1140 ggattatcag gtactgggaa gacgactctg tcaactgatc ctaaccggca gcttattggt    1200
gatgatgagc attgctggag tgacaacgga gtttcaaata ttgagggagg atgctatgca    1260
aaatgcatcg atctttctaa agaaaaggag ccggaaatct ggaatgcaat caagtttgga    1320
accgtgctag aaaatgtggt ctttgaggag cactacaggg aggttgatta caccgataaa    1380
tctgtgaccg agaacacaag ggccgcatac cctattgagt acattcccaa cgtcaggtta    1440
ccatgcgttg gacctcatcc aaagaacatc atcttgcttt cgtgtgatgc ttttggtgtc    1500
ttaccacctg tgagcaaatt gacacatgct caaaccatgt atcacttcat cagtggctac    1560
actgccttgg ttgcaggaac tgtggagggc gtgaaagagc ctacggccac attctcagca    1620
tgctttggag ctgctttcat tatgctgcac cccactaagt atgccaccat gttagcggag    1680
aagatgcagc acatggagc tactgcatgg ttggtcaaca ccggctggtc cggcggcagc    1740
tatggtgtcg gatcaagaat gaaactcgca tatacgagga agatcattaa tgctattcat    1800
gacgggtcat tgtttgggcgc taattatgcg caaactccaa ttttcaacct ggctgtgcca    1860
actgcggtca acggggttcc aagtgaaatc ttgcagccac agaatgcgtg gtcagacaag    1920
acgcaatacg atgctactct gaaaaagctc gcaggtcttt ttcagaagaa ttttgagatt    1980
tatgctgatt accaagttgg tggaaacagc cagcttacgc agcagattct tgcagctggg    2040
cctgttttac ag                                                       2052
```

<210> SEQ ID NO 21
<211> LENGTH: 684
<212> TYPE: PRT
<213> ORGANISM: Physcomitrella patens

<400> SEQUENCE: 21

```
Val Ile Trp Cys Ser Val Thr Leu Ala Glu Arg Val His Leu Phe Ser
  1               5                  10                  15

Ile Lys Met Ala Ser Asn Gly Asn Gly Asn Ala Ser His Asp Phe Glu
             20                  25                  30

Phe Ala Ser Ser His Val Pro Asn Gly Leu Ser Lys Ile Asn Thr Lys
         35                  40                  45

Pro Gly Glu Pro Asp Met Cys Lys Asp Asp Thr Ser Ser Thr Val Lys
     50                  55                  60

Val Ser Asn Leu Glu Gln Leu His Ala Leu Gln Lys Lys Lys Ala Ser
 65                  70                  75                  80

Ala Pro Thr Thr Pro Arg Asn Ala Thr Asn Pro Ser Thr Pro Lys Asn
                 85                  90                  95

Leu Thr Pro Arg Ala Tyr Leu Ser Glu Glu Arg Gln Lys Gln Gln
            100                 105                 110

Met Gln Ser Val Ser Ala Ser Leu Ala Ser Leu Thr Arg Gln Ser Gly
        115                 120                 125

Pro Gln Val Ile Lys Gly Glu Pro Gly Arg Lys Lys Ser Pro Pro Lys
    130                 135                 140

Thr Val Thr Ala Pro Arg Leu Asp Ile Ser Asp Ser Ala Leu Lys Phe
145                 150                 155                 160

Thr His Val Leu Tyr Asn Leu Ser Pro Ser Glu Leu Tyr Glu Gln Ala
                165                 170                 175

Ile Lys Phe Glu Lys Gly Ser Phe Ile Thr Ser Ser Gly Ala Leu Ala
            180                 185                 190
```

-continued

```
Thr Leu Ser Gly Ala Lys Thr Gly Arg Ser Pro Lys Asp Lys Arg Val
            195                 200                 205

Val Lys Glu Glu Thr Ser Lys Asp Asp Leu Trp Trp Gly Arg Gly Ser
        210                 215                 220

Pro Asn Ile Glu Met Asp Glu Glu Thr Phe Leu Val Asn Arg Glu Arg
225                 230                 235                 240

Ala Val Asp Tyr Leu Asn Ser Leu Glu Lys Val Phe Val Asn Asp Gln
                245                 250                 255

Phe Leu Asn Trp Asp Pro Gln Asn Arg Ile Lys Val Arg Ile Ile Ser
            260                 265                 270

Ala Arg Ala Tyr His Ser Leu Phe Met His Asn Met Cys Ile Arg Pro
        275                 280                 285

Thr Pro Glu Glu Leu Glu Asp Phe Gly Thr Pro Asp Phe Thr Ile Tyr
    290                 295                 300

Asn Ala Gly Gln Phe Pro Cys Asn Arg Tyr Thr His Tyr Met Ser Ser
305                 310                 315                 320

Ser Thr Ser Ile Asp Leu Asn Leu Lys Arg Lys Glu Met Val Ile Leu
                325                 330                 335

Gly Thr Gln Tyr Ala Gly Glu Met Lys Lys Gly Leu Phe Ser Leu Met
            340                 345                 350

His Tyr Leu Met Pro Lys Arg Gly Ile Leu Ser Leu His Ser Gly Cys
        355                 360                 365

Asn Met Gly Lys Glu Gly Asp Val Thr Leu Phe Phe Gly Leu Ser Gly
    370                 375                 380

Thr Gly Lys Thr Thr Leu Ser Thr Asp Pro Asn Arg Gln Leu Ile Gly
385                 390                 395                 400

Asp Asp Glu His Cys Trp Ser Asp Asn Gly Val Ser Asn Ile Glu Gly
                405                 410                 415

Gly Cys Tyr Ala Lys Cys Ile Asp Leu Ser Lys Glu Lys Glu Pro Glu
            420                 425                 430

Ile Trp Asn Ala Ile Lys Phe Gly Thr Val Leu Glu Asn Val Val Phe
        435                 440                 445

Glu Glu His Tyr Arg Glu Val Asp Tyr Thr Asp Lys Ser Val Thr Glu
    450                 455                 460

Asn Thr Arg Ala Ala Tyr Pro Ile Glu Tyr Ile Pro Asn Val Arg Leu
465                 470                 475                 480

Pro Cys Val Gly Pro His Pro Lys Asn Ile Ile Leu Leu Ser Cys Asp
                485                 490                 495

Ala Phe Gly Val Leu Pro Pro Val Ser Lys Leu Thr His Ala Gln Thr
            500                 505                 510

Met Tyr His Phe Ile Ser Gly Tyr Thr Ala Leu Val Ala Gly Thr Val
        515                 520                 525

Glu Gly Val Lys Glu Pro Thr Ala Thr Phe Ser Ala Cys Phe Gly Ala
    530                 535                 540

Ala Phe Ile Met Leu His Pro Thr Lys Tyr Ala Thr Met Leu Ala Glu
545                 550                 555                 560

Lys Met Gln Arg His Gly Ala Thr Ala Trp Leu Val Asn Thr Gly Trp
                565                 570                 575

Ser Gly Gly Ser Tyr Gly Val Gly Ser Arg Met Lys Leu Ala Tyr Thr
            580                 585                 590

Arg Lys Ile Ile Asn Ala Ile His Asp Gly Ser Leu Leu Gly Ala Asn
        595                 600                 605

Tyr Ala Gln Thr Pro Ile Phe Asn Leu Ala Val Pro Thr Ala Val Asn
```

```
                610              615              620
Gly Val Pro Ser Glu Ile Leu Gln Pro Gln Asn Ala Trp Ser Asp Lys
625                  630                  635                  640

Thr Gln Tyr Asp Ala Thr Leu Lys Lys Leu Ala Gly Leu Phe Gln Lys
                645                  650                  655

Asn Phe Glu Ile Tyr Ala Asp Tyr Gln Val Gly Gly Asn Ser Gln Leu
            660                  665                  670

Thr Gln Gln Ile Leu Ala Ala Gly Pro Val Leu Gln
        675                  680

<210> SEQ ID NO 22
<211> LENGTH: 1962
<212> TYPE: DNA
<213> ORGANISM: Physcomitrella patens

<400> SEQUENCE: 22
ggcgaagggg aggtgtcgga ggggatttat tgtgccgtag ctgggtttgc aaaaatgtgt       60
tctattccgt tcggtcggaa gaagtccaag aagggggatt tggcgcagga tctgttgggg      120
gatgtgttct cgacttacag cgagaatggg aagctggacg ccgaggggtt gctgaagttc      180
ttgcagacag agcaagggga tagcaagtcc tctctagatg acgccaagca tttagtggag      240
ttgattcgga atgagagaca taagtcgaaa ttccctgggt tcatcgtcag ctcggacctg      300
tcgaagggtg atttttaaaaa ctatgtactg agcccggatt tgaatggggt tcttgaaagc      360
actgtgcatc aagacatgac gcagccgtta tcgcactact tcatattcac tggtcacaac      420
tcgtacttga cgggtaaccca gcttagcagc gacagtagcg acgttcccat tgctgctgca      480
ctgcaacgtg gcgtgcgggt ggtggaactg gatttgtggc ctgacgataa aggcggcatc      540
aaggtcactc acgggaacac actcaccagt ccagttgctt tcgagaagtg cataaaagcc      600
atcaaggcca acgcgttcgt ctcctcgaaa tatcctgtag ttatcactct tgaggatcat      660 cttttcaagtc ctttacaggc ccttgctgca gagactttga cgaacatttt gggagaggac      720
ttgtactatc caccctcatc cgatgggttt aaagaactgc cttctccgga atcattgaaa      780
gggaaaattc taatatctac caaaccgccg aaagaatacc ttgaagccgc tgtcgcacag      840
aagtcggcgt tgaaagatga aaagattttg aatgagttca agaaggcaga taagttgcag      900
gagcagtcaa ctgctcctgt taaaagcccc gttgagaaaa agattgcagt tccaccatca      960
gagaagacaa aatccatttc gaagagaag gacttgagtg aaaaagttgg aaatttacgt     1020
gttgattcag agggtgaatc agctgatcct gcccctgcaa gttcccccga cggtaagaaa     1080
gcaacattga cagcggatag tgaaagtgac gatgacgaca ataagaagaa tcctgagtat     1140
gctcggctta tcactatcca ccaatcgaag ccttcgaaag gaactaccgt ggaagacaga     1200
ctgaaagttg aagggacagt ggtacggatt agtctttcag agactaagct ggagaaggtc     1260
actgaagagt ttcctgaact tgtggtcaag ttcacgcaga ggaacattct acgtgtgtat     1320
cctgctggta accgagtaaa ctcgtccaac tatgatccta ctgcggcttg gattcacgga     1380
gctcaaatgg tggctcaaaa tatgcaaggt tatggcaaag agctctggca agccacggc     1440 aagttcaggg gaaatggtgg ctgtggatac atccttaagc caaagtatct attggaagat     1500
ttgcccaatg gtaaaccttt taaccccttca gctcctggag atacgaagat gatcttgaag     1560
gtaaaggtaa tgacaaccat gggatgggac aaaagcgttcc ccaaatacca tttcgacctt     1620
ttctcgcctc cagatttctt cactaggctg cttgtgactg gagtgcctgc cgatgtggca     1680
aagtggaaaa cttccgttat agatgacgtt tgggaacccc actggaacga ggatcacgag     1740
```

| | |
|---|---:|
| ttttaccttta aatgccctga acttgcactg ctccgaattg aagttagaga tcacgacgag | 1800 |
| gaaagtcaag atgagttcga agggcaggcg tgccttccaa tgcatgaaat taaagacggc | 1860 |
| tatcgatgcg tgcagatgta tgacaaaaag ggcagtgtgt tgaagggcgt gaaaatgttg | 1920 |
| ttccattttc aaaaacgttc gttttctccg gtccagtaat tc | 1962 |

<210> SEQ ID NO 23
<211> LENGTH: 1944
<212> TYPE: DNA
<213> ORGANISM: Physcomitrella patens

<400> SEQUENCE: 23

| | |
|---|---:|
| gtgtcggagg ggatttattg tgccgtagct gggtttgcaa aaatgtgttc tattccgttc | 60 |
| ggtcggaaga agtccaagaa gggggatttg gcgcaggatc tgttggggga tgtgttctcg | 120 |
| acttacagcg agaatgggaa gctggacgcc gaggggttgc tgaagttctt gcagacagag | 180 |
| caagggggata gcaagtcctc tctagatgac gccaagcatt tagtggagtt gattcggaat | 240 |
| gagagacata agtcgaaatt ccctgggttc atcgtcagct cggacctgtc gaagggtgat | 300 |
| tttaaaaact atgtactgag cccggatttg aatgggggttc ttgaaagcac tgtgcatcaa | 360 |
| gacatgacgc agccgttatc gcactacttc atattcactg gtcacaactc gtacttgacg | 420 |
| ggtaaccagc ttagcagcga cagtagcgac gttcccattg ctgctgcact gcaacgtggc | 480 |
| gtgcgggtgg tggaactgga tttgtggcct gacgataaag gcggcatcaa ggtcactcac | 540 |
| gggaacacac tcaccagtcc agttgctttc gagaagtgca taaaagccat caaggccaac | 600 |
| gcgttcgtct cctcgaaata tcctgtagtt atcactcttg aggatcatct ttcaagtcct | 660 |
| ttacaggccc ttgctgcaga gactttgacg aacattttgg gagaggactt gtactatcca | 720 |
| ccctcatccg atgggtttaa agaactgcct tctccggaat cattgaaagg gaaaattcta | 780 |
| atatctacca aaccgccgaa agaataccctt gaagccgctg tcgcacagaa gtcggcgttg | 840 |
| aaagatgaaa agattttgaa tgagttcaag aaggcagata agttgcagga gcagtcaact | 900 |
| gctcctgtta aaagccccgt tgagaaaaag attgcagttc caccatcaga gaagacaaaa | 960 |
| tccatttccg aagagaagga cttgagtgaa aaagttggaa atttacgtgt tgattcagag | 1020 |
| ggtgaatcag ctgatcctgc ccctgcaagt tcccccgacg gtaagaaagc aacattgaca | 1080 |
| gcggatagtg aaagtgacga tgacgacaat aagaagaatc ctgagtatgc tcggcttatc | 1140 |
| actatccacc aatcgaagcc ttcgaaagga actaccgtgg aagacagact gaaagttgaa | 1200 |
| gggacagtgg tacggattag tcttttcagag actaagctgg agaaggtcac tgaagagttt | 1260 |
| cctgaacttg tggtcaagtt cacgcagagg aacattctac gtgtgtatcc tgctggtaac | 1320 |
| cgagtaaaact cgtccaacta tgatcctact gcggcttgga ttcacggagc tcaaatggtg | 1380 |
| gctcaaaata tgcaaggtta tggcaaagag ctctggcaag cccacggcaa gttcagggga | 1440 |
| aatggtggct gtggatacat ccttaagcca agtatctat tggaagattt gcccaatggt | 1500 |
| aaacctttta acccttcagc tcctggagat acgaagatga tcttgaaggt aaaggtaatg | 1560 |
| acaaccatgg gatgggacaa agcgttcccc aaataccatt tcgacctttt ctcgcctcca | 1620 |
| gatttcttca ctaggctgct tgtgactgga gtgcctgccg atgtggcaaa gtggaaaact | 1680 |
| tccgttatag atgacgtttg ggaaccccac tggaacgagg atcacgagtt ttaccttaaa | 1740 |
| tgccctgaac ttgcactgct ccgaattgaa gttagagatc acgacgagga aagtcaagat | 1800 |
| gagttcgaag gcaggcgtg ccttccaatg catgaaatta aagacggcta tcgatgcgtg | 1860 |

-continued

```
cagatgtatg acaaaaaggg cagtgtgttg aagggcgtga aaatgttgtt ccattttcaa    1920
aaacgttcgt tttctccggt ccag                                           1944
```

<210> SEQ ID NO 24
<211> LENGTH: 648
<212> TYPE: PRT
<213> ORGANISM: Physcomitrella patens

<400> SEQUENCE: 24

```
Val Ser Glu Gly Ile Tyr Cys Ala Val Ala Gly Phe Ala Lys Met Cys
 1               5                  10                  15

Ser Ile Pro Phe Gly Arg Lys Lys Ser Lys Lys Gly Asp Leu Ala Gln
            20                  25                  30

Asp Leu Leu Gly Asp Val Phe Ser Thr Tyr Ser Glu Asn Gly Lys Leu
        35                  40                  45

Asp Ala Glu Gly Leu Leu Lys Phe Leu Gln Thr Glu Gln Gly Asp Ser
    50                  55                  60

Lys Ser Ser Leu Asp Asp Ala Lys His Leu Val Glu Leu Ile Arg Asn
65                  70                  75                  80

Glu Arg His Lys Ser Lys Phe Pro Gly Phe Ile Val Ser Ser Asp Leu
                85                  90                  95

Ser Lys Gly Asp Phe Lys Asn Tyr Val Leu Ser Pro Asp Leu Asn Gly
            100                 105                 110

Val Leu Glu Ser Thr Val His Gln Asp Met Thr Gln Pro Leu Ser His
        115                 120                 125

Tyr Phe Ile Phe Thr Gly His Asn Ser Tyr Leu Thr Gly Asn Gln Leu
    130                 135                 140

Ser Ser Asp Ser Ser Asp Val Pro Ile Ala Ala Leu Gln Arg Gly
145                 150                 155                 160

Val Arg Val Val Glu Leu Asp Leu Trp Pro Asp Asp Lys Gly Gly Ile
                165                 170                 175

Lys Val Thr His Gly Asn Thr Leu Thr Ser Pro Val Ala Phe Glu Lys
            180                 185                 190

Cys Ile Lys Ala Ile Lys Ala Asn Ala Phe Val Ser Ser Lys Tyr Pro
        195                 200                 205

Val Val Ile Thr Leu Glu Asp His Leu Ser Ser Pro Leu Gln Ala Leu
    210                 215                 220

Ala Ala Glu Thr Leu Thr Asn Ile Leu Gly Glu Asp Leu Tyr Tyr Pro
225                 230                 235                 240

Pro Ser Ser Asp Gly Phe Lys Glu Leu Pro Ser Pro Glu Ser Leu Lys
                245                 250                 255

Gly Lys Ile Leu Ile Ser Thr Lys Pro Pro Lys Glu Tyr Leu Glu Ala
            260                 265                 270

Ala Val Ala Gln Lys Ser Ala Leu Lys Asp Glu Lys Ile Leu Asn Glu
        275                 280                 285

Phe Lys Lys Ala Asp Lys Leu Gln Glu Gln Ser Thr Ala Pro Val Lys
    290                 295                 300

Ser Pro Val Glu Lys Lys Ile Ala Val Pro Ser Glu Lys Thr Lys
305                 310                 315                 320

Ser Ile Ser Glu Glu Lys Asp Leu Ser Glu Lys Val Gly Asn Leu Arg
                325                 330                 335

Val Asp Ser Glu Gly Glu Ser Ala Asp Pro Ala Pro Ala Ser Ser Pro
            340                 345                 350

Asp Gly Lys Lys Ala Thr Leu Thr Ala Asp Ser Glu Ser Asp Asp Asp
```

```
                355                 360                 365
Asp Asn Lys Lys Asn Pro Glu Tyr Ala Arg Leu Ile Thr Ile His Gln
    370                 375                 380

Ser Lys Pro Ser Lys Gly Thr Thr Val Glu Asp Arg Leu Lys Val Glu
385                 390                 395                 400

Gly Thr Val Val Arg Ile Ser Leu Ser Glu Thr Lys Leu Glu Lys Val
                405                 410                 415

Thr Glu Glu Phe Pro Glu Leu Val Lys Phe Thr Gln Arg Asn Ile
            420                 425                 430

Leu Arg Val Tyr Pro Ala Gly Asn Arg Val Asn Ser Ser Asn Tyr Asp
                435                 440                 445

Pro Thr Ala Ala Trp Ile His Gly Ala Gln Met Val Ala Gln Asn Met
    450                 455                 460

Gln Gly Tyr Gly Lys Glu Leu Trp Gln Ala His Gly Lys Phe Arg Gly
465                 470                 475                 480

Asn Gly Gly Cys Gly Tyr Ile Leu Lys Pro Lys Tyr Leu Leu Glu Asp
                485                 490                 495

Leu Pro Asn Gly Lys Pro Phe Asn Pro Ser Ala Pro Gly Asp Thr Lys
            500                 505                 510

Met Ile Leu Lys Val Lys Val Met Thr Thr Met Gly Trp Asp Lys Ala
    515                 520                 525

Phe Pro Lys Tyr His Phe Asp Leu Phe Ser Pro Pro Asp Phe Phe Thr
    530                 535                 540

Arg Leu Leu Val Thr Gly Val Pro Ala Asp Val Ala Lys Trp Lys Thr
545                 550                 555                 560

Ser Val Ile Asp Asp Val Trp Glu Pro His Trp Asn Glu Asp His Glu
                565                 570                 575

Phe Tyr Leu Lys Cys Pro Glu Leu Ala Leu Leu Arg Ile Glu Val Arg
            580                 585                 590

Asp His Asp Glu Glu Ser Gln Asp Glu Phe Glu Gly Gln Ala Cys Leu
                595                 600                 605

Pro Met His Glu Ile Lys Asp Gly Tyr Arg Cys Val Gln Met Tyr Asp
    610                 615                 620

Lys Lys Gly Ser Val Leu Lys Gly Val Lys Met Leu Phe His Phe Gln
625                 630                 635                 640

Lys Arg Ser Phe Ser Pro Val Gln
                645

<210> SEQ ID NO 25
<211> LENGTH: 2321
<212> TYPE: DNA
<213> ORGANISM: Physcomitrella patens

<400> SEQUENCE: 25
ctgagtgagg aactgggagc gatggaagcg tgcaattgcg tagagccgca atggcctcca    60
gacgatcttc tcatgcggta ccagtacata tcgaattttt tcatcgcgtt ggcatatttc   120
tctattccgc tggagcttat ttactttgtg aagaagtcgt ctattttccc atatcgatgg   180
gttcttgttc agtttggagc cttcattgtg ctgtgcggag caacgcatct aatatccttg   240
tggacgttca gtagccgttc tcgaacagtg gccgtcgttc ttacaatagc gaaggttctt   300
actgctgttg tgtcgtgtgc cacagcactc atgcttgtgc acattattcc agacctcctt   360
agtgtaaaga cccgagaatt gttcttgaag aagaaggctg cagaacttga tcgtgaaatg   420
ggattgatac gtacacagga ggaaacaggt cgtcacgtta ggatgctcac tcatgaaata   480
```

```
cgaagtaccc tagatcgaca tacaattttg aataccaccc tcatagaact cggaaaaacg    540
ctttcgcttg aggagtgtac tttatggatg ccaagcccag atggtcaaga gctacaactc    600
aaaaatgctc ttcgagctga atctcttcat gttacagtcc ccatacatca cccaactatc    660
aagcaagtgt ttagtactcc ccgggcagtg gtgatatctc ctaacagccc agtttgtgtt    720
actcgaattc gtggagcgaa gtacatgact ggggaggtcg tggcaattcg agtcccactt    780
ctgcatctca caaacttcca cttcagtgat tggcctgatg ccggaacacg tccttttgca    840
ttgatggtgc tgatgttgcc tttaaacagt gcacgaaggt ggcacgttca tgaattggag    900
ctagtggaag ttgtggctga tcaggtggct gtggctctat cacacgcaac aattctggag    960
gaatcaatgc ctgctcgaga tcttttgatg aacaaaacg tagcattgga acatgctaga   1020
caggaggcag agacagctat tcgagcccgc aacgactttc tggctgtgat gaatcatgag   1080
atgcgcacgc ccatgcatgc tatcattgct ctttcttctt tattacaaga aacggagtta   1140 accccctgagc agcggtctat ggtggaaact gttttgaaaa gcagtaacct tttggccaca   1200
ttgataaatg acgtgcttga tctctctcgg ctcgaggatg gaagtctgga gctcgatatt   1260
cagacattca accttcctaa tgtcttcaaa gaggttttga accttgtgaa gccaatagcg   1320
tccgtgaaaa ggttacaagt gaacttgact atggggcccg acatccctga aattgcagtt   1380
ggggatgata agcggctttt acaaactgct ctcaatgttg ttggaaatgc ggtgaagttt   1440
actaaggagg ccacgtgaa cgtaattgta ggtctagaaa gacctgaata tccgcgagac   1500
cctcgtcagc cagattttcg gcctttatca ggagacaatc attttacct cagagtccag   1560 gtgcgggaca caggtttagg tctcaatcca caagacatcc ctatgctatt taacaagttt   1620
gtacaagctg actctaccac aactagaaat tacgagggga caggacttgg gttagctatt   1680
tgtaaaagat ttgttaatct catggatggg catatatgga ttgaaagcga gggggttgga   1740
agggggccga ttgtgacctt cattgtgaag ttaaatcttc ccgagacttc aagtcatctc   1800
tctattcata ttgcgcctac ctcgcaacca agtggtagtc agtctcggac agactttct   1860 ggtgtcagaa tcttggtcac cgatgacaat ggtgtgaaca ggatggtaac gcgaggcttg   1920
ctaatgagac tagggcgtga agtgactttg gcggcatctg gacgggaatg tctgcaatta   1980
atccaacagc gaaaccaggc atttaacgtg cttctacttg atgtgtgcat gccggagatg   2040
gatggatatg aagttgctac tcaaattcaa aaaagattaa cacgtcgcga tcggccgctt   2100
cttgttgccc ttacggccaa cactgatcgt atcacccatg agaaatgtct tcgtctgggc   2160
atggacggag tggtcacaaa gcctatttcg ttagaaaaga tgcgattggt gctcacagag   2220
cttttggaac gaggctccat ttctgaactt actcaaagat tatgatatta gttgttgaat   2280
tcatatcccc taatttgaaa ggcaaacgag tactgcaagg g                       2321
```

<210> SEQ ID NO 26
<211> LENGTH: 2241
<212> TYPE: DNA
<213> ORGANISM: Physcomitrella patens

<400> SEQUENCE: 26

```
atggaagcgt gcaattgcgt agagccgcaa tggcctccag acgatcttct catgcggtac     60
cagtacatat cgaattttt catcgcgttg gcatatttct ctattccgct ggagcttatt    120
tactttgtga agaagtcgtc tattttccca tatcgatggg ttcttgttca gtttggagcc    180
ttcattgtgc tgtgcggagc aacgcatcta atatccttgt ggacgttcag tagccgttct    240
```

```
cgaacagtgg ccgtcgttct tacaatagcg aaggttctta ctgctgttgt gtcgtgtgcc     300
acagcactca tgcttgtgca cattattcca gacctcctta gtgtaaagac ccgagaattg     360
ttccttgaaga agaaggctgc agaacttgat cgtgaaatgg gattgatacg tacacaggag    420
gaaacaggtc gtcacgttag gatgctcact catgaaatac gaagtaccct agatcgacat     480
acaattttga ataccaccct catagaactc ggaaaaacgc tttcgcttga ggagtgtact     540
ttatggatgc caagcccaga tggtcaagag ctacaactca aaaatgctct tcagctgaa     600
tctcttcatg ttacagtccc catacatcac ccaactatca agcaagtgtt tagtactccc    660
cgggcagtgg tgatatctcc taacagccca gtttgtgtta ctcgaattcg tggagcgaag    720
tacatgactg gggaggtcgt ggcaattcga gtcccacttc tgcatctcac aaacttccac    780
ttcagtgatt ggcctgatgc cggaacacgt ccttttgcat tgatggtgct gatgttgcct    840
ttaaacagtg cacgaaggtg gcacgttcat gaattggagc tagtggaagt tgtggctgat    900
caggtggctg tggctctatc acacgcaaca attctggagg aatcaatgcc tgctcgagat    960
cttttgatgg aacaaaacgt agcattggaa catgctagac aggaggcaga gacagctatt   1020
cgagcccgca cgactttct ggctgtgatg aatcatgaga tgcgcacgcc catgcatgct    1080
atcattgctc tttcttcttt attacaagaa acggagttaa cccctgagca gcggtctatg    1140
gtggaaactg ttttgaaaag cagtaacctt ttggccacat tgataaatga cgtgcttgat    1200
ctctctcggc tcgaggatgg aagtctggag ctcgatattc agacattcaa ccttcctaat   1260
gtcttcaaag aggttttgaa ccttgtgaag ccaatagcgt ccgtgaaaag gttacaagtg    1320
aacttgacta tggggcccga catccctgaa attgcagttg gggatgataa gcggctttta    1380
caaactgctc tcaatgttgt tggaaatgcg gtgaagttta ctaaggaggg ccacgtgaac    1440
gtaattgtag gtctagaaag acctgaatat ccgcgagacc ctcgtcagcc agattttcgg    1500
cctttatcag gagacaatca ttttttacctc agagtccagg tgcggacac aggtttaggt     1560
ctcaatccac aagacatccc tatgctattt aacaagtttg tacaagctga ctctaccaca    1620
actagaaatt acggagggac aggacttggg ttagctattt gtaaaagatt tgttaatctc    1680
atggatgggc atatatggat tgaaagcgag ggggttggaa ggggccgat tgtgaccttc    1740
attgtgaagt taaatcttcc cgagacttca agtcatctct ctattcatat tgcgcctacc    1800
tcgcaaccaa gtggtagtca gtctcggaca gacttttctg gtgtcagaat cttggtcacc    1860
gatgacaatg tgtgaacag gatggtaacg cgaggcttgc taatgagact agggcgtgaa    1920
gtgactttgg cggcatctgg acgggaatgt ctgcaattaa tccaacagcg aaaccaggca    1980
tttaacgtgc ttctacttga tgtgtgcatg ccggagatgg atggatatga agttgctact    2040
caaattcaaa aaagattaac acgtcgcgat cggccgcttc ttgttgccct tacggccaac    2100
actgatcgta tcacccatga gaaatgtctt cgtctgggca tggacggagt ggtcacaaag    2160
cctatttcgt tagaaaagat gcgattggtg ctcacagagc ttttggaacg aggctccatt    2220
tctgaactta ctcaaagatt a                                               2241
```

<210> SEQ ID NO 27
<211> LENGTH: 747
<212> TYPE: PRT
<213> ORGANISM: Physcomitrella patens

<400> SEQUENCE: 27

Met Glu Ala Cys Asn Cys Val Glu Pro Gln Trp Pro Pro Asp Asp Leu
1               5                   10                  15

```
Leu Met Arg Tyr Gln Tyr Ile Ser Asn Phe Phe Ile Ala Leu Ala Tyr
            20                  25                  30

Phe Ser Ile Pro Leu Glu Leu Ile Tyr Phe Val Lys Lys Ser Ser Ile
        35                  40                  45

Phe Pro Tyr Arg Trp Val Leu Val Gln Phe Gly Ala Phe Ile Val Leu
    50                  55                  60

Cys Gly Ala Thr His Leu Ile Ser Leu Trp Thr Phe Ser Ser Arg Ser
 65                  70                  75                  80

Arg Thr Val Ala Val Val Leu Thr Ile Ala Lys Val Leu Thr Ala Val
                85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Lys Ala Ala Glu
            115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Thr Ile Leu Asn Thr Thr Leu Ile Glu Leu Gly Lys Thr Leu Ser Leu
                165                 170                 175

Glu Glu Cys Thr Leu Trp Met Pro Ser Pro Asp Gly Gln Glu Leu Gln
            180                 185                 190

Leu Lys Asn Ala Leu Arg Ala Glu Ser Leu His Val Thr Val Pro Ile
        195                 200                 205

His His Pro Thr Ile Lys Gln Val Phe Ser Thr Pro Arg Ala Val Val
    210                 215                 220

Ile Ser Pro Asn Ser Pro Val Cys Val Thr Arg Ile Arg Gly Ala Lys
225                 230                 235                 240

Tyr Met Thr Gly Glu Val Val Ala Ile Arg Val Pro Leu Leu His Leu
                245                 250                 255

Thr Asn Phe His Phe Ser Asp Trp Pro Asp Ala Gly Thr Arg Pro Phe
            260                 265                 270

Ala Leu Met Val Leu Met Leu Pro Leu Asn Ser Ala Arg Arg Trp His
        275                 280                 285

Val His Glu Leu Glu Leu Val Glu Val Val Ala Asp Gln Val Ala Val
    290                 295                 300

Ala Leu Ser His Ala Thr Ile Leu Glu Glu Ser Met Pro Ala Arg Asp
305                 310                 315                 320

Leu Leu Met Glu Gln Asn Val Ala Leu Glu His Ala Arg Gln Glu Ala
                325                 330                 335

Glu Thr Ala Ile Arg Ala Arg Asn Asp Phe Leu Ala Val Met Asn His
            340                 345                 350

Glu Met Arg Thr Pro Met His Ala Ile Ile Ala Leu Ser Ser Leu Leu
        355                 360                 365

Gln Glu Thr Glu Leu Thr Pro Glu Gln Arg Ser Met Val Glu Thr Val
    370                 375                 380

Leu Lys Ser Ser Asn Leu Leu Ala Thr Leu Ile Asn Asp Val Leu Asp
385                 390                 395                 400

Leu Ser Arg Leu Glu Asp Gly Ser Leu Glu Leu Asp Ile Gln Thr Phe
                405                 410                 415

Asn Leu Pro Asn Val Phe Lys Glu Val Leu Asn Leu Val Lys Pro Ile
            420                 425                 430

Ala Ser Val Lys Arg Leu Gln Val Asn Leu Thr Met Gly Pro Asp Ile
```

```
                435                 440                 445
Pro Glu Ile Ala Val Gly Asp Asp Lys Arg Leu Leu Gln Thr Ala Leu
    450                 455                 460
Asn Val Val Gly Asn Ala Val Lys Phe Thr Lys Glu Gly His Val Asn
465                 470                 475                 480
Val Ile Val Gly Leu Glu Arg Pro Glu Tyr Pro Arg Asp Pro Arg Gln
                485                 490                 495
Pro Asp Phe Arg Pro Leu Ser Gly Asp Asn His Phe Tyr Leu Arg Val
            500                 505                 510
Gln Val Arg Asp Thr Gly Leu Gly Leu Asn Pro Gln Asp Ile Pro Met
        515                 520                 525
Leu Phe Asn Lys Phe Val Gln Ala Asp Ser Thr Thr Thr Arg Asn Tyr
    530                 535                 540
Gly Gly Thr Gly Leu Gly Leu Ala Ile Cys Lys Arg Phe Val Asn Leu
545                 550                 555                 560
Met Asp Gly His Ile Trp Ile Glu Ser Glu Gly Val Gly Arg Gly Pro
                565                 570                 575
Ile Val Thr Phe Ile Val Lys Leu Asn Leu Pro Glu Thr Ser Ser His
            580                 585                 590
Leu Ser Ile His Ile Ala Pro Thr Ser Gln Pro Ser Gly Ser Gln Ser
        595                 600                 605
Arg Thr Asp Phe Ser Gly Val Arg Ile Leu Val Thr Asp Asp Asn Gly
    610                 615                 620
Val Asn Arg Met Val Thr Arg Gly Leu Leu Met Arg Leu Gly Arg Glu
625                 630                 635                 640
Val Thr Leu Ala Ala Ser Gly Arg Glu Cys Leu Gln Leu Ile Gln Gln
                645                 650                 655
Arg Asn Gln Ala Phe Asn Val Leu Leu Leu Asp Val Cys Met Pro Glu
            660                 665                 670
Met Asp Gly Tyr Glu Val Ala Thr Gln Ile Gln Lys Arg Leu Thr Arg
        675                 680                 685
Arg Asp Arg Pro Leu Leu Val Ala Leu Thr Ala Asn Thr Asp Arg Ile
    690                 695                 700
Thr His Glu Lys Cys Leu Arg Leu Gly Met Asp Gly Val Val Thr Lys
705                 710                 715                 720
Pro Ile Ser Leu Glu Lys Met Arg Leu Val Leu Thr Glu Leu Leu Glu
                725                 730                 735
Arg Gly Ser Ile Ser Glu Leu Thr Gln Arg Leu
            740                 745

<210> SEQ ID NO 28
<211> LENGTH: 1072
<212> TYPE: DNA
<213> ORGANISM: Physcomitrella patens

<400> SEQUENCE: 28
agtgggtggt tggactgtaa ggagctagcg ttttagagct acagtgcggt ttgctgtgtg      60
agtgagtgag tgagtgagtg cgtgagtgag gatgtctgtt tctggtatgg acaactatga     120
gaagctggag aaggtaggag agggacttac ggaaaggtg tataaggccc gtgataaacg      180
ctccgggcag ctggtggcgc tcaagaagac taggttggag atggaggaag aaggcgtccc     240
ttccaccgct ttgcgcgaag tttcgttgct acaaatgctc tcccacagca tgtatatcgt     300
caggctactt tgcgtggagc acgtcgagaa aggcagcaag cccatgctct acttggtctt     360
```

```
tgaatatatg gacactgatc ttaagaagta tattgacttg cacggtcgtg gtccgagcgg      420
gaagcctctg cctcccaaag tggtccagag tttcatgtat caattgtgca cagggcttgc      480
ccactgtcat ggccacggag taatgcacag ggatctgaaa ccccagaatt tgctcgtcga      540
caagcaaacc cgtcgtctta agattgccga ccttggtctc ggtcgggcat tcacagtgcc      600
aatgaagagt tacacacacg agattgttac tctatggtac cgagctcctg aagttcttct      660
tggagcgacc cactactctc tacctgtgga tatctggtct gttgggtgca tcttcgctga      720
actcgtccgg aaaatgccgc tcttcactgg agactccgaa cttcagcagc ttcttcacat      780
cttcaggttg cttggcaccc cgaatgagac aatctggcct ggtgttagcc agcaccgtga      840
ttggcacgag tttcctcaat ggagaccaca agatctgtcc cttgctgttc ccggactcag      900
cgcggttggc ttagaccttc tcgccaaaat gttggtattc gagccctcaa agagaatctc      960
tgccaaagcc gccttgagcc atacttattt cgctgatgtt gataagmcag caacctaaac     1020
acaacagaac aattcaagag aaccaggtaa cctctacctg tccaagacga ag             1072
```

<210> SEQ ID NO 29
<211> LENGTH: 930
<212> TYPE: DNA
<213> ORGANISM: Physcomitrella patens

<400> SEQUENCE: 29

```
gtgaggatgt ctgtttctgg tatggacaac tatgagaagc tggagaaggt aggagagggg       60
acttacggaa aggtgtataa ggcccgtgat aaacgctccg ggcagctggt ggcgctcaag      120
aagactaggt tggagatgga ggaagaaggc gtcccttcca ccgcttttgcg cgaagtttcg     180 ttgctacaaa tgctctccca cagcatgtat atcgtcaggc tactttgcgt ggagcacgtc      240
gagaaaggca gcaagcccat gctctacttg gtctttgaat atatggacac tgatcttaag      300
aagtatattg acttgcacgg tcgtggtccg agcgggaagc ctctgcctcc caaagtggtc      360
cagagtttca tgtatcaatt gtgcacaggg cttgcccact gtcatggcca cggagtaatg      420
cacagggatc tgaaacccca gaatttgctc gtcgacaagc aaacccgtcg tcttaagatt      480
gccgaccttg gtctcggtcg ggcattcaca gtgccaatga agagttacac acacgagatt      540
gttactctat ggtaccgagc tcctgaagtt cttcttggag cgacccacta ctctctacct      600
gtggatatct ggtctgttgg gtgcatcttc gctgaactcg tccggaaaat gccgctcttc      660
actggagact ccgaacttca gcagcttctt cacatcttca ggttgcttgg cacccccgaat     720 gagacaatct ggcctggtgt tagccagcac cgtgattggc acgagtttcc tcaatggaga      780
ccacaagatc tgtcccttgc tgttcccgga ctcagcgcgg ttggcttaga ccttctcgcc      840
aaaatgttgg tattcgagcc ctcaaagaga atctctgcca aagccgcctt gagccatact      900
tatttcgctg atgttgataa gmcagcaacc                                       930
```

<210> SEQ ID NO 30
<211> LENGTH: 310
<212> TYPE: PRT
<213> ORGANISM: Physcomitrella patens
<220> FEATURE:
<221> NAME/KEY: MOD_RES
<222> LOCATION: (308)
<223> OTHER INFORMATION: Variable amino acid

<400> SEQUENCE: 30

```
Val Arg Met Ser Val Ser Gly Met Asp Asn Tyr Glu Lys Leu Glu Lys
 1               5                  10                  15
```

-continued

```
Val Gly Glu Gly Thr Tyr Gly Lys Val Tyr Lys Ala Arg Asp Lys Arg
             20                  25                  30

Ser Gly Gln Leu Val Ala Leu Lys Lys Thr Arg Leu Glu Met Glu Glu
         35                  40                  45

Glu Gly Val Pro Ser Thr Ala Leu Arg Glu Val Ser Leu Leu Gln Met
     50                  55                  60

Leu Ser His Ser Met Tyr Ile Val Arg Leu Leu Cys Val Glu His Val
 65                  70                  75                  80

Glu Lys Gly Ser Lys Pro Met Leu Tyr Leu Val Phe Glu Tyr Met Asp
                 85                  90                  95

Thr Asp Leu Lys Lys Tyr Ile Asp Leu His Gly Arg Gly Pro Ser Gly
            100                 105                 110

Lys Pro Leu Pro Pro Lys Val Val Gln Ser Phe Met Tyr Gln Leu Cys
        115                 120                 125

Thr Gly Leu Ala His Cys His Gly His Gly Val Met His Arg Asp Leu
    130                 135                 140

Lys Pro Gln Asn Leu Leu Val Asp Lys Gln Thr Arg Arg Leu Lys Ile
145                 150                 155                 160

Ala Asp Leu Gly Leu Gly Arg Ala Phe Thr Val Pro Met Lys Ser Tyr
                165                 170                 175

Thr His Glu Ile Val Thr Leu Trp Tyr Arg Ala Pro Glu Val Leu Leu
            180                 185                 190

Gly Ala Thr His Tyr Ser Leu Pro Val Asp Ile Trp Ser Val Gly Cys
        195                 200                 205

Ile Phe Ala Glu Leu Val Arg Lys Met Pro Leu Phe Thr Gly Asp Ser
    210                 215                 220

Glu Leu Gln Gln Leu Leu His Ile Phe Arg Leu Leu Gly Thr Pro Asn
225                 230                 235                 240

Glu Thr Ile Trp Pro Gly Val Ser Gln His Arg Asp Trp His Glu Phe
                245                 250                 255

Pro Gln Trp Arg Pro Gln Asp Leu Ser Leu Ala Val Pro Gly Leu Ser
            260                 265                 270

Ala Val Gly Leu Asp Leu Leu Ala Lys Met Leu Val Phe Glu Pro Ser
        275                 280                 285

Lys Arg Ile Ser Ala Lys Ala Leu Ser His Thr Tyr Phe Ala Asp
    290                 295                 300

Val Asp Lys Xaa Ala Thr
305                 310
```

<210> SEQ ID NO 31
<211> LENGTH: 1275
<212> TYPE: DNA
<213> ORGANISM: Physcomitrella patens

<400> SEQUENCE: 31

```
gctctcctgt ggcctcaagc tctggcatcg cccagaggaa gcccgcatcc gctaacttgg    60
caggtttgcc cggcaccgca ttcaagggct ccgtcgctgg tttgcgatgg acagcaatg   120 gatccgttca agtctccaag tcttcactgg acgtcggcgt cttcaaggaa ggacgcacct   180
cttcgcgccg gctgtcgtg cgcgcctcag cagactcagg ctctgagtcc aagaacattc   240
tgatgatggg cggcactcga ttcatcggac tcttccttgc ccgcgagctt gtgaaggcag   300
gccaccaggt tacattgttc acaagaggaa aagctcccat cacccagcaa ctgccaggag   360
aatctgatga ggagtacgcc gagtactcgt ccaaggtgaa gcaccttcaa ggcgatcgtc   420
```

```
aagatttga cggcctgaag gagaagctta aaggcaccaa cttcaacatt gtctacgaca    480
tcaacggtag ggagggtaag gaagtggagc ccatcttgga ggctctacca ggactggagc    540
agtacatttt ctgctcatcg gccggtgttt acctgaaatc cgaccaactt cctcacttcg    600
aggttgacgc agtcgacccc aagagccgac acaaagggaa gttggacacg gaaacgctgc    660
tgcagagcaa gggagttgcg tggacttcca tcagacctgt gtacatttac gggcctctca    720
actacaaccc tgtggaggag tggttctttc agcgcctcaa ggagggacgc cccattccgg    780
tccccaactc cggaatgcag atcacgcagc tcggccacgt caaggacctg gccagagcgt    840
tcgtgttagt gctggcgaat gagaaggctt acggccagat ttacaacatc agcggtgcca    900
agtatgtgac cttcgatggt atcgccaagg catgtgctct tgctggtggg ttccccgagc    960
ctcaaatcgt acactacaac cccaaggact tcgacttcgg caagaagaag ctttcccac    1020 ttcgtgacca gcatttcttt acctccgtcg agaaggccga aaggagcta ggcttcacac    1080 ccgaattcgg attggtcgag ggacttaagg attcctacag cctggacttt gggcgtggaa    1140
cattccgcaa agccgccgac ttctctactg atgatatgat cctggagaaa cttggcatca    1200
agaccaccgt agctgcctag atttctcgtt tccagtgatc aaagttgtag ggagggaatt    1260
gtgcagcaga cgccg                                                     1275

<210> SEQ ID NO 32
<211> LENGTH: 1209
<212> TYPE: DNA
<213> ORGANISM: Physcomitrella patens

<400> SEQUENCE: 32
gtggcctcaa gctctggcat cgcccagagg aagcccgcat ccgctaactt ggcaggtttg     60
cccggcaccg cattcaaggg ctccgtcgct ggtttgcgat gggacagcaa tggatccgtt    120
caagtctcca gtcttcact ggacgtcggc gtcttcaagg aaggacgcac ctcttcgcgc    180
cgggctgtcg tgcgcgcctc agcagactca ggctctgagt ccaagaacat tctgatgatg    240
ggcggcactc gattcatcgg actcttcctt gcccgcgagc ttgtgaaggc aggccaccag    300
gttacattgt tcacaagagg aaaagctccc atcacccagc aactgccagg agaatctgat    360
gaggagtacg ccgagtactc gtccaaggtg aagcaccttc aaggcgatcg tcaagatttt    420
gacggcctga aggagaagct taaaggcacc aacttcaaca ttgtctacga catcaacggt    480
agggagggta aggaagtgga gcccatcttg gaggctctac caggactgga gcagtacatt    540
ttctgctcat cggccggtgt ttacctgaaa tccgaccaac ttcctcactt cgaggttgac    600
gcagtcgacc ccaagagccg acacaaaggg aagttggaca cggaaacgct gctgcagagc    660
aagggagttg cgtggacttc catcagacct gtgtacattt acgggcctct caactacaac    720
cctgtggagg agtggttctt tcagcgcctc aaggagggac gccccattcc ggtccccaac    780
tccggaatgc agatcacgca gctcggccac gtcaaggacc tggccagagc gttcgtgtta    840
gtgctggcga atgagaaggc ttacggccag atttacaaca tcagcggtgc caagtatgtg    900
accttcgatg gtatcgccaa ggcatgtgct cttgctggtg ggttccccga gcctcaaatc    960
gtacactaca accccaagga cttcgacttc ggcaagaaga aggctttccc acttcgtgac   1020
cagcatttct ttacctccgt cgagaaggcc gagaaggagc taggcttcac acccgaattc   1080
ggattggtcg agggacttaa ggattcctac agcctggact ttgggcgtgg aacattccgc   1140
aaagccgccg acttctctac tgatgatatg atcctggaga aacttggcat caagaccacc   1200
gtagctgcc                                                           1209
```

<210> SEQ ID NO 33
<211> LENGTH: 403
<212> TYPE: PRT
<213> ORGANISM: Physcomitrella patens

<400> SEQUENCE: 33

```
Val Ala Ser Ser Gly Ile Ala Gln Arg Lys Pro Ala Ser Ala Asn
  1               5                  10                  15

Leu Ala Gly Leu Pro Gly Thr Ala Phe Lys Gly Ser Val Ala Gly Leu
                 20                  25                  30

Arg Trp Asp Ser Asn Gly Ser Val Gln Val Ser Lys Ser Ser Leu Asp
             35                  40                  45

Val Gly Val Phe Lys Glu Gly Arg Thr Ser Ser Arg Arg Ala Val Val
         50                  55                  60

Arg Ala Ser Ala Asp Ser Gly Ser Glu Ser Lys Asn Ile Leu Met Met
 65                  70                  75                  80

Gly Gly Thr Arg Phe Ile Gly Leu Phe Leu Ala Arg Glu Leu Val Lys
                 85                  90                  95

Ala Gly His Gln Val Thr Leu Phe Thr Arg Gly Lys Ala Pro Ile Thr
                100                 105                 110

Gln Gln Leu Pro Gly Glu Ser Asp Glu Glu Tyr Ala Glu Tyr Ser Ser
            115                 120                 125

Lys Val Lys His Leu Gln Gly Asp Arg Gln Asp Phe Asp Gly Leu Lys
        130                 135                 140

Glu Lys Leu Lys Gly Thr Asn Phe Asn Ile Val Tyr Asp Ile Asn Gly
145                 150                 155                 160

Arg Glu Gly Lys Glu Val Glu Pro Ile Leu Glu Ala Leu Pro Gly Leu
                165                 170                 175

Glu Gln Tyr Ile Phe Cys Ser Ser Ala Gly Val Tyr Leu Lys Ser Asp
                180                 185                 190

Gln Leu Pro His Phe Glu Val Asp Ala Val Asp Pro Lys Ser Arg His
            195                 200                 205

Lys Gly Lys Leu Asp Thr Glu Thr Leu Leu Gln Ser Lys Gly Val Ala
        210                 215                 220

Trp Thr Ser Ile Arg Pro Val Tyr Ile Tyr Gly Pro Leu Asn Tyr Asn
225                 230                 235                 240

Pro Val Glu Glu Trp Phe Phe Gln Arg Leu Lys Glu Gly Arg Pro Ile
                245                 250                 255

Pro Val Pro Asn Ser Gly Met Gln Ile Thr Gln Leu Gly His Val Lys
                260                 265                 270

Asp Leu Ala Arg Ala Phe Val Leu Val Leu Ala Asn Glu Lys Ala Tyr
            275                 280                 285

Gly Gln Ile Tyr Asn Ile Ser Gly Ala Lys Tyr Val Thr Phe Asp Gly
        290                 295                 300

Ile Ala Lys Ala Cys Ala Leu Ala Gly Gly Phe Pro Glu Pro Gln Ile
305                 310                 315                 320

Val His Tyr Asn Pro Lys Asp Phe Asp Phe Gly Lys Lys Lys Ala Phe
                325                 330                 335

Pro Leu Arg Asp Gln His Phe Phe Thr Ser Val Glu Lys Ala Glu Lys
            340                 345                 350

Glu Leu Gly Phe Thr Pro Glu Phe Gly Leu Val Glu Gly Leu Lys Asp
        355                 360                 365

Ser Tyr Ser Leu Asp Phe Gly Arg Gly Thr Phe Arg Lys Ala Ala Asp
```

|       | 370 |     |     | 375 |     |     |     | 380 |     |     |
|-------|-----|-----|-----|-----|-----|-----|-----|-----|-----|-----|

Phe Ser Thr Asp Asp Met Ile Leu Glu Lys Leu Gly Ile Lys Thr Thr
385                 390                 395                 400

Val Ala Ala

<210> SEQ ID NO 34
<211> LENGTH: 1939
<212> TYPE: DNA
<213> ORGANISM: Physcomitrella patens

<400> SEQUENCE: 34

```
gcccttatcc cgggctagtc gcattcacag agcagctgat ttagagtctc caccgaattc      60
caccatgttg gcgctcttcg agacgcccgc ggggttcgcc ctgttcaagg ttttgaatga     120
gggtaaactc gatgcctccg aggaattgta caaggagttt gagactgcgg acctcgcccg     180
taagatggtg aagttgaaag cctttgaaaa attcgagaat accacagatg ccctgaatgc     240
tgcgtcacac cttgtggaaa gcaagttgcc aaagggtctg cgcaagttcc ttaagaaaga     300
atgccaaggg gagactctag ctatagctga ctcgaagctt ggaaaagcta ttagtgacaa     360
gctggaaatc aactgtgtta caatgcggc agtggcagag ctgatgaggg gtctaagatc     420
acaattgtcg gaactaattt ctggtcttgc tggtcatgat atggctccca tgagtctggg     480
actgtctcac agtttatcgc gatacaaact taaattcagc cctgacaagg tggacaccat     540
gatcgtgcaa gccattggac tcttggacga tttggacaag gagctaaata cttatgctat     600
gagagtgcgt gaatggtatg gttggcattt tccagagctt gctaagatcg ttcaagataa     660
tgttcaatac gctaagtcag tgaagctgat gggcagtcgc actaacgccg cagacctgga     720
tttctctggg atattgcaag aggaagtaga gtctgaaatg aaagaagctg cagtcatttc     780
catgggtacg gaagttagtg accacgatat gttgaacatc aagtccttgt gcgaccaagt     840
cattgctctc tcagagtacc gaggccaact ttttgactac ttgaggagtc gtatgaatgc     900
tattgcgcct aatcttactg tcatggttgg ggagttagta ggtgctaggt taattgccca     960
tgctggaagt ctcattaact ggcaaaaca cccggcaagc actgttcaaa ttttgggtgc    1020
tgaaaaggca cttttttaggg cattgaagac caaacatgaa cctcgaaat atgggcttat    1080
ttatcacgcc tcttttgatag acaagcggc acctaaattc aagggtaaaa tttctcgagt    1140
ccttgctgca agtcggcgc tgtcgatccg tatggatgct ctgggagagg gctcggaagc    1200
tagcattggt attgaaagcc gcgctaaggc tgaagcaagg ttaaggcaac ttgaaggtag    1260
agctcttgga aaaactcctg tctctgcatc caagggcaag cccaatattc aggcttatga    1320
aaaagatagg aaatctggaa ctcctggatt gctttctgcc gccaaggttt acaatccctc    1380
cgctgatgtt actatggatg aacctactga tgccacccc gctaagaaga aaaagatcaa    1440
ggaggctgca gaggagccag ctgctgaacc agcagccgaa gacactttac cgaagaagaa    1500
aagaaatct aaggaagctg cagcagaggc agaacctgaa ccaactacgg atgccacttc    1560
acccaagaag aagaagaaga atccaagca agccgcagaa gaggcagctg ctgaacctac    1620
cacagaggcc actcctccac caagaagaa gaaatcaaag gatgctgtca cacctaccgt    1680
tgcggttgcc gtggctgtca caccagagct caccaagtct gggaagaaga ggaaagctga    1740
gactgaagct gccgccgggg ctgcagtaga ggccgcagtg gaggcagtca ctggagtaga    1800
gaagaagaag aaaaagaaaa agagcaagga agaatctgcc taagcaagag gcgcccaagg    1860
atagtagtta ggttacttgt agtgtataca tggagcgaaa tatgtcattg aagggtcaaa    1920
```

<210> SEQ ID NO 35
<211> LENGTH: 1776
<212> TYPE: DNA
<213> ORGANISM: Physcomitrella patens

<400> SEQUENCE: 35

```
atgttggcgc tcttcgagac gcccgcgggg ttcgccctgt tcaaggtttt gaatgagggt      60
aaactcgatg cctccgagga attgtacaag gagtttgaga ctgcggacct cgcccgtaag     120
atggtgaagt tgaaagcctt tgaaaaattc gagaatacca cagatgccct gaatgctgcg     180
tcacaccttg tggaaagcaa gttgccaaag ggtctgcgca agttccttaa gaaagaatgc     240
caagggagac tctagctat agctgactcg aagcttggaa aagctattag tgacaagctg     300
gaaatcaact gtgttaacaa tgcggcagtg gcagagctga tgagggtct aagatcacaa     360
ttgtcggaac taatttctgg tcttgctggt catgatatgg ctcccatgag tctgggactg     420
tctcacagtt atcgcgata caaacttaaa ttcagccctg acaaggtgga caccatgatc     480
gtgcaagcca ttggactctt ggacgatttg acaaggagc taaatactta tgctatgaga     540
gtgcgtgaat ggtatggttg gcattttcca gagcttgcta agatcgttca agataatgtt     600
caatacgcta gtcagtgaa gctgatgggc agtcgcacta cgccgcaga cctggatttc     660
tctgggatat tgcaagagga agtagagtct gaaatgaaag aagctgcagt catttccatg     720
ggtacggaag ttagtgacca cgatatgttg aacatcaagt ccttgtgcga ccaagtcatt     780
gctctctcag agtaccgagg ccaacttttt gactacttga ggagtcgtat gaatgctatt     840
gcgcctaatc ttactgtcat ggttggggag ttagtaggtg ctaggttaat tgcccatgct     900
ggaagtctca ttaacttggc aaaacacccg gcaagcactg ttcaaatttt gggtgctgaa     960
aaggcacttt ttagggcatt gaagaccaaa catgaacctc cgaaatatgg gcttatttat    1020
cacgcctctt tgataggaca agcggcacct aaattcaagg gtaaaatttc tcgagtcctt    1080
gctgcaaagt cggcgctgtc gatccgtatg gatgctctgg gagagggctc ggaagctagc    1140
attggtattg aaagccgcgc taaggctgaa gcaaggttaa ggcaacttga aggtagagct    1200
cttggaaaaa ctcctgtctc tgcatccaag ggcaagccca atattcaggc ttatgaaaaa    1260
gataggaaat ctggaactcc tggattgctt tctgccgcca aggtttacaa tccctccgct    1320
gatgttacta tggatgaacc tactgatgcc accccgcta agaagaaaaa gatcaaggag    1380
gctgcagagg agccagctgc tgaaccagca gccgaagaca ctttaccgaa gaagaaaaag    1440
aaatctaagg aagctgcagc agaggcagaa cctgaaccaa ctacggatgc cacttcaccc    1500
aagaagaaga agaagaaatc caagcaagcc gcagaagagg cagctgctga acctaccaca    1560
gaggccactc ctccaccaaa gaagaagaaa tcaaaggatg ctgtcacacc taccgttgcg    1620
gttgccgtgg ctgtcacacc agagctcacc aagtctggga agaagaggaa agctgagact    1680
gaagctgccg ccgggctgc agtagaggcc gcagtggagg cagtcactgg agtagagaag    1740
aagaagaaaa agaaaaagag caaggaagaa tctgcc                              1776
```

<210> SEQ ID NO 36
<211> LENGTH: 592
<212> TYPE: PRT
<213> ORGANISM: Physcomitrella patens

<400> SEQUENCE: 36

Met Leu Ala Leu Phe Glu Thr Pro Ala Gly Phe Ala Leu Phe Lys Val

-continued

```
  1               5               10              15
Leu Asn Glu Gly Lys Leu Asp Ala Ser Glu Glu Leu Tyr Lys Glu Phe
             20                  25                  30

Glu Thr Ala Asp Leu Ala Arg Lys Met Val Lys Leu Lys Ala Phe Glu
             35                  40                  45

Lys Phe Glu Asn Thr Thr Asp Ala Leu Asn Ala Ala Ser His Leu Val
             50                  55                  60

Glu Ser Lys Leu Pro Lys Gly Leu Arg Lys Phe Leu Lys Lys Glu Cys
 65                  70                  75                  80

Gln Gly Glu Thr Leu Ala Ile Ala Asp Ser Lys Leu Gly Lys Ala Ile
                 85                  90                  95

Ser Asp Lys Leu Glu Ile Asn Cys Val Asn Asn Ala Ala Val Ala Glu
                100                 105                 110

Leu Met Arg Gly Leu Arg Ser Gln Leu Ser Glu Leu Ile Ser Gly Leu
                115                 120                 125

Ala Gly His Asp Met Ala Pro Met Ser Leu Gly Leu Ser His Ser Leu
                130                 135                 140

Ser Arg Tyr Lys Leu Lys Phe Ser Pro Asp Lys Val Asp Thr Met Ile
145                 150                 155                 160

Val Gln Ala Ile Gly Leu Leu Asp Asp Leu Asp Lys Glu Leu Asn Thr
                165                 170                 175

Tyr Ala Met Arg Val Arg Glu Trp Tyr Gly Trp His Phe Pro Glu Leu
                180                 185                 190

Ala Lys Ile Val Gln Asp Asn Val Gln Tyr Ala Lys Ser Val Lys Leu
                195                 200                 205

Met Gly Ser Arg Thr Asn Ala Ala Asp Leu Asp Phe Ser Gly Ile Leu
                210                 215                 220

Gln Glu Glu Val Glu Ser Glu Met Lys Glu Ala Ala Val Ile Ser Met
225                 230                 235                 240

Gly Thr Glu Val Ser Asp His Asp Met Leu Asn Ile Lys Ser Leu Cys
                245                 250                 255

Asp Gln Val Ile Ala Leu Ser Glu Tyr Arg Gly Gln Leu Phe Asp Tyr
                260                 265                 270

Leu Arg Ser Arg Met Asn Ala Ile Ala Pro Asn Leu Thr Val Met Val
                275                 280                 285

Gly Glu Leu Val Gly Ala Arg Leu Ile Ala His Ala Gly Ser Leu Ile
                290                 295                 300

Asn Leu Ala Lys His Pro Ala Ser Thr Val Gln Ile Leu Gly Ala Glu
305                 310                 315                 320

Lys Ala Leu Phe Arg Ala Leu Lys Thr Lys His Glu Pro Pro Lys Tyr
                325                 330                 335

Gly Leu Ile Tyr His Ala Ser Leu Ile Gly Gln Ala Ala Pro Lys Phe
                340                 345                 350

Lys Gly Lys Ile Ser Arg Val Leu Ala Ala Lys Ser Ala Leu Ser Ile
                355                 360                 365

Arg Met Asp Ala Leu Gly Glu Gly Ser Glu Ala Ser Ile Gly Ile Glu
                370                 375                 380

Ser Arg Ala Lys Ala Glu Ala Arg Leu Arg Gln Leu Glu Gly Arg Ala
385                 390                 395                 400

Leu Gly Lys Thr Pro Val Ser Ala Ser Lys Gly Lys Pro Asn Ile Gln
                405                 410                 415

Ala Tyr Glu Lys Asp Arg Lys Ser Gly Thr Pro Gly Leu Leu Ser Ala
                420                 425                 430
```

```
Ala Lys Val Tyr Asn Pro Ser Ala Asp Val Thr Met Asp Glu Pro Thr
            435                 440                 445

Asp Ala Thr Pro Ala Lys Lys Lys Ile Lys Glu Ala Ala Glu Glu
        450                 455                 460

Pro Ala Ala Glu Pro Ala Ala Glu Asp Thr Leu Pro Lys Lys Lys Lys
465                 470                 475                 480

Lys Ser Lys Glu Ala Ala Ala Glu Ala Glu Pro Glu Pro Thr Thr Asp
                485                 490                 495

Ala Thr Ser Pro Lys Lys Lys Lys Lys Ser Lys Gln Ala Ala Glu
        500                 505                 510

Glu Ala Ala Ala Glu Pro Thr Thr Glu Ala Thr Pro Pro Lys Lys
        515                 520                 525

Lys Lys Ser Lys Asp Ala Val Thr Pro Thr Val Ala Val Ala Val Ala
        530                 535                 540

Val Thr Pro Glu Leu Thr Lys Ser Gly Lys Lys Arg Lys Ala Glu Thr
545                 550                 555                 560

Glu Ala Ala Ala Gly Ala Ala Val Glu Ala Ala Val Glu Ala Val Thr
                565                 570                 575

Gly Val Glu Lys Lys Lys Lys Lys Lys Ser Lys Glu Glu Ser Ala
                580                 585                 590

<210> SEQ ID NO 37
<211> LENGTH: 1522
<212> TYPE: DNA
<213> ORGANISM: Physcomitrella patens

<400> SEQUENCE: 37
aattcccaga ttccctcaca cacccactat gcaatcccgc attctcattg cgtgcccacc     60
tctcgaacgc ccaggtctgg gtttgaaatc ctggtaattg gacgatttgg aggtaaaagg    120
aggtgcgcaa tttggcagat agtttggagg tttggataat cgttgcgtag aggtggccat    180
ggcgggtgtg cgctgggact cgtgggaccc ggtttggaa ttggtggcca gcaagagggc     240
actgtgccct ggagcttctt tctcttctcc gttttgcctc agttgctctg cgtctgtgtc    300
atccaacagc agtactcgtg ccaggtctcc caaggccctt gtcctcagga gctcctttgt    360
ctcgcggacc acccattcca gcttctggga tggtggagtg ggagcctgtg tgctcgcgct    420
tgcggtggag gactcaatta agcaaaggaa acgcggtggt gccctttgtg ctcaagcgaa    480 tattttttgag cgtgtggtca gaattgtgag gtcctacgca aatgctatag tgagctcagc    540
tgaagaccct gaaaagttac tggatcagac tgtgttggaa atgaatgaag acctgataaa    600
aatgcgtcag gcatcggcac aggtgctagc ttcccaaaag cagttggaga taagtataa    660 agcagctcaa acagctgcag atgattggta taggagagcg aaattagcac ttgaaaaagg    720
tgatgaggac ttagctaggg aggctcttaa acgccgtaag gattatgagg aaagtgccaa    780
ggcattgaaa agtcagctgg atcagcagaa gggtgtcgtg ataagctga tatcgaacac     840 tcggctgcta gaaagcaaga tctcagaggc taagtcgaag aaggacactt tgaaagcacg    900
agcacaatct gccaagactt cccagaaggt taatgagatg ttgggaaata tcaatactag    960
cggtgctctt gcggcatttg agaagatgga agaaaaagtt actgcattag aggcagaatc   1020
ggaggcgctc aatcaactca gtactgatga tttggctgcc aagttcgctc ttttagaaag   1080
tgattctgta gatgacgact tggcatcctt aaagcaagac gtgctgggtt catcgaagag   1140
aaaaggagag ctgccggaag gccggtccca agcagtttca gtagcagca aaactcccta   1200
```

```
tcctttcaag gactcggaga ttgaaaggga attgaatgag ctacgaaaga gggccaacga   1260 ttttttaagtc ttcattttga ttttctctgc tgtttagcag caaatcggaa ttcttatgat   1320
tgtgtatttt agagtgaagg gtggttgctg gtcactgctg tatcttaaat cattgacgat   1380
ttgaaggtcg ggaacgtgag tctttagcaa ttggtcatgc aagctacggc tatacaattt   1440
aatttgtgca atacctcaa tatctgctga aacagatttt gtggtgatca ttaaaaatct   1500
tgattcgact cgtgccgaat tc                                            1522

<210> SEQ ID NO 38
<211> LENGTH: 1092
<212> TYPE: DNA
<213> ORGANISM: Physcomitrella patens

<400> SEQUENCE: 38
gtggccatgg cgggtgtggc gctgggactc gtgggacccg gtttggaatt ggtggccagc     60
aagagggcac tgtgccctgg agcttctttc tcttctccgt tttgcctcag ttgctctgcg    120
tctgtgtcat ccaacagcag tactcgtgcc aggtctccca aggcccttgt cctcaggagc    180
tcctttgtct cgcggaccac ccattccagc ttctgggatg gtggagtggg agcctgtgtg    240
ctcgcgcttg cggtggagga ctcaattaag caaaggaaac gcggtggtgc cctttgtgct    300
caagcgaata ttttttgagcg tgtggtcaga attgtgaggt cctacgcaaa tgctatagtg    360
agctcagctg aagaccctga aaagttactg gatcagactg tgttggaaat gaatgaagac    420
ctgataaaaa tgcgtcaggc atcggcacag gtgctagctt cccaaaagca gttggagaat    480
aagtataaag cagctcaaac agctgcagat gattggtata ggagagcgaa attagcactt    540
gaaaaaggtg atgaggactt agctaggag gctcttaaac gccgtaagga ttatgaggaa    600
agtgccaagg cattgaaaag tcagctggat cagcagaagg gtgtcgtgga taagctgata    660
tcgaacactc ggctgctaga aagcaagatc tcagaggcta agtcgaagaa ggacactttg    720
aaagcacgag cacaatctgc caagacttcc cagaaggtta atgagatgtt gggaaatatc    780
aatactagcg gtgctcttgc ggcatttgag aagatggaag aaaaagttac tgcattagag    840
gcagaatcgg aggcgctcaa tcaactcagt actgatgatt tggctgccaa gttcgctctt    900
ttagaaagtg attctgtaga tgacgacttg gcatccttaa agcaagacgt gctgggttca    960
tcgaagagaa aaggagagct gccggaaggc cggtcccaag cagtttcaag tagcagcaaa   1020
actccctatc ctttcaagga ctcggagatt gaaagggaat tgaatgagct acgaaagagg   1080
gccaacgatt tt                                                       1092

<210> SEQ ID NO 39
<211> LENGTH: 364
<212> TYPE: PRT
<213> ORGANISM: Physcomitrella patens

<400> SEQUENCE: 39

Val Ala Met Ala Gly Val Ala Leu Gly Leu Val Gly Pro Gly Leu Glu
 1               5                  10                  15

Leu Val Ala Ser Lys Arg Ala Leu Cys Pro Gly Ala Ser Phe Ser Ser
            20                  25                  30

Pro Phe Cys Leu Ser Cys Ser Ala Ser Val Ser Ser Asn Ser Ser Thr
        35                  40                  45

Arg Ala Arg Ser Pro Lys Ala Leu Val Leu Arg Ser Ser Phe Val Ser
    50                  55                  60

Arg Thr Thr His Ser Ser Phe Trp Asp Gly Gly Val Gly Ala Cys Val
```

```
                65                  70                  75                  80
Leu Ala Leu Ala Val Glu Asp Ser Ile Lys Gln Arg Lys Arg Gly Gly
                    85                  90                  95
Ala Leu Cys Ala Gln Ala Asn Ile Phe Glu Arg Val Val Arg Ile Val
                100                 105                 110
Arg Ser Tyr Ala Asn Ala Ile Val Ser Ser Ala Glu Asp Pro Glu Lys
                115                 120                 125
Leu Leu Asp Gln Thr Val Leu Glu Met Asn Glu Asp Leu Ile Lys Met
                130                 135                 140
Arg Gln Ala Ser Ala Gln Val Leu Ala Ser Gln Lys Gln Leu Glu Asn
145                 150                 155                 160
Lys Tyr Lys Ala Ala Gln Thr Ala Ala Asp Asp Trp Tyr Arg Arg Ala
                165                 170                 175
Lys Leu Ala Leu Glu Lys Gly Asp Glu Asp Leu Ala Arg Glu Ala Leu
                180                 185                 190
Lys Arg Arg Lys Asp Tyr Glu Ser Ala Lys Ala Leu Lys Ser Gln
                195                 200                 205
Leu Asp Gln Gln Lys Gly Val Val Asp Lys Leu Ile Ser Asn Thr Arg
                210                 215                 220
Leu Leu Glu Ser Lys Ile Ser Glu Ala Lys Ser Lys Lys Asp Thr Leu
225                 230                 235                 240
Lys Ala Arg Ala Gln Ser Ala Lys Thr Ser Gln Lys Val Asn Glu Met
                245                 250                 255
Leu Gly Asn Ile Asn Thr Ser Gly Ala Leu Ala Ala Phe Glu Lys Met
                260                 265                 270
Glu Glu Lys Val Thr Ala Leu Glu Ala Glu Ser Glu Ala Leu Asn Gln
                275                 280                 285
Leu Ser Thr Asp Asp Leu Ala Ala Lys Phe Ala Leu Leu Glu Ser Asp
                290                 295                 300
Ser Val Asp Asp Asp Leu Ala Ser Leu Lys Gln Asp Val Leu Gly Ser
305                 310                 315                 320
Ser Lys Arg Lys Gly Glu Leu Pro Glu Gly Arg Ser Gln Ala Val Ser
                325                 330                 335
Ser Ser Ser Lys Thr Pro Tyr Pro Phe Lys Asp Ser Glu Ile Glu Arg
                340                 345                 350
Glu Leu Asn Glu Leu Arg Lys Arg Ala Asn Asp Phe
                355                 360

<210> SEQ ID NO 40
<211> LENGTH: 1275
<212> TYPE: DNA
<213> ORGANISM: Physcomitrella patens

<400> SEQUENCE: 40
gctctcctgt ggcctcaagc tctggcatcg cccagaggaa gcccgcatcc gctaacttgg      60
caggtttgcc cggcaccgca ttcaagggct ccgtcgctgg tttgcgatgg acagcaatg     120
gatccgttca gtctccaag tcttcactgg acgtcggcgt cttcaaggaa ggacgcacct     180
cttcgcgccg ggctgtcgtg cgcgcctcag cagactcagg ctctgagtcc aagaacattc     240
tgatgatggg cggcactcga ttcatcggac tcttccttgc ccgcgagctt gtgaaggcag     300
gccaccaggt tacattgttc acaagaggaa aagctcccat cacccagcaa ctgccaggag     360
aatctgatga ggagtacgcc gagtactcgt ccaaggtgaa gcaccttcaa ggcgatcgtc     420
aagatttga cggcctgaag gagaagctta aaggcaccaa cttcaacatt gtctacgaca     480
```

```
tcaacggtag ggagggtaag gaagtggagc ccatcttgga ggctctacca ggactggagc    540
agtacatttt ctgctcatcg gccggtgttt acctgaaatc cgaccaactt cctcacttcg    600
aggttgacgc agtcgacccc aagagccgac acaaagggaa gttggacacg gaaacgctgc    660
tgcagagcaa gggagttgcg tggacttcca tcagacctgt gtacatttac gggcctctca    720
actacaaccc tgtggaggag tggttctttc agcgcctcaa ggagggacgc cccattccgg    780
tccccaactc cggaatgcag atcacgcagc tcggccacgt caaggacctg ccagagcgt    840 tcgtgttagt gctggcgaat gagaaggctt acggccagat ttacaacatc agcggtgcca    900
agtatgtgac cttcgatggt atcgccaagg catgtgctct tgctggtggg ttccccgagc    960
ctcaaatcgt acactacaac cccaaggact cgacttcgg caagaagaag ctttcccac    1020 ttcgtgacca gcatttcttt acctccgtcg agaaggccga aaggagcta ggcttcacac    1080 ccgaattcgg attggtcgag ggacttaagg attcctacag cctggacttt gggcgtggaa    1140
cattccgcaa agccgccgac ttctctactg atgatatgat cctggagaaa cttggcatca    1200
agaccaccgt agctgcctag atttctcgtt ccagtgatc aaagttgtag ggagggaatt    1260
gtgcagcaga cgccg                                                    1275

<210> SEQ ID NO 41
<211> LENGTH: 1209
<212> TYPE: DNA
<213> ORGANISM: Physcomitrella patens

<400> SEQUENCE: 41
gtggcctcaa gctctggcat cgcccagagg aagcccgcat ccgctaactt ggcaggtttg     60
cccggcaccg cattcaaggg ctccgtcgct ggtttgcgat gggacagcaa tggatccgtt    120
caagtctcca gtcttcact ggacgtcggc gtcttcaagg aaggacgcac ctcttcgcgc    180
cgggctgtcg tgcgcgcctc agcagactca ggctctgagt ccaagaacat tctgatgatg    240 gcggcactc gattcatcgg actcttcctt gcccgcgagc ttgtgaaggc aggccaccag    300
gttacattgt tcacaagagg aaaagctccc atcacccagc aactgccagg agaatctgat    360
gaggagtacg ccgagtactc gtccaaggtg aagcaccttc aaggcgatcg tcaagatttt    420
gacggcctga aggagaagct taaaggcacc aacttcaaca ttgtctacga catcaacggt    480
agggagggta aggaagtgga gcccatcttg gaggctctac caggactgga gcagtacatt    540
ttctgctcat cggccggtgt ttacctgaaa tccgaccaac ttcctcactt cgaggttgac    600
gcagtcgacc ccaagagccg acacaaaggg aagttggaca cggaaacgct gctgcagagc    660
aagggagttg cgtggacttc atcagacct gtgtacattt acgggcctct caactacaac    720
cctgtggagg agtggttctt tcagcgcctc aaggagggac gccccattcc ggtccccaac    780
tccggaatgc agatcacgca gctcggccac gtcaaggacc tggccagagc gttcgtgtta    840
gtgctggcga atgagaaggc ttacggccag atttacaaca tcagcggtgc caagtatgtg    900
accttcgatg gtatcgccaa ggcatgtgct cttgctggtg ggttccccga gcctcaaatc    960
gtacactaca accccaagga cttcgacttc ggcaagaaga aggctttccc acttcgtgac    1020
cagcatttct ttacctccgt cgagaaggcc gagaaggagc taggcttcac acccgaattc    1080
ggattggtcg agggacttaa ggattcctac agcctggact ttgggcgtgg aacattccgc    1140
aaagccgccg acttctctac tgatgatatg atcctggaga aacttggcat caagaccacc    1200
gtagctgcc                                                           1209
```

<210> SEQ ID NO 42
<211> LENGTH: 403
<212> TYPE: PRT
<213> ORGANISM: Physcomitrella patens

<400> SEQUENCE: 42

```
Val Ala Ser Ser Gly Ile Ala Gln Arg Lys Pro Ala Ser Ala Asn
 1               5                  10                  15

Leu Ala Gly Leu Pro Gly Thr Ala Phe Lys Gly Ser Val Ala Gly Leu
                20                  25                  30

Arg Trp Asp Ser Asn Gly Ser Val Gln Val Ser Lys Ser Ser Leu Asp
         35                  40                  45

Val Gly Val Phe Lys Glu Gly Arg Thr Ser Ser Arg Arg Ala Val Val
     50                  55                  60

Arg Ala Ser Ala Asp Ser Gly Ser Glu Ser Lys Asn Ile Leu Met Met
 65                  70                  75                  80

Gly Gly Thr Arg Phe Ile Gly Leu Phe Leu Ala Arg Glu Leu Val Lys
                 85                  90                  95

Ala Gly His Gln Val Thr Leu Phe Thr Arg Gly Lys Ala Pro Ile Thr
            100                 105                 110

Gln Gln Leu Pro Gly Glu Ser Asp Glu Glu Tyr Ala Glu Tyr Ser Ser
        115                 120                 125

Lys Val Lys His Leu Gln Gly Asp Arg Gln Asp Phe Asp Gly Leu Lys
    130                 135                 140

Glu Lys Leu Lys Gly Thr Asn Phe Asn Ile Val Tyr Asp Ile Asn Gly
145                 150                 155                 160

Arg Glu Gly Lys Glu Val Glu Pro Ile Leu Glu Ala Leu Pro Gly Leu
                165                 170                 175

Glu Gln Tyr Ile Phe Cys Ser Ser Ala Gly Val Tyr Leu Lys Ser Asp
            180                 185                 190

Gln Leu Pro His Phe Glu Val Asp Ala Val Asp Pro Lys Ser Arg His
        195                 200                 205

Lys Gly Lys Leu Asp Thr Glu Thr Leu Leu Gln Ser Lys Gly Val Ala
    210                 215                 220

Trp Thr Ser Ile Arg Pro Val Tyr Ile Tyr Gly Pro Leu Asn Tyr Asn
225                 230                 235                 240

Pro Val Glu Glu Trp Phe Phe Gln Arg Leu Lys Glu Gly Arg Pro Ile
                245                 250                 255

Pro Val Pro Asn Ser Gly Met Gln Ile Thr Gln Leu Gly His Val Lys
            260                 265                 270

Asp Leu Ala Arg Ala Phe Val Leu Val Leu Ala Asn Glu Lys Ala Tyr
        275                 280                 285

Gly Gln Ile Tyr Asn Ile Ser Gly Ala Lys Tyr Val Thr Phe Asp Gly
    290                 295                 300

Ile Ala Lys Ala Cys Ala Leu Ala Gly Gly Phe Pro Glu Pro Gln Ile
305                 310                 315                 320

Val His Tyr Asn Pro Lys Asp Phe Asp Phe Gly Lys Lys Lys Ala Phe
                325                 330                 335

Pro Leu Arg Asp Gln His Phe Phe Thr Ser Val Glu Lys Ala Glu Lys
            340                 345                 350

Glu Leu Gly Phe Thr Pro Glu Phe Gly Leu Val Glu Gly Leu Lys Asp
        355                 360                 365

Ser Tyr Ser Leu Asp Phe Gly Arg Gly Thr Phe Arg Lys Ala Ala Asp
    370                 375                 380
```

```
Phe Ser Thr Asp Asp Met Ile Leu Glu Lys Leu Gly Ile Lys Thr Thr
385                 390                 395                 400

Val Ala Ala

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 43
caggaaacag ctatgacc                                              18

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 44
ctaaagggaa caaaagctg                                             19

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 45
tgtaaaacga cggccagt                                              18

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 46
atggcgcgcc cgatggtgcg ttcgagatcg                                 30

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 47
gcttaattaa gcgttaacga gctttctcgc agtgcc                          36

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 48
atggcgcgcc tgggtttggg tagttgcttg acgac                           35
```

<210> SEQ ID NO 49
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 49
gcttaattaa ggttcaagga ccgcctgcct atac                             34

<210> SEQ ID NO 50
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 50
atggcgcgcc gagctgctgt cagttcgtca acgg                             34

<210> SEQ ID NO 51
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 51
atttaattaa gttgaccagg acgacagcag tagc                             34

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 52
atggcgcgcc cgcagcatgt gactcgtcac ctg                              33

<210> SEQ ID NO 53
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 53
cgttaattaa agctactact tgctctagga agctg                            35

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 54
atggcgcgcc agcacgaggg caagaggg                                    28

<210> SEQ ID NO 55
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 55
atttaattaa gttgacgttg gattgcacat ggtgg    35

<210> SEQ ID NO 56
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 56
atggcgcgcc ggccttcaag cactctctgc at    32

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 57
atttaattaa tctcatggac gacccacc    28

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 58
taggcgcgcc gttgcgttct ctgcttcctt cga    33

<210> SEQ ID NO 59
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 59
gcttaattaa ctgtatccaa acctctgccg gtgg    34

<210> SEQ ID NO 60
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 60
atggcgcgcc ggcgaagggg aggtgtcgg    29

<210> SEQ ID NO 61
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 61
ggttaattaa gaattactgg accggagaaa acg    33

<210> SEQ ID NO 62
<211> LENGTH: 35

```
<212> TYPE: DNA
<213> ORGANISM: Artificial Sequence
<220> FEATURE:
<223> OTHER INFORMATION: Description of Artificial Sequence: Primer

<400> SEQUENCE: 62
atggcgcgcc ctgagtgagg aactgggagc gatgg                              35

<210> SEQ ID NO 63
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 63
gcttaattaa cccttgcagt actcgtttgc ctttc                              35

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 64
taggcgcgcc agtgggtggt tggactgtaa gga                                33

<210> SEQ ID NO 65
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 65
gcttaattaa cttcgtcttg gacaggtaga ggttac                             36

<210> SEQ ID NO 66
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 66
atggcgcgcc gcctctcctg tggcctcaag c                                  31

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 67
atttaattaa cgtcgtctgc tgcacaattc cctccc                             36

<210> SEQ ID NO 68
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 68
```

```
atggcgcgcc ggctagtcgc attcacagag cagct                                35
```

<210> SEQ ID NO 69
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 69

```
cgttaattaa gcccttgcga tatccagcgt ttgac                                35
```

<210> SEQ ID NO 70
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 70

```
atggcgcgcc gataatcgtt gcgtagaggt ggcc                                 34
```

<210> SEQ ID NO 71
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 71

```
gcttaattaa gacttaaaaa tcgttggccc tctttcg                              37
```

<210> SEQ ID NO 72
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 72

```
atggcgcgcc gcgaaagaac cgattgggat tagg                                 34
```

<210> SEQ ID NO 73
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 73

```
atttaattaa cgaacataga ccgtaagtcg tgaggc                               36
```

SUGAR AND LIPID METABOLISM REGULATORS IN PLANTS

CROSS REFERENCE TO RELATED APPLICATIONS

This application is a divisional application of U.S. Nonprovisional patent application Ser. No. 10/100,294, which was filed on Mar. 18, 2002 now U.S. Pat. No. 7,105,723 and which claims priority benefit of U.S. Provisional Patent Application Ser. No. 60/276,993 filed Mar. 16, 2001, both of which are hereby incorporated in their entirety.

BACKGROUND OF THE INVENTION

1. Field of the Invention

A characteristic of seed development in most plants is the accumulation of storage compounds such as proteins, sugars and oil. This invention relates generally to nucleic acid sequences encoding proteins that are related to the presence of seed storage compounds in plants. More specifically, the present invention relates to nucleic acid sequences encoding sugar and lipid metabolism regulator proteins and the use of these sequences in transgenic plants.

2. Background Art

The study and genetic manipulation of plants has a long history that began even before the famed studies of Gregor Mendel. In perfecting this science, scientists have accomplished modification of particular traits in plants ranging from potato tubers having increased starch content to oilseed plants such as canola and sunflower having increased or altered fatty acid content. With the increased consumption and use of plant oils, the modification of seed oil content and seed oil levels has become increasingly widespread (e.g. Töpfer et al. 1995, Science 268: 681-686). Manipulation of biosynthetic pathways in transgenic plants provides a number of opportunities for molecular biologists and plant biochemists to affect plant metabolism giving rise to the production of specific higher-value products. The seed oil production or composition has been altered in numerous traditional oilseed plants such as soybean (U.S. Pat. No. 5,955,650), canola (U.S. Pat. No. 5,955,650), sunflower (U.S. Pat. No. 6,084,164) and rapeseed (Töpfer et al. 1995, Science 268: 681-686), and non-traditional oil seed plants such as tobacco (Cahoon et al. 1992, Proc. Natl. Acad. Sci. USA 89: 11184-11188).

Plant seed oils comprise both neutral and polar lipids (see Table 1). The neutral lipids contain primarily triacylglycerol, which is the main storage lipid that accumulates in oil bodies in seeds. The polar lipids are mainly found in the various membranes of the seed cells, e.g. the endoplasmic reticulum, microsomal membranes and the cell membrane. The neutral and polar lipids contain several common fatty acids (see Table 2) and a range of less common fatty acids. The fatty acid composition of membrane lipids is highly regulated and only a select number of fatty acids are found in membrane lipids. On the other hand, a large number of unusual fatty acids can be incorporated into the neutral storage lipids in seeds of many plant species (Van de Loo F. J. et al. 1993, Unusual Fatty Acids in Lipid Metabolism in Plants pp. 91-126, editor T S Moore Jr. CRC Press; Millar et al. 2000, Trends Plant Sci. 5: 95-101).

TABLE 1

| Plant Lipid Classes | |
| --- | --- |
| Neutral Lipids | Triacylglycerol (TAG) |
| | Diacylglycerol (DAG) |
| | Monoacylglycerol (MAG) |
| Polar Lipids | Monogalactosyldiacylglycerol (MGDG) |
| | Digalactosyldiacylglycerol (DGDG) |
| | Phosphatidylglycerol (PG) |
| | Phosphatidylcholine (PC) |
| | Phosphatidylethanolamine (PE) |
| | Phosphatidylinositol (PI) |
| | Phosphatidylserine (PS) |
| | Sulfoquinovosyldiacylglycerol |

TABLE 2

| Common Plant Fatty Acids | |
| --- | --- |
| 16:0 | Palmitic acid |
| 16:1 | Palmitoleic acid |
| 16:3 | Palmitolenic acid |
| 18:0 | Stearic acid |
| 18:1 | Oleic acid |
| 18:2 | Linoleic acid |
| 18:3 | Linolenic acid |
| γ-18:3 | Gamma-linolenic acid* |
| 20:0 | Arachidic acid |
| 22:6 | Docosahexanoic acid (DHA)* |
| 20:2 | Eicosadienoic acid |
| 20:4 | Arachidonic acid (AA)* |
| 20:5 | Eicosapentaenoic acid (EPA)* |
| 22:1 | Erucic acid |

*These fat acids do not normally occur in plant seed oils, but their production in transgenic plant seed oil is of importance in plant biotechnology.

Lipids are synthesized from fatty acids and their synthesis may be divided into two parts: the prokaryotic and the eukaryotic pathway (Browse et al. 1986, Biochemical J. 235: 25-31; Ohlrogge & Browse 1995, Plant Cell 7: 957-970). The prokaryotic pathway is located in plastids that are the primary site of fatty acid biosynthesis. Fatty acid synthesis begins with the conversion of acetyl-CoA to malonyl-CoA by acetyl-CoA carboxylase (ACCase). Malonyl-CoA is converted to malonyl-acyl carrier protein (ACP) by the malonyl-CoA:ACP transacylase. The enzyme beta-keto-acyl-ACP-synthase III (KAS III) catalyzes a condensation reaction in which the acyl group from acetyl-CoA is transferred to malonyl-ACP to form 3-ketobutyryl-ACP. In a subsequent series of condensation, reduction and dehydration reactions, the nascent fatty acid chain on the ACP cofactor is elongated by the step-by-step addition (condensation) of two carbon atoms donated by malonyl-ACP until a 16- or 18-carbon saturated fatty acid chain is formed. The plastidial delta-9 acyl-ACP desaturase introduces the first unsaturated double bond into the fatty acid. Thioesterases cleave the fatty acids from the ACP cofactor and free fatty acids are exported to the cytoplasm where they participate as fatty acyl-CoA esters in the eukaryotic pathway. In this pathway, the fatty acids are esterified by glycerol-3-phosphate acyltransferase and lysophosphatidic acid acyltransferase to the sn-1 and sn-2 positions of glycerol-3-phosphate, respectively, to yield phosphatidic acid (PA). The PA is the precursor for other polar and neutral lipids, the latter being formed in the Kennedy pathway (Voelker 1996, Genetic Engineering ed.: Setlow 18: 111-113; Shanklin & Cahoon 1998, Annu. Rev. Plant Physiol. Plant Mol. Biol. 49: 611-641; Frentzen 1998, Lipids 100: 161-166; Millar et al. 2000, Trends Plant Sci. 5: 95-101).

Acetyl-CoA in the plastids is the central precursor for lipid biosynthesis. Acetyl-CoA can be formed in the plastids by different reactions and the exact contribution of each reaction is still being debated (Ohlrogge & Browse 1995, Plant Cell 7: 957-970). It is however accepted that a large part of the acetyl-CoA is derived from glucose-6-phosphate and pyruvate that are imported from the cytoplasm into the plastids. Sucrose is produced in the source organs (leaves, or anywhere that photosynthesis occurs) and is transported to the developing seeds that are also termed sink organs. In the developing seeds, the sucrose is the precursor for all the storage compounds, i.e. starch, lipids and partly the seed storage proteins. Therefore, it is clear that carbohydrate metabolism in which sucrose plays a central role is very important to the accumulation of seed storage compounds.

Although lipid and fatty acid content of seed oil can be modified by the traditional methods of plant breeding, the advent of recombinant DNA technology has allowed for easier manipulation of the seed oil content of a plant, and in some cases, has allowed for the alteration of seed oils in ways that could not be accomplished by breeding alone (see, e.g., Töpfer et al. 1995, Science 268: 681-686). For example, introduction of a $\Delta^{12}$-hydroxylase nucleic acid sequence into transgenic tobacco resulted in the introduction of a novel fatty acid, ricinoleic acid, into the tobacco seed oil (Van de Loo et al. 1995, Proc. Natl. Acad. Sci. USA 92: 6743-6747). Tobacco plants have also been engineered to produce low levels of petroselinic acid by the introduction and expression of an acyl-ACP desaturase from coriander (Cahoon et al. 1992, Proc. Natl. Acad. Sci USA 89: 11184-11188).

The modification of seed oil content in plants has significant medical, nutritional and economic ramifications. With regard to the medical ramifications, the long chain fatty acids (C18 and longer) found in many seed oils have been linked to reductions in hypercholesterolemia and other clinical disorders related to coronary heart disease (Brenner 1976, Adv. Exp. Med. Biol. 83: 85-101). Therefore, consumption of a plant having increased levels of these types of fatty acids may reduce the risk of heart disease. Enhanced levels of seed oil content also increase large-scale production and thereby reduce the cost of these oils.

In order to increase or alter the levels of compounds such as seed oils in plants, nucleic acid sequences and proteins regulating lipid and fatty acid metabolism must be identified. As mentioned earlier, several desaturase nucleic acids such as the $\Delta^6$-desaturase nucleic acid, $\Delta^{12}$-desaturase nucleic acid and acyl-ACP desaturase nucleic acid have been cloned and demonstrated to encode enzymes required for fatty acid synthesis in various plant species. Oleosin nucleic acid sequences from such different species as *Brassica*, soybean, carrot, pine and *Arabidopsis thaliana* have also been cloned and determined to encode proteins associated with the phospholipid monolayer membrane of oil bodies in those plants.

Storage lipids in seeds are synthesized from carbohydrate derived precursors. Plants do have a complete glycolytic pathway in the cytosol (Plaxton 1996, Annu. Rev. Plant Physiol. Plant Mol. Biol. 47: 185-214) and it has been shown that a complete pathway also exists in the plastids of rapeseeds (Kang & Rawsthorne 1994, Plant J. 6: 795-805). Sucrose is the primary source of carbon and energy, transported from the leaves into the developing seeds. During the storage phase of seeds, sucrose is converted in the cytosol to provide the metabolic precursors glucose-6-phosphate and pyruvate. These are transported into the plastids and converted into acetyl-CoA that serves as the primary precursor for the synthesis of fatty acids. Although several nucleic acids that are involved in enzymatic steps of the metabolism of lipids, fatty acids and starch have been cloned and identified, there are likely a multitude of such plant nucleic acids that have yet to be identified. Phenotypic analysis of several oilseed plants and other mutated plants has revealed other putative proteins involved in plant lipid metabolism, but the prior art has yet to describe the genomic location of these proteins or the sequence of the nucleic acids that encode them.

An exemplary study is that of the oilseed plant *Arabidopsis thaliana*. Focks and Benning (1998, Plant Physiol. 118: 91-101) isolated and characterized a wrinkled mutant of *Arabidopsis thaliana* designated wri1. The wri1 mutant has a decreased seed oil content that was speculated to be due to a defect in the seed-specific regulation of carbohydrate metabolism. In the wri1 mutant, the activities of several glycoltic enzymes were reduced and the mutant seeds were impaired in the incorporation of sucrose and glucose into triacylglycerol lipids, while important precursor molecules for plastidial lipid biosynthesis, like pyruvate and acetate, were incorporated at increased rates. This biochemical evidence was interpreted by Focks & Benning (1998, Plant Physiol. 118: 91-101) as indication that the WRI1 protein could be a regulatory protein governing carbohydrate metabolism during seed development.

The regulation of protein phosphorylation by kinases and phosphatases is accepted as a universal mechanism of cellular control (Cohen 1992, Trends Biochem. Sci, 17: 408-413), and $Ca^{2+}$ and calmodulin signals are frequently transduced via $Ca^{2+}$ and calmodulin-dependent kinases and phosphatases (Roberts & Harmon 1992, Annu. Rev. Plant Physiol. Plant Mol. Biol. 43: 375-414.). Okadaic acid, a protein phosphatase inhibitor, has been found to affect both gibberellic (GA) and absisic acid (ABA) pathways (Kuo et al. 1996, Plant Cell. 8: 259-269). Although the molecular basis of GA and ABA signal transduction remains poorly understood, it seems well established that the two phytohormones are involved in overall regulatory processes in seed development (e.g. Ritchie & Gilroy 1998, Plant Physiol. 116: 765-776).

There is a clear need to specifically identify factors that are more specific for the developmental regulation of storage compound accumulation. In order to find specific key regulatory genes controlling seed oil and sugar biosynthesis, transcription factors, protein kinases and phosphates provide proteins which can alter seed storage compound production. Elucidating the function of genes directly and/or indirectly involved in oil production provides important information for designing new strategies for crop improvement. There is a need, therefore, to identify genes which have the capacity to confer altered or increased oil production to its host plant and to other plant species. Particularly well suited plants for this purpose are oilseed plants containing high amounts of lipid compounds like rapeseed, canola, linseed, soybean, sunflower maize, oat, rye, barley, wheat, sugarbeet, tagetes, cotton, oil palm, coconut palm, flax, castor and peanut, for example.

SUMMARY OF THE INVENTION

The present invention provides novel isolated nucleic acid and amino acid sequences associated with the metabolism of seed storage compounds in plants. More particularly, the present invention provides an isolated nucleic acid from a moss encoding a Lipid Metabolism Protein (LMP), or a portion thereof. The moss can be, but is not limited to, *Physcomitrella patens* or *Ceratodon purpureus*. These sequences may be used to modify or increase lipids or oil and/or fatty acids, cofactors, carbohydrates, and enzymes in microorganisms and plants.

Mosses and algae are the only known plant systems that produce considerable amounts of fatty acids like arachidonic acid and/or eicosapentaenoic acid and/or docosahexaenoic acid (see, e.g., Table 2). Therefore, nucleic acid molecules originating from a moss like *Physcomitrella patens* are especially suited to modify the lipid and fatty acid metabolism in a host, especially in microorganisms and plants. Furthermore, nucleic acids from the moss *Physcomitrella patens* can be used to identify those DNA sequences and enzymes in other species which are useful to modify the biosynthesis of precursor molecules of fatty acids in the respective organisms.

The present invention further provides an isolated nucleic acid comprising a fragment of at least 15 nucleotides of a nucleic acid from a moss encoding a Lipid Metabolism Protein (LMP), or a portion thereof.

Also provided by the present invention are polypeptides encoded by the nucleic acids, and heterologous polypeptides comprising polypeptides encoded by the nucleic acids, and antibodies to those polypeptides.

More particularly, the present invention relates to the use of LMP nucleic acids in the production of transgenic plants having a modified level of a seed storage compound. A method of producing a transgenic plant with a modified level of a seed storage compound includes the steps of transforming a plant cell with an expression vector comprising a LMP nucleic acid, and generating a plant with a modified level of the seed storage compound from the plant cell. In a preferred embodiment, the plant is an oil producing species selected from the group consisting of rapeseed, canola, linseed, soybean, sunflower, maize, oat, rye, barley, wheat, sugarbeet, tagetes, cotton, oil palm, coconut palm, flax, castor and peanut, for example.

Also included herein is a seed produced by a transgenic plant transformed by a LMP DNA sequence, wherein the seed contains the LMP DNA sequence and wherein the plant is true breeding for a modified level of a seed storage compound. The present invention additionally includes a seed oil produced by the aforementioned seed.

Further provided by the present invention are vectors comprising the nucleic acids, host cells containing the vectors, and descendent plant materials produced by transforming a plant cell with the nucleic acids and/or vectors.

According to the present invention, the compounds, compositions, and methods described herein can be used to increase or decrease the level of a lipid in a seed oil, or to increase or decrease the level of a fatty acid in a seed oil, or to increase or decrease the level of a starch or other carbohydrate in a seed or plant. A method of producing a higher or lower than normal or typical level of storage compound in a transgenic plant, comprises expressing a LMP nucleic acid from *Physcomitrella patens* in the transgenic plant, wherein the transgenic plant is a species different from *Physcomitrella patens*. Also included herein are compositions and methods of the modification of the efficiency of production of a seed storage compound.

Accordingly, it is an object of the present invention to provide novel isolated LMP nucleic acids and isolated LMP amino acid sequences from *Physcomitrella patens*, as well as active fragments, analogs, and orthologs thereof and allelic variants and active fragments, analogs, and orthologs thereof.

It is another object of the present invention to provide transgenic plants having modified levels of seed storage compounds, and in particular, modified levels of a lipid, a fatty acid or a starch.

It is a further object of the present invention to provide methods for producing such aforementioned transgenic plants.

It is another object of the present invention to provide descendants, seeds, reproducible cell material, and seed oils from such aforementioned transgenic plants.

It is another object of the present invention to provide a method of producing a polypeptide comprising culturing the host cell provided herein under conditions appropriate for the host cell to express the nucleic acid and thereby produce the polypeptide.

It is another object of the present invention to provide an isolated LMP polypeptide from mosses, plants, or algae, or a portion thereof especially wherein the polypeptide is involved in increased or altered fatty acid production, or allelic variants thereof, and compounds further comprising heterologous polypeptides thereof.

It is another object of the present invention to provide an antibody which specifically binds to a LMP polypeptide provided herein or a compound derived therefrom, or a portion thereof. These antibodies can be used, for example, to identify and/or purify LMP polypeptides or fragments thereof. These antibodies can be used as part of a kit.

It is another object of the present invention to provide a test kit comprising a portion and/or a complement of the nucleic acid provided herein, which can be used, for example, as a probe or primer for identifying and/or cloning nucleic acid molecules involved in increased or altered fatty acid production.

It is another object of the present invention to provide a method of increasing or altering the fatty acid production of a cell comprising culturing a cell containing a vector as provided herein such that the fatty acid composition of the cell is altered or increased.

It is another object of the present invention to provide a method for increasing or altering fatty acid production of a cell, comprising culturing a cell whose genomic DNA has been altered by the inclusion of a nucleic acid molecule provided herein.

These and other objects, features and advantages of the present invention will become apparent after a review of the following detailed description of the disclosed embodiments and the appended claims.

BRIEF DESCRIPTION OF THE FIGURES

FIGS. 1A-C: FIG. 1A shows the polynucleotide sequences of Clone ID NO: s_pp001031077f from *Physcomitrella patens* (SEQ ID NO:1) of the present invention. The polynucleotide sequence contains a sequence of 2908 nucleotides. FIG. 1B shows the polynucleotide sequences of the open reading frame of SEQ ID NO:1 from *Physcomitrella patens* (SEQ ID NO:2) (Clone ID NO: s_pp001031077f) of the present invention. The polynucleotide sequence contains a sequence of 2493 nucleotides. FIG. 1C shows the deduced amino acid sequence of SEQ ID NO:2 (SEQ ID NO:3) (Clone ID NO: s_pp001031077f) of the present invention. The polypeptide sequence contains a sequence of 831 amino acids. The standard one-letter abbreviation for amino acids is used to illustrate the deduced amino acid sequence.

FIG. 2A-C: FIG. 2A shows the polynucleotide sequences of Clone ID NO: s_pp001117032r from *Physcomitrella patens* (SEQ ID NO:4) of the present invention. The polynucleotide sequence contains a sequence of 1122 nucleotides. FIG. 2B shows the polynucleotide sequences of the open reading frame of SEQ ID NO:4 from *Physcomitrella patens* (SEQ ID NO:5) (Clone ID NO: s_pp001117032r) of the present invention. The polynucleotide sequence contains a sequence of 933 nucleotides. FIG. 2C shows the deduced amino acid sequence of SEQ ID NO:5 (SEQ ID NO:6) (Clone ID NO:

s_pp001117032r) of the present invention. The polypeptide sequence contains a sequence of 311 amino acids. The standard one-letter abbreviation for amino acids is used to illustrate the deduced amino acid sequence.

FIGS. 3A-C: FIG. 3A shows the polynucleotide sequences of Clone ID NO: c_pp001113065r from *Physcomitrella patens* (SEQ ID NO:7) of the present invention. The polynucleotide sequence contains a sequence of 2417 nucleotides. FIG. 3B shows the polynucleotide sequences of the open reading frame of SEQ ID NO:7 from *Physcomitrella patens* (SEQ ID NO:8) (Clone ID NO: c_pp001113065r) of the present invention. The polynucleotide sequence contains a sequence of 1323 nucleotides. FIG. 3C shows the deduced amino acid sequence of SEQ ID NO:8 (SEQ ID NO:9) (Clone ID NO: c_pp001113065r) of the present invention. The polypeptide sequence contains a sequence of 441 amino acids. The standard one-letter abbreviation for amino acids is used to illustrate the deduced amino acid sequence.

FIGS. 4A-C: FIG. 4A shows the polynucleotide sequences of Clone ID NO: c_pp004047195r from *Physcomitrella patens* (SEQ ID NO:10) of the present invention. The polynucleotide sequence contains a sequence of 1818 nucleotides. FIG. 4B shows the polynucleotide sequences of the open reading frame of SEQ ID NO:10 from *Physcomitrella patens* (SEQ ID NO:11) (Clone ID NO: c_pp004047195r) of the present invention. The polynucleotide sequence contains a sequence of 1419 nucleotides. FIG. 4C shows the deduced amino acid sequence of SEQ ID NO:11 (SEQ ID NO:12) (Clone ID NO: c_pp004047195r) of the present invention. The polypeptide sequence contains a sequence of 473 amino acids. The standard one-letter abbreviation for amino acids is used to illustrate the deduced amino acid sequence.

FIGS. 5A-C: FIG. 5A shows the polynucleotide sequences of Clone ID NO: c_pp001058012r from *Physcomitrella patens* (SEQ ID NO:13) of the present invention. The polynucleotide sequence contains a sequence of 1274 nucleotides. FIG. 5B shows the polynucleotide sequences of the open reading frame of SEQ ID NO:13 from *Physcomitrella patens* (SEQ ID NO:14) (Clone ID NO: c_pp001058012r) of the present invention. The polynucleotide sequence contains a sequence of 1017 nucleotides. FIG. 5C shows the deduced amino acid sequence of SEQ ID NO:14 (SEQ ID NO:15) (Clone ID NO: c_pp001058012r) of the present invention. The polypeptide sequence contains a sequence of 339 amino acids. The standard one-letter abbreviation for amino acids is used to illustrate the deduced amino acid sequence.

FIGS. 6A-C: FIG. 6A shows the polynucleotide sequences of Clone ID NO: c_pp001009079f from *Physcomitrella patens* (SEQ ID NO:16) of the present invention. The polynucleotide sequence contains a sequence of 1626 nucleotides. FIG. 6B shows the polynucleotide sequences of the open reading frame of SEQ ID NO:16 from *Physcomitrella patens* (SEQ ID NO:17) (Clone ID NO: c_pp001009079f) of the present invention. The polynucleotide sequence contains a sequence of 1455 nucleotides. FIG. 6C shows the deduced amino acid sequence of SEQ ID NO:17 (SEQ ID NO:18) (Clone ID NO: c_pp001009079f) of the present invention. The polypeptide sequence contains a sequence of 485 amino acids. The standard one-letter abbreviation for amino acids is used to illustrate the deduced amino acid sequence.

FIGS. 7A-C: FIG. 7A shows the polynucleotide sequences of Clone ID NO: c_pp004076330r from *Physcomitrella patens* (SEQ ID NO:19) of the present invention. The polynucleotide sequence contains a sequence of 2291 nucleotides. FIG. 7B shows the polynucleotide sequences of the open reading frame of SEQ ID NO:19 from *Physcomitrella patens* (SEQ ID NO:20) (Clone ID NO: c_pp004076330r) of the present invention. The polynucleotide sequence contains a sequence of 2052 nucleotides. FIG. 7C shows the deduced amino acid sequence of SEQ ID NO:20 (SEQ ID NO:21) (Clone ID NO: c_pp004076330r) of the present invention. The polypeptide sequence contains a sequence of 684 amino acids. The standard one-letter abbreviation for amino acids is used to illustrate the deduced amino acid sequence.

FIGS. 8A-C: FIG. 8A shows the polynucleotide sequences of Clone ID NO: c_pp004040301r from *Physcomitrella patens* (SEQ ID NO:22) of the present invention. The polynucleotide sequence contains a sequence of 1962 nucleotides. FIG. 5B shows the polynucleotide sequences of the open reading frame of SEQ ID NO:22 from *Physcomitrella patens* (SEQ ID NO:23) (Clone ID NO: c_pp004040301r) of the present invention. The polynucleotide sequence contains a sequence of 1944 nucleotides. FIG. 5C shows the deduced amino acid sequence of SEQ ID NO:23 (SEQ ID NO:24) (Clone ID NO: c_pp004040301r) of the present invention. The polypeptide sequence contains a sequence of 648 amino acids. The standard one-letter abbreviation for amino acids is used to illustrate the deduced amino acid sequence.

FIGS. 9A-C: FIG. 9A shows the polynucleotide sequences of Clone ID NO: c_pp002024092r from *Physcomitrella patens* (SEQ ID NO:25) of the present invention. The polynucleotide sequence contains a sequence of 2321 nucleotides. FIG. 9B shows the polynucleotide sequences of the open reading frame of SEQ ID NO:25 from *Physcomitrella patens* (SEQ ID NO:26) (Clone ID NO: c_pp002024092r) of the present invention. The polynucleotide sequence contains a sequence of 2241 nucleotides. FIG. 9C shows the deduced amino acid sequence of SEQ ID NO:26 (SEQ ID NO:27) (Clone ID NO: c_pp002024092r) of the present invention. The polypeptide sequence contains a sequence of 747 amino acids. The standard one-letter abbreviation for amino acids is used to illustrate the deduced amino acid sequence.

FIGS. 10A-C: FIG. 10A shows the polynucleotide sequences of Clone ID NO: c_pp001031042f from *Physcomitrella patens* (SEQ ID NO:28) of the present invention. The polynucleotide sequence contains a sequence of 1072 nucleotides. FIG. 10B shows the polynucleotide sequences of the open reading frame of SEQ ID NO:28 from *Physcomitrella patens* (SEQ ID NO:29) (Clone ID NO: c_pp001031042f) of the present invention. The polynucleotide sequence contains a sequence of 930 nucleotides. FIG. 10C shows the deduced amino acid sequence of SEQ ID NO:29 (SEQ ID NO:30) (Clone ID NO: c_pp001031042f) of the present invention. The polypeptide sequence contains a sequence of 310 amino acids. The standard one-letter abbreviation for amino acids is used to illustrate the deduced amino acid sequence.

FIGS. 11A-C. FIG. 11A shows the polynucleotide sequences of Clone ID NO: c_pp032010072r from *Physcomitrella patens* (SEQ ID NO:31) of the present invention. The polynucleotide sequence contains a sequence of 1275 nucleotides. FIG. 11B shows the polynucleotide sequences of the open reading frame of SEQ ID NO:31 from *Physcomitrella patens* (SEQ ID NO:32) (Clone ID NO: c_pp032010072r) of the present invention. The polynucleotide sequence contains a sequence of 1209 nucleotides. FIG. 11C shows the deduced amino acid sequence of SEQ ID NO:32 (SEQ ID NO:33) (Clone ID NO: c_pp032010072r) of the present invention. The polypeptide sequence contains a sequence of 403 amino acids. The standard one-letter abbreviation for amino acids is used to illustrate the deduced amino acid sequence.

FIGS. 12A-C. FIG. 12A shows the polynucleotide sequences of Clone ID NO: s_pp001068093r from *Physcomi-* trella patens (SEQ ID NO:34) of the present invention. The polynucleotide sequence contains a sequence of 1939 nucleotides. FIG. 12B shows the polynucleotide sequences of the open reading frame of SEQ ID NO:34 from Physcomitrella patens (SEQ ID NO:35) (Clone ID NO: s_pp001068093r) of the present invention. The polynucleotide sequence contains a sequence of 1776 nucleotides. FIG. 12C shows the deduced amino acid sequence of SEQ ID NO:35 (SEQ ID NO:36) (Clone ID NO: s_pp001068093r) of the present invention. The polypeptide sequence contains a sequence of 592 amino acids. The standard one-letter abbreviation for amino acids is used to illustrate the deduced amino acid sequence.

FIGS. 13A-C. FIG. 13A shows the polynucleotide sequences of Clone ID NO: s_pp013010011r from Physcomitrella patens (SEQ ID NO:37) of the present invention. The polynucleotide sequence contains a sequence of 1522 nucleotides. FIG. 13B shows the polynucleotide sequences of the open reading frame of SEQ ID NO:37 from Physcomitrella patens (SEQ ID NO:38) (Clone ID NO: s_pp013010011r) of the present invention. The polynucleotide sequence contains a sequence of 1092 nucleotides. FIG. 13C shows the deduced amino acid sequence of SEQ ID NO:38 (SEQ ID NO:39) (Clone ID NO: s_pp013010011 r) of the present invention. The polypeptide sequence contains a sequence of 364 amino acids. The standard one-letter abbreviation for amino acids is used to illustrate the deduced amino acid sequence.

FIGS. 14A-C. FIG. 14A shows the polynucleotide sequences of Clone ID NO: c_pp004096088r from Physcomitrella patens (SEQ ID NO:40) of the present invention. The polynucleotide sequence contains a sequence of 1275 nucleotides. FIG. 14B shows the polynucleotide sequences of the open reading frame of SEQ ID NO:40 from Physcomitrella patens (SEQ ID NO:41) (Clone ID NO: c_pp004096088r) of the present invention. The polynucleotide sequence contains a sequence of 1209 nucleotides. FIG. 14C shows the deduced amino acid sequence of SEQ ID NO:41 (SEQ ID NO:42) (Clone ID NO: c_pp004096088r) of the present invention. The polypeptide sequence contains a sequence of 403 amino acids. The standard one-letter abbreviation for amino acids is used to illustrate the deduced amino acid sequence.

DETAILED DESCRIPTION OF THE INVENTION

The present invention is directed to novel isolated nucleic acid and amino acid sequences associated with the metabolism of seed storage compounds in plants. The present invention may be understood more readily by reference to the following detailed description of the preferred embodiments of the invention and the Examples included therein.

Before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing particular embodiments only and is not intended to be limiting.

As used in the specification and in the claims, "a" or "an" can mean one or more, depending upon the context in which it is used. Thus, for example, reference to "a cell" can mean that at least one cell can be utilized.

In accordance with the purpose(s) of this invention, as embodied and broadly described herein, this invention, in one aspect, provides an isolated nucleic acid from a moss encoding a Lipid Metabolism Protein (LMP), or a portion thereof. One aspect of the invention pertains to isolated nucleic acid molecules that encode LMP polypeptides or biologically active portions thereof, as well as nucleic acid fragments sufficient for use as hybridization probes or primers for the identification or amplification of LMP-encoding nucleic acid (e.g., LMP DNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of the gene: at least about 1000 nucleotides of sequence upstream from the 5 end of the coding region and at least about 200 nucleotides of sequence downstream from the 3' end of the coding region of the gene. The nucleic acid molecule can be single-stranded or double-stranded, but preferably is double-stranded DNA.

An "isolated" nucleic acid molecule is one which is substantially separated from other nucleic acid molecules which are present in the natural source of the nucleic acid. Preferably, an "isolated" nucleic acid is substantially free of sequences which naturally flank the nucleic acid (i.e., sequences located at the 5' and 3' ends of the nucleic acid) in the genomic DNA of the organism from which the nucleic acid is derived. For example, in various embodiments, the isolated LMP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g, a Physcomitrella patens cell). Moreover, an "isolated" nucleic acid molecule, such as a cDNA molecule, can be substantially free of other cellular material, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

In a preferred embodiment, an isolated nucleic acid of the invention comprises one of the polynucleotide sequences shown in SEQ ID NO:1, SEQ ID NO:2, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, SEQ ID NO:17, SEQ ID NO:19, SEQ ID NO:20, SEQ ID NO:22, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:38, SEQ ID NO:40 or SEQ ID NO:41. These polynucleotide sequences correspond to the *Physcomitrella patens* LMP cDNAs of the invention. These cDNAs comprise sequences encoding LMPs (i.e., the "coding region"), as well as 5' untranslated sequences and 3' untranslated sequences or can contain whole genomic fragments isolated from genomic DNA. Alternatively, the nucleic acid molecules can comprise only the coding region of any of the polynucleotide sequences described herein. Examples of polynucleotides comprising only the coding region or open reading frame (ORF) are shown in SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, or SEQ ID NO:41.

In another preferred embodiment an isolated nucleic acid molecule of the present invention encodes a polypeptide that is able to participate in the metabolism of seed storage compounds such as lipids, starch and seed storage proteins and that contains a transcription factor domain, a protein kinase domain or a signal transduction domain. Examples of isolated LMPs that contain such domains can be found in Table 4: LMPs containing a transcription factor domain include those shown in SEQ ID NO:3, SEQ ID NO:6, SEQ ID NO:9, SEQ ID NO:15 and SEQ ID NO:36; LMPs containing a protein kinase domain include those shown in SEQ ID NO:12, SEQ ID NO:18, SEQ ID NO:21, SEQ ID NO:30 and SEQ ID NO:42; LMPs containing a signal transduction domain include those shown in SEQ ID NO:24, SEQ ID NO:27, SEQ ID NO:33 and SEQ ID NO:39.

In yet another preferred embodiment, an isolated nucleic acid molecule of the invention comprises a nucleic acid molecule which is a complement of one of the nucleotide sequences shown in SEQ ID NO:1, SEQ ID NO:2, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, SEQ ID NO:17, SEQ ID NO:19, SEQ ID NO:20, SEQ ID NO:22, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:38, SEQ ID NO:40 or SEQ ID NO:41, or a portion thereof. As used herein, the term "complementary" refers to a nucleotide sequence that can hybridize to one of the nucleotide sequences shown in SEQ ID NO:1, SEQ ID NO:2, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, SEQ ID NO:17, SEQ ID NO:19, SEQ ID NO:20, SEQ ID NO:22, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:38, SEQ ID NO:40 or SEQ ID NO:41, thereby forming a stable duplex.

In still another preferred embodiment, an isolated nucleic acid molecule of the invention comprises a polynucleotide sequence which is at least about 50-60%, preferably at least about 60-70%, more preferably at least about 70-80%, 80-90%, or 90-95%, and even more preferably at least about 95%, 96%, 97%, 98%, 99% or more homologous to a nucleotide sequence shown in SEQ ID NO:1, SEQ ID NO:2, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, SEQ ID NO:17, SEQ ID NO:19, SEQ ID NO:20, SEQ ID NO:22, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:38, SEQ ID NO:40 or SEQ ID NO:41, or a portion thereof. In an additional preferred embodiment, an isolated nucleic acid molecule of the invention comprises a nucleotide sequence which hybridizes, e.g., hybridizes under stringent conditions, to one of the nucleotide sequences shown in SEQ ID NO:1, SEQ ID NO:2, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, SEQ ID NO:17, SEQ ID NO:19, SEQ ID NO:20, SEQ ID NO:22, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:38, SEQ ID NO:40 or SEQ ID NO:41, or a portion thereof. These hybridization conditions include washing with a solution having a salt concentration of about 0.02 molar at pH 7 at about 60° C.

Moreover, the nucleic acid molecule of the invention can comprise only a portion of one of the polynucleotide sequences shown in SEQ ID NO:1, SEQ ID NO:2, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, SEQ ID NO:17, SEQ ID NO:19, SEQ ID NO:20, SEQ ID NO:22, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:38, SEQ ID NO:40 or SEQ ID NO:41, for example a fragment which can be used as a probe or primer or a fragment encoding a biologically active portion of a LMP. The nucleotide sequences determined from the cloning of the LMP genes from *P. patens* allows for the generation of probes and primers designed for use in identifying and/or cloning LMP homologues in other cell types and organisms, as well as LMP homologues from other mosses or related species.

Therefore, this invention also provides compounds comprising the nucleic acids disclosed herein, or fragments thereof. These compounds include the nucleic acids attached to a moiety. These moieties include, but are not limited to, detection moieties, hybridization moieties, purification moieties, delivery moieties, reaction moieties, binding moieties, and the like. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the LMP polynucleotide sequences described herein, an anti-sense sequence of one of the LMP polynucleotide sequences described herein, or naturally occurring mutants thereof. Primers based on a LMP polynucleotide sequence described herein can be used in PCR reactions to clone LMP homologues. Probes based on the LMP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a LMP, such as by measuring a level of a LMP-encoding nucleic acid in a sample of cells, e.g., detecting LMP mRNA levels or determining whether a genomic LMP gene has been mutated or deleted.

In one embodiment, the nucleic acid molecule of the invention encodes a protein or portion thereof which includes an amino acid sequence which is sufficiently homologous to a LMP amino acid sequence shown in SEQ ID NO:3, SEQ ID NO:6, SEQ ID NO:9, SEQ ID NO:12, SEQ ID NO:15, SEQ ID NO:18, SEQ ID NO:21, SEQ ID NO:24, SEQ ID NO:27, SEQ ID NO:30, SEQ ID NO:33, SEQ ID NO:36, SEQ ID NO:39, or SEQ ID NO:42 such that the protein or portion thereof maintains the same or a similar function as the LMP amino acid sequence. As used herein, the language "sufficiently homologous" refers to proteins or portions thereof that have amino acid sequences that include a minimum number of identical or equivalent amino acid residues when compared to an amino acid sequence of SEQ ID NO:3, SEQ ID NO:6, SEQ ID NO:9, SEQ ID NO:12, SEQ ID NO:15, SEQ ID NO:18, SEQ ID NO:21, SEQ ID NO:24, SEQ ID NO:27, SEQ ID NO:30, SEQ ID NO:33, SEQ ID NO:36, SEQ ID NO:39, or SEQ ID NO:42 such that the protein or portion thereof is able to participate in the metabolism of seed storage compounds such as lipids, starch and seed storage proteins or has an activity described in Table 3.

As altered or increased fatty acid production is a general trait wished to be inherited into a wide variety of plants like maize, wheat, rye, oat, triticale, rice, barley, soybean, peanut, cotton, rapeseed and canola, sunflower, tagetes, sugarbeet, solanaceous plants like potato, tobacco, eggplant, and tomato, Vicia species, pea, alfalfa, bushy plants (coffee, cacao, tea), Salix species, trees (oil palm, coconut) and perennial grasses and forage crops, these crops plants are also preferred target plants for genetic engineering as one further embodiment of the present invention.

Portions of proteins encoded by the LMP nucleic acid molecules of the invention are preferably biologically active portions of one of the LMPs. As used herein, the term "biologically active portion of a LMP" is intended to include a portion, e.g., a domain/motif, of a LMP that participates in the metabolism of compounds necessary for the production of seed storage compounds, for the construction of cellular membranes in microorganisms or plants, or in the transport of molecules across these membranes, or has an activity as set forth in Table 3. To determine whether a LMP or a biologically active portion thereof can participate in the metabolism of compounds necessary for the production of seed storage compounds and cellular membranes, an assay of enzymatic activity may be performed. Such assay methods are well known to those skilled in the art, as detailed in Example 14.

Biologically active portions of a LMP include peptides comprising amino acid sequences derived from the amino acid sequence of a LMP (e.g., an amino acid sequence of SEQ ID NO:3, SEQ ID NO:6, SEQ ID NO:9, SEQ ID NO:12, SEQ ID NO:15, SEQ ID NO:18, SEQ ID NO:21, SEQ ID NO:24, SEQ ID NO:27, SEQ ID NO:30, SEQ ID NO:33, SEQ ID NO:36, SEQ ID NO:39, or SEQ ID NO:42 or the amino acid sequence of a protein homologous to a LMP, which include fewer amino acids than a full length LMP or the full length protein which is homologous to a LMP) and exhibit at least one activity of a LMP. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of a LMP. Moreover, other biologically active portions, in which other regions of the protein are deleted, can be prepared by recombinant techniques and evaluated for one or more of the activities described herein. Preferably, the biologically active portions of a LMP include one or more selected domains/motifs or portions thereof having biological activity.

Additional nucleic acid fragments encoding biologically active portions of a LMP can be prepared by isolating a portion of one of the sequences, expressing the encoded portion of the LMP or peptide (e.g., by recombinant expression in vitro) and assessing the activity of the encoded portion of the LMP or peptide.

The invention further encompasses nucleic acid molecules that differ from one of the polynucleotide sequences shown in SEQ ID NO:1, SEQ ID NO:2, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, SEQ ID NO:17, SEQ ID NO:19, SEQ ID NO:20, SEQ ID NO:22, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:38, SEQ ID NO:40 or SEQ ID NO:41 (and portions thereof) due to degeneracy of the genetic code and thus encode the same LMP as that encoded by the aforementioned polynucleotide sequences. In a further embodiment, the nucleic acid molecule of the invention encodes a full length Physcomitrella patens protein which is substantially homologous to an amino acid sequence of a polypeptide encoded by an open reading frame shown in SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, or SEQ ID NO:41.

In addition to the Physcomitrella patens LMP nucleotide sequences described herein, it will be appreciated by those skilled in the art that DNA sequence polymorphisms that lead to changes in the amino acid sequences of LMPs may exist within a population (e.g., the Physcomitrella patens population). Such genetic polymorphism in the LMP gene may exist among individuals within a population due to natural variation. As used herein, the terms "gene" and "recombinant gene" refer to nucleic acid molecules comprising an open reading frame encoding a LMP, preferably a Physcomitrella patens LMP. Such natural variations can typically result in 1-5% variance in the nucleotide sequence of the LMP gene. Any and all such nucleotide variations and resulting amino acid polymorphisms in LMP that are the result of natural variation and that do not alter the functional activity of LMPs are intended to be within the scope of the invention.

Nucleic acid molecules corresponding to natural variants and non-Physcomitrella patens orthologs of the Physcomitrella patens LMP cDNA of the invention can be isolated based on their homology to Physcomitrella patens LMP nucleic acid disclosed herein using the Physcomitrella patens cDNA, or a portion thereof, as a hybridization probe according to standard hybridization techniques under stringent hybridization conditions. As used herein with regard to hybridization for DNA to DNA blot, the term "stringent conditions" refers to hybridization overnight at 60° C. in 10× Denhart's solution, 6×SSC, 0.5% SDS and 100 µg/ml denatured salmon sperm DNA. Blots are washed sequentially at 62° C. for 30 minutes each time in 3×SSC/0.1% SDS, followed by 1×SSC/0.1% SDS and finally 0.1×SSC/0.1% SDS. As also used herein, "highly stringent conditions" refers to hybridization overnight at 65° C. in 10× Denhart's solution, 6×SSC, 0.5% SDS and 100 g/ml denatured salmon sperm DNA. Blots are washed sequentially at 65° C. for 30 minutes each time in 3×SSC/0.1% SDS, followed by 1×SSC/0.1% SDS and finally 0.1×SSC/0.1% SDS. Methods for nucleic acid hybridizations are described in Meinkoth and Wahl, 1984 Anal. Biochem. 138:267-284; Current Protocols in Molecular Biology, Chapter 2, Ausubel et al. Eds., Greene Publishing and Wiley-Interscience, New York, 1995; and Tijssen, Laboratory Techniques in Biochemistry and Molecular Biology: Hybridization with Nucleic Acid Probes, Part I, Chapter 2, Elsevier, New York, 1993. Preferably, an isolated nucleic acid molecule of the invention that hybridizes under stringent or highly stringent conditions to a sequence of SEQ ID NO:1, SEQ ID NO:2, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, SEQ ID NO:17, SEQ ID NO:19, SEQ ID NO:20, SEQ ID NO:22, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:38, SEQ ID NO:40 or SEQ ID NO:41 corresponds to a naturally occurring nucleic acid molecule. In one embodiment, the nucleic acid encodes a natural *Physcomitrella patens* LMP.

Accordingly, in another embodiment, an isolated nucleic acid molecule of the invention is at least 15 nucleotides in length and hybridizes under stringent conditions to the nucleic acid molecule comprising a nucleotide sequence of SEQ ID NO:1, SEQ ID NO:2, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, SEQ ID NO:17, SEQ ID NO:19 SEQ ID NO:20, SEQ ID NO:22, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:38, SEQ ID NO:40 or SEQ ID NO:41. In other embodiments, the nucleic acid is at least 30, 50, 100, 250 or more nucleotides in length.

In addition to naturally-occurring variants of the LMP sequence that may exist in the population, the skilled artisan will further appreciate that changes can be introduced by mutation into a LMP polynucleotide sequence provided herein, thereby leading to changes in the amino acid sequence of the encoded LMP, without altering the functional ability of the LMP. For example, nucleotide substitutions leading to amino acid substitutions at "non-essential" amino acid residues can be made in a LMP polynucleotide sequence. A "non-essential" amino acid residue is a residue that can be altered from the wild-type sequence of one of the LMPs provided herein without altering the activity of said LMP, whereas an "essential" amino acid residue is required for LMP activity. Other amino acid residues, however, (e.g., those that are not conserved or only semi-conserved in the domain having LMP activity) may not be essential for activity and thus are likely to be amenable to alteration without altering LMP activity.

Accordingly, another aspect of the invention pertains to nucleic acid molecules encoding LMPs that contain changes in amino acid residues that are not essential for LMP activity. Such LMPs differ in amino acid sequence from a sequence yet retain at least one of the LMP activities described herein. In one embodiment, the isolated nucleic acid molecule comprises a nucleotide sequence encoding a protein, wherein the protein comprises an amino acid sequence at least about 50% homologous to an amino acid sequence shown in SEQ ID NO:3, SEQ ID NO:6, SEQ ID NO:9, SEQ ID NO:12, SEQ ID NO:15, SEQ ID NO:18, SEQ ID NO:21, SEQ ID NO:24, SEQ ID NO:27, SEQ ID NO:30, SEQ ID NO:33, SEQ ID NO:36, SEQ ID NO:39, or SEQ ID NO:42 and is capable of participation in the metabolism of compounds necessary for the production of seed storage compounds in *Physcomitrella patens*, or cellular membranes, or has one or more activities set forth in Table 3. Preferably, the protein encoded by the nucleic acid molecule is at least about 50-60% homologous, more preferably at least about 60-70% homologous, even more preferably at least about 70-80%, 80-90%, 90-95% homologous, and most preferably at least about 96%, 97%, 98%, or 99% homologous to one of the amino acid sequences shown in SEQ ID NO:3, SEQ ID NO:6, SEQ ID NO:9, SEQ ID NO:12, SEQ ID NO:15, SEQ ID NO:18, SEQ ID NO:21, SEQ ID NO:24, SEQ ID NO:27, SEQ ID NO:30, SEQ ID NO:33, SEQ ID NO:36, SEQ ID NO:39, or SEQ ID NO:42.

To determine the percent homology of two amino acid sequences (e.g., the sequences of SEQ ID NO:3, SEQ ID NO:6, SEQ ID NO:9, SEQ ID NO:12, SEQ ID NO:15, SEQ ID NO, 18, SEQ ID NO:21, SEQ ID NO:24, SEQ ID NO:27, SEQ ID NO:30, SEQ ID NO:33, SEQ ID NO:36, SEQ ID NO:39, or SEQ ID NO:42, and a mutant or homolog thereof), the sequences are aligned for optimal comparison purposes (e.g., gaps can be introduced in the sequence of one polypeptide for optimal alignment with the other polypeptide). The amino acid residues at corresponding amino acid positions are then compared. When a position in one sequence (e.g., SEQ ID NO:3, SEQ ID NO:6, SEQ ID NO:9, SEQ ID NO:12 SEQ ID NO:15 SEQ ID NO:18, SEQ ID NO:21, SEQ ID NO:24, SEQ ID NO:27, SEQ ID NO:30, SEQ ID NO:33, SEQ ID NO:36, SEQ ID NO:39, or SEQ ID NO:42) is occupied by the same amino acid residue as the corresponding position in the other sequence (e.g., a mutant or homolog of the sequence shown in SEQ ID NO:3, SEQ ID NO:6, SEQ ID NO:9, SEQ ID NO:12, SEQ ID NO:15, SEQ ID NO:18, SEQ ID NO:21, SEQ ID NO:24, SEQ ID NO:27, SEQ ID NO:30, SEQ ID NO:33, SEQ ID NO:36, SEQ ID NO:39, or SEQ ID NO:42), then the molecules are identical at that position. The same type of comparison can be made between two nucleic acid sequences.

As used herein amino acid or nucleic acid "homology" is equivalent to amino acid or nucleic acid "identity". Accordingly, the percent sequence identity between the two sequences is a function of the number of identical positions shared by the sequences (i.e., percent sequence identity=numbers of identical positions/total numbers of positions×100). For the purposes of the invention, the percent sequence identity between two polynucleotide or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two polynucleotides. A gap opening penalty of 10 and a gap extension penalty of 0.1 are used for determining the percent identity of two polypeptides. All other parameters are set at the default settings. It is to be understood that for the purposes of determining sequence identity when comparing a DNA sequence to an RNA sequence, a thymidine nucleotide is equivalent to a uracil nucleotide.

An isolated LMP homolog or mutant can also be created by introducing one or more nucleotide substitutions, additions or deletions into a nucleotide sequence of SEQ ID NO:1, SEQ ID NO:2, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, SEQ ID NO:17, SEQ ID NO:19, SEQ ID NO:20, SEQ ID NO:22, SEQ ID NO:23, SEQ ID NO:25, SEQ ID NO:26, SEQ ID NO:28, SEQ ID NO:29, SEQ ID NO:31, SEQ ID NO:32, SEQ ID NO:34, SEQ ID NO:35, SEQ ID NO:37, SEQ ID NO:38, SEQ ID NO:40 or SEQ ID NO:41 such that one or more amino acid substitutions, additions or deletions are introduced into the encoded protein. Mutations can be introduced into one of the LMP polynucleotide sequences of the present invention by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a LMP is preferably replaced with another amino acid residue from the same side chain family. Alternatively, in another embodiment, mutations can be introduced randomly along all or part of a LMP coding sequence, such as by saturation mutagenesis, and the resultant mutants can be screened for a LMP activity described herein to identify mutants that retain LMP activity. Following mutagenesis of one of the LMP polynucleotide sequences, the encoded protein can be expressed recombinantly and the activity of the protein can be determined using, for example, assays described in the Examples below.

LMPs are preferably produced by recombinant DNA techniques. For example, a nucleic acid molecule encoding the protein is cloned into an expression vector, the expression vector is introduced into a host cell and the LMP is expressed in the host cell using methods known to those of skill in the art. The LMP can then be isolated from the cells by an appropriate purification scheme using standard protein purification techniques. Alternative to recombinant expression, a LMP, polypeptide or peptide, can be synthesized chemically using standard peptide synthesis techniques. Moreover, native LMP can be isolated from cells (e.g., *Physcomitrella patens* cells), for example using an anti-LMP antibody, which can be produced by standard techniques utilizing a LMP or fragment thereof of this invention.

The invention also provides LMP chimeric or fusion proteins. As used herein, a LMP "chimeric protein" or "fusion protein" comprises a IMP polypeptide operatively linked to a non-LMP polypeptide. An "LMP polypeptide" refers to a polypeptide having an amino acid sequence corresponding to a LMP, whereas a "non-LMP polypeptide" refers to a polypeptide having an amino acid sequence corresponding to a protein which is not substantially homologous to the LMP, e.g., a protein which is different from the LMP and which is derived from the same or a different organism. Within the fusion protein, the term "operatively linked" is intended to indicate that the LMP polypeptide and the non-LMP polypeptide are fused to each other so that both sequences fulfill the proposed function attributed to the sequence used. The non-LMP polypeptide can be fused to the N-terminus or C-terminus of the LMP polypeptide. For example, in one embodiment, the fusion protein is a GST-LMP fusion protein in which the LMP sequences are fused to the C-terminus of the GST sequences. Such fusion proteins can facilitate the purification of recombinant LMPs. In another embodiment, the fusion protein is a LMP containing a heterologous signal sequence at its N-terminus. In certain host cells (e.g., mammalian host cells), expression and/or secretion of a LMP can be increased through use of a heterologous signal sequence.

Preferably, a LMP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al., John Wiley & Sons: 1992). Moreover, many expression vectors are commercially available that already encode a fusion moiety (e.g., a GST polypeptide). An LMP-encoding nucleic acid can be cloned into such an expression vector such that the fusion moiety is linked in-frame to the LMP.

In addition to the nucleic acid molecules encoding LMPs described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire LMP coding strand, or to only a portion thereof. In one embodiment, an antisense nucleic acid molecule is antisense to a "coding region" of the coding strand of a nucleotide sequence encoding a LMP. The term "coding region" is defined above. In another embodiment, the antisense nucleic acid molecule is antisense to a "noncoding region" of the coding strand of a nucleotide sequence encoding LMP. The term "noncoding region" refers to 5' and 3' sequences which flank the coding region that are not translated into amino acids (i.e., also referred to as 5' and 3' untranslated regions).

Given the coding strand sequences encoding LMPs disclosed herein, antisense nucleic acids of the invention can be designed according to the rules of Watson and Crick base pairing. The antisense nucleic acid molecule can be complementary to the entire coding region of LMP mRNA, but more preferably is an oligonucleotide which is antisense to only a portion of the coding or noncoding region of LMP mRNA. For example, the antisense oligonucleotide can be complementary to the region surrounding the translation start site of LMP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylamino-methyl-2-thiouridine, 5-carboxymethylaminomethyluracil, dihydrouracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methyl-cytosine, N-6-adenine, 7-methylguanine, 5-methylaminomethyluracil, 5-methoxyamino-methyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding a LMP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic including plant promoters are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. 1987, Nucleic Acids Res. 15: 6625-6641). The antisense nucleic acid molecule can also comprise a 2'-o-methylribonucleotide (Inoue et al. 1987, Nucleic Acids Res. 15: 6131-6148) or a chimeric RNA-DNA analogue (Inoue et al. 1987, FEBS Lett. 215: 327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff & Gerlach 1988, Nature 334: 585-591)) can be used to catalytically cleave LMP mRNA transcripts to thereby inhibit translation of LMP mRNA. A ribozyme having specificity for a LMP-encoding nucleic acid can be designed based upon the nucleotide sequence of a LMP cDNA disclosed herein (i.e., s_pp001031077f) or on the basis of a heterologous sequence to be isolated according to methods taught in this invention. For example, a derivative of a *Tetrahymena* L-19 IVS RNA can be constructed in which the nucleotide sequence of the active site is complementary to the nucleotide sequence to be cleaved in a LMP-encoding mRNA (see, e.g., Cech et al., U.S. Pat. No. 4,987,071 and Cech et al., U.S. Pat. No. 5,116,742). Alternatively, LMP mRNA can be used to select a catalytic RNA having a specific ribonuclease activity from a pool of RNA molecules (see, e.g., Bartel, D. & Szostak J. W. 1993, Science 261: 1411-1418).

Alternatively, LMP gene expression can be inhibited by targeting nucleotide sequences complementary to the regulatory region of a LMP nucleotide sequence (e.g., a LMP promoter and/or enhancers) to form triple helical structures that prevent transcription of a LMP gene in target cells (See generally, Helene C. 1991, Anticancer Drug Des. 6: 569-84; Helene C. et al. 1992, Ann. N.Y. Acad. Sci. 660: 27-36; and Maher, L. J. 1992, Bioassays 14: 807-15).

Another aspect of the invention pertains to vectors, preferably expression vectors, containing a nucleic acid encoding a LMP (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used inter-changeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequencers) in a manner which allows for expression of the nucleotide sequence are fused to each other so that both sequences fulfill the proposed function addicted to the sequence used. (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990) or see: Gruber and Crosby, in: Methods in Plant Molecular Biology and Biotechnology, CRC Press, Boca Raton, Fla., eds.: Glick & Thompson, Chapter 7, 89-108 including the references therein. Regulatory sequences include those which direct constitutive expression of a nucleotide sequence in many types of host cell and those which direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., LMPs, mutant forms of LMPs, fusion proteins, etc.).

The recombinant expression vectors of the invention can be designed for expression of LMPs in prokaryotic or eukaryotic cells. For example, LMP genes can be expressed in bacterial cells, insect cells (using baculovirus expression vectors), yeast and other fungal cells (see Romanos M. A. et al. 1992, Foreign gene expression in yeast: a review. Yeast 8: 423-488; van den Hondel, C. A. M. J. J. et al. 1991, Heterologous gene expression in filamentous fungi, in: More Gene Manipulations in Fungi, Bennet & Lasure, eds., p. 396-428: Academic Press: San Diego; and van den Hondel & Punt 1991, Gene transfer systems and vector development for filamentous fungi, in: Applied Molecular Genetics of Fungi, Peberdy et al., eds., p. 1-28, Cambridge University Press: Cambridge), algae (Falciatore et al. 1999, Marine Biotechnology 1: 239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella,* and *Stylonychia,* especially of the genus *Stylonychia lemnae* with vectors following a transformation method as described in WO 98/01572 and multicellular plant cells (see Schmidt & Willmitzer 1988, High efficiency *Agrobacterium tumefaciens*-mediated transformation of *Arabidopsis thaliana* leaf and cotyledon explants, Plant Cell Rep.: 583-586); Plant Molecular Biology and Biotechnology, C Press, Boca Raton, Fla., chapter 6/7, S.71-119 (1993); White, Jenes et al., Techniques for Gene Transfer, in: Transgenic Plants, Vol. 1, Engineering and Utilization, eds.: Kung and Wu, Academic Press 1993, 128-43; Potrykus 1991, Annu, Rev. Plant Physiol. Plant Mol. Biol. 42: 205-225 (and references cited therein) or mammalian cells. Suitable host cells are discussed further in Goeddel, Gene Expression Technology: Methods in Enzymology 185, Academic Press, San Diego, Calif. 1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith & Johnson 1988, Gene 67: 31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the LMP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant LMP unfused to GST can be recovered by cleavage of the fusion protein with thrombin.

Examples of suitable inducible non-fusion *E. coli* expression vectors include pTrc (Amann et al. 1988, Gene 69: 301-315) and pET 11d (Studier et al. 1990, Gene Expression Technology: Methods in Enzymology 185, Academic Press, San Diego, Calif. 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman S. 1990, Gene Expression Technology: Methods in Enzymology 185: 119-128, Academic Press, San Diego, Calif.). Another strategy is to alter the nucleic acid sequence of the nucleic acid to be inserted into an expression vector so that the individual codons for each amino acid are those preferentially utilized in the bacterium chosen for expression (Wada et al. 1992, Nucleic Acids Res. 20: 2111-2118). Such alteration of nucleic acid sequences of the invention can be carried out by standard DNA synthesis techniques.

In another embodiment, the LMP expression vector is a yeast expression vector. Examples of vectors for expression in yeast *S. cerevisiae* include pYepSec1 (Baldari et al. 1987, Embo J. 6: 229-234), pMFa (Kurjan & Herskowitz 1982, Cell 30: 933-943), pJRY88 (Schultz et al. 1987, Gene 54: 113-123), and pYES2 (Invitrogen Corporation, San Diego, Calif.). Vectors and methods for the construction of vectors appropriate for use in other fungi, such as the filamentous fungi, include those detailed in: van den Hondel & Punt 1991, "Gene transfer systems and vector development for filamentous fungi, in: Applied Molecular Genetics of Fungi, Peberdy et al., eds., p. 1-28, Cambridge University Press: Cambridge.

Alternatively, the LMPs of the invention can be expressed in insect cells using baculovirus expression vectors. Baculovirus vectors available for expression of proteins in cultured insect cells (e.g., Sf 9 cells) include the pAc series (Smith et al. 1983, Mol. Cell Biol. 3: 2156-2165) and the pVL series (Lucklow & Summers 1989, Virology 170: 31-39).

In yet another embodiment, a nucleic acid of the invention is expressed in mammalian cells using a mammalian expression vector. Examples of mammalian expression vectors include pCDM8 (Seed 1987, Nature 329: 840) and pMT2PC (Kaufman et al. 1987, EMBO J. 6: 187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, Fritsh and Maniatis, *Molecular Cloning: A Laboratory Manual. 2nd, ed., Cold Spring Harbor Laboratory,* Cold Spring Harbor Laboratory Press, Cold Spring Harbor, N.Y., 1989.

In another embodiment, the LMPs of the invention may be expressed in uni-cellular plant cells (such as algae, see Falciatore et al. (1999, Marine Biotechnology 1: 239-251) and references therein and plant cells from higher plants (e.g., the spermato-phytes, such as crop plants)). Examples of plant expression vectors include those detailed in: Becker, Kemper, Schell and Masterson (1992, "New plant binary vectors with selectable markers located proximal to the left border", Plant Mol. Biol. 20: 1195-1197) and Bevan (1984, "Binary *Agrobacterium* vectors for plant transformation, Nucleic Acids Res. 12: 8711-8721; Vectors for Gene Transfer in Higher Plants; in: Transgenic Plants, Vol. 1, Engineering and Utilization, eds.: Kung und R. Wu, Academic Press, 1993, S. 15-38).

A plant expression cassette preferably contains regulatory sequences capable to drive gene expression in plants cells and which are operably linked so that each sequence can fulfill its function such as termination of transcription such as polyadenylation signals. Preferred polyadenylation signals are those originating from *Agrobacterium tumefaciens* t-DNA such as the gene 3 known as octopine synthase of the Ti-plasmid pTiACH5 (Gielen et al. 1984, EMBO J. 3: 835 ff) or functional equivalents thereof but also all other terminators functionally active in plants are suitable.

As plant gene expression is very often not limited on transcriptional levels a plant expression cassette preferably contains other operably linked sequences like translational enhancers such as the overdrive-sequence containing the 5'-untranslated leader sequence from tobacco mosaic virus enhancing the protein per RNA ratio (Gallie et al. 1987, Nucleic Acids Res. 15: 8693-8711).

Plant gene expression has to be operably linked to an appropriate promoter conferring gene expression in a timely, cell or tissue specific manner. Preferred are promoters driving constitutive expression (Benfey et al. 1989, EMBO J. 8: 2195-2202) like those derived from plant viruses like the 35S CAMV (Franck et al. 1980, Cell 21: 285-294), the 19S CaMV (see also U.S. Pat. No. 5,352,605 and WO8402913) or plant promoters like those from Rubisco small subunit described in U.S. Pat. No. 4,962,028. Even more preferred are seed-specific promoters driving expression of LMP proteins during all or selected stages of seed development. Seed-specific plant promoters are know to the art and are identified and characterized using seed-specific mRNA libraries and expression profiling techniques. Seed-specific promoters include the napin-gene promoter from rapeseed_(U.S. Pat. No. 5,608, 152), the USP-promoter from *Vicia faba* (Baeumlein et al. 1991, Mol. Gen. Genetics 225: 459-67), the oleosin-promoter from *Arabidopsis* (WO9845461), the phaseolin-promoter from *Phaseolus vulgaris* (U.S. Pat. No. 5,504,200), the Bce4-promoter from *Brassica* (WO9113980) or the legumin B4 promoter (LeB4; Baeumlein et al. 1992, Plant J. 2: 233-239) as well as promoters conferring seed specific expression in monocot plants like *maize*, barley, wheat, rye, rice etc. Suitable promoters to note are the lpt2 or lpt1-gene promoter from barley (WO 95/15389 and WO 95/23230) or those described in WO 99/16890 (promoters from the barley hordein-gene, the rice glutelin gene, the rice oryzin gene, the rice prolamin gene, the wheat gliadin gene, wheat glutelin gene, the maize zein gene, the oat glutelin gene, the Sorghum kasirin-gene, the rye secalin gene).

Plant gene expression can also be facilitated via an inducible promoter (for review see Gatz 1997, Annu. Rev. Plant Physiol. Plant Mol. Biol. 48: 89-108). Chemically inducible promoters are especially suitable if gene expression is wanted to occur in a time specific manner. Examples for such promoters are a salicylic acid inducible promoter (WO 95/19443), a tetracycline inducible promoter (Gatz et al. 1992, Plant J. 2: 397-404) and an ethanol inducible promoter (WO 93/21334).

Also promoters responding to biotic or abiotic stress conditions are suitable promoters such as the pathogen inducible PRP1-gene promoter (Ward et al., 1993, Plant. Mol. Biol. 22: 361-366), the heat inducible hsp80-promoter from tomato (U.S. Pat. No. 5,187,267), cold inducible alpha-amylase promoter from potato (WO 96/12814) or the wound-inducible pinII-promoter (EP 375091).

Other preferred sequences for use in plant gene expression cassettes are targeting-sequences necessary to direct the gene-product in its appropriate cell compartment (for review see Kermode 1996, Crit. Rev. Plant Sci. 15: 285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells. Also especially suited are promoters that confer plastid-specific gene expression as plastids are the compartment where precursors and some end products of lipid biosynthesis are synthesized. Suitable promoters such as the viral RNA-polymerase promoter are described in WO 95/16783 and WO 97/06250 and the clpP-promoter from *Arabidopsis* described in WO 99/46394.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to LMP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986, Antisense RNA as a molecular tool for genetic analysis, Reviews—Trends in Genetics, Vol. 1) and Mol et al. (1990, FEBS Lett. 268: 427-430).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact be identical to the parent cell, but are still included within the scope of the term as used herein. A host cell can be any prokaryotic or eukaryotic cell. For example, a LMP can be expressed in bacterial cells, insect cells, fungal cells or mammalian cells (such as Chinese hamster ovary cells (CHO) or COS cells), algae, ciliates, plant cells and fungi. Other suitable host cells are known to those skilled in the art.

Vector DNA can be introduced into prokaryotic or eukaryotic cells via conventional transformation or transfection techniques. As used herein, the terms "transformation" and "transfection", conjugation and transduction are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells including plant cells can be found in Sambrook et al. (1989, *Molecular Cloning: A Laboratory Manual. 2nd, ed, Cold Spring Harbor Laboratory*, Cold Spring Harbor Laboratory Press, Cold Spring Harbor, N.Y.) and other laboratory manuals such as Methods in Molecular Biology 1995, Vol. 44, *Agrobacterium* protocols, ed: Gartland and Davey, Humana Press, Totowa, N.J.

For stable transfection of mammalian and plant cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, kanamycin and methotrexate or in plants that confer resistance towards a herbicide such as glyphosate or glufosinate. Nucleic acid encoding a selectable marker can be introduced into a host cell on the same vector as that encoding a LMP or can be introduced on a separate vector. Cells stably transfected with the introduced nucleic acid can be identified by, for example, drug selection (e.g., cells that have incorporated the selectable marker gene will survive, while the other cells die).

To create a homologous recombinant microorganism, a vector is prepared which contains at least a portion of a LMP gene into which a deletion, addition or substitution has been introduced to thereby alter, e.g., functionally disrupt, the LMP gene. Preferably, this LMP gene is a *Physcomitrella patens* LMP gene, but it can be a homologue from a related plant or even from a mammalian, yeast, or insect source. In a preferred embodiment, the vector is designed such that, upon homologous recombination, the endogenous LMP gene is functionally disrupted (i.e., no longer encodes a functional protein; also referred to as a knock-out vector). Alternatively, the vector can be designed such that, upon homologous recombination, the endogenous LMP gene is mutated or otherwise altered but still encodes functional protein (e.g., the upstream regulatory region can be altered to thereby alter the expression of the endogenous LMP). To create a point mutation via homologous recombination, DNA-RNA hybrids can be used in a technique known as chimeraplasty (Cole-Strauss et al. 1999, Nucleic Acids Res. 27: 1323-1330 and Kmiec 1999, American Scientist 87: 240-247). Homologous recombination procedures in *Physcomitrella patens* are also well known in the art and are contemplated for use herein.

In a homologous recombination vector, the altered portion of the LMP gene is flanked at its 5' and 3' ends by additional nucleic acid of the LMP gene to allow for homologous recombination to occur between the exogenous LMP gene carried by the vector and an endogenous LMP gene in a microorganism or plant. The additional flanking LMP nucleic acid is of sufficient length for successful homologous recombination with the endogenous gene. Typically, several hundreds of base pairs up to kilobases of flanking DNA (both at the 5' and 3' ends) are included in the vector (see e.g., Thomas & Capecchi 1987, Cell 51: 503, for a description of homologous recombination vectors or Strepp et al. 1998, Proc. Natl. Acad. Sci. USA 95: 4368-4373 for cDNA based recombination in *Physcomitrella patens*). The vector is introduced into a microorganism or plant cell (e.g., via polyethylene glycol mediated DNA). Cells in which the introduced LMP gene has homologously recombined with the endogenous LMP gene are selected using art-known techniques.

In another embodiment, recombinant microorganisms can be produced which contain selected systems which allow for regulated expression of the introduced gene. For example, inclusion of a LMP gene on a vector placing it under control of the lac operon permits expression of the LMP gene only in the presence of IPTG. Such regulatory systems are well known in the art.

A host cell of the invention, such as a prokaryotic or eukaryotic host cell in culture, can be used to produce (i.e., express) a LMP. Accordingly, the invention further provides methods for producing LMPs using the host cells of the invention. In one embodiment, the method comprises culturing the host cell of invention (into which a recombinant expression vector encoding a LMP has been introduced, or which contains a wild-type or altered LMP gene in it's genome) in a suitable medium until LMP is produced. In another embodiment, the method further comprises isolating LMPs from the medium or the host cell.

Another aspect of the invention pertains to isolated LMPs, and biologically active portions thereof. An "isolated" or "purified" protein or biologically active portion thereof includes a protein that is substantially free of cellular material when produced by recombinant DNA techniques, or chemical precursors or other chemicals when chemically synthesized. The language "substantially free of cellular material" includes preparations of LMP in which the protein is separated from cellular components of the cells in which it is naturally or recombinantly produced. In one embodiment, the language "substantially free of cellular material" includes preparations of LMP having less than about 30% (by dry weight) of non-LMP (also referred to herein as a "contaminating protein"), more preferably less than about 20% of non-LMP, still more preferably less than about 10% of non-LMP, and most preferably less than about 5% non-LMP. When the LMP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of LMP in which the protein is separated from chemical precursors or other chemicals which are involved in the synthesis of the protein. In one embodiment, the language "substantially free of chemical precursors or other chemicals" includes preparations of LMP having less than about 30% (by dry weight) of chemical precursors or non-LMP chemicals, more preferably less than about 20% chemical precursors or non-LMP chemicals, still more preferably less than about 10% chemical precursors or non-LMP chemicals, and most preferably less than about 5% chemical precursors or non-LMP chemicals. In preferred embodiments, isolated proteins or biologically active portions thereof lack contaminating proteins from the same organism from which the LMP is derived. Typically, such proteins are produced by recombinant expression of, for example, a *Physcomitrella patens* LMP in other plants than *Physcomitrella patens* or microorganisms, algae or fungi.

An isolated LMP or a portion thereof of the invention can participate in the metabolism of compounds necessary for the production of storage compounds such as fatty acids, triacylglyceride lipids, starch and storage proteins in *Physcomitrella patens*, or of cellular membranes, or has one or more of the activities set forth in Table 3. In preferred embodiments, the protein or portion thereof comprises an amino acid sequence which is sufficiently homologous to an amino acid sequence shown in SEQ ID NO:3, SEQ ID NO:6, SEQ ID NO:9, SEQ ID NO:12, SEQ ID NO:15, SEQ ID NO:18, SEQ ID NO:21, SEQ ID NO:24, SEQ ID NO:27, SEQ ID NO:30, SEQ ID NO:33, SEQ ID NO:36, SEQ ID NO:39, or SEQ ID NO:42 such that the protein or portion thereof maintains the ability to participate in the metabolism of compounds necessary for the construction of cellular membranes in *Physcomitrella patens*, or in the transport of molecules across these membranes. The portion of the protein is preferably a biologically active portion as described herein. In another preferred embodiment, a LMP of the invention has an amino acid sequence encoded by a nucleic acid shown in SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, or SEQ ID NO:41.

In yet another preferred embodiment, the LMP has an amino acid sequence which is encoded by a nucleotide sequence which hybridizes, e.g., hybridizes under stringent conditions, to a LMP nucleotide sequence described herein. In still another preferred embodiment, the LMP has an amino acid sequence which is encoded by a nucleotide sequence that is at least about 50-60%, preferably at least about 60-70%, more preferably at least about 70-80%, 80-90%, 90-95%, and even more preferably at least about 96%, 97%, 98%, 99% or more homologous to one of the amino acid sequences encoded by a LMP nucleic acid shown in SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, or SEQ ID NO:41. The preferred LMPs of the present invention also preferably possess at least one of the LMP activities described herein. For example, a preferred LMP of the present invention includes an amino acid sequence encoded by a nucleotide sequence which hybridizes, e.g., hybridizes under stringent conditions, to a nucleotide sequence shown in SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, or SEQ ID NO:41, and which can participate in the metabolism of compounds necessary for the construction of cellular membranes in *Physcomitrella patens*, or in the transport of molecules across these membranes, or which has one or more of the activities set forth in Table 3.

In other embodiments, the LMP homologue is substantially homologous to an LMP amino acid sequence shown in SEQ ID NO:3, SEQ ID NO:6, SEQ ID NO:9, SEQ ID NO:12, SEQ ID NO:15, SEQ ID NO:18, SEQ ID NO:21, SEQ ID NO:24, SEQ ID NO:27, SEQ ID NO:30, SEQ ID NO:33, SEQ ID NO:36, SEQ ID NO:39, or SEQ ID NO:42 and retains the functional activity of the LMP yet differs in amino acid sequence due to natural variation or mutagenesis, as described in detail above. Accordingly, in another embodiment, the LMP is a protein which comprises an amino acid sequence which is at least about 50-60%, preferably at least about 60-70%, and more preferably at least about 70-80, 80-90, 90-95%, and most preferably at least about 96%, 97%, 98%, 99% or more homologous to an entire amino acid sequence and which has at least one of the LMP activities described herein. In another embodiment, the invention pertains to a full *Physcomitrella patens* protein which is substantially homologous to an LMP described herein.

Homologues of the LMP can be generated by mutagenesis, e.g., discrete point mutation or truncation of the LMP. As used herein, the term "homologue" refers to a variant form of the LMP which acts as an agonist or antagonist of the activity of the LMP. An agonist of the LMP can retain substantially the same, or a subset, of the biological activities of the LMP. An antagonist of the LMP can inhibit one or more of the activities of the naturally occurring form of the LMP, by, for example, competitively binding to a downstream or upstream member of the cell membrane component metabolic cascade which includes the LMP, or by binding to a LMP which mediates transport of compounds across such membranes, thereby preventing translocation from taking place.

In an alternative embodiment, homologues of the LMP can be identified by screening combinatorial libraries of mutants, e.g., truncation mutants, of the LMP for LMP agonist or antagonist activity. In one embodiment, a variegated library of LMP variants is generated by combinatorial mutagenesis at the nucleic acid level and is encoded by a variegated gene library. A variegated library of LMP variants can be produced by, for example, enzymatically ligating a mixture of synthetic oligonucleotides into gene sequences such that a degenerate set of potential LMP sequences is expressible as individual polypeptides, or alternatively, as a set of larger fusion proteins (e.g., for phage display) containing the set of LMP sequences therein. There are a variety of methods which can be used to produce libraries of potential LMP homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential LMP sequences. Methods for synthesizing degenerate oligonucleotides are known in the art (see, e.g., Narang 1983, Tetrahedron 39: 3; Itakura et al. 1984, Annu. Rev. Biochem. 53: 323; Itakura et al. 1984, Science 198: 1056; Ike et al. 1983, Nucleic Acids Res. 11: 477).

In addition, libraries of fragments of the LMP coding sequences can be used to generate a variegated population of LMP fragments for screening and subsequent selection of homologues of a LMP. In one embodiment, a library of coding sequence fragments can be generated by treating a double stranded PCR fragment of a LMP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the LMP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of LMP homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify LMP homologues (Arkin & Yourvan 1992, Proc. Natl. Acad. Sci. USA 89: 7811-7815; Delgrave et ale 1993, Protein Engineering 6: 327-331).

In another embodiment, cell based assays can be exploited to analyze a variegated LMP library, using methods well known in the art.

The nucleic acid molecules, proteins, protein homologues, fusion proteins, primers, vectors, and host cells described herein can be used in one or more of the following methods: identification of *Physcomitrella patens* and related or other organisms; mapping of genomes of organisms related to *Physcomitrella patens*; identification and localization of *Physcomitrella patens* sequences of interest; evolutionary studies; determination of LMP regions required for function; modulation of a LMP activity; modulation of the metabolism of one or more cell functions; modulation of the transmembrane transport of one or more compounds; and modulation of seed storage compound accumulation.

The moss *Physcomitrella patens* represents one member of the mosses. It is related to other mosses such as *Ceratodon purpureus* which is capable to grow in the absence of light. Mosses like *Ceratodon* and *Physcomitrella* share a high degree of homology on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The LMP nucleic acid molecules of the invention have a variety of uses. First, they may be used to identify an organism as being *Physcomitrella patens* or a close or related relative thereof. Also, they may be used to identify the presence of *Physcomitrella patens* or a relative thereof in a mixed population of microorganisms. The invention provides the nucleic acid sequences of a number of *Physcomitrella patens* genes; by probing the extracted genomic DNA of a culture of a unique or mixed population of microorganisms under stringent conditions with a probe spanning a region of a *Physcomitrella patens* gene which is unique to this organism, one can ascertain whether this organism is present or a related gene is present regardless of the host.

Further, the nucleic acid and protein molecules of the invention may serve as markers for specific regions of the genome. This has utility not only in the mapping of the genome, but also for functional studies of *Physcomitrella patens* and related proteins. For example, to identify the region of the genome to which a particular *Physcomitrella patens* or related DNA-binding protein binds, a genome, such as that of *Physcomitrella patens*, could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *Physcomitrella patens*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related mosses. One skilled in the art will appreciate that the methods and other aspects of the invention and this disclosure related thereto also relates to other species of plants and are not restricted to *Physcomitrella patens*.

The LMP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the LMP nucleic acid molecules of the invention may result in the production of LMPs having functional differences from the wild-type LMPs. These proteins may be improved in efficiency or activity, may be present in greater numbers in the cell than is usual, or may be decreased in efficiency or activity.

There are a number of mechanisms by which the alteration of a LMP of the invention may directly affect the accumulation of seed storage compounds. In the case of plants expressing LMPs increased transport can lead to altered accumulation of compounds and/or solute partitioning within the plant tissue and organs. An example is provided by Mitsukawa et al. (1997, Proc. Natl. Acad. Sci. USA 94: 7098-7102), where overexpression of an *Arabidopsis* high-affinity phosphate transporter gene in tobacco cultured cells enhanced cell growth under phosphate-limited conditions. Phosphate availability also affects significantly the production of sugars and metabolic intermediates (Hurry et al. 2000, Plant J. 24: 383-396) and the lipid composition in leaves and roots (Härtel et al. 2000, Proc. Natl. Acad. Sci. USA 97: 10649-10654). Likewise, the activity of the plant ACCase has been demonstrated to be regulated by phosphorylation (Savage & Ohlrogge 1999, Plant J. 18: 521-527). Moreover, the presence of lipid kinase activities in chloroplast envelope membranes suggests that signal transduction pathways and/or membrane protein regulation occur in envelopes (see, e.g., Müller et al. 2000, J. Biol. Chem. 275: 19475-19481 and literature cited therein). The ABI1 and ABI2 genes encode two protein serine/threonine phosphatases 2C, which are regulators in abscisic acid signaling pathway, and thereby in early and late seed development (e.g. Merlot et al. 2001, Plant J. 25: 295-303). For more examples see also the section entitled 'background of the invention'.

The effect of the genetic modification in plants on a desired seed storage compound (such as sugars, lipids and fatty acids) can be assessed by growing the modified plant under suitable conditions and analyzing the seeds or any other plant organ for increased production of the desired product (i.e., a lipid or a fatty acid). Such analysis techniques are well known to one skilled in the art, and include spectroscopy, thin layer chromatography, staining methods of various kinds, enzymatic and microbiological methods, and analytical chromatography such as high performance liquid chromatography (see, for example, Ullman 1985, Encyclopedia of Industrial Chemistry, vol. A2, pp. 89-90 and 443-613, VCH: Weinheim; Fallon, A. et al. 1987, Applications of HPLC in Biochemistry in: Laboratory Techniques in Biochemistry and Molecular Biology, vol. 17; Rehm et al. 1993 Product recovery and purification, Biotechnology, vol. 3, Chapter III, pp. 469-714, VCH: Weinheim; Belter, P. A. et al., 1988 Bioseparations: downstream processing for biotechnology, John Wiley & Sons; Kennedy J. F. & Cabral J. M. S. 1992, Recovery processes for biological materials, John Wiley and Sons; Shaeiwitz J. A. & Henry J. D. 1988, Biochemical separations in: Ulmann's Encyclopedia of Industrial Chemistry, Separation and purification techniques in biotechnology, vol. B3, Chapter 11, pp. 1-27, VCH: Weinheim; and Dechow F. J. 1989).

Besides the above-mentioned methods, plant lipids can be extracted from plant material as described by Cahoon et al. (1999, Proc. Natl. Acad. Sci. USA 96, 22: 12935-12940) and Browse et al. (1986, Anal. Biochemistry 442: 141-145). Qualitative and quantitative lipid or fatty acid analysis is described in Christie, William W., Advances in Lipid Methodology. Ayr/Scotland: Oily Press.—(Oily Press Lipid Library; 2); Christie, William W., Gas Chromatography and Lipids. A Practical Guide—Ayr, Scotland: Oily Press, 1989 Repr. 1992.—IX,307 S.—(Oily Press Lipid Library; 1); "Progress in Lipid Research", Oxford: Pergamon Press, 1 (1952)-16 (1977) Progress in the Chemistry of Fats and Other Lipids CODEN.

Determination of the presence of fatty acid products can be obtained by the analysis of transgenic plants following standard analytical procedures: GC, CC-MS or TLC as variously described by Christie and references therein (1997 in: Advances on Lipid Methodology 4th ed.: Christie, Oily Press, Dundee, pp. 119-169; 1998). Detailed methods are described for leaves by Demieux et al (1990, Theor. Appt. Genet. 80: 234-240) and for seeds by Focks & Benning (1998, Plant Physiol. 118: 91-101).

Positional analysis of the fatty acid composition at the C-1, C-2 or C-3 positions of the glycerol backbone can be determined by lipase digestion (see, e.g., Siebertz & Heinz 1977, Z. Naturforsch. 32c: 193-205, and Christie 1987, Lipid Analysis $2^{nd}$ Edition, Pergamon Press, Exeter, ISBN 0-08-023791-6).

A typical way to gather information of the influence of increased or decreased protein activities on lipid and sugar biosynthetic pathways is, for example, via analyzing the carbon fluxes by labeling studies with leaves or seeds using $^{14}C$-acetate or $^{14}C$-pyruvate (see, e.g. Focks & Benning 1998, Plant Physiol. 118: 91-101; Eccleston & Ohlrogge 1998, Plant Cell 10: 613-621). The distribution of carbon-14 into lipids and aqueous soluble components can be determined by liquid scintillation counting after the respective separation (for example on TLC plates) including standards like $^{14}C$-sucrose and $^{14}C$-malate (Eccleston & Ohlrogge 1998, Plant Cell 10: 613-621).

Material to be analyzed can be disintegrated via sonication, glass milling, liquid nitrogen and grinding or via other applicable methods. The material has to be centrifuged after disintegration. The sediment is re-suspended in distilled water, heated for 10 minutes at 100° C., cooled on ice and centrifuged again followed by extraction in 0.5 M sulfuric acid in methanol containing 2% dimethoxypropane for 1 hour at 90° C. leading to hydrolyzed oil and lipid compounds resulting in transmethylated lipids. These fat acid methyl esters are extracted in petrolether and finally subjected to GC analysis using a capillary column (Chrompack, WCOT Fused Silica, CP-Wax-52 CB, 25 m, 0.32 mm) at a temperature gradient between 170° C. and 240° C. for 20 minutes and 5 min. at 240° C. The identity of resulting fatty acid methylesters is defined by the use of standards available form commercial sources (i.e., Sigma).

In case of fatty acids where standards are not available, molecule identity can be shown via derivatization and subsequent CC-MS analysis. For example, the localization of triple bond fatty acids is shown via GC-MS after derivatization via 4,4-Dimethoxy-oxazolin-Derivaten (Christie, Oily Press, Dundee, 1998).

A common standard method for analyzing sugars, especially starch, is published by Stitt et al. (1989, "Determination of metabolite levels in specific cells and subcellular compartments of plant leaves" Methods Enzymol. 174: 518-552; for other methods see also Hartel et al. 1998, Plant Physiol. Biochem. 36: 407-417 and Focks & Benning 1998, Plant Physiol. 118: 91-101).

The present invention also provides antibodies which specifically binds to a LMP-polypeptide, or a portion thereof as encoded by a nucleic acid disclosed herein or as described herein. Antibodies can be made by many well-known methods (see, e.g. Harlow and Lane, "Antibodies; A Laboratory Manual" Cold Spring Harbor Laboratory, Cold Spring Harbor, N.Y., 1988). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced (see, for example, Kelly et al. 1992, Bio/Technology 10: 163-167; Bebbington et al., 1992, Bio/Technology 10:169-175).

The phrase "selectively binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and Examples be considered as exemplary only, with a true scope and spirit of the invention being indicated by the claims included herein.

EXAMPLES

Example 1

General Processes a) General Cloning Processes:

Cloning processes such as, for example, restriction cleavages, agarose gel electrophoresis, purification of DNA fragments, transfer of nucleic acids to nitrocellulose and nylon membranes, linkage of DNA fragments, transformation of *Escherichia coli* and yeast cells, growth of bacteria and sequence analysis of recombinant DNA were carried out as described in Sambrook et al. (1989, Cold Spring Harbor Laboratory Press: ISBN 0-87969-309-6) or Kaiser, Michaelis and Mitchell (1994, Methods in Yeast Genetics", Cold Spring Harbor Laboratory Press: ISBN 0-87969-451-3).

b) Chemicals:

The chemicals used were obtained, if not mentioned otherwise in the text, in p.a. quality from the companies Fluka eu-Ulm), Merck (Darmstadt), Roth (Karlsruhe), Serva (Heidelberg) and Sigma (Deisenhofen). Solutions were prepared using purified, pyrogen-free water, designated as $H_2O$ in the following text, from a Milli-Q water system water purification plant (Millipore, Eschborn). Restriction endonucleases, DNA-modifying enzymes and molecular biology kits were obtained from the companies AGS (Heidelberg), Amersham (Braunschweig), Biometra (Gottingen), Boehringer (Mannheim), Genomed (Bad Oeynnhausen), New England Biolabs (Schwalbach/Taunus), Novagen (Madison, Wis., USA), Perkin-Elmer (Weiterstadt), Pharmacia (Freiburg), Qiagen (Hilden) and Stratagene (Amsterdam, Netherlands). They were used, if not mentioned otherwise, according to the manufacturer's instructions.

c) Plant Material:

For this study, moss of the species *Physcomitrella patens* (Hedw.) B.S.G. from the collection of the genetic studies section of the University of Hamburg were used. They originate from the strain 16/14 collected by H.L.K. Whitehouse in Gransden Wood, Huntingdonshire (England), which was subcultured from a spore by Engel (1968, Am. J. Bot. 55: 438-446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores mature.

d) Cultivation Conditions:

Culturing was carried out in a climatic chamber at an air temperature of 25° C. and light intensity of 55 µmol $m^{-2}$ $s^{-1}$ (white light; Philips TL 65W/25 fluorescent tube) and a light/dark change of 16/8 hours. The moss was either modified in liquid culture using Knop medium according to Reski & Abel (1985, Planta 165: 354-358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material.
CTAB buffer: 2% (w/v) N-cethyl-N,N,N-trimethylammonium bromide (CTAB); 100 mM Tris HCl pH 8.0; 1.4 M NaCl; 20 mM EDTA.
N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000 g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 µl of TE buffer (Sambrook et al. 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of $H_2O$+RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of Total RNA and Poly-(A)+ RNA from Plants

For the investigation of transcripts, both total RNA and poly-$(A)^+$ RNA were isolated. The total RNA was obtained from wild-type 9-d-old protonemata following the GTC-method (Reski et al. 1994, Mol. Gen. Genet. 244: 352-359). Poly-(A)+ RNA was isolated using Dyna Beads$^R$ (Dynal, Oslo, Norway) following the instructions of the manufacturer's protocol. After determination of the concentration of the RNA or of the poly(A)+ RNA, the RNA was precipitated by addition of ⅒ volumes of 3 M sodium acetate pH 4.6 and 2 volumes of ethanol and stored at −70° C.

Example 4 cDNA Library Construction

For cDNA library construction first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 basepairs were eluted from the gel, phenol extracted, concentrated on Elutip-D-columns (Schleicher and Schuell, Dassel, Germany) and were ligated to vector arms and packed into lambda ZAPS phages or lambda ZAP-Express phages using the Gigapack Gold Kit (Stratagene, Amsterdam, Netherlands) using material and following the instructions of the manufacturer.

Example 5

DNA Sequencing and Computational Functional Analysis cDNA libraries as described in Example 4 were used for DNA sequencing according to standard methods, in particular by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands. Plasmid DNA was prepared from overnight grown E. coli cultures grown in Luria-Broth medium containing ampicillin (see Sambrook et al. (1989, Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

```
5'-CAGGAAACAGCTATGACC-3'     (SEQ ID NO:43)
5'-CTAAAGGGAACAAAAGCTG-3'    (SEQ ID NO:44)
5'-TGTAAAACGACGGCCAGT-3'     (SEQ ID NO:45)
```

Sequences were processed and annotated using the software package EST-MAX commercially provided by Bio-Max (Munich, Germany). The program incorporates practically all bioinformatics methods important for functional and structural characterization of protein sequences. For reference see the website pedant.mips.biochem.mpg.de.

The most important algorithms incorporated in EST-MAX are: FASTA: Very sensitive protein sequence database searches with estimates of statistical significance (Pearson W. R. 1990, Rapid and sensitive sequence comparison with FASTP and FASTA. Methods Enzymol. 183: 63-98). BLAST: Very sensitive protein sequence database searches with estimates of statistical significance (Altschul S. F., Gish W., Miller W., Myers E. W. and Lipman D. J. Basic local alignment search tool. J. Mol. Biol. 215: 403-410). PREDATOR: High-accuracy protein secondary structure prediction from single and multiple sequences. (Frishman & Argos 1997, 75% accuracy in protein secondary structure prediction. Proteins 27: 329-335). CLUSTALW: Multiple sequence alignment (Thompson, J. D., Higgins, D. G. and Gibson, T. J. 1994, CLUSTAL W: improving the sensitivity of progressive multiple sequence alignment through sequence weighting, positions-specific gap penalties and weight matrix choice, Nucleic Acids Res. 22: 4673-4680). TMAP: Transmembrane region prediction from multiply aligned sequences (Persson B. & Argos P. 1994, Prediction of transmembrane segments in proteins utilizing multiple sequence alignments, J. Mol. Biol. 237: 182-192). ALOM2: Transmembrane region prediction from single sequences (Klein P., Kanehisa M., and DeLisi C. 1984, Prediction of protein function from sequence properties: A discriminant analysis of a database. Biochim. Biophys. Acta 787: 221-226. Version 2 by Dr. K. Nakai). PROSEARCH: Detection of PROSITE protein sequence patterns. Kolakowski L. F. Jr., Leunissen J. A. M. and Smith J. E. 1992, ProSearch: fast searching of protein sequences with regular expression patterns related to protein structure and function. Biotechniques 13: 919-921). BLIMPS: Similarity searches against a database of ungapped blocks (Wallace & Henikoff 1992, PATMAT: A searching and extraction program for sequence, pattern and block queries and databases, CABIOS 8: 249-254. Written by Bill Alford).

Example 6

Cloning of Full-Length cDNAs and Binary Plasmids for Plant Transformation

RACE-PCR to Determine Full-Length Sequences

Full-length sequences of the *Physcomitrella patens* partial cDNAs (ESTs) that were identified in the *Physcomitrella patens* EST sequencing program using the annotation program EST-Max were isolated by RACE PCR using the SMART RACE cDNA amplification kit from Clontech allowing both 5'- and 3' rapid amplification of cDNA ends (RACE). The isolation of cDNAs and the RACE PCR protocol used were based on the manufacturer's conditions. The RACE product fragments were extracted from agarose gels with a QIAquick® Gel Extraction Kit (Qiagen) and ligated into the TOPO® pCR 2.1 vector (Invitrogen) following manufacturer's instructions. Recombinant vectors were transformed into TOP10 cells (Invitrogen) using standard conditions (Sambrook et al. 1989). Transformed cells are grown overnight at 37° C. on LB agar containing 50 μg/ml kanamycin and spread with 40 μl of a 40 mg/ml stock solution of X-gal in dimethylformamide for blue-white selection. Single white colonies are selected and used to inoculate 3 ml of liquid LB containing 50 μg/ml kanamycin and grown overnight at 37° C. Plasmid DNA was extracted using the QIAprep® Spin Miniprep Kit (Qiagen) following manufacturer's instructions. Subsequent analyses of clones and restriction mapping was performed according to standard molecular biology techniques (Sambrook et al. 1989). The sequences obtained from the RACE reactions were compiled to give the nucleotide sequences for the LMP genes (SEQ ID NOs: 1, 4, 7, 10, 13, 16, 19, 22, 25, 28, 31, 34, 37 and 40).

RT-PCR and Cloning of *Physcomitrella* LMP Genes

Full-length LMP cDNAs were isolated by RT-PCR from *Physcomitrella patens* RNA. The synthesis of the first strand cDNA was achieved using AMV Reverse Transcriptase (Roche, Mannheim, Germany). The resulting single-stranded cDNA was amplified via Polymerase Chain Reaction (PCR) utilizing two gene-specific primers. The conditions for the reaction were standard conditions with Expand High Fidelity PCR system (Roche). The parameters for the reaction were: five minutes at 94° C. followed by five cycles of 40 seconds at 94° C., 40 seconds at 50° C. and 1.5 minutes at 72° C. This was followed by thirty cycles of 40 seconds at 94° C., 40 seconds at 65° C. and 1.5 minutes at 72° C. The fragments generated under these RT-PCR conditions were analyzed by agarose gel electrophoresis to make sure that PCR products of the expected length had been obtained.

Full-length LMP cDNA were isolated by using synthetic oligonucleotide primers (MWG-Biotech) designed based on the LMP gene specific DNA sequence that was determined by EST sequencing and by sequencing of RACE PCR products. All 5' PCR primers ("forward primer", F) contained an AscI restriction site 5' upstream of the ATG start codon. All 3' PCR primers ("reverse primers", R) contained a Pact restriction site 3' downstream of the stop codon. The restriction sites were added so that the RT-PCR amplification products could be cloned into the AscI and Pact restriction sites located in the multiple cloning site of the binary vector pBPS-GB1. The first 2 nucleotides are used as spacers so the restriction enzymes cut properly. The following "forward" (F) and "reverse" (R) primers were used to amplify the full-length Physcomitrella cDNAs by RT-PCR using RNA from Physcomitrella as original template:

```
For amplification of SEQ ID NO:1
pp29F
                                       (SEQ ID NO:46)
(5'-ATGGCGCGCCCGATGGTGCGTTCGAGATCG-3')

pp29R
                                       (SEQ ID NO:47)
(5'-GCTTAATTAAGCGTTAACGAGCTTTCTCGCAGTGCC-3')

For amplification of SEQ ID NO:4
pp07F
                                       (SEQ ID NO:48)
(5'-ATGGCGCGCCTGGGTTTGGGTAGTTGCTTGACGAC-3')

pp07R
                                       (SEQ ID NO:49)
(5'-GCTTAATTAAGGTTCAAGGACCGCCTGCCTATAC-3')

For amplification of SEQ ID NO:7
pp27F
                                       (SEQ ID NO:50)
(5'-ATGGCGCGCCGAGCTGCTGTCAGTTCGTCAACGG-3')

pp27R
                                       (SEQ ID NO:51)
(5'-ATTTAATTAAGTTGACCAGGACGACAGCAGTAGC-3')

For amplification of SEQ ID NO:10
pp63F
                                       (SEQ ID NO:52)
(5'-ATGGCGCGCCCGCAGCATGTGACTCGTCACCTG-3')

pp63R
                                       (SEQ ID NO:53)
(3'-CGTTAATTAAAGCTACTACTTGCTCTAGGAAGCTG-5')

For amplification of SEQ ID NO:13
pp31F
                                       (SEQ ID NO:54)
(5'-ATGGCGCGCCAGCACGAGGGCAAGAGGG-3')

pp31R
                                       (SEQ ID NO:55)
(5'-ATTTAATTAAGTTGACGTTGGATTGCACATGGTTG-3')

For amplification of SEQ ID NO:16
pp37F
                                       (SEQ ID NO:56)
(5'-ATGGCGCGCCGGCCTTCAAGCACTCTCTGCAT-3')

pp37R
                                       (SEQ ID NO:57)
(5'-ATTTAATTAATCTCATGGACGACCCACC-3')

For amplification of SEQ ID NO:19
pp11F
                                       (SEQ ID NO:58)
(5'-TAGGCGCGCCGTTGCGTTCTCTGCTTCCTTCGA-3')

pp11R
                                       (SEQ ID NO:59)
(5'-GCTTAATTAACTGTATCCAAACCTCTGCCGGTGG-3')

For amplification of SEQ ID NO:22
pp58F
                                       (SEQ ID NO:60)
(5'-ATGGCGGGCCGGCGAAGGGGAGGTGTCGG-3')

pp58R
                                       (SEQ ID NO:61)
(5'-GGTTAATTAAGAATTACTGGACCGGAGAAAACG-3')

For amplification of SEQ ID NO:25
pp48F
                                       (SEQ ID NO:62)
(5'-ATGGCGCGCCCTGAGTGAGGAACTGGGAGCGATGG-3')

pp48R
                                       (SEQ ID NO:63)
(5'-GCTTAATTAACCCTTGCAGTACTCGTTTGCCTTTC-3')

For amplification of SEQ ID NO:28
pp74F
                                       (SEQ ID NO:64)
(5'-TAGGCGCCCCAGTGGGTGGTTGGACTGTAAGGA-3')

pp74R
                                       (SEQ ID NO:65)
(5'-GCTTAATTAACTTCGTCTTGGACAGGTAGAGGTTAC-3')

For amplification of SEQ ID NO:31
pp08F
                                       (SEQ ID NO:66)
(5'-ATGGCGCGCCGCCTCTCCTGTGGCCTCAAGC-3')

pp08R
                                       (SEQ ID NO:67)
(5'-ATTTAATTAACGTCGTCTGCTGCACAATTCCCTCCC-3')

For amplification of SEQ ID NO:34
pp84F
                                       (SEQ ID NO:68)
(5'-ATGGCGCGCCGGCTAGTCGCATTCACAGAGCAGCT-3')

pp84R
                                       (SEQ ID NO:69)
(5'-CGTTAATTAAGCCCTTGCGATATCCAGCGTTTGAC-3')

For amplification of SEQ ID NO:37
pp100F
                                       (SEQ ID NO:70)
(5'-ATGGCGCGCCGATAATCGTTGCGTAGAGGTGGCC-3')

pp100R
                                       (SEQ ID NO:71)
(5'-GCTTAATTAAGACTTAAAAATCGTTGGCCCTCTTTCG-3')

For amplification of SEQ ID NO:40
pp12F
                                       (SEQ ID NO:72)
(5'-ATGGCGCGCCGCGAAAGAACCGATTGGGATTAGG-3')

pp12R
                                       (SEQ ID NO:73)
(5'-ATTTAATTAACGAACATAGACCGTAAGTCGTGAGCC-3')
```

For plant transformation, binary vectors such as pBinAR can be used (Höfgen & Willmitzer 1990, Plant Sci. 66: 221-230). Plant binary vectors encoding LMP genes were constructed with the aim to achieve the overexpression of functionally active proteins in transgenic plants. All LMP gene candidates were cloned into the plant binary vector pBPS-GB1 vector. The binary vector contains a selectable marker gene driven under the control of the AtAct2-I promoter (Ann Y-Q et al. 1996, Plant Journal 10:107-121) and a USP (unknown seed protein, Bäumlein et al., Mol Gen Genet 225: 459-467, 1991) seed-specific promoter driving the candidate LMP gene with the NOSpA terminator. Full-length LMP cDNA were cloned into AscI and PacI restriction sites in the multiple cloning site of pBPS-GB1 in sense orientation behind the USP seed-specific promoter. The recombinant binary vectors (based on pBPS-GB1) containing the genes of interest were transformed into *E. coli* Top10 cells (Invitrogen) using standard conditions. Transformed cells were selected for on LB agar containing 50 μg/ml kanamycin grown overnight at 37° C. Plasmid DNA was extracted using the QIAprep Spin Miniprep Kit (Qiagen) following manufacturer's instructions. Analysis of subsequent clones and restriction mapping was performed according to standard molecular biology techniques (Sambrook et al. 1989, Molecular Cloning, A Laboratory Manual. 2$^{nd}$ Edition. Cold Spring Harbor Laboratory Press. Cold Spring Harbor, N.Y.). The nucleotide sequence of the inserted LMP genes was verified by "2+1" sequencing (the insert DNA was sequence by determining the nucleotide sequence of one DNA stand with two independent sequence reactions and the complementary DNA strand with on sequencing reaction according to the Bermuda convention). The full length sequences are shown as SEQ ID NOs: 1, 4, 7, 10, 13, 16, 19, 22, 25, 28, 31, 34, 37 and 40.

TABLE 3

Putative LMP Functions

| Functional categories | Function | Sequence code | ORF position | SEQ ID NO: |
|---|---|---|---|---|
| Transcription factor | Putative DNA-binding protein - *Arabidopsis thaliana* | s_pp001031077f | 339-2493 | 1 |
| Transcription factor | Probable transcription initiation factor TFIIB - soybean | s_pp001117032r | 133-1065 | 4 |
| Transcription factor | BZIP DNA-binding protein HBF-1 - soybean | c_pp001113065r | 721-2043 | 7 |
| Protein kinase | Probable kasein kinase (EC 2.7.1) - *Arabidopsis* | c_pp004047195r | 14-1432 | 10 |
| Transcription factor | Homeodomain leucine zipper protein - *Oryza sativa* | c_pp001058012r | 134-1150 | 13 |
| Protein kinase | putative protein kinase - *Arabidopsis thaliana* (thale) | s_pp001009079f | 132-1455 | 16 |
| Protein kinase | Phosphoenolpyruvate carboxykinase-like protein | c_pp004076330r | 136-2187 | 19 |
| Signal Transduction | Phosphoinositide-specific phospholipase C - *Nicotiana* | c_pp004040301r | 13-1956 | 22 |
| Signal Transduction | Ethylene receptor homolog - *Pelargonium* x *hortorum* | s_pp002024092r | 22-2262 | 25 |
| Protein kinase | Probable cdc2-like protein kinase cdc2MsF - *alfalfa* | s_pp001031042f | 86-1015 | 28 |
| Signal Transduction | Product: "putative RNA binding protein"; | c_pp032010072r | 278-1588 | 31 |
| Transcription factor | Transcription factor SAR DNA binding protein | s_pp001068093r | 65-1840 | 34 |
| Signal Transduction | Lipid transfer protein | s_pp013010011r | 173-1264 | 37 |
| Kinase | Acetylglutamate kinase (EC 2.7.2.8) - *Synechocystis* | c_pp004096088r | 9-1217 | 40 |

TABLE 4

Grouping of LMPs based on Functional protein domains

| Functional category | SEQ ID NO: | Functional domain | Domain position |
|---|---|---|---|
| Transcription factors | 3 | Helicase domain | 683-759 |
| | 3 | SNF2 domain | 270-535 |
| | 6 | Transcription factor 2 domain | 110-178 |
| | 6 | Transcription factor 2 domain | 211-275 |
| | 15 | Homeobox domain | 92-144 |
| | 9 | bZIP domain | 255-319 |
| | 36 | Nop domain | 251-395 |
| Kinases | 12 | pkinase domain | 9-210 |
| | 21 | PEPCK domain | 159-613 |
| | 18 | Galactokinase | 24-35 |
| | 18 | Shikimate kinase | 141-154 |
| | 30 | pkinase domain | 11-282 |
| | 42 | Kinase domain | 57-215 |
| Signal Transduction | 33 | Retinoic acid receptor signature | 162-181 |
| | 33 | EDG1 orphan receptor signature | 56-76 |
| | 27 | Response regulatory domain | 615-729 |
| | 27 | H-ATPase domain | 454-571 |
| | 39 | Protein sensory transduction domain | 189-203 |
| | 39 | Alpha-1B adrenergic receptor signature | 312-329 |
| | 24 | PI-Phospholipase C—X domain | 121-257 |
| | 24 | PI-Phospholipase C—Y domain | 407-485 |

Example 7

*Agrobacterium* Mediated Plant Transformation

*Agrobacterium* mediated plant transformation with binary vectors encoding the LMP nucleic acids described herein was performed using standard transformation and regeneration techniques (Gelvin, Stanton B. & Schilperoort R. A, Plant Molecular Biology Manual, 2nd ed. Kluwer Academic Publ., Dordrecht 1995 in Sect., Ringbuc Zentrale Signatur: BT11-P; Glick, Bernard R. and Thompson, John E. Methods in Plant Molecular Biology and Biotechnology, S. 360, CRC Press, Boca Raton 1993).

The *Agrobacterium* mediated transformation of *Arabidopsis thaliana* was performed using the GV3 (pMP90) (Koncz & Schell, 1986, Mol. Gen. Genet. 204: 383-396) *Agrobacterium tumefaciens* strain. *Arabidopsis thaliana* ecotype Col-2 was grown and transformed according to standard conditions (Bechtold 1993, Acad. Sci. Paris. 316: 1194-1199; Bent et al. 1994, Science 265: 1856-1860). Kanamycin was used as antibiotic selection marker for *Agrobacterium* transformation. The presence and correct orientation of the LMP-encoding binary vectors in *Agrobacterium* cultures was verified by PCR using the LMP gene-specific primers described in Example 6. For the plant transformation flowering *Arabidopsis* plants were dipped into the recombinant *Agrobacterium* cultures and allowed to go to seed. Transgenic *Arabidopsis* T1 plants were identified by growing the seeds on Petri plates containing the selection agent appropriate for the selection marker present on the T-DNA. Surviving healthy seedlings were transferred to soil and grown in a growth chamber under controlled conditions. T2 seeds were harvested from these T1 plants. The transgenic lines were propagated through successive generations and T3 and T4 seeds were obtained. The segregation ratio of the presence or absence of the T-DNA was monitored in order to determine whether the lines contained single-locus or multi-locus insertions and whether the lines were homozygous or heterozygous for the T-DNA insertion. T2, T3 and T4 seeds were analyzed for seed oil content (see also example 14).

*Agrobacterium* mediated plant transformation is also applicable to *Brassica* and other crops. In particular, seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. The seed coats are removed and the seeds are air dried overnight in a half-open sterile Petri dish. During this period, the seeds lose approximately 85% of their water content. The seeds are then stored at room temperature in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and re-suspended in MS (Murashige & Skoog 1962, Physiol. Plant. 15: 473-497) medium supplemented with 100 µM acetosyringone. Bacteria cultures are incubated in this pre-induction medium for 2 hours at room temperature before use. The axis of soybean zygotic seed embryos at approximately 44% moisture content are imbibed for 2 hours at room temperature with the pre-induced *Agrobacterium* suspension culture. (The imbibition of dry embryos with a culture of *Agrobacterium* is also applicable to maize embryo axes). The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/l carbenicillin or 300 mg/l cefotaxime to kill the agrobacteria. The liquid medium is used to moisten the sterile filter paper. The embryos are incubated during 4 weeks at 25° C., under 440 µmol m$^{-2}$ sec$^{-1}$ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 440 mmol m$^{-2}$ s$^{-1}$ light intensity and 12 h photoperiod for about 80 days.

Samples of the primary transgenic plants (T$_0$) are analyzed by PCR to confirm the presence of T-DNA. These results are confirmed by Southern hybridization wherein DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labeled probe by PCR, and used as recommended by the manufacturer.

Transformation of soybean can be performed using for example a technique described in EP 424 047, U.S. Pat. No. 5,322,783 (Pioneer Hi-Bred International) or in EP 0397 687, U.S. Pat. No. 5,376,543 or U.S. Pat. No. 5,169,770 (University Toledo). Soybean seeds are surface sterilized with 70% ethanol for 4 minutes at room temperature with continuous shaking, followed by 20% (v/v) Clorox supplemented with 0.05% (v/v) Tween for 20 minutes with continuous shaking. Then the seeds are rinsed 4 times with distilled water and placed on moistened sterile filter paper in a Petri dish at room temperature for 6 to 39 hours. The seed coats are peeled off and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

Example 8

Analysis of the Impact of Recombinant LMPs on the Production of a Desired Seed Storage Compound: Fatty Acid Production Total fatty acid of seeds of control and transgenic plants was measured with bulked seeds (usually 5 mg seed weight) of a single plant. Three different types of controls have been used: Col-2 or Col-0 (Columbia-2 or Columbia-0, the *Arabidopsis* ecotypes LMP gene of interest have been transformed in), C-24 (an *Arabidopsis* ecotype found to accumulate high amounts of total fatty acids in seeds) and BPS empty (without LMP gene of interest) binary vector construct. The controls indicated in the tables below have been grown side by side with the transgenic lines. Differences in the total values of the controls are explained either by differences in the growth conditions, which were found to be very sensitive to small variations in the plant cultivation, or by differences in the standards added to quantify the fatty acid content. Because of the seed bulking all values obtained with T2 seeds and in part also with T3 seeds are the result of a mixture of homozygous (for the gene of interest) and heterozygous events, implying that these data underestimate the LMP gene effect.

TABLE 5

Determination of the T4 seed total fatty acid content of transgenic lines of s_pp001031077f (containing SEQ ID NO: 1). Shown are the means (± standard deviation) of four independent transgenic events. (Average mean values are shown ± standard deviation, number of individual measurements per plant line: 15-18, Col-2 is the *Arabidopsis* ecotype the LMP gene has been transformed in, C-24 is a high-oil *Arabidopsis* ecotype used as another control)

| Genotype | g total fatty acids/ g seed weight |
|---|---|
| C-42 wild-type seeds | 0.368 ± 0.026 |
| Col-2 wild-type seeds | 0.343 ± 0.028 |
| pp29-19-1 transgenic seeds | 0.386 ± 0.027 |
| pp29-19-3 transgenic seeds | 0.377 ± 0.032 |
| pp29-20-12 transgenic seeds | 0.371 ± 0.017 |
| pp29-20-7 transgenic seeds | 0.366 ± 0.030 |
| pp29-2-4 transgenic seeds | 0.384 ± 0.037 |
| pp29-4-4 transgenic seeds | 0.364 ± 0.021 |
| pp29-4-5 transgenic seeds | 0.362 ± 0.022 |

TABLE 6

Determination of the T4 seed total fatty acid content of transgenic lines of s_pp001117032r (containing SEQ ID NO: 4) Shown are the means (± standard deviation) of 10-18 individual plants per line.

| Genotype | g total fatty acids/ g seed weiht |
|---|---|
| C-42 wild-type seeds | 0.368 ± 0.026 |
| Col-2 wild-type seeds | 0.343 ± 0.028 |
| pp07-4-2 transgenic seeds | 0.366 ± 0.042 |
| pp07-6-3 transgenic seeds | 0.370 ± 0.021 |

TABLE 7

Determination of the T3 seed total fatty acid content of transgenic lines of c_pp001113065r (containing SEQ ID NO: 7). Shown are the means (± standard deviation) of 11-18 individual plants per line.

| Genotype | g total fatty acids/ g seed weight |
|---|---|
| C-24 wild-type seeds | 0.490 ± 0.026 |
| Col-2 wild-type seeds | 0.444 ± 0.045 |
| pp27-14 transgenic seeds | 0.484 ± 0.041 |
| pp27-2 transgenic seeds | 0.474 ± 0.036 |

TABLE 8

Determination of the T3 seed total fatty acid content of transgenic lines of c_pp004047195r (containing SEQ ID NO: 10). Shown are the means (± standard deviation) of 12-19 individual plants per line.

| Genotype | g total fatty acids/ g seed weight |
|---|---|
| Col-2 wild-type seeds | 0.290 ± 0.026 |
| BPS empty vector transgenic seeds | 0.294 ± 0.020 |
| C-24 wild-type seeds | 0.311 ± 0.016 |
| pp63-1 transgenic seeds | 0.325 ± 0.022 |
| pp63-3 transgenic seeds | 0.328 ± 0.026 |
| pp63-4 transgenic seeds* | 0.332 ± 0.021 |
| pp63-6 transgenic seeds* | 0.303 ± 0.018 |

TABLE 9

Determination of the T3 seed total fatty acid content of transgenic lines of c_pp001058012r (containing SEQ ID NO: 13). Shown are the means (± standard deviation) of 12-19 individual plants per line.

| Genotype | g total fatty acids/ g seed weight |
|---|---|
| Col-2 wild-type seeds | 0.406 ± 0.047 |
| C-24 wild-type seeds | 0.488 ± 0.047 |
| pp31-17 transgenic seeds | 0.416 ± 0.033 |
| pp31-18 transgenic seeds | 0.441 ± 0.043 |

TABLE 10

Determination of the T3 seed total fatty acid content of transgenic lines of c_pp001009079f (containing SEQ ID NO: 16). Shown are the means (± standard deviation) of 12-18 individual plants per line.

| Genotype | g total fatty acids/ g seed weight |
|---|---|
| Col-2 wild-type seeds | 0.406 ± 0.047 |
| C-24 wild-type seeds | 0.488 ± 0.047 |
| pp37-2 transgenic seeds | 0.434 ± 0.032 |

TABLE 11

Determination of the T2 seed total fatty acid content of transgenic lines of c_pp004076330r (containing SEQ ID NO: 19). Shown are the means (± standard deviation) of 15-18 individual plants per line.

| Genotype | g total fatty acids/g seed weight |
|---|---|
| Col-2 wild-type seeds | 0.487 ± 0.023 |
| C-24 wild-type seeds | 0.513 ± 0.031 |
| pp11 transgenic seeds | 0.509 ± 0.032 |

TABLE 12

Determination of the T2 seed total fatty acid content of transgenic lines of c_pp004040301r (containing SEQ ID NO: 22). Shown are the means (± standard deviation) of 17-18 individual plants per line.

| Genotype | g total fatty acids/g seed weight |
|---|---|
| Col-2 wild-type seeds | 0.487 ± 0.023 |
| C-24 wild-type seeds | 0.513 ± 0.031 |
| pp58 transgenic seeds | 0.496 ± 0.019 |

TABLE 13

Determination of the T2 seed total fatty acid content of transgenic lines of c_pp002024092r (containing SEQ ID NO: 25). Shown are the means (± standard deviation) of 16-19 individual plants per line.

| Genotype | g total fatty acids/g seed weight |
|---|---|
| Col-2 wild-type seeds | 0.533 ± 0.020 |
| C-24 wild-type seeds | 0.622 ± 0.058 |
| pp48 transgenic seeds | 0.555 ± 0.042 |

TABLE 14

Determination of the T2 seed total fatty acid content of transgenic
lines of c_pp001031042f (containing SEQ ID NO: 28).
Shown are the means (± standard deviation)
of 15-19 individual plants per line.

| Genotype | g total fatty acids/g seed weight |
|---|---|
| Col-2 wild-type seeds | 0.451 ± 0.038 |
| C-24 wild-type seeds | 0.483 ± 0.040 |
| pp74 transgenic seeds | 0.468 ± 0.043 |

TABLE 15

Determination of the T3 seed total fatty acid content of transgenic
lines of c_pp032010072r (containing SEQ ID NO: 31).
Shown are the means (± standard deviation) of
14-17 individual plants per line.

| Genotype | g total fatty acids/g seed weight |
|---|---|
| C-24 wild-type seeds | 0.430 ± 0.034 |
| Col-2 wild-type seeds | 0.398 ± 0.029 |
| pp08-12 transgenic seeds | 0.414 ± 0.023 |

TABLE 16

Determination of the T2 seed total fatty acid content of transgenic
lines of s_pp001068093r (containing SEQ ID NO: 34).
Shown are the means (± standard deviation) of
14-19 individual plants per line.

| Genotype | g total fatty acids/g seed weight |
|---|---|
| C-24 wild-type seeds | 0.439 ± 0.036 |
| Col-2 wild-type seeds | 0.419 ± 0.034 |
| pp84 transgenic seeds | 0.442 ± 0.037 |

TABLE 17

Determination of the T4 seed total fatty acid content of transgenic
lines of s_pp013010011r (containing SEQ ID NO: 37).
Shown are the means (± standard deviation) of
14-20 individual plants per line.

| Genotype | g total fatty acids/g seed weight |
|---|---|
| Col-0 wild-type seeds | 0.366 ± 0.024 |
| pp100-5-3 transgenic seeds | 0.499 ± 0.054 |
| pp100-5-4 transgenic seeds | 0.447 ± 0.040 |
| pp100-5-9 transgenic seeds | 0.463 ± 0.051 |

TABLE 18

Determination of the T2 seed total fatty acid content of transgenic
lines of c_pp004096088r (containing SEQ ID NO: 40).
Shown are the means (± standard deviation) of
14-20 individual plants per line.

| Genotype | g total fatty acids/g seed weight |
|---|---|
| Col-2 wild-type seeds | 0.365 ± 0.028 |
| pp12 transgenic seeds | 0.375 ± 0.013 |

Example 9

Analysis of the Impact of Recombinant LMPs on the Production of a Desired Seed Storage Compound: Soluble Sugars, Starch and Proteins For the extraction of soluble sugars and starch, 50 seeds are homogenized in 500 µl of 80% (v/v) ethanol in a 1.5-ml polypropylene test tube and incubated at 70° C. for 90 minutes. Following centrifugation at 16,000 g for 5 minutes, the supernatant is transferred to a new test tube. The pellet is extracted twice with 500 µl of 80% ethanol. The solvent of the combined supernatants is evaporated at room temperature under a vacuum. The residue is dissolved in 50 µl of water, representing the soluble carbohydrate fraction. The pellet left from the ethanol extraction, which contains the insoluble carbohydrates including starch, is homogenized in 200 µl of 0.2 N KOH, and the suspension is incubated at 95° C. for 1 hour to dissolve the starch. Following the addition of 35 µl of 1 N acetic acid and centrifugation for 5 minutes at 16,000 g, the supernatant is used for starch quantification.

To quantify soluble sugars, 10 µl of the sugar extract is added to 990 µl of reaction buffer containing 100 mM imidazole, pH 6.9, 5 mM $MgCl_2$, 2 mM NADP, 1 mM ATP, and 2 units 2 $ml^{-1}$ of Glucose-6-P-dehydrogenase. For enzymatic determination of glucose, fructose and sucrose, 4.5 units of hexokinase, 1 unit of phosphoglucoiso-merase, and 2 µl of a saturated fructosidase solution are added in succession. The production of NADPH is photometrically monitored at a wavelength of 340 nm. Similarly, starch is assayed in 30 µl of the insoluble carbohydrate fraction with a kit from Boehringer Mannheim.

An example for analyzing the protein content in leaves and seeds can be found by Bradford M. M. (1976, "A rapid and sensitive method for the quantification of microgram quantities of protein using the principle of protein dye binding" Anal. Biochem. 72: 248-254). For quantification of total seed protein, 15-20 seeds are homogenized in 250 µl of acetone in a 1.5-ml polypropylene test tube. Following centrifugation at 16,000 g, the supernatant is discarded and the vacuum-dried pellet is resuspended in 250 Pl of extraction buffer containing 50 mM Tris-HCl, pH 8.0, 250 mM NaCl, 1 mM EDTA, and 1% (w/v) SDS. Following incubation for 2 hours at 25° C., the homogenate is centrifuged at 16,000 g for 5 minutes and 200 ml of the supernatant will be used for protein measurements. In the assay γ-globulin is used for calibration. For protein measurements Lowry DC protein assay (Bio-Rad) or Bradford-assay (Bio-Rad) can be used.

Enzymatic assays of hexokinase and fructokinase are performed spectrophoto-metrically according to Renz et al. (1993, Planta 190: 156-165), of phosphogluco-isomerase, ATP-dependent 6-phosphofructokinase, pyrophosphate-dependent 6-phospho-fructokinase, fructose-1,6-bisphosphate aldolase, triose phosphate isomerase, glyceral-3-P dehydrogenase, phosphoglycerate kinase, phosphoglycerate mutase, enolase and pyruvate kinase can be performed according to Burrell et al. (1994, Planta 194: 95-101) and of UDP-Glucose-pyrophosphorylase according to Zrenner et al. (1995, Plant J. 7: 97-107).

Intermediates of the carbohydrate metabolism, like glucose-1-phosphate, glucose-6-phosphate, fructose-6-phosphate, phosphoenolpyruvate, pyruvate, and ATP can be measured as described in Hartel et al. (1998, Plant Physiol. Biochem. 36: 407-417) and metabolites are measured as described in Jelitto et al. (1992, Planta 188: 238-244).

In addition to the measurement of the final seed storage compound (i.e., lipid, starch or storage protein) it is also possible to analyze other components of the metabolic pathways utilized for the production of a desired seed storage compound, such as intermediates and side-products, to determine the overall efficiency of production of the compound (Fiehn et al. 2000, Nature Biotech. 18: 1447-1161).

For example, yeast expression vectors comprising the nucleic acids disclosed herein, or fragments thereof, can be constructed and transformed into *Saccharomyces cerevisiae* using standard protocols. The resulting transgenic cells can then be assayed for alterations in sugar, oil, lipid or fatty acid contents.

Similarly, plant expression vectors comprising the nucleic acids disclosed herein, or fragments thereof, can be constructed and transformed into an appropriate plant cell such as *Arabidopsis*, soy, rape, *maize*, wheat, *Medicago truncatula*, etc., using standard protocols. The resulting transgenic cells and/or plants derived therefrom can then be assayed for alterations in sugar, oil, lipid or fatty acid contents.

Additionally, the sequences disclosed herein, or fragments thereof, can be used to generate knockout mutations in the genomes of various organisms, such as bacteria, mammalian cells, yeast cells, and plant cells (Girke at al. 1998, Plant J. 15: 39-48). The resultant knockout cells can then be evaluated for their composition and content in seed storage compounds, and the effect on the phenotype and/or genotype of the mutation. For other methods of gene inactivation include U.S. Pat. No. 6,004,804 "Non-Chimeric Mutational Vectors" and Puttaraju et al. (1999, "Spliceosome-mediated RNA trans-splicing as a tool for gene therapy" Nature Biotech. 17:246-252).

Example 10

Purification of the LMPs from Transformed Organisms

A LMP can be recovered from plant material by various methods well known in the art. Organs of plants can be separated mechanically from other tissue or organs prior to isolation of the seed storage compound from the plant organ. Following homogenization of the tissue cellular debris is removed by centrifugation, and the supernatant fraction containing the soluble proteins is retained for further purification of the desired compound. If the product is secreted from cells grown in culture, then the cells are removed from the culture by low-speed centrifugation and the supernate fraction is retained for further purification.

The supernatant fraction from either purification method is subjected to chromatography with a suitable resin, in which the desired molecule is either retained on a chromatography resin while many of the impurities in the sample are not or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There are a wide array of purification methods known to the art and the preceding method of purification is not meant to be limiting. Such purification techniques are described, for example, in Bailey J. E. & Ollis D. F. 1986, Biochemical Engineering Fundamentals, McGraw-Hill: New York).

The identity and purity of the isolated compounds may be assessed by techniques standard in the art. These include high-performance liquid chromatography (HPLC), spectroscopic methods, staining methods, thin layer chromatography, analytical chromatography such as high performance liquid chromatography, NIRS, enzymatic assay, or microbiologically. Such analysis methods are reviewed in: Patek et al. (1994, Appl. Environ. Microbiol. 60: 133-140), Malakhova et al. (1996, Biotekhnologiya 11: 27-32) and Schmidt et al. (1998, Bioprocess Engineer 19: 67-70), Ulmann's Encyclopedia of Industrial Chemistry (1996, Vol. A27, VCH: Weinheim, p. 89-90, p. 521-540, p. 540-547, p. 559-566, 575-581 and p. 581-587) and Michal G. (1999, Biochemical Pathways: An Atlas of Biochemistry and Molecular Biology, John Wiley and Sons; Fallon, A. et al. 1987, Applications of HPLC in Biochemistry in: Laboratory Techniques in Biochemistry and Molecular Biology, vol. 17).

Example 11

In Vitro Analysis of the Function of LMP Genes in Transgenic Plants

The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M. & Webb, E. C. 1979, Enzymes. Longmans: London; Fersht, (1985) Enzyme Structure and Mechanism. Freeman: New York; Walsh (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, $3^{rd}$ ed. Academic Press: New York; Bisswanger, H., (1994) Enzymkinetik, $2^{nd}$ ed. VCH: Weinheim (ISBN 3527300325); Bergmeyer, H. U., Bergmeyer, J., Graβl, M., eds. (1983-1986) Methods of Enzymatic Analysis, $3^{rd}$ ed., vol. I-XII, Verlag Chemie: Weinheim; and Ullmann's Encyclopedia of Industrial Chemistry (1987) vol. A9, Enzymes. VCH: Weinheim, p. 352-363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar H. et al. 1995, EMBO J. 14: 3895-3904 and references cited therein). Reporter gene test systems are well known and established for applications in both pro- and eukaryotic cells, using enzymes such as β-galactosidase, green fluorescent protein, and several others.

The determination of activity of membrane-transport proteins can be performed according to techniques such as those described in Gennis R. B. (1989, Pores, Channels and Transporters, in Biomembranes, Molecular Structure and Function, Springer: Heidelberg, p. 85-137, 199-234, and 270-322).

Example 12

Assessment of the mRNA Expression and Activity of a Recombinant Gene Product in the Transformed Organism The activity of a recombinant gene product in the transformed host organism can be measured on the transcriptional or/and on the translational level. A useful method to ascertain the level of transcription of the gene (an indicator of the amount of mRNA available for translation to the gene product) is to perform a Northern blot (for reference see, for example, Ausubel et al. 1988, Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information at least partially demonstrates the degree of transcription of the transformed gene. Total cellular RNA can be prepared from cells, tissues or organs by several methods, all well-known in the art, such as that described in Bormann et al. (1992, Mol. Microbiol. 6: 317-326).

To assess the presence or relative quantity of protein translated from this mRNA, standard techniques, such as a Western blot, may be employed (see, for example, Ausubel et al. 1988, Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or calorimetric label which may be readily detected. The presence and quantity of label observed indicates the presence and quantity of the desired mutant protein present in the cell.

The activity of LMPs that bind to DNA can be measured by several well-established methods, such as DNA band-shift assays (also called gel retardation assays). The effect of such LMP on the expression of other molecules can be measured using reporter gene assays (such as that described in Kolmar H. et al. 1995, EMBO J. 14: 3895-3904 and references cited therein). Reporter gene test systems are well known and established for applications in both prokaryotic and eukaryotic cells, using enzymes such as beta-galactosidase, green fluorescent protein, and several others.

The determination of activity of lipid metabolism membrane-transport proteins can be performed according to techniques such as those described in Gennis R. B. (1989 Pores, Channels and Transporters, in Biomembranes, Molecular Structure and Function, Springer: Heidelberg, pp. 85-137, 199-234 and 270-322)

Example 13

In Vivo Mutagenesis

In vivo mutagenesis of microorganisms can be performed by incorporation and passage of the plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g. mutHLS, mutD, mutT, etc.; for reference, see Rupp W. D. 1996, DNA repair mechanisms, in: *Escherichia coli* and *Salmonella*, p. 2277-2294, ASM: Washington.) Such strains are well known to those skilled in the art. The use of such strains is illustrated, for example, in Greener and Callahan 1994, Strategies 7: 32-34. Transfer of mutated DNA molecules into plants is preferably done after selection and testing in microorganisms. Transgenic plants are generated according to various examples within the exemplification of this document.

Northern-Hybridization

For RNA hybridization, 20 µg of total RNA or 1 µg of poly-(A)+ RNA is separated by gel electrophoresis in 1.25% strength agarose gels using formaldehyde as described in Amasino (1986, Anal. Biochem. 152: 304), transferred by capillary attraction using 10×SSC to positively charged nylon membranes (Hybond N+, Amersham, Braunschweig), immobilized by UV light and prehybridized for 3 hours at 68° C. using hybridization buffer (10% dextran sulfate w/v, 1 M NaCl, 1% SDS, 100 µg/ml of herring sperm DNA). The labeling of the DNA probe with the Highprime DNA labeling kit (Roche, Mannheim, Germany) is carried out during the prehybridization using alpha-$^{32}$P dCTP (Amersham, Braunschweig, Germany). Hybridization is carried out after addition of the labeled DNA probe in the same buffer at 68° C. overnight. The washing steps are carried out twice for 15 minutes using 2×SSC and twice for 30 minutes using 1×SSC, 1% SDS at 68° C. The exposure of the sealed filters is carried out at −70° C. for a period of 1 day to 14 days.

Example 14

Identification of LMP Homologues

Gene sequences can be used to identify homologous or heterologous genes from cDNA or genomic libraries. Homologous genes (e.g. full-length cDNA clones) can be isolated via nucleic acid hybridization using for example cDNA libraries: Depended on the abundance of the gene of interest, 100,000 up to 1,000,000 recombinant bacteriophages are plated and transferred to nylon membranes. After denaturation with alkali, DNA is immobilized on the membrane by e.g. UV cross linking. Hybridization is carried out at high stringency conditions. In aqueous solution hybridization and washing is performed at an ionic strength of 1 M NaCl and a temperature of 68° C. Hybridization probes are generated by e.g. radioactive ($^{32}$P) nick transcription labeling (High Prime, Roche, Mannheim. Germany). Signals are typically detected by autoradiography.

Partially homologous or heterologous genes that are related but not identical can be identified analog to the above-described procedure using low stringency hybridization and washing conditions. For aqueous hybridization the ionic strength is normally kept at 1 M NaCl while the temperature is progressively lowered from 68 to 42° C.

Isolation of gene sequences with homologies (or sequence identity/similarity) only in a distinct domain of (for example 10-20 amino acids) can be carried out by using synthetic radio labeled oligonucleotide probes. Radio labeled oligonucleotides are prepared by phosphorylation of the 5'-prime end of two complementary oligonucleotides with T4 polynucleotide kinase. The complementary oligonucleotides are annealed and ligated to form concatemers. The double stranded concatemers are than radiolabeled by for example nick transcription. Hybridization is normally performed at low stringency conditions using high oligonucleotide concentrations.

Oligonucleotide Hybridization Solution:

6×SSC 0.01 M sodium phosphate 1 mM EDTA (pH 8)

0.5% SDS

100 µg/ml denatured salmon sperm DNA 0.1% nonfat dried milk

During hybridization, temperature is lowered stepwise to 5-10° C. below the estimated oligonucleotide Tm or down to room temperature followed by washing steps and autoradiography. Washing is performed with low stringency such as 3 washing steps using 4×SSC. Further details are described by Sambrook et al. (1989, "Molecular Cloning: A Laboratory Manual", Cold Spring Harbor Laboratory Press) or Ausubel et al. (1994, "Current Protocols in Molecular Biology", John Wiley & Sons).

We claim:

1. An isolated Lipid Metabolism Protein (LMP) nucleic acid comprising a polynucleotide sequence selected from the group consisting of:
   a) the full-length polynucleotide sequence as shown in SEQ ID NO:19 or SEQ ID NO:20; and
   b) a polynucleotide sequence encoding the full-length polypeptide as shown in SEQ ID NO:21.

2. An isolated nucleic acid comprising a polynucleotide of at least 100 consecutive nucleotides of the LMP nucleic acid of claim 1.

3. An isolated nucleic acid comprising a polynucleotide sequence having at least 90% sequence identity with a polynucleotide sequence selected from the group consisting of the full-length polynucleotide as shown in SEQ ID NO:19 or SEQ ID NO:20 and a full-length polynucleotide encoding the full-length polypeptide as shown in SEQ ID NO:21, wherein said polynucleotide encodes a polypeptide having phosphoenolpyruvate carboxykinase (PEPCK) activity, wherein expression of the LMP nucleic acid in a plant results in a modified level of a lipid in the plant as compared to a control plant, and wherein the control plant has not been transformed with the LMP nucleic acid.

4. An isolated nucleic acid comprising a polynucleotide complementary to the full-length LMP nucleic acid of claim 1.

5. The isolated LMP nucleic acid of claim 1, wherein the nucleic acid encodes a polypeptide that increases the amount of a lipid in a plant when the polypeptide is expressed in the plant.

6. The isolated LMP nucleic acid of claim 5, wherein the nucleic acid encodes a polypeptide that contains a PEPCK domain.

7. The isolated LMP nucleic acid of claim 6, wherein the nucleic acid encodes the full-length polypeptide as shown in SEQ ID NO:21.

8. A first isolated nucleic acid that hybridizes under stringent conditions to a second nucleic acid selected from the group consisting of:
 a) a second nucleic acid comprising the full-length polynucleotide of SEQ ID NO:19 or SEQ ID NO:20; and
 b) a second nucleic acid encoding the full-length polypeptide of SEQ ID NO:21; wherein the first nucleic acid encodes a polypeptide that has phosphoenolpyruvate carboxykinase activity and that functions as a modulator of a lipid in a plant.

9. A recombinant expression vector comprising the LMP nucleic acid of claim 1, wherein expression of the vector in a host cell modifies a level of a lipid in the host cell.

10. A transgenic plant cell comprising the LMP nucleic acid of claim 1.

11. The transgenic plant cell of claim 10, wherein expression of the LMP nucleic acid in the plant cell results in a modified level of a lipid in the plant cell as compared to a control plant cell, and wherein the control plant cell is of the same ecotype as the transgenic plant cell but has not been transformed with the LMP nucleic acid.

12. A transgenic plant comprising the LMP nucleic acid of claim 1.

13. The transgenic plant of claim 12, wherein the plant is a dicotyledonous plant.

14. The transgenic plant of claim 12, wherein the plant is a monocotyledonous plant.

15. The transgenic plant of claim 12, wherein the plant is selected from the group consisting of rapeseed, canola, linseed, soybean, sunflower, *maize*, oat, rye, barley, wheat, sugarbeet, tagetes, cotton, oil palm, coconut palm, flax, castor and peanut.

16. The transgenic plant of claim 12, wherein expression of the LMP nucleic acid in the plant results in a modified level of a lipid in the plant as compared to a control plant, and wherein the control plant is of the same ecotype as the transgenic plant cell but has not been transformed with the LMP nucleic acid.

17. The transgenic plant of claim 12, wherein the level of the lipid is increased.

18. A seed produced by the transgenic plant of claim 12, wherein the plant is true breeding for a modified level of the lipid as compared to a control plant, and wherein the control plant is of the same ecotype as the transgenic plant but has not been transformed with the LMP nucleic acid.

19. A method of producing a transgenic plant having a modified level of a lipid comprising, transforming a plant cell with an expression vector comprising a Lipid Metabolism Protein (LMP) nucleic acid and generating from the plant cell the transgenic plant, wherein the LMP nucleic acid comprises a polynucleotide sequence selected from the group consisting of:
 a) the full-length polynucleotide sequence as shown in SEQ ID NO:19 or SEQ ID NO:20; and
 b) a polynucleotide sequence encoding the full-length polypeptide as shown in SEQ ID NO:21.

20. The method of claim 19, wherein the plant is a dicotyledonous plant.

21. The method of claim 19, wherein the plant is a monocotyledonous plant.

22. The method of claim 19, wherein the plant is selected from the group consisting of rapeseed, canola, linseed, soybean, sunflower, *maize*, oat, rye, barley, wheat, sugarbeet, tagetes, cotton, oil palm, coconut palm, flax, castor and peanut.

23. The method of claim 19, wherein the level of the lipid is increased.

24. A method of increasing the level of a lipid in a plant comprising, increasing the expression of a Lipid Metabolism Protein (LMP) nucleic acid in the plant, wherein the LMP nucleic acid is selected from the group consisting of:
 a) the full-length polynucleotide sequence as shown in SEQ ID NO:19 or SEQ ID NO:20; and
 b) a polynucleotide sequence encoding the full-length polypeptide as shown in SEQ ID NO:21.

25. The method of claim 24, wherein the plant is a dicotyledonous plant.

26. The method of claim 24, wherein the plant is a monocotyledonous plant.

27. The method of claim 24, wherein the plant is selected from the group consisting of rapeseed, canola, linseed, soybean, sunflower, *maize*, oat, rye, barley, wheat, sugarbeet, tagetes, cotton, oil palm, coconut palm, flax, castor and peanut.

28. The method of claim 24, wherein the level of the lipid is increased.

29. The method of claim 24, wherein the plant is transgenic.

30. The method of claim 24, wherein the plant is not transgenic.

31. An isolated nucleic acid comprising a polynucleotide sequence having at least 90% sequence identity with the full-length polynucleotide as shown in SEQ ID NO:19 or SEQ ID NO:20 or with a polynucleotide encoding the full-length polypeptide as shown in SEQ ID NO:21.

* * * * *